(12) United States Patent
Grembecka et al.

(10) Patent No.: US 12,285,490 B2
(45) Date of Patent: *Apr. 29, 2025

(54) ASH1L DEGRADERS AND METHODS OF TREATMENT THEREWITH

(71) Applicant: The Regents of the University of Michigan, Ann Arbor, MI (US)

(72) Inventors: Jolanta Grembecka, Ann Arbor, MI (US); Szymon Klossowski, Ann Arbor, MI (US); Jing Deng, Ann Arbor, MI (US); Tomasz Cierpicki, Ann Arbor, MI (US); Hao Li, Ann Arbor, MI (US); Hongzhi Miao, Ann Arbor, MI (US); Trupta Purohit, Ann Arbor, MI (US); EunGi Kim, Ann Arbor, MI (US); Dong Chen, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/488,912

(22) Filed: Oct. 17, 2023

(65) Prior Publication Data

US 2024/0366774 A1 Nov. 7, 2024

Related U.S. Application Data

(63) Continuation of application No. 17/468,308, filed on Sep. 7, 2021, now Pat. No. 11,786,602, which is a continuation of application No. 16/186,012, filed on Nov. 9, 2018, now Pat. No. 11,110,177.

(60) Provisional application No. 62/584,473, filed on Nov. 10, 2017.

(51) Int. Cl.
| | |
|---|---|
| *A61K 47/64* | (2017.01) |
| *A61K 9/00* | (2006.01) |
| *A61K 31/404* | (2006.01) |
| *A61K 31/454* | (2006.01) |
| *A61K 31/4545* | (2006.01) |
| *A61K 38/45* | (2006.01) |
| *A61K 47/54* | (2017.01) |
| *A61P 35/02* | (2006.01) |
| *C07D 209/24* | (2006.01) |
| *C07D 471/04* | (2006.01) |

(52) U.S. Cl.
CPC ............ *A61K 47/64* (2017.08); *A61K 9/0019* (2013.01); *A61K 9/0053* (2013.01); *A61K 31/404* (2013.01); *A61K 31/454* (2013.01); *A61K 31/4545* (2013.01); *A61K 38/45* (2013.01); *A61K 47/545* (2017.08); *A61K 47/556* (2017.08); *A61P 35/02* (2018.01); *C07D 209/24* (2013.01); *C07D 471/04* (2013.01); *C12Y 203/02* (2013.01)

(58) Field of Classification Search
CPC .... A61K 47/64; A61K 47/545; A61K 47/556; A61K 9/0019; A61K 9/0053; A61K 31/404; A61K 31/454; A61K 31/4545; A61K 38/45; A61P 35/02
See application file for complete search history.

(56) References Cited

U.S. PATENT DOCUMENTS

| | | | |
|---|---|---|---|
| 3,598,122 | A | 8/1971 | Zaffaroni |
| 3,598,123 | A | 8/1971 | Zaffaroni |
| 3,710,795 | A | 1/1973 | Higuchi et al. |
| 3,731,683 | A | 5/1973 | Zaffaroni |
| 3,742,951 | A | 7/1973 | Zaffaroni |
| 3,814,097 | A | 6/1974 | Ganderton et al. |
| 3,921,636 | A | 11/1975 | Zaffaroni |
| 3,972,995 | A | 8/1976 | Tsuk et al. |
| 3,993,072 | A | 11/1976 | Zaffaroni |
| 3,993,073 | A | 11/1976 | Zaffaroni |
| 3,996,934 | A | 12/1976 | Zaffaroni |
| 4,031,894 | A | 6/1977 | Urquhart et al. |
| 4,060,084 | A | 11/1977 | Chandrasekaran et al. |
| 4,069,307 | A | 1/1978 | Higuchi et al. |
| 4,077,407 | A | 3/1978 | Theeuwes et al. |
| 4,151,273 | A | 4/1979 | Riegelman et al. |
| 4,201,211 | A | 5/1980 | Chandrasekaran et al. |
| 4,229,447 | A | 10/1980 | Porter |
| 4,230,105 | A | 10/1980 | Harwood |
| 4,292,299 | A | 9/1981 | Suzuki et al. |
| 4,292,303 | A | 9/1981 | Keith et al. |
| 4,343,789 | A | 8/1982 | Kawata et al. |

(Continued)

FOREIGN PATENT DOCUMENTS

| | | |
|---|---|---|
| EP | 0606046 | 7/1994 |
| EP | 0780386 | 6/1997 |

(Continued)

OTHER PUBLICATIONS

Adams et al., Application of fragment-based screening to the design of inhibitors of *Escherichia coli* DsbA. Angew Chem Int Ed Engl. Feb. 9, 2015;54(7):2179-84.

Andreeff et al., HOX expression patterns identify a common signature for favorable AML. Leukemia. Nov. 2008;22(11):2041-7.

Antonini et al., N*-N*-S* tridentate ligand system as potential antitumor agents. J Med Chem. Oct. 1981;24(10):1181-4.

Cabianca et al., A long ncRNA links copy number variation to a polycomb/trithorax epigenetic switch in FSHD muscular dystrophy. Cell. May 11, 2012;149(4):819-31.

(Continued)

*Primary Examiner* — Timothy R Rozof
(74) *Attorney, Agent, or Firm* — David W. Staple; Casimir Jones, S.C.

(57) ABSTRACT

Provided herein are small molecules comprising a first domain that binds to ASH1L and a second domain that facilitates ASH1L degradation. In particular, ASH1L-targeting proteolysis targeting chimeras (PROTACs) and methods of use thereof for the treatment of disease (e.g., acute leukemia, solid cancers and other diseases dependent on activity of ASH1L) are provided.

19 Claims, 5 Drawing Sheets

(56) References Cited

U.S. PATENT DOCUMENTS

| | | | |
|---|---|---|---|
| 4,476,116 A | 10/1984 | Anik | |
| 4,596,795 A | 6/1986 | Pitha | |
| 4,755,386 A | 7/1988 | Hsiao et al. | |
| 4,755,389 A | 7/1988 | Jones et al. | |
| 5,033,252 A | 7/1991 | Carter | |
| 5,052,558 A | 10/1991 | Carter | |
| 5,116,817 A | 5/1992 | Anik | |
| 5,124,342 A | 6/1992 | Kerdesky et al. | |
| 5,281,420 A | 1/1994 | Kelm et al. | |
| 5,323,907 A | 6/1994 | Kalvelage | |
| 5,336,168 A | 8/1994 | Sibalis | |
| 5,340,591 A | 8/1994 | Nakano et al. | |
| 5,391,452 A | 2/1995 | Sacripante et al. | |
| 5,456,923 A | 10/1995 | Nakamichi et al. | |
| 5,665,378 A | 9/1997 | Davis et al. | |
| 5,700,485 A | 12/1997 | Berde et al. | |
| 5,723,269 A | 3/1998 | Akagi et al. | |
| 5,739,136 A | 4/1998 | Ellinwood, Jr. et al. | |
| 5,837,280 A | 11/1998 | Kenealy et al. | |
| 5,858,401 A | 1/1999 | Bhalani et al. | |
| 5,861,510 A | 1/1999 | Piscopio et al. | |
| 5,863,949 A | 1/1999 | Robinson et al. | |
| 5,869,090 A | 2/1999 | Rosenbaum | |
| 6,083,518 A | 7/2000 | Lindahl | |
| 6,337,344 B1 | 1/2002 | Defossa et al. | |
| 6,391,452 B1 | 5/2002 | Antonsen et al. | |
| 6,511,993 B1 | 1/2003 | Dack et al. | |
| 6,667,048 B1 | 12/2003 | Lambert et al. | |
| 6,923,983 B2 | 8/2005 | Morgan et al. | |
| 6,929,801 B2 | 8/2005 | Klose et al. | |
| 6,946,144 B1 | 9/2005 | Jordan | |
| 6,960,563 B2 | 11/2005 | Egbaria et al. | |
| 7,030,242 B2 | 4/2006 | Noe et al. | |
| 7,998,966 B2 | 8/2011 | Bearss et al. | |
| 8,314,140 B2 | 11/2012 | Wallace et al. | |
| 10,632,209 B2 * | 4/2020 | Grembecka | C07D 471/04 |
| 11,110,177 B2 * | 9/2021 | Grembecka | A61K 9/0019 |
| 11,147,885 B2 * | 10/2021 | Grembecka | C12Y 203/02 |
| 11,786,602 B2 * | 10/2023 | Grembecka | A61K 47/556 546/277.4 |
| 2004/0013734 A1 | 1/2004 | Babcock et al. | |
| 2010/0311811 A1 | 12/2010 | Sauer | |
| 2010/0317863 A1 | 12/2010 | Kuzmich et al. | |
| 2012/0028831 A1 | 2/2012 | Croce | |
| 2012/0053345 A1 | 3/2012 | Ericson et al. | |
| 2019/0142799 A1 | 5/2019 | Grembecka et al. | |
| 2019/0142961 A1 | 5/2019 | Grembecka et al. | |
| 2019/0144442 A1 | 5/2019 | Grembecka et al. | |
| 2020/0246474 A1 | 8/2020 | Grembecka et al. | |
| 2022/0089570 A1 | 3/2022 | Crew et al. | |

FOREIGN PATENT DOCUMENTS

| | | |
|---|---|---|
| EP | 0818442 | 1/1998 |
| EP | 0931788 | 7/1999 |
| EP | 1004578 | 5/2000 |
| JP | 2017-513862 | 6/2017 |
| WO | WO 1990/05719 | 5/1990 |
| WO | WO 1996/27583 | 9/1996 |
| WO | WO 1996/33172 | 10/1996 |
| WO | WO 1998/03516 | 1/1998 |
| WO | WO 1998/07697 | 2/1998 |
| WO | WO 1998/30566 | 7/1998 |
| WO | WO 1998/33768 | 8/1998 |
| WO | WO 1998/34915 | 8/1998 |
| WO | WO 1998/34918 | 8/1998 |
| WO | WO 1999/07675 | 2/1999 |
| WO | WO 1999/29667 | 6/1999 |
| WO | WO 1999/52889 | 10/1999 |
| WO | WO 1999/52910 | 10/1999 |
| WO | WO 2008/128072 | 10/2008 |
| WO | WO 2009/051956 | 4/2009 |
| WO | WO 2011/018415 | 2/2011 |
| WO | WO 2014/077784 | 5/2014 |
| WO | WO 2017/025868 | 2/2017 |
| WO | WO 2017/176958 | 10/2017 |
| WO | WO 2017/185023 | 10/2017 |
| WO | WO 2017/197240 | 11/2017 |
| WO | WO 2019/094772 | 5/2019 |
| WO | WO 2019/094773 | 5/2019 |

OTHER PUBLICATIONS

Chemical Abstract Service, Accession No. 1930:37386, 1930, 1 page.
Chemical Abstract Service, Accession No. 1993:38871, 1993, 1 page.
Chemical Abstract Service, Accession No. 1996:132307, 1996, 1 page.
Chemical Abstract Service, Accession No. 1996:175895, 1996, 1 page.
Chemical Abstract Service, Accession No. 1999:661868, 1999, 1 page.
Chemical Abstract Service, Accession No. 1999:797879, 1999, 1 page.
Chemical Abstract Service, Accession No. 2000:675083, 2000, 1 page.
Chemical Abstract Service, Accession No. 2004:559860, 2004, 1 page.
Chemical Abstract Service, Accession No. 2004:819180, 2004, 1 page.
Chemical Abstract Service, Accession No. 2006:600185, 2006, 1 page.
Chemical Abstract Service, Accession No. 2011:1243461, 2011, 1 page.
Chemical Abstract Service, Accession No. 2012:485967, 2012, 1 page.
Chemical Abstract Service, Accession No. 2013:1474439, 2013, 1 page.
Chemical Abstract Service, Accession No. 2013:273371, 2013, 1 page.
Colamaio et al., miR-142-3p down-regulation contributes to thyroid follicular tumorigenesis by targeting ASH1L and MLL1. J Clin Endocrinol Metab. Jan. 2015;100(1): E59-69.
Dumaitre et al., Synthesis and cyclic GMP phosphodiesterase inhibitory activity of a series of 6-phenylpyrazolo[3,4-d]pyrimidones. J. Med. Chem. 1996;39(8):1635-44.
Eram et al., Kinetic characterization of human histone H3 lysine 36 methyltrasferases, ASH1L and SETD2. Biochimica et Biophysica Acta 2015;1850:1842-8.
Faber et al., HOXA9 is required for survival in human MLL-rearranged acute leukemias. Blood. Mar. 12, 2009;113(11):2375-85.
Fujimoto et al., Whole-genome mutational landscape and characterization of noncoding and structural mutations in liver cancer. Nat Genet. May 2016;48(5):500-9.
Irwin et al., ZINC—a free database of commercially available compounds for virtual screening. J. Chem. Inf. Model. 2005;45(1):177-82.
Jones et al., Ash11 controls quiescence and self-renewal potential in hematopoietic stem cells. J Clin Invest. May 2015;125(5):2007-20.
Kanellopoulou et al., Reprogramming of Polycomb-Mediated Gene Silencing in Embryonic Stem Cells by the miR-290 Family and the Methyltransferase Ash11. Stem Cell Reports. Dec. 8, 2015;5(6):971-978.
Kroon et al., Hoxa9 transforms primary bone marrow cells through specific collaboration with Meis1a but not Pbx1b. EMBO J. Jul. 1, 1998;17(13):3714-25.
Liu et al., Genetic alterations of histone lysine methyltransferases and their significance in breast cancer. Oncotarget. Feb. 2015; 6(4): 2466-2482.
Miyazaki et al., Ash11 methylates Lys36 of histone H3 independently of transcriptional elongation to counteract polycomb silencing. PLoS Genet. Nov. 2013;9(11):e1003897.
Perugorria et al., Histone methyltransferase ASH1 orchestrates fibrogenic gene transcription during myofibroblast transdifferentiation. Hepatology. Sep. 2012;56(3):1129-39.

(56) References Cited

OTHER PUBLICATIONS

PubChem SID 292557486, Aurora Fine Chemicals LLC, Deposit Date Jan. 20, 2016, 5 pages.

Rogawski et al., Two Loops Undergoing Concerted Dynamics Regulate the Activity of the ASH1L Histone Methyltransferase. Biochemistry. Sep. 8, 2015;54(35):5401-13.

Rogawski et al., The function of the ASH1L histone methyltransferase in cancer: A chemical biology approach. A dissertation submitted in partial fulfillment of the requirements for the degree of Doctor of Philosophy, U.S., 2016, Abstract, pp. 56-77, https://deepblue.lib.umich.edu/bitstream/handle/2027.42/143998/rogawski_1/pdf?sequence=1.

Shah et al., The Hox genes and their roles in oncogenesis. Nat Rev Cancer. May 2010;10(5):361-71.

STN Registry, RN 1175821-79-0, 2'-Methoxy[1,1'-biphenyl]-3-carbothioamide, Entered Aug. 26, 2009, 1 page.

STN Registry, RN 1175743-53-9, 4'-Methoxy[1,1'-biphenyl]-3-carbothioamide, Entered Aug. 26, 2009, 1 page.

STN Registry, RN 1174708-56-5, 5-Phenyl-2-thiophenecarbothioamide, Entered Aug. 20, 2009, 1 page.

Tanaka et al., Dual function of histone H3 lysine 36 methyltransferase ASH1 in regulation of Hox gene expression. PLoS One. 2011;6(11):e28171.

Von Der Saal et al., Syntheses and Selective Inhibitory Activities or Terphenyl-Bisamidines for Serine Proteases. Arch Pharm Pharm Med Chem 1996;329(2):73-82.

Wang et al., Small molecule epigenetic inhibitors targeted to histone lysine methyltransferases and demethylases. Q Rev Biophys. Nov. 2013;46(4):349-73.

Yao et al., Selective Inhibitors of Histone Methyltransferase DOT1L: Design, Synthesis, and Crystallographic Studies. J Am Chem Soc. 2015;133(42):16746-9.

Zhu et al., ASH1L Links Histone H3 Lysine 36 Dimethylation to MLL Leukemia. Cancer Discov. Jul. 2016;6(7):770-83.

Extended European Search Report for EP 17796920.1, mailed Nov. 15, 2019, 24 pages.

International Search Report and Written Opinion for PCT/US2017/032365, mailed Sep. 12, 2017, 10 pages.

International Search Report and Written Opinion for PCT/US2018/060101, mailed Jan. 16, 2019, 8 pages.

International Search Report and Written Opinion for PCT/US2018/060102, mailed Jan. 29, 2019, 9 pages.

Japanese Office Action, corresponding to 2020-526059, issued on Dec. 6, 2022.

* cited by examiner

| Cell line | Compound 1 GI50 (µM), 7d |
|---|---|
| MV4;11 | 0.2 |
| SEM | 0.4 |
| MOLM13 | 2.5 |
| KOPN8 | 1.2 |
| U937 | 1.5 |
| REH | 0.4 |
| K562 | 10 |
| MCF7 | >10 |

ASH1L DEGRADERS AND METHODS OF TREATMENT THEREWITH

CROSS-REFERENCE TO RELATED APPLICATIONS

The present invention is a continuation of U.S. patent application Ser. No. 17/468,308, filed Sep. 7, 2021, now U.S. Pat. No. 11,786,602, which is a continuation of U.S. patent application Ser. No. 16/186,012, filed Nov. 9, 2018, now U.S. Pat. No. 11,110,177, which claims the priority benefit of U.S. Provisional Patent Application 62/584,473, filed Nov. 10, 2017, each of which is incorporated by reference in its entirety.

FIELD

Provided herein are small molecules comprising a first domain that binds to ASH1L and a second domain that facilitates ASH1L degradation. In particular, ASH1L-targeting proteolysis targeting chimeras (PROTACs) and methods of use thereof for the treatment of disease (e.g., acute leukemia, solid cancers and other diseases dependent on activity of ASH1L) are provided.

BACKGROUND

ASH1L (Absent small and homeotic disks protein 1 homolog; EC:2.1.1.43) is a histone-lysine N-methyltransferase (KMTase), which methylates histone 3, lysine 36 (H3K36). ASH1L is required for chromatin association of MLL fusion proteins at crucial leukemia target genes and for MLL fusion protein mediated oncogenic transformation, implying that ASH1L represents a therapeutic target in MLL leukemias and other leukemias with high HOX expression (ref. 1; incorporated by reference in their entireties). ASH1L is also overexpressed in a variety of solid tumors, including thyroid and breast cancer (refs. 2, 3; incorporated by reference in their entireties). In thyroid cancer, ASH1L is overexpressed in tumor-specific truncated forms. The tumor suppressor microRNA miR-142-3p inhibits ASH1L protein expression by binding to the ASH1L 3'UTR, an effect correlated with inhibition of colony formation and slowing of thyroid cancer cell growth (ref. 2; incorporated by reference in its entirety). In addition, the ASH1L gene frequently undergoes copy number amplification in aggressive basal-like breast cancer, and high expression of ASH1L mRNA is associated with shorter survival of breast cancer patients (ref. 3; incorporated by reference in its entirety). Finally, in hepatocellular carcinoma (HCC), structural variations are found near the ASH1L gene, and knockdown of ASH1L in HCC cells slows proliferation (ref. 4; incorporated by reference in its entirety).

In multiple developmental and oncogenic contexts, ASH1L activates HOXA-B, -C, and -D genes and MEIS1 (refs. 5-8; incorporated by reference in their entireties). ASH1L's KMTase activity is required for at least some of its gene activating function, as deletion of the ASH1L SET domain in differentiating mouse embryonic stem cells leads to loss of expression of 152 genes, including members of the Hox and Wnt families (ref. 8; incorporated by reference in its entirety). These findings are highly relevant because HOX genes are oncogenic drivers in many different blood and solid tumors (ref. 9; incorporated by reference in its entirety). For example, overexpression of HOXA9 is highly associated with a poor prognosis in AML (ref. 10; incorporated by reference in its entirety), and HOXA9 and its collaborator MEIS1 are required for survival of MLL-rearranged leukemia cells (refs. 11, 12; incorporated by reference in their entireties). ASH1L deficiency causes a major reduction in long-term hematopoietic stem cells (HSC) in mouse bone marrow, but has very modest effects on peripheral blood counts due to increased proliferation of progenitors downstream of HSCs (ref. 5; incorporated by reference in its entirety). ASH1L also plays important roles in diseases beyond cancer. For example, in facioscapulohumeral muscular dystrophy, ASH1L is recruited by a noncoding RNA to chromosome region 4q35, where it causes H3K36 dimethylation, chromatin remodeling, and abnormal transcription of 4q35 genes (ref. 13; incorporated by reference in its entirety). In liver fibrosis, during the transdifferentiation of hepatic stellate cells to fibrogenic myofibroblasts, ASH1L is upregulated and binds to and activates profibrogenic genes (ref. 14; incorporated by reference in its entirety).

SUMMARY

Provided herein are small molecules comprising a first domain that binds to ASH1L and a second domain that facilitates ASH1L degradation. In particular, ASH1L-targeting proteolysis targeting chimeras (PROTACs) and methods of use thereof for the treatment of disease (e.g., acute leukemia, solid cancers and other diseases dependent on activity of ASH1L) are provided.

In some embodiments, provided herein are compounds that bind to ASH1L. In some embodiments, compounds herein comprise (i) an ASH1L binding moiety and (ii) a second moiety that facilitates the degradation of the bound ASH1L (e.g., degradation moiety). In some embodiments, binding of a compound herein to ASH1L inhibits ASH1L activity. In some embodiments, binding of a compound herein to ASH1L does not inhibit ASH1L activity. In some embodiments, binding of a compound herein to ASH1L facilitates ASH1L degradation. In some embodiments, binding of a compound herein to ASH1L inhibits ASH1L activity and facilitates ASH1L degradation. An understanding of the mechanism of action of the compounds herein with respect to ASH1L is not necessary to practice the embodiments described herein. In some embodiments, the second moiety (e.g., degradation moiety) comprises a ligand for a ubiquitin ligase (e.g., Cereblon E3 ubiquitin ligase, von Hippel-Lindau (VHL) E3 ligase or any other E3 ubiquitin ligase). In some embodiments, the E3 ubiquitin ligase ligand and the ASH1L binding moiety are connected by an appropriate linker.

In some embodiments, provided herein are compounds comprising a structure of:

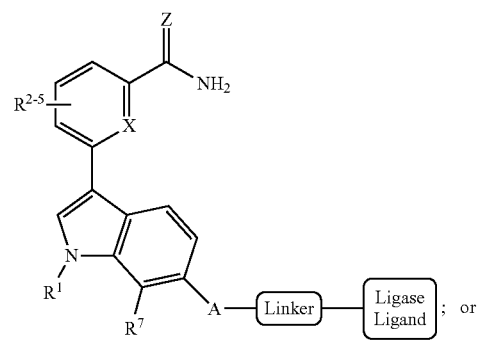

[Formula (Ia)]

-continued

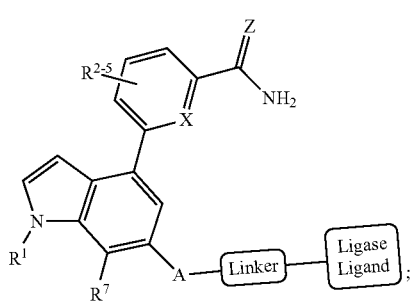
[Formula (Ic)]

wherein X, Z, A, Linker, Ligase Ligand, and $R^1$-$R^7$ are selected from any combination of the suitable substituents and moieties described and/or depicted herein;

or a salt thereof. In some embodiments, a compound of Formula (Ic) comprises any moieties and substituents described herein for Formula (Ia).

In some embodiments, provided herein are compounds comprising a structure of:

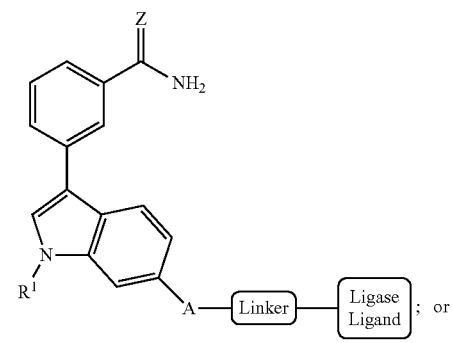
[Formula (Ib)]

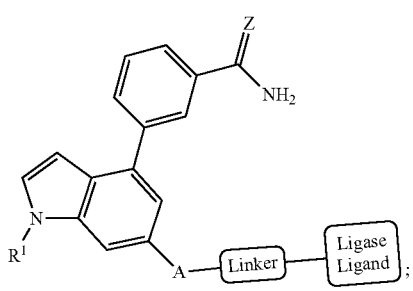
[Formula (Id)]

wherein Z, A, Linker, Ligase Ligand, and $R^1$ are selected from any combination of the suitable substituents and moieties described and/or depicted herein;

or a salt thereof. In some embodiments, a compound of Formula (Id) comprises any moieties and substituents described herein for Formula (Ib).

In some embodiments, provided herein are compounds comprising a structure of:

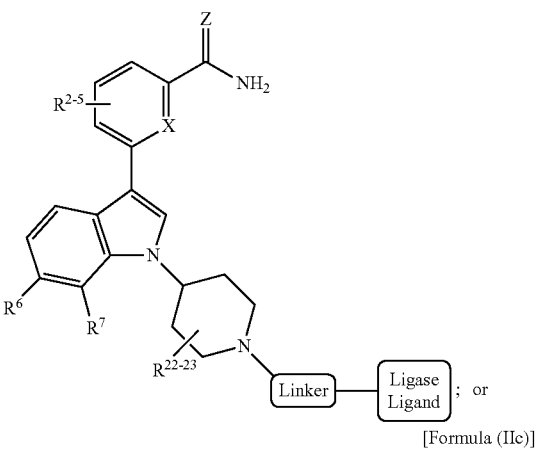
[Formula (IIa)]

[Formula (IIc)]

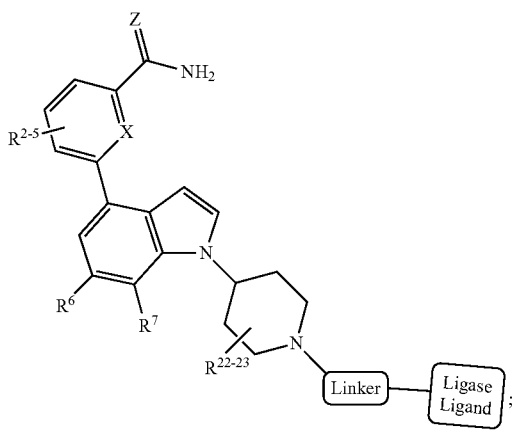

wherein X, Z, A, Linker, Ligase Ligand, $R^2$-$R^7$, and $R^{22}$-$R^{23}$ are selected from any combination of the suitable substituents and moieties described and/or depicted herein;

or a salt thereof. In some embodiments, a compound of Formula (IIc) comprises any moieties and substituents described herein for Formula (IIa).

In some embodiments, provided herein are compounds comprising a structure of:

[Formula (IIb)]

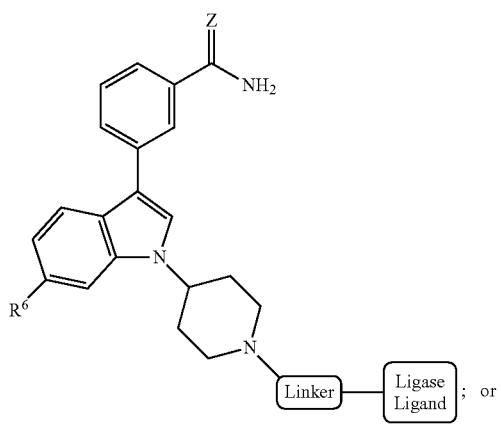

-continued

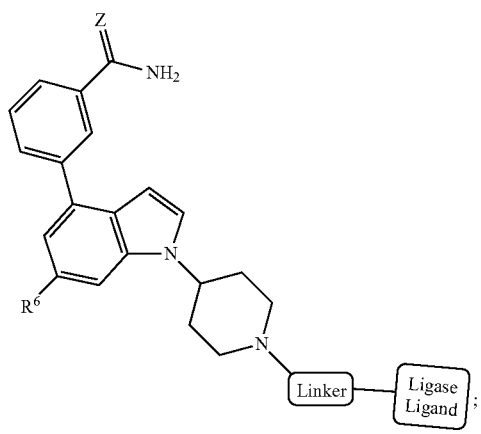
[Formula (IId)]

wherein Z, Linker, Ligase Ligand, and R⁶ are selected from any combination of the suitable substituents and moieties described and/or depicted herein;

or a salt thereof. In some embodiments, a compound of Formula (IId) comprises any moieties and substituents described herein for Formula (IIb).

In some embodiments, provided herein are compounds comprising a structure of:

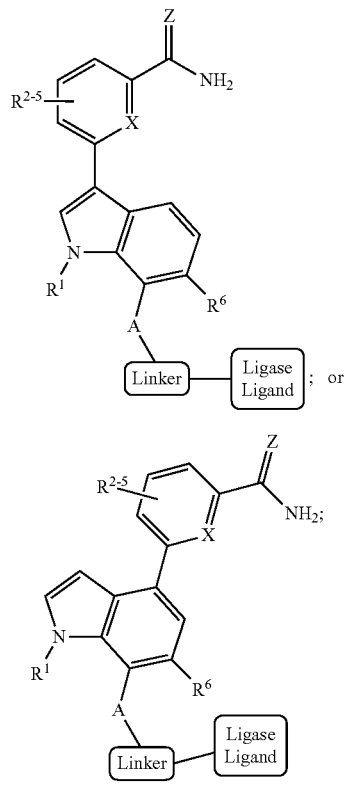
[Formula (IIIa)]

[Formula (IIIc)]

wherein X, Z, A, Linker, Ligase Ligand, and $R^1$-$R^6$ are selected from any combination of the suitable substituents and moieties described and/or depicted herein;

or a salt thereof. In some embodiments, a compound of Formula (IIIc) comprises any moieties and substituents described herein for Formula (IIIa).

In some embodiments, provided herein are compounds comprising a structure of:

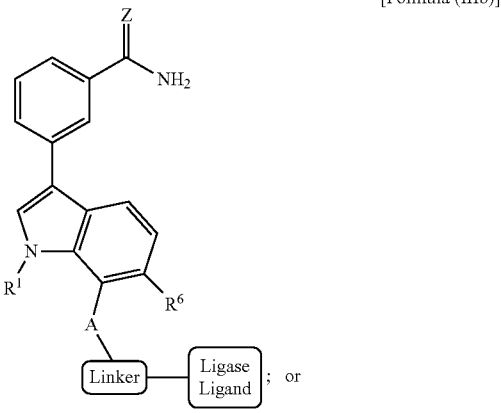
[Formula (IIIb)]

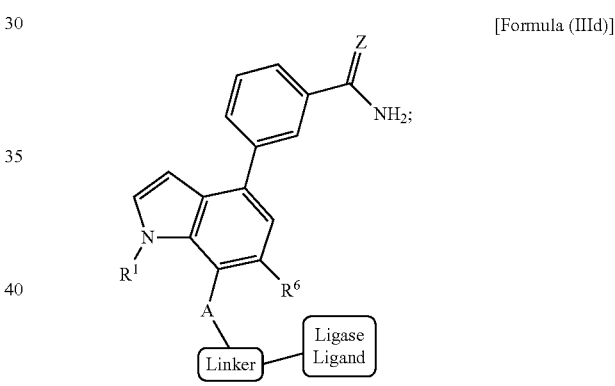
[Formula (IIId)]

wherein Z, A, Linker, Ligase Ligand, $R^1$, and $R^6$ are selected from any combination of the suitable substituents and moieties described and/or depicted herein;

or a salt thereof. In some embodiments, a compound of Formula (IIId) comprises any moieties and substituents described herein for Formula (IIIb).

In some embodiments, provided herein are compounds 1-182 (e.g., compounds 1-91 of Table 8 and alternately connected versions thereof (e.g., compounds 92-182)), salts thereof, or pharmaceutical composition thereof. In some embodiments, provided herein are compounds or one of Formulas (Ia-d), (IIa-d), or (IIIa-d), wherein X, Z, A, the Linker, the Ligase Ligand, and $R^1$-$R^7$, when present, are selected from the X, Z, A, the Linker, the Ligase Ligand, and $R^1$-$R^7$ groups of compounds 1-91, in any combination.

In some embodiments, provided herein are pharmaceutical compositions comprising a compound described herein and a pharmaceutically acceptable carrier. In some embodiments, the pharmaceutical composition is formulated for oral administration. In some embodiments, the pharmaceutical composition is formulated for injection.

In some embodiments, provided herein are compounds inducing ASH1L degradation comprising a structure of Formula (Ia):

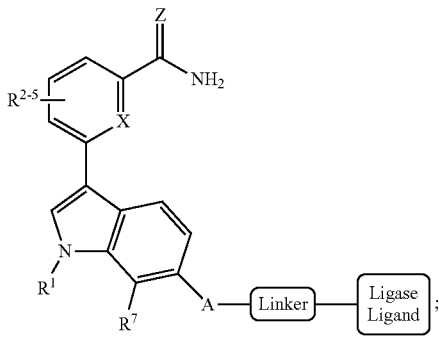

wherein X is CH or N;

wherein Z is O or S;

wherein R¹ is selected from H, alkyl, substituted alkyl (e.g. halogen substituted alkyl), branched alkyl, a substituted branched alkyl (e.g. halogen substituted branched alkyl), alkoxy, amine, substituted amine, thioalkyl, ketone, amide, a substituted amide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring (e.g. piperidine, methylpiperidine, bridged piperidine, tetrahydropyran, alkylsulfonyl substituted piperidine, sulfonamide substituted piperidine, arylsulfonyl substituted piperidine, 1-((trifluoromethyl)sulfonyl)piperidine), difluorocyclohexane, monofluorocyclohexane, cyclohexane, substituted difluorocyclohexane, bicyclooctane, cycloheptane, carbocyclic or heterocyclic aromatic ring fused to another aromatic ring, a hydrogen bond donor, a hydrogen bond acceptor, and combinations thereof; and wherein R², R³, R⁴, R⁵, and R⁷ are independently selected from H, halogen (e.g., Cl, F, Br, I), $CH_3$, OH, SH, $NH_2$, CN, $CF_3$, $CCl_3$, —$CH_2$—$CH_3$, —$CH_2$—OH, —$CH_2NH_2$, $CH_3SH$, $CH_2Cl$, $CH_2Br$, $CH_2F$, $CHF_2$, $CH_2CN$, $CH_2CF_3$, and $CH_2Cl_3$, alkyl, haloalkyl, alkohol;

wherein A is a covalent bond (i.e., no atom present) or is selected from the structures listed in Table 1 (wherein n is 0, 1, 2, 3, 4, 5, 6, 7, 8, 9 or 10; wherein m, when present, is 0, 1, 2, 3, 4, 5, 6, 7, 8, 9, 10, 11, 12, 13, 14 or 15 or ranges therebetween; wherein k, when present is 0, 1, 2, 3, 4, 5, 6, 7, 8, 9 or 10; wherein l, when present is 0, 1, 2, 3, 4, 5, 6, 7, 8, 9 or 10);

wherein the linker is selected from the structures listed in Table 2 (wherein n, when present, is 0, 1, 2, 3, 4, 5, 6, 7, 8, 9, 10, 11, 12, 13, 14, 15; wherein m, when present, is 0, 1, 2, 3, 4, 5, 6, 7, 8, 9, 10, 11, 12, 13, 14 or 15 or ranges therebetween); wherein k, when present is 0, 1, 2, 3, 4, 5, 6, 7, 8, 9 or 10; wherein l, when present is 0, 1, 2, 3, 4, 5, 6, 7, 8, 9 or 10; and wherein the ligase ligand is selected from those listed in Table 3.

TABLE 1

Exemplary A groups from Formulas (Ia-d) and (IIIa-d).

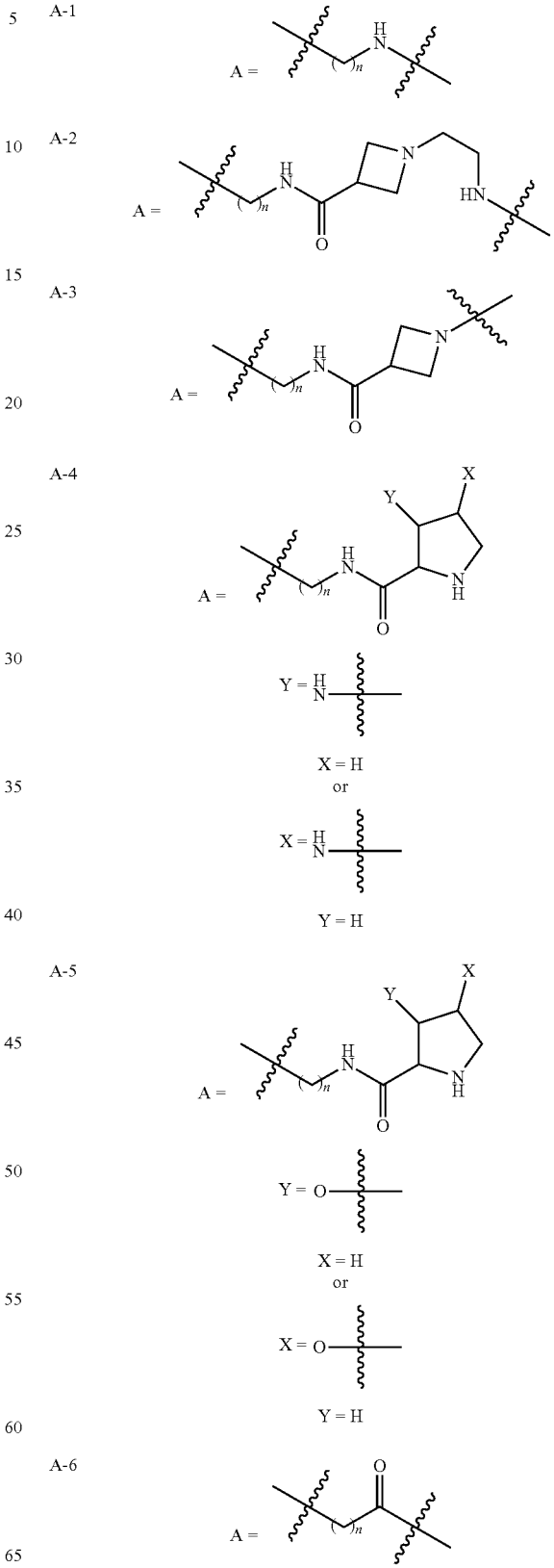

TABLE 1-continued

Exemplary A groups from Formulas (Ia-d) and (IIIa-d).

A-7
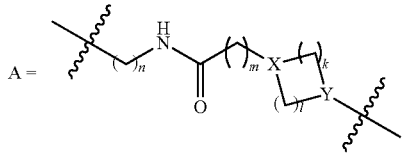
X, Y = CH or N

A-8
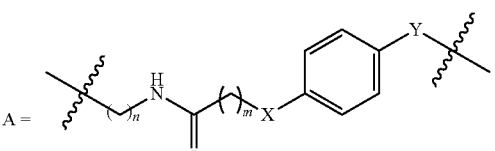
X, Y = O, NH, or CH$_2$

A-9
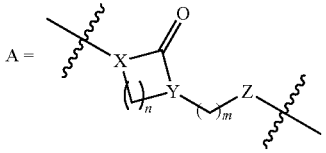
X, Y = N, or CH
Z = O, NH, or CH$_2$

TABLE 2

Exemplary linkers for Formulas (Ia-d) and (IIIa-d).

La-1
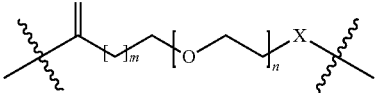
X = O, NH, or CH$_2$

La-2
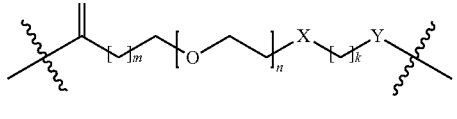
X, Y = O, NH or CH$_2$

La-3
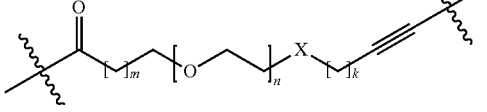
X = O, NH or CH$_2$

La-4
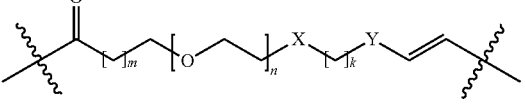
X, Y = O, NH or CH$_2$

TABLE 2-continued

Exemplary linkers for Formulas (Ia-d) and (IIIa-d).

La-5
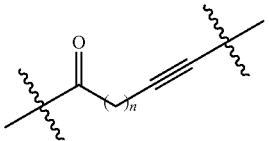

La-6
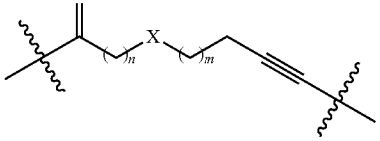
X = O, NH or CH$_2$

La-7
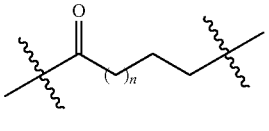

La-8
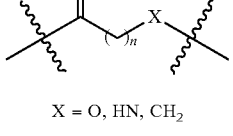
X = O, HN, CH$_2$

La-9
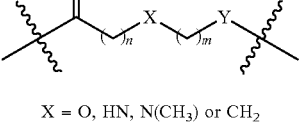
X = O, HN, N(CH$_3$) or CH$_2$

La-10
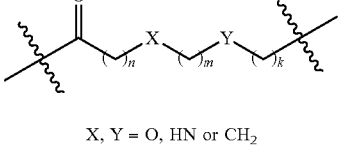
X, Y = O, HN or CH$_2$

La-11
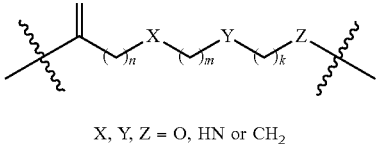
X, Y, Z = O, HN or CH$_2$

La-12
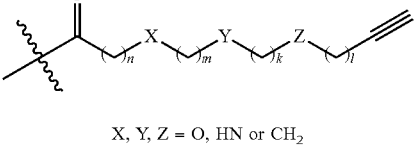
X, Y, Z = O, HN or CH$_2$

La-13
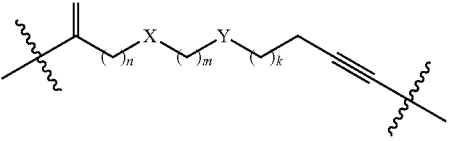
X, Y = O, HN or CH$_2$

TABLE 2-continued

Exemplary linkers for Formulas (Ia-d) and (IIIa-d).

La-14

X, Y, Z = O, HN or $CH_2$

La-15

X, = O, HN, $CH_2$

La-16

X, = O, HN, $CH_2$

La-17

X = O, HN, $CH_2$

La-18

X = O, HN, $CH_2$

La-19

X, Y = O, HN, $CH_2$

La-20

X, Y = O, HN, $CH_2$

La-21

X, Y = O, HN, $CH_2$

La-22

X, Y = O, HN, $CH_2$

La-23

X, Y = O, HN, $CH_2$

La-24

La-25

X, Y, Z = O, HN or $CH_2$

La-26

X, Y, Z = O, HN or $CH_2$

La-27

X, Y = O, HN or $CH_2$

La-28

X, Y = O, HN, $CH_2$

La-29

X, Y = O, HN, $CH_2$

La-30

X, Y = O, HN or $CH_2$

TABLE 2-continued

Exemplary linkers for Formulas (Ia-d) and (IIIa-d).

La-31 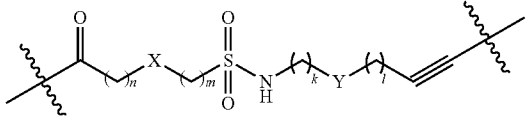

X, Y = O, HN or CH$_2$

La-32 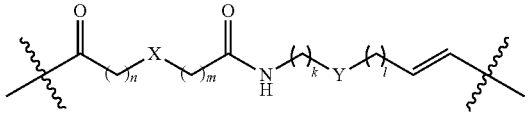

X, Y = O, HN or CH$_2$

La-33 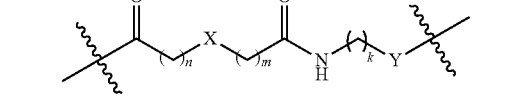

X, Y = O, HN, CH$_2$

La-34 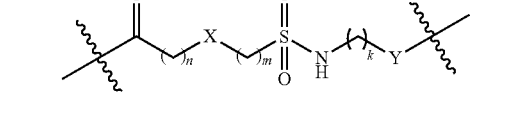

X, Y = O, HN, CH$_2$

La-35 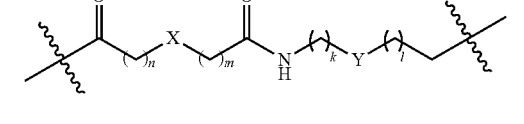

X, Y = O, HN, CH$_2$

La-36 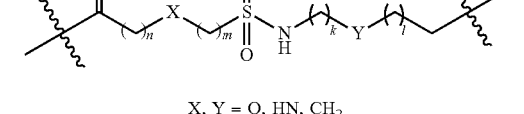

X, Y = O, HN, CH$_2$

La-37 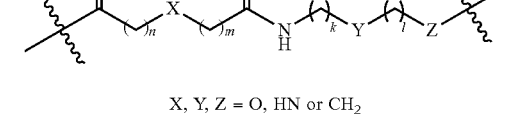

X, Y, Z = O, HN or CH$_2$

La-38 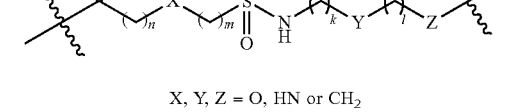

X, Y, Z = O, HN or CH$_2$

La-38 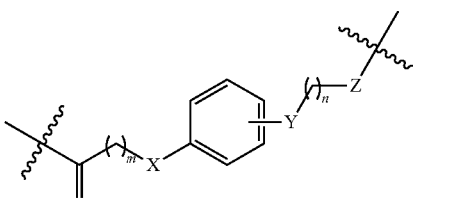

X = O, NH, or CH$_2$

TABLE 2-continued

Exemplary linkers for Formulas (Ia-d) and (IIIa-d).

La-39 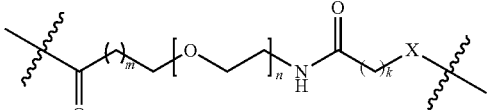

X, Y, Z = O, NH or CH$_2$.

La-40 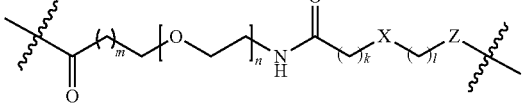

X = O, NH, CH$_2$

La-41 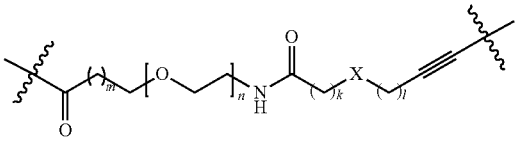

X, Y, Z = O, NH, CH$_2$

La-42 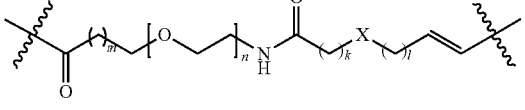

X = O, NH, CH$_2$

La-43 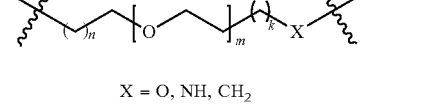

X = O, NH, CH$_2$

La-44 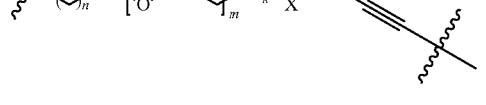

X = O, NH, CH$_2$

La-45

X = O, NH, CH$_2$

La-46 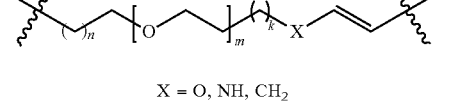

X = O, NH, CH$_2$

TABLE 2-continued
Exemplary linkers for Formulas (Ia-d) and (IIIa-d).
La-47
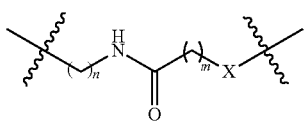
X = O, HN, CH$_2$
La-48
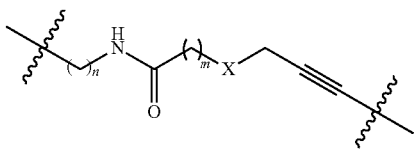
X = O, HN, CH$_2$
La-49
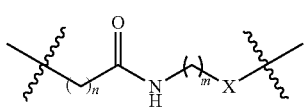
X = O, HN, CH$_2$
La-50
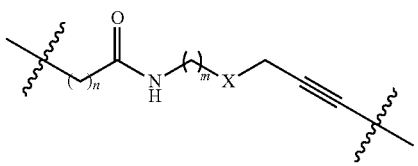
X = O, HN, CH$_2$
La-51
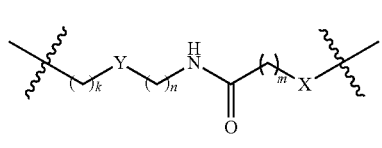
X = O, HN, CH$_2$
La-52
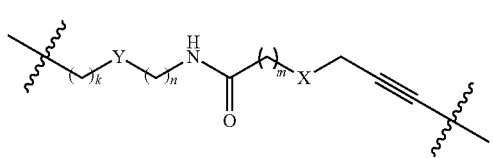
X, Y = O, HN or CH$_2$
La-53
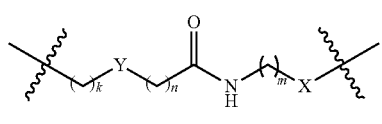
X = O, HN, CH$_2$
La-54
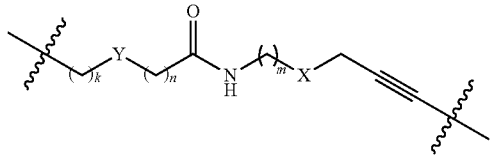
X, Y = O, HN or CH$_2$
La-55
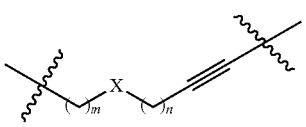
X = O, NH or CH$_2$
La-56
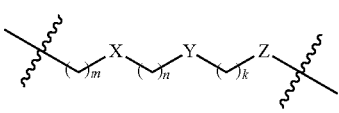
X, Y, Z = O, NH or CH$_2$
La-57
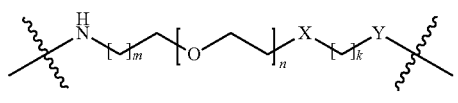
X, Y = O, NH or CH$_2$
La-58
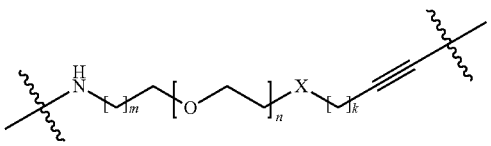
X = O, NH or CH$_2$
La-59
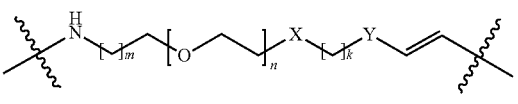
X, Y = O, NH or CH$_2$
La-60
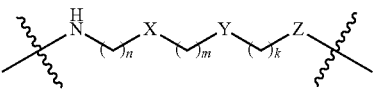
X, Y, Z = O, HN or CH$_2$
La-61
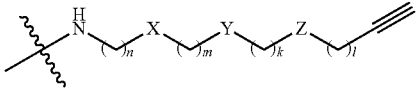
X, Y, Z = O, HN or CH$_2$
La-62
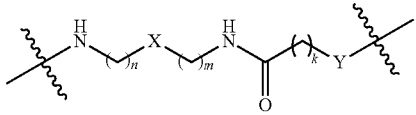
X, Y = O, HN, CH$_2$
La-63
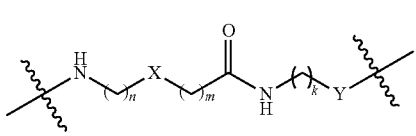
X, Y = O, HN, CH$_2$ TABLE 2-continued Exemplary linkers for Formulas (Ia-d) and (IIIa-d).

La-64

X, Y = O, HN, CH$_2$

La-65

X, Y = O, HN, CH$_2$

La-66

X, Y = O, HN, CH$_2$

La-67

X, Y = O, HN, CH$_2$

La-68

X, Y = O, HN, CH$_2$

La-69

X, Y = O, HN, CH$_2$

La-70

X = O, NH, or CH$_2$

La-71

La-72

X, Y = O, NH or CH$_2$

La-73

X = O, NH or CH$_2$

La-74

X, Y = O, NH or CH$_2$

La-75

X, Y, Z = O, HN or CH$_2$

La-76

X, Y, Z = O, HN or CH$_2$

La-77

X, Y = O, HN, CH$_2$

La-78

X, Y = O, HN, CH$_2$

La-79

X, Y = O, HN, CH$_2$

La-80

X, Y = O, HN, CH$_2$

TABLE 2-continued

Exemplary linkers for Formulas (Ia-d) and (IIIa-d).

La-81

X, Y = O, HN, CH$_2$

La-82

X, Y = O, HN, CH$_2$

La-83

X, Y = O, HN, CH$_2$

La-84

X, Y = O, HN, CH$_2$

La-85

X = O, NH, CH$_2$

La-86

\* X, Y, and Z groups, when present in the linkers above (Table 2), are independently O, NH, or CH$_2$, and do not need to be the same group when present in the same linker.

TABLE 3

Exemplary ligase ligands for Formulas (Ia-d) and (IIIa-d).

LLa-1

LLa-2

LLa-3

LLa-4

LLa-5

LLa-6

LLa-7

In some embodiments, the $R^1$ substituent of Formula (Ia) is one of Formulas (a-q):

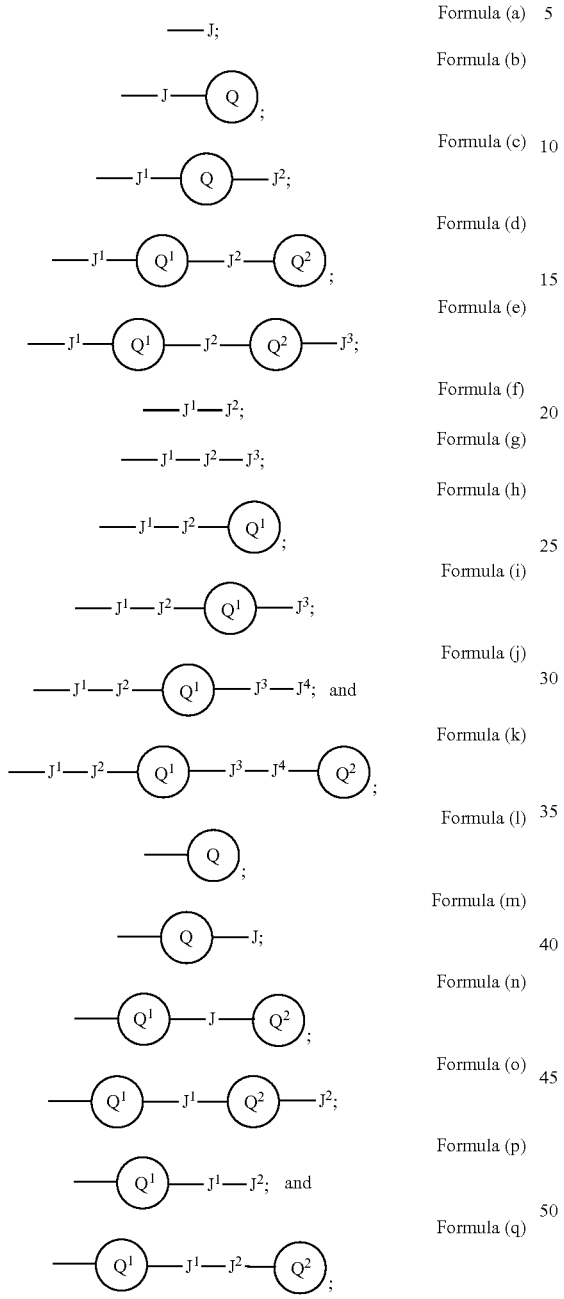

Formula (a)
Formula (b)
Formula (c)
Formula (d)
Formula (e)
Formula (f)
Formula (g)
Formula (h)
Formula (i)
Formula (j)
Formula (k)
Formula (l)
Formula (m)
Formula (n)
Formula (o)
Formula (p)
Formula (q)

wherein one of J, $Q^1$, or $J^1$, when present, is linked to the main scaffold;

wherein each J, $J^1$, $J^2$, $J^3$, and $J^4$, when present, are independently selected from the group consisting of: a covalent bond, H, $alkyl_{1-15}$, $alkenyl_{1-6}$, $alkynyl_{1-6}$, $(CH_2)_{0-6}C(S)NH_2$, $(CH_2)_{0-6}C(O)NH_2$, O, S, NH, $(CH_2)_{0-6}C(O)NH(CH_2)_{0-6}$, $(CH_2)_{0-6}NHC(O)(CH_2)_{1-6}$, alkylsulfonyl, sulfonamide, alkylsulfonamide, $(CH_2)_{0-6}C(S)NH(CH_2)_{1-6}$, $(CH_2)_{0-6}O(CH_2)_{1-6}$, $(CH_2)_{0-6}OH$, $(CH_2)_{0-6}S(CH_2)_{1-6}$, $(CH_2)_{0-6}SH$, $(CH_2)_{0-6}NH(CH_2)_{1-6}$, $(CH_2)_{0-6}N(CH_2)_{1-6}(CH_2)_{1-6}$, $(CH_2)_{0-6}NH_2$, $(CH_2)_{0-6}SO_2(CH_2)_{1-6}$, $(CH_2)_{0-6}NHSO_2(CH_2)_{1-6}$, $(CH_2)_{0-6}SO_2NH_2$, halogen (e.g., F, Cl, Br, or I), haloalkyl (e.g., $(CH_2)_{0-6}$ $CH_2F$, $(CH_2)_{0-3}CHF(CH_2)_{0-2}CH_3$, or similar with Br, Cl, or I), dihaloalkyl (e.g., $(CH_2)_{0-6}$ $CF_2H$, $(CH_2)_{0-3}$ $CF_2(CH_2)_{0-2}CH_3$, or similar with Br, Cl, or I), trihaloalkyl (e.g., $(CH_2)_{0-6}$ $CF_3$, or similar with Br, Cl, or I), alkyl with 1-3 halogens at two or more positons along its length, $(CH_2)_{1-4}SP(Ph)_2=S$, $(CH_2)_{0-6}NH(CH_2)_{1-5}OH$, $(CH_2)_{0-6}NH(CH_2)_{1-5}NH_2$, $(CH_2)_{0-6}NH(CH_2)_{1-5}SH$, $(CH_2)_{0-6}O(CH_2)_{1-5}OH$, $(CH_2)_{0-6}O(CH_2)_{1-5}NH_2$, $(CH_2)_{0-6}O(CH_2)_{1-5}SH$, $(CH_2)_{0-6}S(CH_2)_{1-5}OH$, $(CH_2)_{0-6}S(CH_2)_{1-5}NH_2$, $(CH_2)_{0-6}S(CH_2)_{1-5}SH$, $(CH_2)_{0-6}O(CH_2)_{1-6}NH(CH_2)_{1-5}OH$, $(CH_2)_{0-6}O(CH_2)_{1-6}NH(CH_2)_{1-5}NH_2$, $(CH_2)_{0-6}O(CH_2)_{1-6}NH(CH_2)_{1-5}SH$, $(CH_2)_{0-6}O(CH_2)_{1-6}O(CH_2)_{1-5}OH$, $(CH_2)_{0-6}O(CH_2)_{1-6}O(CH_2)_{1-5}NH_2$, $(CH_2)_{0-6}O(CH_2)_{1-6}O(CH_2)_{1-5}SH$, $(CH_2)_{0-6}O(CH_2)_{1-6}S(CH_2)_{1-5}OH$, $(CH_2)_{0-6}O(CH_2)_{1-6}S(CH_2)_{1-5}NH_2$, $(CH_2)_{0-6}O(CH_2)_{1-6}S(CH_2)_{1-5}SH$, $(CH_2)_{0-6}S(CH_2)_{1-6}NH(CH_2)_{1-5}OH$, $(CH_2)_{0-6}S(CH_2)_{1-6}NH(CH_2)_{1-5}NH_2$, $(CH_2)_{0-6}S(CH_2)_{1-6}NH(CH_2)_{1-5}SH$, $(CH_2)_{0-6}S(CH_2)_{1-6}O(CH_2)_{1-5}OH$, $(CH_2)_{0-6}S(CH_2)_{1-6}O(CH_2)_{1-5}NH_2$, $(CH_2)_{0-6}S(CH_2)_{1-6}O(CH_2)_{1-5}SH$, $(CH_2)_{0-6}S(CH_2)_{1-6}S(CH_2)_{1-5}OH$, $(CH_2)_{0-6}S(CH_2)_{1-6}S(CH_2)_{1-5}NH_2$, $(CH_2)_{0-6}S(CH_2)_{1-6}S(CH_2)_{1-5}SH$, $(CH_2)_{0-6}NH(CH_2)_{1-6}NH(CH_2)_{1-5}OH$, $(CH_2)_{0-6}NH(CH_2)_{1-6}NH(CH_2)_{1-5}NH_2$, $(CH_2)_{0-6}NH(CH_2)_{1-6}NH(CH_2)_{1-5}SH$, $(CH_2)_{0-6}NH(CH_2)_{1-6}O(CH_2)_{1-5}OH$, $(CH_2)_{0-6}NH(CH_2)_{1-6}O(CH_2)_{1-5}NH_2$, $(CH_2)_{0-6}NH(CH_2)_{1-6}O(CH_2)_{1-5}SH$, $(CH_2)_{0-6}NH(CH_2)_{1-6}S(CH_2)_{1-5}OH$, $(CH_2)_{0-6}NH(CH_2)_{1-6}S(CH_2)_{1-5}NH_2$, $(CH_2)_{0-6}NH(CH_2)_{1-6}S(CH_2)_{1-5}SH$, $(CH_2)_{0-3}C(O)O(CH_2)_{0-3}$, $(CH_2)_{0-3}C(S)O(CH_2)_{0-3}$, $(CH_2)_{0-3}C(O)S(CH_2)_{0-3}$, $(CH_2)_{0-3}C(S)S(CH_2)_{0-3}$, $(CH_2)_{0-3}C(O)NH(CH_2)_{0-3}$, $(CH_2)_{0-3}C(S)NH(CH_2)_{0-3}$, $(CH_2)_{0-3}NHC(O)(CH_2)_{0-3}$, $(CH_2)_{0-3}NHC(S)(CH_2)_{0-3}$, $(CH_2)_{0-3}OC(O)(CH_2)_{0-3}$, $(CH_2)_{0-3}OC(S)(CH_2)_{0-3}$, $(CH_2)_{0-3}SC(O)(CH_2)_{0-3}$, $(CH_2)_{0-3}SC(S)(CH_2)_{0-3}$, $(CH_2)_{0-3}NHC(O)NH(CH_2)_{0-3}$, $(CH_2)_{0-3}NHC(S)NH(CH_2)_{0-3}$, $(CH_2)_{0-3}OC(O)NH(CH_2)_{0-3}$, $(CH_2)_{0-3}OC(S)NH(CH_2)_{0-3}$, $(CH_2)_{0-3}SC(O)NH(CH_2)_{0-3}$, $(CH_2)_{0-3}SC(S)NH(CH_2)_{0-3}$, $(CH_2)_{0-3}NHC(O)O(CH_2)_{0-3}$, $(CH_2)_{0-3}NHC(S)O(CH_2)_{0-3}$, $(CH_2)_{0-3}OC(O)O(CH_2)_{0-3}$, $(CH_2)_{0-3}OC(S)O(CH_2)_{0-3}$, $(CH_2)_{0-3}SC(O)O(CH_2)_{0-3}$, $(CH_2)_{0-3}SC(S)O(CH_2)_{0-3}$, $(CH_2)_{0-3}NHC(O)S(CH_2)_{0-3}$, $(CH_2)_{0-3}NHC(S)S(CH_2)_{0-3}$, $(CH_2)_{0-3}OC(O)S(CH_2)_{0-3}$, $(CH_2)_{0-3}OC(S)S(CH_2)_{0-3}$, $(CH_2)_{0-3}SC(O)S(CH_2)_{0-3}$, $(CH_2)_{0-3}SC(S)S(CH_2)_{0-3}$, $(CH_2O)_{1-6}$, and trimethyl methane;

wherein each Q, $Q^1$, and $Q^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), thiadiazole, aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, thiethane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, any suitable $C^3$-$C^7$ cycloalkyl group, and any of the ring structures depicted in Table 4;

wherein each Q, $Q^1$, and $Q^2$, when present, may display one or more additional J groups at any position on the Q ring;

wherein any alkyl or $(CH_2)_{x-y}$ groups above may be straight or branched;

wherein any alkyl or $(CH_2)_{x-y}$ groups above may additionally comprise OH, =O, $NH_2$, CN, dihaloalkyl (e.g., $CF_2H$), trihaloalkyl (e.g., $CF_3$), or halogen (e.g., F) substituents at one or more carbons; and wherein the number of hydrogens on terminal positions of the groups above may be adjusted if the group is linked to an additional group (e.g., $CH_3$ adjusted to $CH_2$, OH adjusted to O, etc.) or if the group is terminal (e.g., $CH_2$ adjusted to $CH_3$, O adjusted to OH, etc.).

TABLE 4

| Non-limiting examples of ring structures. | |
|---|---|
| R-1 |  |
| R-2 |  |
| R-3 | 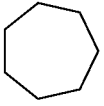 |
| R-4 |  |
| R-5 |  |
| R-6 | 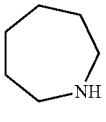 |
| R-7 | 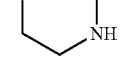 |
| R-8 |  |
| R-9 | 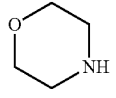 |
| R-10 |  |

TABLE 4-continued

| Non-limiting examples of ring structures. | |
|---|---|
| R-11 |  |
| R-12 |  |
| R-13 |  |
| R-14 |  |
| R-15 |  |
| R-16 |  |
| R-17 |  |
| R-18 |  |
| R-19 |  |
| R-20 |  |
| R-21 |  |
| R-22 |  |
| R-23 |  |
| R-24 |  |
| R-25 |  |

TABLE 4-continued
Non-limiting examples of ring structures.
| | | |
|---|---|---|
| R-26 |  | |
| R-27 |  | |
| R-28 |  | |
| R-29 |  | |
| R-30 |  | |
| R-31 |  | |
| R-32 |  | |
| R-33 |  | |
| R-34 |  | |
| R-35 |  | |
| R-36 |  | |
| R-37 |  | |
| R-38 |  | |
| R-39 |  | |
| R-40 |  | |
| R-41 |  | |
| R-42 |  | |
| R-43 |  | |
| R-44 |  | |
| R-45 |  | |
| R-46 |  | |
| R-47 |  | |
| R-48 |  | |
| R-49 |  | |
| R-50 |  | |
| R-51 |  | |
| R-52 |  | |

TABLE 4-continued

Non-limiting examples of ring structures.

| | |
|---|---|
| R-53 | [oxazine ring structure] |
| R-54 | [oxazine ring structure] |
| R-55 | [oxazine ring structure] |
| R-56 | [cycloheptatriene] |
| R-57 | [azepine] |
| R-58 | [oxepine] |
| R-59 | [thiepine] |
| R-60 | [diazepine] |
| R-61 | [diazepine] |
| R-62 | [diazepine] |
| R-63 | [thiazepine] |
| R-64 | [bicyclic amine] |
| R-65 | [bicyclic amine] |
| R-66 | [bicyclic amine] |
| R-67 | [bicyclic amine] |
| R-68 | [bicyclic amine] |
| R-69 | [bicyclic amine] |
| R-70 | [cyclohexene] |
| R-71 | [cyclohexene] |
| R-72 | [cyclohexene] |
| R-73 | [dihydropyridine] |
| R-74 | [dihydropyridine] |
| R-75 | [dihydropyran] |
| R-76 | [dihydrothiopyran] |
| R-77 | [piperazine] |

TABLE 4-continued
Non-limiting examples of ring structures.
| | |
|---|---|
| R-78 | 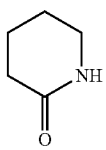 |
| R-79 | 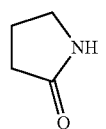 |
| R-80 | 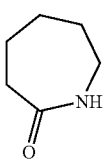 |
| R-81 | 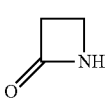 |
| R-82 | 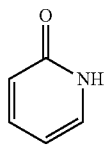 |
| R-83 | 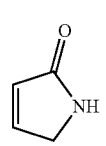 |
| R-84 | 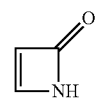 |
| R-85 | 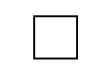 |
In some embodiments, the linker and A are selected from one or the combinations listed in Table 5.
TABLE 5
Exemplary linker and A combinations for Formulas (Ia-d) and (IIIa-d).
| | A | Linker |
|---|---|---|
| AL-1 | 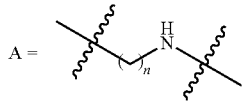<br>n = 0-5 | 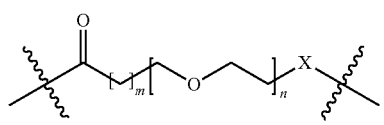<br>X = O, N, C<br>m = 0-15; n = 0-15<br>(the same values for n, m apply to the linkers below) |
| AL-2 | 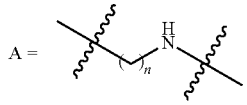 | 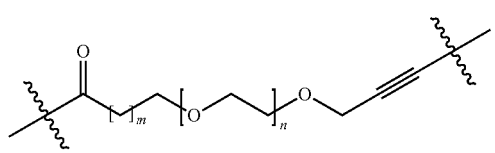 |
| AL-3 | 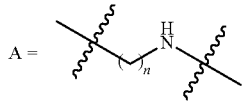 | 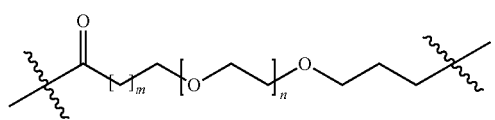 |
| AL-4 | 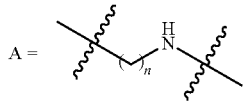 | 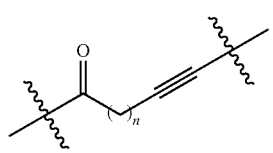 |
| AL-5 | 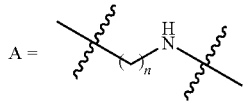 | 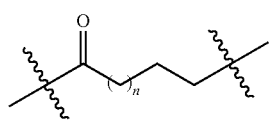 |

TABLE 5-continued
Exemplary linker and A combinations for Formulas (Ia-d) and (IIIa-d).
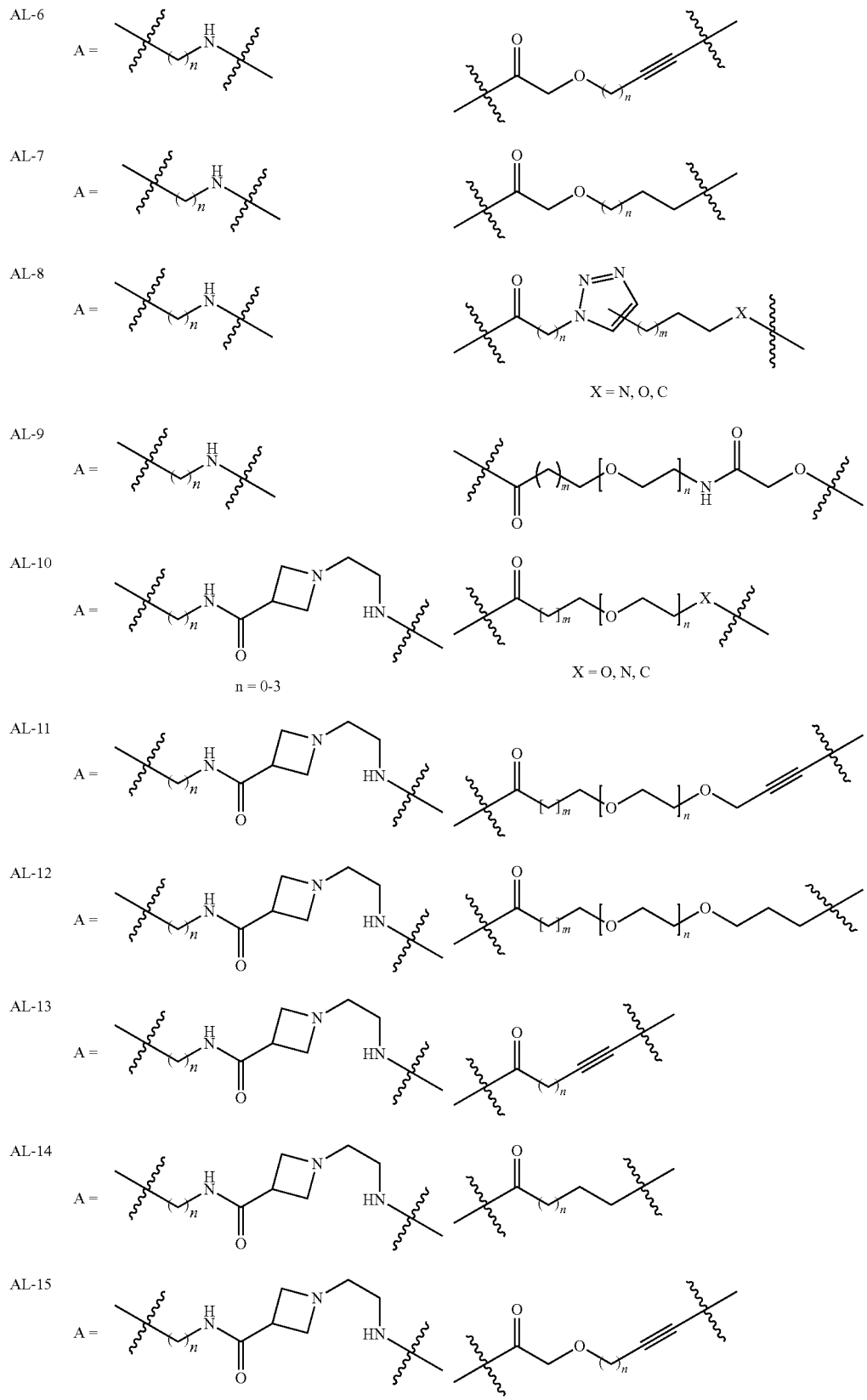

TABLE 5-continued
Exemplary linker and A combinations for Formulas (Ia-d) and (IIIa-d).
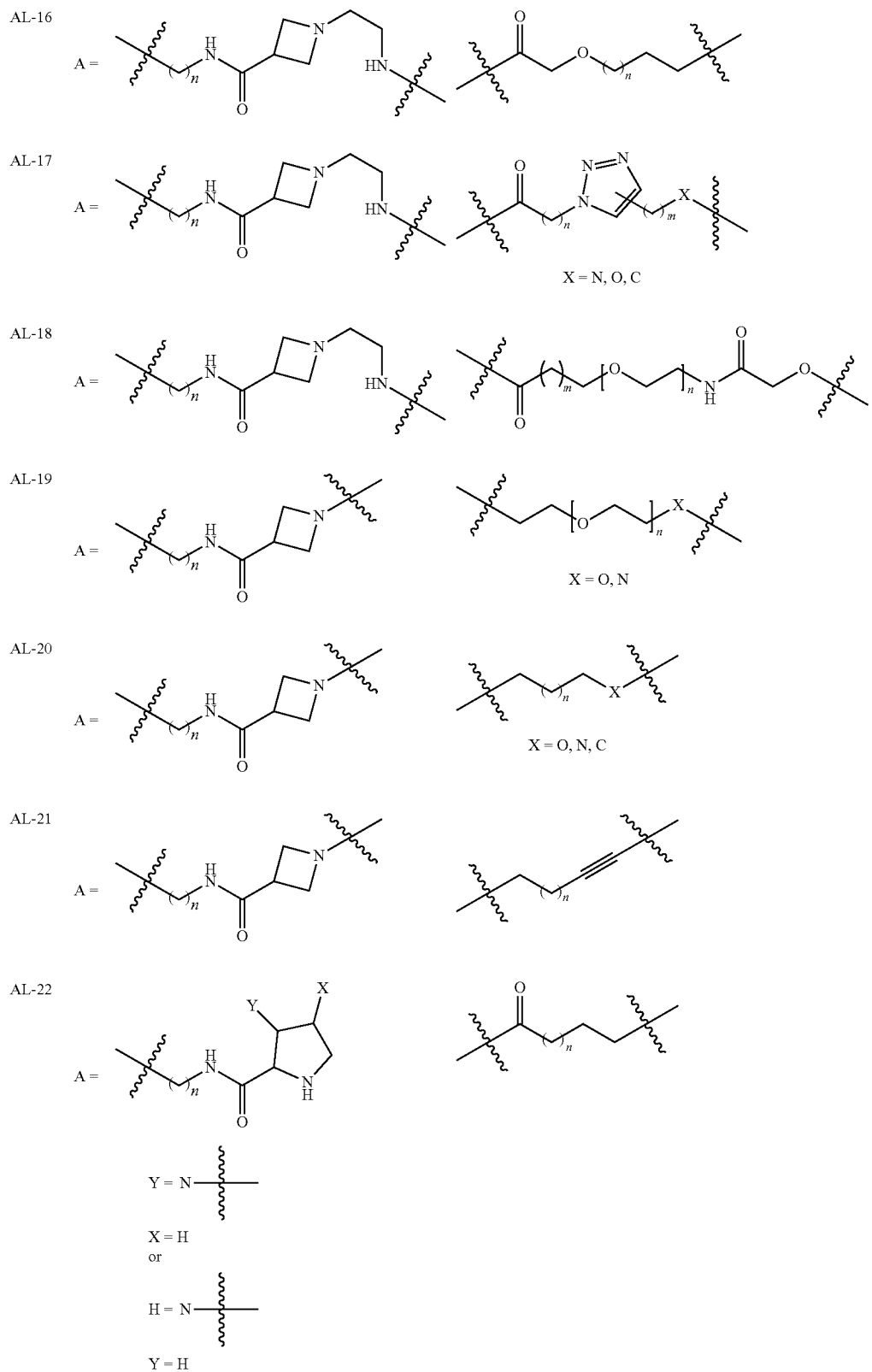

TABLE 5-continued
Exemplary linker and A combinations for Formulas (Ia-d) and (IIIa-d).
AL-23 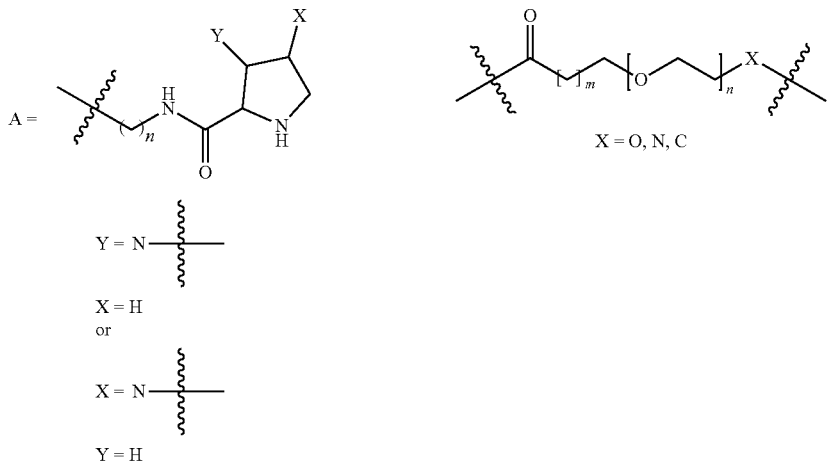
AL-24 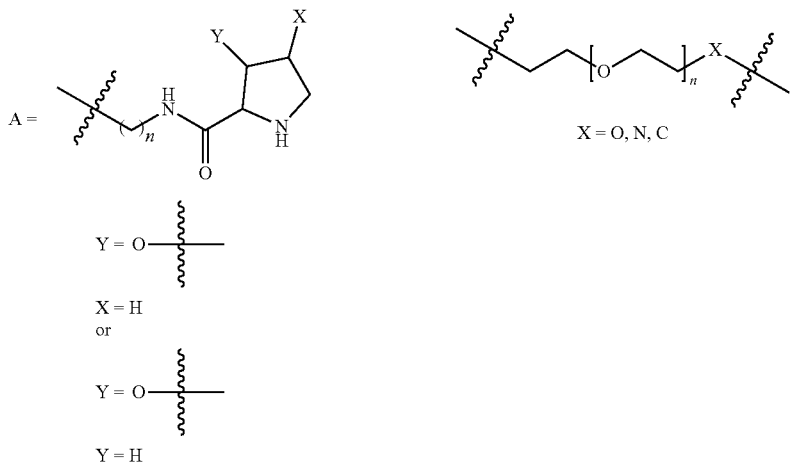
AL-25 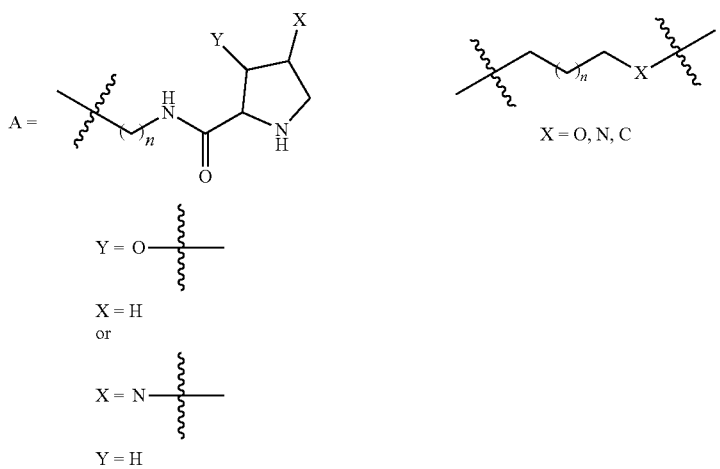
AL-26 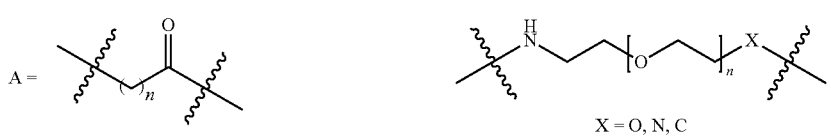

TABLE 5-continued

Exemplary linker and A combinations for Formulas (Ia-d) and (IIIa-d).

AL-27

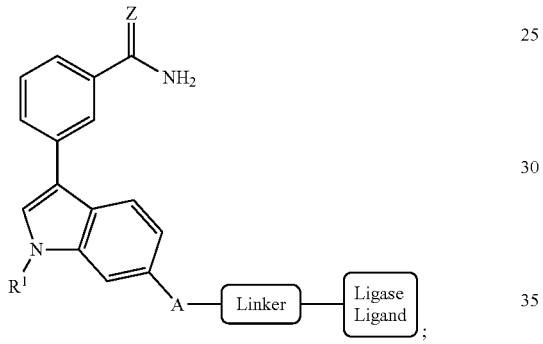

X = O, N, C

AL-28

*The above linker and A combinations are exemplary and do not include all possible combinations within the scope herein. Any suitable linkers and A groups described herein may be combined in embodiments herein. For example, any linkers of Table 2 and A groups of Table 1 may be combined in any suitable combination within the scope herein.

In some embodiments, provided herein are compounds inducing ASH1L degradation comprising a structure of Formula (Ib):

wherein Z is O or S;
wherein $R^1$ is selected from H, alkyl, substituted alkyl (e.g. halogen substituted alkyl), branched alkyl, a substituted branched alkyl (e.g. halogen substituted branched alkyl), alkoxy, amine, substituted amine, thioalkyl, ketone, amide, a substituted amide, cyano, sulfonyl, carboxy, dialkylphosphine oxide, a carbocyclic ring, s substituted carbocyclic ring, an aromatic ring, a substituted aromatic ring, a heterocyclic aromatic ring, a substituted heterocyclic aromatic ring, a substituted or non-substituted heterocyclic non-aromatic ring (e.g. piperidine, methylpiperidine, bridged piperidine, tetrahydropyran, alkylsulfonyl substituted piperidine, sulfonamide substituted piperidine, arylsulfonyl substituted piperidine, 1-((trifluoromethyl)sulfonyl)piperidine), difluorocyclohexane, monofluorocyclohexane, cyclohexane, substituted difluorocyclohexane, bicyclooctane, cycloheptane, carbocyclic or heterocyclic aromatic ring fused to another aromatic ring, a hydrogen bond donor, a hydrogen bond acceptor, and combinations thereof; and
wherein A is a covalent bond (i.e., no atom present) or is selected from the structures listed in Table 1 (wherein n is 0, 1, 2, 3, 4, 5, 6, 7, 8, 9 or 10; wherein m, when present, is 0, 1, 2, 3, 4, 5, 6, 7, 8, 9, 10, 11, 12, 13, 14 or 15 or ranges therebetween; wherein k, when present is 0, 1, 2, 3, 4, 5, 6, 7, 8, 9 or 10; wherein l, when present is 0, 1, 2, 3, 4, 5, 6, 7, 8, 9 or 10);

wherein the linker is selected from the structures listed in Table 2 (wherein n, when present, is 0, 1, 2, 3, 4, 5, 6, 7, 8, 9, 10, 11, 12, 13, 14, 15; wherein m, when present, is 0, 1, 2, 3, 4, 5, 6, 7, 8, 9, 10, 11, 12, 13, 14 or 15 or ranges therebetween); wherein k, when present is 0, 1, 2, 3, 4, 5, 6, 7, 8, 9 or 10; wherein l, when present is 0, 1, 2, 3, 4, 5, 6, 7, 8, 9 or 10; and wherein the ligase ligand is selected from those listed in Table 3.

In some embodiments, the $R^1$ substituent of Formula (Ib) is one of Formulas (a-q);
wherein one of J, $Q^1$, or $J^1$, when present, is linked to the main scaffold;
wherein each J, $J^1$, $J^2$, $J^3$, and $J^4$, when present, are independently selected from the group consisting of: a covalent bond, H, $alkyl_{1-15}$, $alkenyl_{1-6}$, $alkynyl_{1-6}$, $(CH_2)_{0-6}C(S)NH_2$, $(CH_2)_{0-6}C(O)NH_2$, O, S, NH, $(CH_2)_{0-6}C(O)NH(CH_2)_{1-6}$, $(CH_2)_{0-6}NHC(O)(CH_2)_{1-6}$, alkylsulfonyl, sulfonamide, alkylsulfonamide, $(CH_2)_{0-6}C(S)NH(CH_2)_{1-6}$, $(CH_2)_{0-6}O(CH_2)_{1-6}$, $(CH_2)_{0-6}OH$, $(CH_2)_{0-6}S(CH_2)_{1-6}$, $(CH_2)_{0-6}SH$, $(CH_2)_{0-6}NH(CH_2)_{1-6}$, $(CH_2)_{0-6}N(CH_2)_{1-6}$, $(CH_2)_{1-6}$, $(CH_2)_{0-6}NH_2$, $(CH_2)_{0-6}SO_2(CH_2)_{1-6}$, $(CH_2)_{0-6}NHSO_2(CH_2)_{1-6}$, $(CH_2)_{0-6}SO_2NH_2$, halogen (e.g., F, Cl, Br, or I), haloalkyl (e.g., $(CH_2)_{0-6}$ $CH_2F$, $(CH_2)_{0-3}CHF(CH_2)_{0-2}CH_3$, or similar with Br, Cl, or I), dihaloalkyl (e.g., $(CH_2)_{0-6}$ $CF_2H$, $(CH_2)_{0-3}$ $CF_2(CH_2)_{0-2}CH_3$, or similar with Br, Cl, or I), trihaloalkyl (e.g., $(CH_2)_{0-6}$ $CF_3$, or similar with Br, Cl, or I), alkyl with 1-3 halogens at two or more positons along its length, $(CH_2)_{1-4}SP(Ph)_2=S$, $(CH_2)_{0-6}NH(CH_2)_{1-5}OH$, $(CH_2)_{0-6}NH(CH_2)_{1-5}NH_2$, $(CH_2)_{0-6}NH(CH_2)_{1-5}SH$, $(CH_2)_{0-6}O(CH_2)_{1-5}OH$, $(CH_2)_{0-6}O(CH_2)_{1-5}NH_2$, $(CH_2)_{0-6}O(CH_2)_{1-5}SH$, $(CH_2)_{0-6}S(CH_2)_{1-5}OH$, $(CH_2)_{0-6}S(CH_2)_{1-5}NH_2$, $(CH_2)_{0-6}S(CH_2)_{1-5}SH$, $(CH_2)_{0-6}O(CH_2)_{1-6}NH(CH_2)_{1-5}OH$, $(CH_2)_{0-6}O(CH_2)_{1-6}NH(CH_2)_{1-5}NH_2$, $(CH_2)_{0-6}O(CH_2)_{1-6}NH(CH_2)_{1-5}SH$, $(CH_2)_{0-6}O(CH_2)_{1-6}O(CH_2)_{1-5}OH$, $(CH_2)_{0-6}O(CH_2)_{1-6}O(CH_2)_{1-5}NH_2$, $(CH_2)_{0-6}O(CH_2)_{1-6}O(CH_2)_{1-5}SH$, $(CH_2)_{0-6}O(CH_2)_{1-6}S(CH_2)_{1-5}OH$, $(CH_2)_{0-6}O(CH_2)_{1-6}S(CH_2)_{1-5}NH_2$, $(CH_2)_{0-6}O(CH_2)_{1-6}S(CH_2)_{1-5}SH$, $(CH_2)_{0-6}S(CH_2)_{1-6}NH(CH_2)_{1-5}OH$, $(CH_2)_{0-6}S(CH_2)_{1-6}NH(CH_2)_{1-5}NH_2$, $(CH_2)_{0-6}S(CH_2)_{1-6}NH(CH_2)_{1-5}SH$, $(CH_2)_{0-6}S(CH_2)_{1-6}O(CH_2)_{1-5}OH$, $(CH_2)_{0-6}S(CH_2)_{1-6}O(CH_2)_{1-5}NH_2$, $(CH_2)_{0-6}S(CH_2)_{1-6}O(CH_2)_{1-5}SH$, $(CH_2)_{0-6}S(CH_2)_{1-6}S(CH_2)_{1-5}OH$, $(CH_2)_{0-6}S(CH_2)_{1-6}(CH_2)_{1-5}NH_2$, $(CH_2)_{0-6}S(CH_2)_{1-6}(CH_2)_{1-5}SH$, (CH$_2$)$_{0-6}$NH(CH$_2$)$_{1-6}$NH(CH$_2$)$_{1-5}$OH, (CH$_2$)$_{0-6}$NH(CH$_2$)$_{1-6}$NH(CH$_2$)$_{1-5}$NH$_2$, (CH$_2$)$_{0-6}$NH(CH$_2$)$_{1-6}$NH(CH$_2$)$_{1-5}$SH, (CH$_2$)$_{0-6}$NH(CH$_2$)$_{1-6}$O(CH$_2$)$_{1-5}$OH, (CH$_2$)$_{0-6}$NH(CH$_2$)$_{1-6}$O(CH$_2$)$_{1-5}$NH$_2$, (CH$_2$)$_{0-6}$NH(CH$_2$)$_{1-6}$O(CH$_2$)$_{1-5}$SH, (CH$_2$)$_{0-6}$NH(CH$_2$)$_{1-6}$S(CH$_2$)$_{1-5}$OH, (CH$_2$)$_{0-6}$NH(CH$_2$)$_{1-6}$S(CH$_2$)$_{1-5}$NH$_2$, (CH$_2$)$_{0-6}$NH(CH$_2$)$_{1-6}$(CH$_2$)$_{1-5}$SH, (CH$_2$)$_{0-3}$C(O)O(CH$_2$)$_{0-3}$, (CH$_2$)$_{0-3}$C(S)O(CH$_2$)$_{0-3}$, (CH$_2$)$_{0-3}$C(O)S(CH$_2$)$_{0-3}$, (CH$_2$)$_{0-3}$C(S)S(CH$_2$)$_{0-3}$, (CH$_2$)$_{0-3}$C(O)NH(CH$_2$)$_{0-3}$, (CH$_2$)$_{0-3}$C(S)NH(CH$_2$)$_{0-3}$, (CH$_2$)$_{0-3}$NHC(O)(CH$_2$)$_{0-3}$, (CH$_2$)$_{0-3}$NHC(S)(CH$_2$)$_{0-3}$, (CH$_2$)$_{0-3}$OC(O)(CH$_2$)$_{0-3}$, (CH$_2$)$_{0-3}$OC(S)(CH$_2$)$_{0-3}$, (CH$_2$)$_{0-3}$SC(O)(CH$_2$)$_{0-3}$, (CH$_2$)$_{0-3}$SC(S)(CH$_2$)$_{0-3}$, (CH$_2$)$_{0-3}$NHC(O)NH(CH$_2$)$_{0-3}$, (CH$_2$)$_{0-3}$NHC(S)NH(CH$_2$)$_{0-3}$, (CH$_2$)$_{0-3}$OC(O)NH(CH$_2$)$_{0-3}$, (CH$_2$)$_{0-3}$OC(S)NH(CH$_2$)$_{0-3}$, (CH$_2$)$_{0-3}$SC(O)NH(CH$_2$)$_{0-3}$, (CH$_2$)$_{0-3}$SC(S)NH(CH$_2$)$_{0-3}$, (CH$_2$)$_{0-3}$NHC(O)O(CH$_2$)$_{0-3}$, (CH$_2$)$_{0-3}$NHC(S)O(CH$_2$)$_{0-3}$, (CH$_2$)$_{0-3}$OC(O)O(CH$_2$)$_{0-3}$, (CH$_2$)$_{0-3}$OC(S)O(CH$_2$)$_{0-3}$, (CH$_2$)$_{0-3}$SC(O)O(CH$_2$)$_{0-3}$, (CH$_2$)$_{0-3}$SC(S)O(CH$_2$)$_{0-3}$, (CH$_2$)$_{0-3}$NHC(O)S(CH$_2$)$_{0-3}$, (CH$_2$)$_{0-3}$NHC(S)S(CH$_2$)$_{0-3}$, (CH$_2$)$_{0-3}$OC(O)S(CH$_2$)$_{0-3}$, (CH$_2$)$_{0-3}$OC(S)S(CH$_2$)$_{0-3}$, (CH$_2$)$_{0-3}$SC(O)S(CH$_2$)$_{0-3}$, (CH$_2$)$_{0-3}$SC(S)S(CH$_2$)$_{0-3}$, (CH$_2$O)$_{1-6}$, and trimethyl methane;

- wherein each Q, Q$^1$, and Q$^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), thiadiazole, aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, thiethane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, any suitable C$^3$-C$^7$ cycloalkyl group, and any of the ring structures depicted in Table 4;
- wherein each Q, Q$^1$, and Q$^2$, when present, may display one or more additional J groups at any position on the Q ring;
- wherein any alkyl or (CH$_2$)$_{x-y}$ groups above may be straight or branched;
- wherein any alkyl or (CH$_2$)$_{x-y}$ groups above may additionally comprise OH, =O, NH$_2$, CN, dihaloalkyl (e.g., CF$_2$H), trihaloalkyl (e.g., CF$_3$), or halogen (e.g., F) substituents at one or more carbons; and
- wherein the number of hydrogens on terminal positions of the groups above may be adjusted if the group is linked to an additional group (e.g., CH$_3$ adjusted to CH$_2$, OH adjusted to O, etc.) or if the group is terminal (e.g., CH$_2$ adjusted to CH$_3$, O adjusted to OH, etc.).

In some embodiments, provided herein are ASH1L-degrading compounds comprising a structure of Formula (IIa):

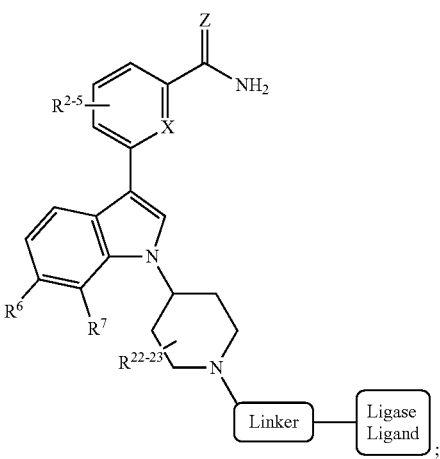

- wherein X is CH or N;
- wherein Z is O or S;
- wherein R$^2$, R$^3$, R$^4$, R$^5$, and R$^7$ are independently selected from H, halogen (e.g., Cl, F, Br, I), CH$_3$, OH, SH, NH$_2$, CN, CF$_3$, CCl$_3$, —CH$_2$—CH$_3$, —CH$_2$—OH, —CH$_2$NH$_2$, CH$_3$SH, CH$_2$Cl, CH$_2$Br, CH$_2$F, CHF$_2$, CH$_2$CN, CH$_2$CF$_3$, and CH$_2$Cl$_3$;
- wherein R$^6$ is selected from H, alkyl, substituted alkyl (e.g. halogen substituted alkyl), branched alkyl, a substituted branched alkyl (e.g. halogen substituted branched alkyl) hydroxy, alkoxy, amine, substituted amine, thioalkyl, halogen, ketone, amide, a substituted amide, cyano, sulfonyl, carboxy, dialkylphosphine oxide, a carbocyclic ring, s substituted carbocyclic ring, an aromatic ring, a substituted aromatic ring, a heterocyclic aromatic ring, a substituted heterocyclic aromatic ring, a substituted or non-substituted heterocyclic non-aromatic ring (e.g. piperidine, methylpiperidine, bridged piperidine, tetrahydropyran, alkylsulfonyl substituted piperidine, sulfonamide substituted piperidine, arylsulfonyl substituted piperidine), carbocyclic or heterocyclic aromatic ring fused to another aromatic ring, a hydrogen bond donor, a hydrogen bond acceptor, and combinations thereof;
- wherein R$^{22}$ and R$^{23}$ are independently selected from H, halogen (e.g., Cl, F, Br, I), CH$_3$, OH, SH, NH$_2$, CN, CF$_3$, CCl$_3$, —CH$_2$—CH$_3$, —CH$_2$—OH, —CH$_2$NH$_2$, CH$_3$SH, CH$_2$Cl, CH$_2$Br, CH$_2$F, CHF$_2$, CH$_2$CN, CH$_2$CF$_3$, and CH$_2$Cl$_3$;
- wherein the linker is selected from the structures listed in Table 6 (wherein n, when present, is 0, 1, 2, 3, 4, 5, 6, 7, 8, 9, 10, 11, 12, 13, 14, 15; wherein m, when present, is 0, 1, 2, 3, 4, 5, 6, 7, 8, 9, 10, 11, 12, 13, 14 or 15 or ranges therebetween); wherein k, when present is 0, 1, 2, 3, 4, 5, 6, 7, 8, 9 or 10; wherein l, when present is 0, 1, 2, 3, 4, 5, 6, 7, 8, 9 or 10); and
- wherein the ligase ligand is selected from those listed in Table 7.

TABLE 6
Exemplary linkers for Formulas (IIa), (IIb), (IIc), and (IId).
Lb-1
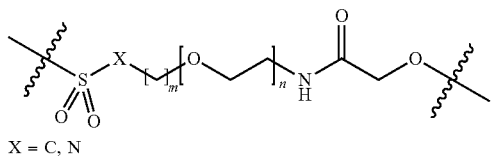
X = C, N
Lb-2
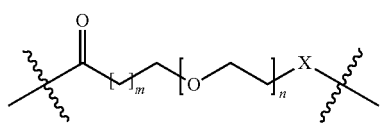
X = O, N, C
Lb-3
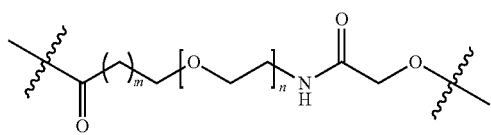
Lb-4
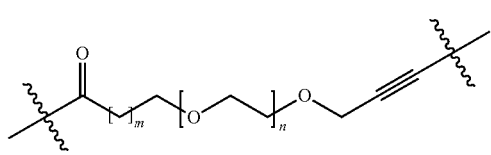
Lb-5
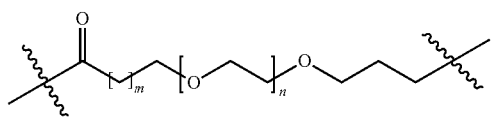
Lb-6
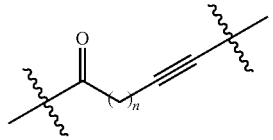
Lb-7
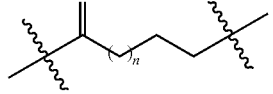
Lb-8
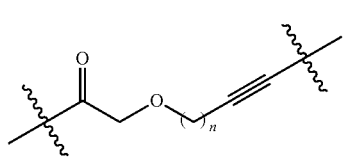
Lb-9
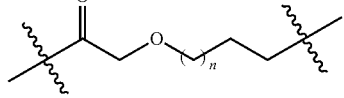
Lb-10
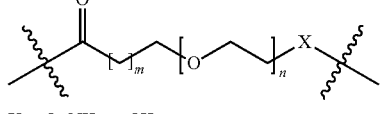
X = O, NH, or CH$_2$
Lb-11
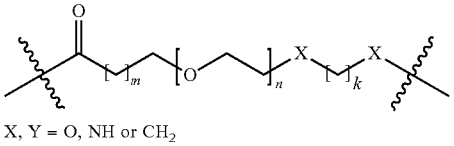
X, Y = O, NH or CH$_2$
Lb-12
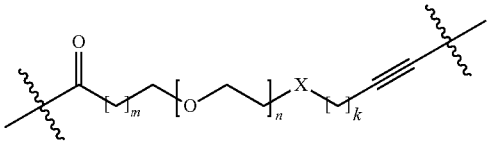
X = O, NH or CH$_2$
Lb-13
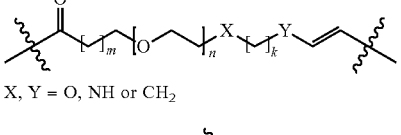
X, Y = O, NH or CH$_2$
Lb-14
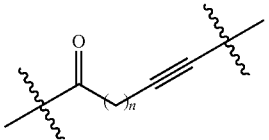
Lb-15
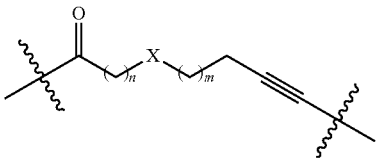
X = O, NH or CH$_2$
Lb-16
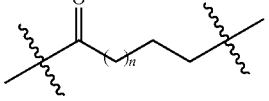
Lb-17
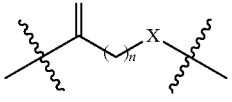
X = O, HN, CH$_2$
Lb-18
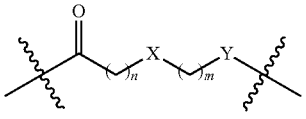
X = O, HN, N(CH$_3$) or CH$_2$
Lb-19
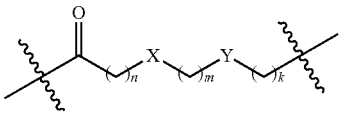
X, Y = O, HN or CH$_2$
Lb-20
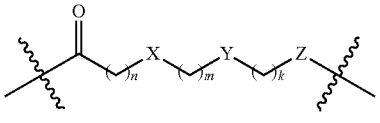
X, Y, Z = O, HN or CH$_2$ TABLE 6-continued
Exemplary linkers for Formulas (IIa), (IIb), (IIc), and (IId).
Lb-21 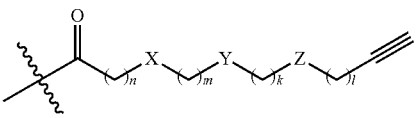
X, Y, Z = O, HN or CH$_2$
Lb-22 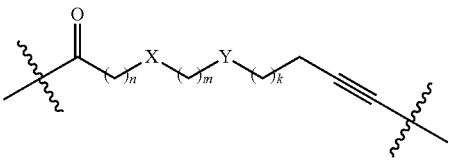
X, Y = O, HN or CH$_2$
Lb-23 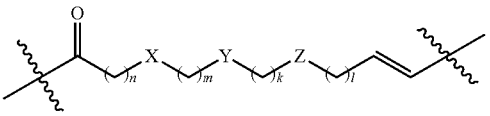
X, Y Z = O, HN or CH$_2$
Lb-24 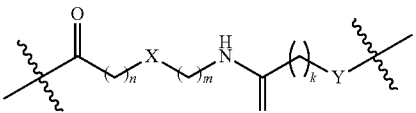
X = O, HN, CH$_2$
Lb-25 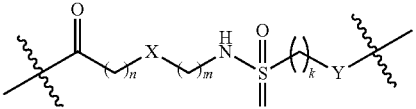
X = O, HN, CH$_2$
Lb-26 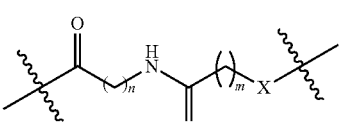
X = O, HN, CH$_2$
Lb-28 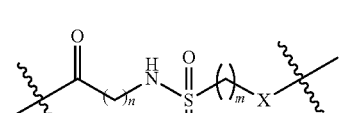
X = O, HN, CH$_2$
Lb-29 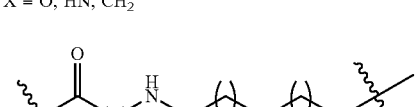
X, Y = O, HN or CH$_2$
Lb-30 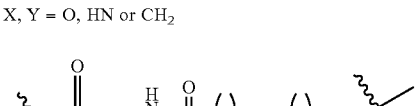
X, Y = O, HN or CH$_2$
Lb-31 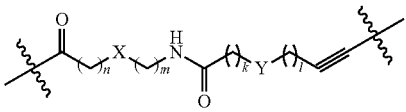
X, Y = O, HN or CH$_2$
Lb-32 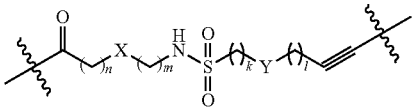
X, Y = O, HN, CH$_2$
Lb-33 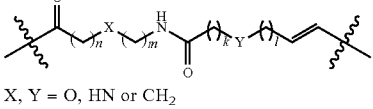
X, Y = O, HN or CH$_2$
Lb-34 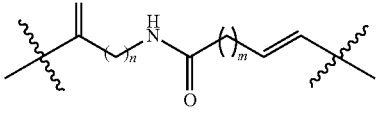
Lb-35 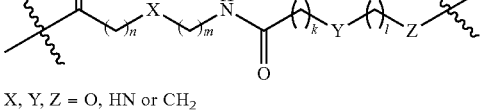
X, Y, Z = O, HN or CH$_2$
Lb-36 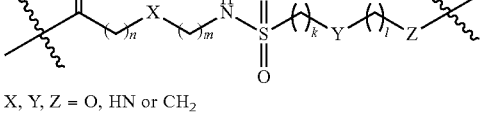
X, Y, Z = O, HN or CH$_2$
Lb-37 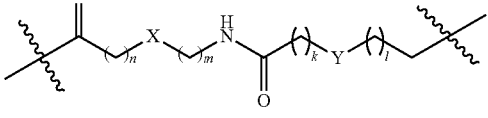
X, Y = O, HN or CH$_2$
Lb-38 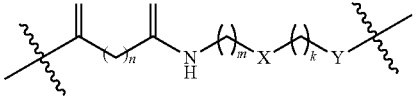
X, Y = O, HN, CH$_2$
Lb-39 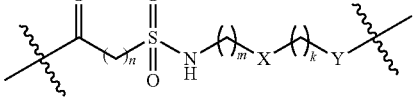
X, Y = O, HN, CH$_2$
Lb-40 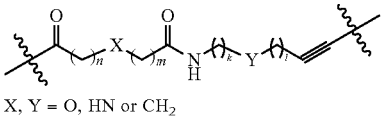
X, Y = O, HN or CH$_2$ TABLE 6-continued Exemplary linkers for Formulas (IIa), (IIb), (IIc), and (IId).

Lb-41
X, Y = O, HN or CH$_2$

Lb-42
X, Y = O, HN or CH$_2$

Lb-43
X, Y = O, HN, CH$_2$

Lb-44
X, Y = O, HN, CH$_2$

Lb-45
X, Y = O, HN, CH$_2$

Lb-46
X, Y = O, HN. CH$_2$

Lb-47
X, Y, Z = O, HN or CH$_2$

Lb-48
X, Y, Z = O, HN or CH$_2$

Lb-49
X, Y = O, NH, or CH$_2$

Lb-50
X, Y = O, NH or CH$_2$

Lb-51
X = O, NH, CH$_2$

Lb-52
X, Y, Z = O, NH, CH$_2$

Lb-53
X = O, NH, CH$_2$

Lb-54
X = O, NH, CH$_2$

Lb-55
X = O, NH, CH$_2$

Lb-56
X = O, NH, CH$_2$

Lb-57
X = O, NH, CH$_2$

Lb-58
X = O, HN, CH$_2$

Lb-59
X = O, HN, CH$_2$

Lb-60
X = O, HN, CH$_2$

TABLE 6-continued

Exemplary linkers for Formulas (IIa), (IIb), (IIc), and (IId).

Lb-61: [structure]
X = O, HN, CH$_2$

Lb-62: [structure]
X = O, HN, CH$_2$

Lb-63: [structure]
X, Y = O, HN or CH$_2$

Lb-64: [structure]
X = O, HN, CH$_2$

Lb-65: [structure]
X, Y = O, HN or CH$_2$

L6-66: [structure]
X = O, NH or CH$_2$

Lb-67: [structure]
X, Y, Z = O, NH or CH$_2$

Lb-68: [structure]
X, Y = O, NH or CH$_2$

Lb-69: [structure]
X = O, NH or CH$_2$

Lb-70: [structure]
X, Y = O, NH or CH$_2$

Lb-71: [structure]
X, Y, Z = O, HN or CH$_2$

Lb-72: [structure]
X, Y, Z = O, HN or CH$_2$

Lb-73: [structure]
X, Y = O, HN, CH$_2$

Lb-74: [structure]
X, Y = O, HN, CH$_2$

Lb-75: [structure]
X, Y = O, HN, CH$_2$

Lb-76: [structure]
X, Y = O, HN, CH$_2$

Lb-77: [structure]
X, Y = O, HN, CH$_2$

Lb-78: [structure]
X, Y = O, HN, CH$_2$

Lb-79: [structure]
X, Y = O, HN, CH$_2$

TABLE 6-continued

Exemplary linkers for Formulas (IIa), (IIb), (IIc), and (IId).

Lb-80 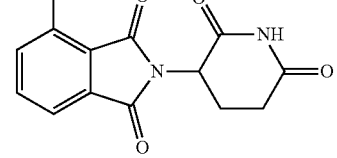
X, Y = O, HN, CH₂

Lb-81 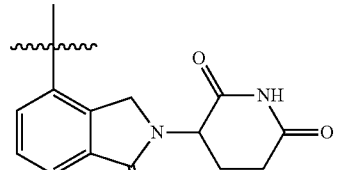
X, Y = O, NH, CH₂

Lb-82 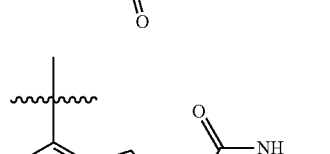

*X, Y, and Z groups, when present in the linkers above (Table 6), are independently O, NH, or CH₂, and do not need to be the same group when present in the same linker.

TABLE 7

Exemplary ligase ligands for Formulas (IIa), (IIb), (IIc), and (IId).

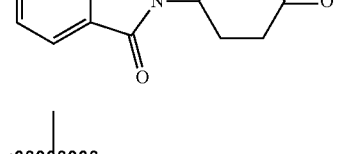

In some embodiments, the $R^6$ substituent of Formula (IIa) is one of Formulas (a-q); wherein one of J, $Q^1$, or $J^1$, when present, is linked to the main scaffold;

wherein each J, $J^1$, $J^2$, $J^3$, and $J^4$, when present, are independently selected from the group consisting of: a covalent bond, H, $alkyl_{1-15}$, $alkenyl_{1-6}$, $alkynyl_{1-6}$, $(CH_2)_{0-6}C(S)NH_2$, $(CH_2)_{0-6}C(O)NH_2$, O, S, NH, $(CH_2)_{0-6}C(O)NH(CH_2)_{1-6}$, $(CH_2)_{0-6}NHC(O)(CH_2)_{1-6}$, alkylsulfonyl, sulfonamide, alkylsulfonamide, $(CH_2)_{0-6}C(S)NH(CH_2)_{1-6}$, $(CH_2)_{0-6}O(CH_2)_{1-6}$, $(CH_2)_{0-6}OH$, $(CH_2)_{0-6}S(CH_2)_{1-6}$, $(CH_2)_{0-6}SH$, $(CH_2)_{0-6}NH(CH_2)_{1-6}$, $(CH_2)_{0-6}N(CH_2)_{1-6}(CH_2)_{1-6}$, $(CH_2)_{0-6}NH_2$, $(CH_2)_{0-6}SO_2(CH_2)_{1-6}$, $(CH_2)_{0-6}NHSO_2(CH_2)_{1-6}$, $(CH_2)_{0-6}SO_2NH_2$, halogen (e.g., F, Cl, Br, or I), haloalkyl (e.g., $(CH_2)_{0-6}$ $CH_2F$, $(CH_2)_{0-3}CHF(CH_2)_{0-2}CH_3$, or similar with Br, Cl, or I), dihaloalkyl (e.g., $(CH_2)_{0-6}$ $CF_2H$, $(CH_2)_{0-3}$ $CF_2(CH_2)_{0-2}CH_3$, or similar with Br, Cl, or I), trihaloalkyl (e.g., $(CH_2)_{0-6}$ $CF_3$, or similar with Br, Cl, or I), alkyl with 1-3 halogens at two or more positons along its length, $(CH_2)_{1-4}SP(Ph)_2=S$, $(CH_2)_{0-6}NH(CH_2)_{1-5}OH$, $(CH_2)_{0-6}NH(CH_2)_{1-5}NH_2$, $(CH_2)_{0-6}NH(CH_2)_{1-5}SH$, $(CH_2)_{0-6}O(CH_2)_{1-5}OH$, $(CH_2)_{0-6}O(CH_2)_{1-5}NH_2$, $(CH_2)_{0-6}O(CH_2)_{1-5}SH$, $(CH_2)_{0-6}S(CH_2)_{1-5}OH$, $(CH_2)_{0-6}S(CH_2)_{1-5}NH_2$, $(CH_2)_{0-6}S(CH_2)_{1-5}SH$, $(CH_2)_{0-6}O(CH_2)_{1-6}NH(CH_2)_{1-5}OH$, $(CH_2)_{0-6}O(CH_2)_{1-6}NH(CH_2)_{1-5}NH_2$, $(CH_2)_{0-6}O(CH_2)_{1-6}NH(CH_2)_{1-5}SH$, $(CH_2)_{0-6}O(CH_2)_{1-6}O(CH_2)_{1-5}OH$, $(CH_2)_{0-6}O(CH_2)_{1-6}O(CH_2)_{1-5}NH_2$, $(CH_2)_{0-6}O(CH_2)_{1-6}O(CH_2)_{1-5}SH$, $(CH_2)_{0-6}O(CH_2)_{1-6}S(CH_2)_{1-5}OH$, $(CH_2)_{0-6}O(CH_2)_{1-6}S(CH_2)_{1-5}NH_2$, $(CH_2)_{0-6}O(CH_2)_{1-6}S(CH_2)_{1-5}SH$, $(CH_2)_{0-6}S(CH_2)_{1-6}NH(CH_2)_{1-5}OH$, $(CH_2)_{0-6}S(CH_2)_{1-6}NH(CH_2)_{1-5}NH_2$, $(CH_2)_{0-6}S(CH_2)_{1-6}NH(CH_2)_{1-5}SH$, $(CH_2)_{0-6}S(CH_2)_{1-6}O(CH_2)_{1-5}OH$, $(CH_2)_{0-6}S(CH_2)_{1-6}O(CH_2)_{1-5}NH_2$, $(CH_2)_{0-6}S(CH_2)_{1-6}O(CH_2)_{1-5}SH$, $(CH_2)_{0-6}S(CH_2)_{1-6}S(CH_2)_{1-5}OH$, $(CH_2)_{0-6}S(CH_2)_{1-6}S(CH_2)_{1-5}NH_2$, $(CH_2)_{0-6}S(CH_2)_{1-6}S(CH_2)_{1-5}SH$, (CH$_2$)$_{0-6}$NH(CH$_2$)$_{1-6}$NH(CH$_2$)$_{1-5}$OH, (CH$_2$)$_{0-6}$NH(CH$_2$)$_{1-6}$NH(CH$_2$)$_{1-5}$NH$_2$, (CH$_2$)$_{0-6}$NH(CH$_2$)$_{1-6}$NH(CH$_2$)$_{1-5}$SH, (CH$_2$)$_{0-6}$NH(CH$_2$)$_{1-6}$O(CH$_2$)$_{1-5}$OH, (CH$_2$)$_{0-6}$NH(CH$_2$)$_{1-6}$O(CH$_2$)$_{1-5}$NH$_2$, (CH$_2$)$_{0-6}$NH(CH$_2$)$_{1-6}$O(CH$_2$)$_{1-5}$SH, (CH$_2$)$_{0-6}$NH(CH$_2$)$_{1-6}$S(CH$_2$)$_{1-5}$OH, (CH$_2$)$_{0-6}$NH(CH$_2$)$_{1-6}$S(CH$_2$)$_{1-5}$NH$_2$, (CH$_2$)$_{0-6}$NH(CH$_2$)$_{1-6}$S(CH$_2$)$_{1-5}$SH, (CH$_2$)$_{0-3}$C(O)O(CH$_2$)$_{0-3}$, (CH$_2$)$_{0-3}$C(S)O(CH$_2$)$_{0-3}$, (CH$_2$)$_{0-3}$C(O)S(CH$_2$)$_{0-3}$, (CH$_2$)$_{0-3}$C(S)S(CH$_2$)$_{0-3}$, (CH$_2$)$_{0-3}$C(O)NH(CH$_2$)$_{0-3}$, (CH$_2$)$_{0-3}$C(S)NH(CH$_2$)$_{0-3}$, (CH$_2$)$_{0-3}$NHC(O)(CH$_2$)$_{0-3}$, (CH$_2$)$_{0-3}$NHC(S)(CH$_2$)$_{0-3}$, (CH$_2$)$_{0-3}$OC(O)(CH$_2$)$_{0-3}$, (CH$_2$)$_{0-3}$OC(S)(CH$_2$)$_{0-3}$, (CH$_2$)$_{0-3}$SC(O)(CH$_2$)$_{0-3}$, (CH$_2$)$_{0-3}$SC(S)(CH$_2$)$_{0-3}$, (CH$_2$)$_{0-3}$NHC(O)NH(CH$_2$)$_{0-3}$, (CH$_2$)$_{0-3}$NHC(S)NH(CH$_2$)$_{0-3}$, (CH$_2$)$_{0-3}$OC(O)NH(CH$_2$)$_{0-3}$, (CH$_2$)$_{0-3}$OC(S)NH(CH$_2$)$_{0-3}$, (CH$_2$)$_{0-3}$SC(O)NH(CH$_2$)$_{0-3}$, (CH$_2$)$_{0-3}$SC(S)NH(CH$_2$)$_{0-3}$, (CH$_2$)$_{0-3}$NHC(O)O(CH$_2$)$_{0-3}$, (CH$_2$)$_{0-3}$NHC(S)O(CH$_2$)$_{0-3}$, (CH$_2$)$_{0-3}$OC(O)O(CH$_2$)$_{0-3}$, (CH$_2$)$_{0-3}$OC(S)O(CH$_2$)$_{0-3}$, (CH$_2$)$_{0-3}$SC(O)O(CH$_2$)$_{0-3}$, (CH$_2$)$_{0-3}$SC(S)O(CH$_2$)$_{0-3}$, (CH$_2$)$_{0-3}$NHC(O)S(CH$_2$)$_{0-3}$, (CH$_2$)$_{0-3}$NHC(S)S(CH$_2$)$_{0-3}$, (CH$_2$)$_{0-3}$OC(O)S(CH$_2$)$_{0-3}$, (CH$_2$)$_{0-3}$OC(S)S(CH$_2$)$_{0-3}$, (CH$_2$)$_{0-3}$SC(O)S(CH$_2$)$_{0-3}$, (CH$_2$)$_{0-3}$SC(S)S(CH$_2$)$_{0-3}$, (CH$_2$O)$_{1-6}$, and trimethyl methane;

wherein each Q, Q$^1$, and Q$^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), thiadiazole, aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, thiethane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, any suitable C$^3$-C$^7$ cycloalkyl group, and any of the ring structures depicted in Table 4;

wherein each Q, Q$^1$, and Q$^2$, when present, may display one or more additional J groups at any position on the Q ring;

wherein any alkyl or (CH$_2$)$_{x-y}$ groups above may be straight or branched;

wherein any alkyl or (CH$_2$)$_{x-y}$ groups above may additionally comprise OH, =O, NH$_2$, CN, dihaloalkyl (e.g., CF$_2$H), trihaloalkyl (e.g., CF$_3$), or halogen (e.g., F) substituents at one or more carbons; and wherein the number of hydrogens on terminal positions of the groups above may be adjusted if the group is linked to an additional group (e.g., CH$_3$ adjusted to CH$_2$, OH adjusted to O, etc.) or if the group is terminal (e.g., CH$_2$ adjusted to CH$_3$, O adjusted to OH, etc.).

In some embodiments, provided herein are ASH1L-degrading compounds comprising a structure of Formula (IIb):

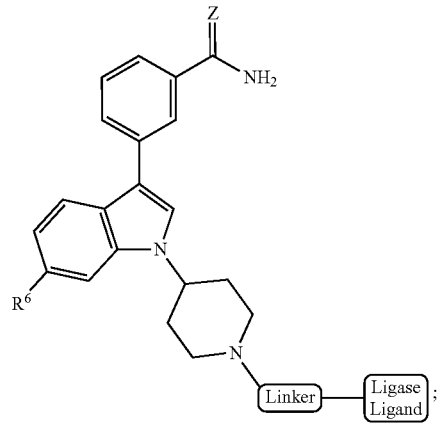

wherein Z is O or S;

wherein R$^6$ is selected from H, alkyl, substituted alkyl, hydroxy, alkoxy, amine, substituted amine, alkylamine, substituted alkylamine, thioalkyl, halogen, ketone, amide, substituted amide, alkylamide, substituted alkylamide, cyano, sulfonyl, carboxy, dialkylphosphine oxide, a carbocyclic ring, a substituted carbocyclic ring an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof;

wherein the linker is selected from the structures listed in Table 6 (wherein n, when present, is 0, 1, 2, 3, 4, 5, 6, 7, 8, 9, 10, 11, 12, 13, 14, 15; wherein m when present, is 0, 1, 2, 3, 4, 5, 6, 7, 8, 9, 10, 11, 12, 13, 14 or 15 or ranges therebetween); wherein k, when present is 0, 1, 2, 3, 4, 5, 6, 7, 8, 9 or 10; wherein l, when present is 0, 1, 2, 3, 4, 5, 6, 7, 8, 9 or 10); wherein the ligase ligand is selected from those listed in Table 7.

In some embodiments, the R$^6$ substituent of Formula (IIb) is one of Formulas (a-q)

wherein one of J, Q$^1$, or J$^1$, when present, is linked to the main scaffold;

wherein each J, J$^1$, J$^2$, J$^3$, and J$^4$, when present, are independently selected from the group consisting of: a covalent bond, H, alkyl$_{1-15}$, alkenyl$_{1-6}$, alkynyl$_{1-6}$, (CH$_2$)$_{0-6}$C(S)NH$_2$, (CH$_2$)$_{0-6}$C(O)NH$_2$, O, S, NH, (CH$_2$)$_{0-6}$C(O)NH(CH$_2$)$_{1-6}$, (CH$_2$)$_{0-6}$NHC(O)(CH$_2$)$_{1-6}$, alkylsulfonyl, sulfonamide, alkylsulfonamide, (CH$_2$)$_{0-6}$C(S)NH(CH$_2$)$_{1-6}$, (CH$_2$)$_{0-6}$O(CH$_2$)$_{1-6}$, (CH$_2$)$_{0-6}$OH, (CH$_2$)$_{0-6}$S(CH$_2$)$_{1-6}$, (CH$_2$)$_{0-6}$SH, (CH$_2$)$_{0-6}$NH(CH$_2$)$_{1-6}$, (CH$_2$)$_{0-6}$N(CH$_2$)$_{1-6}$(CH$_2$)$_{1-6}$, (CH$_2$)$_{0-6}$NH$_2$, (CH$_2$)$_{0-6}$SO$_2$(CH$_2$)$_{1-6}$, (CH$_2$)$_{0-6}$NHSO$_2$(CH$_2$)$_{1-6}$, (CH$_2$)$_{0-6}$SO$_2$NH$_2$, halogen (e.g., F, Cl, Br, or I), haloalkyl (e.g., (CH$_2$)$_{0-6}$ CH$_2$F, (CH$_2$)$_{0-3}$CHF (CH$_2$)$_{0-2}$CH$_3$, or similar with Br, Cl, or I), dihaloalkyl (e.g., (CH$_2$)$_{0-6}$ CF$_2$H, (CH$_2$)$_{0-3}$ CF$_2$(CH$_2$)$_{0-2}$CH$_3$, or similar with Br, Cl, or I), trihaloalkyl (e.g., (CH$_2$)$_{0-6}$CF$_3$, or similar with Br, Cl, or I), alkyl with 1-3 halogens at two or more positons along its length, (CH$_2$)$_{1-4}$SP(Ph)$_2$=S, (CH$_2$)$_{0-6}$NH(CH$_2$)$_{1-5}$OH, (CH$_2$)$_{0-6}$NH(CH$_2$)$_{1-5}$NH$_2$, (CH$_2$)$_{0-6}$NH(CH$_2$)$_{1-5}$SH, (CH$_2$)$_{0-6}$O(CH$_2$)$_{1-5}$OH, (CH$_2$)$_{0-6}$O(CH$_2$)$_{1-5}$NH$_2$, (CH$_2$)$_{0-6}$O(CH$_2$)$_{1-5}$SH, (CH$_2$)$_{0-6}$S(CH$_2$)$_{1-5}$OH, (CH$_2$)$_{0-6}$S(CH$_2$)$_{1-5}$NH$_2$, (CH$_2$)$_{0-6}$S(CH$_2$)$_{1-5}$SH, (CH$_2$)$_{0-6}$O(CH$_2$)$_{1-6}$NH(CH$_2$)$_{1-5}$OH, (CH$_2$)$_{0-6}$O(CH$_2$)$_{1-6}$NH(CH$_2$)$_{1-5}$NH$_2$, (CH$_2$)$_{0-6}$O(CH$_2$)$_{1-6}$NH(CH$_2$)$_{1-5}$SH, (CH$_2$)$_{0-6}$O(CH$_2$)$_{1-6}$O(CH$_2$)$_{1-5}$OH, (CH$_2$)$_{0-6}$O(CH$_2$)$_{0-6}$O(CH$_2$)$_{1-5}$NH$_2$, (CH$_2$)$_{0-6}$O(CH$_2$)$_{1-6}$O(CH$_2$)$_{1-5}$SH, (CH$_2$)$_{0-6}$O(CH$_2$)$_{1-6}$S(CH$_2$)$_{1-5}$OH, (CH$_2$)$_{0-6}$O(CH$_2$)$_{1-6}$S(CH$_2$)$_{1-5}$NH$_2$, (CH$_2$)$_{0-6}$O(CH$_2$)$_{1-6}$S(CH$_2$)$_{1-5}$SH, (CH$_2$)$_{0-6}$S(CH$_2$)$_{1-6}$NH(CH$_2$)$_{1-5}$OH, (CH$_2$)$_{0-6}$S(CH$_2$)$_{1-6}$NH(CH$_2$)$_{1-5}$NH$_2$, (CH$_2$)$_{0-6}$S(CH$_2$)$_{1-6}$NH(CH$_2$)$_{1-5}$SH, (CH$_2$)$_{0-6}$S(CH$_2$)$_{1-6}$O(CH$_2$)$_{1-5}$OH, (CH$_2$)$_{0-6}$S(CH$_2$)$_{1-6}$O(CH$_2$)$_{1-5}$NH$_2$, (CH$_2$)$_{0-6}$S(CH$_2$)$_{1-6}$O(CH$_2$)$_{1-5}$SH, (CH$_2$)$_{0-6}$S(CH$_2$)$_{1-6}$S(CH$_2$)$_{1-5}$OH, (CH$_2$)$_{0-6}$S(CH$_2$)$_{1-6}$S(CH$_2$)$_{1-5}$NH$_2$, (CH$_2$)$_{0-6}$S(CH$_2$)$_{1-6}$S(CH$_2$)$_{1-5}$SH, (CH$_2$)$_{0-6}$NH(CH$_2$)$_{1-6}$NH(CH$_2$)$_{1-5}$OH, (CH$_2$)$_{0-6}$NH(CH$_2$)$_{1-6}$NH(CH$_2$)$_{1-5}$NH$_2$, (CH$_2$)$_{0-6}$NH(CH$_2$)$_{1-6}$NH(CH$_2$)$_{1-5}$SH, (CH$_2$)$_{0-6}$NH(CH$_2$)$_{1-6}$O(CH$_2$)$_{1-5}$OH, (CH$_2$)$_{0-6}$NH(CH$_2$)$_{1-6}$O(CH$_2$)$_{1-5}$NH$_2$, (CH$_2$)$_{0-6}$NH(CH$_2$)$_{1-6}$O(CH$_2$)$_{1-5}$SH, (CH$_2$)$_{0-6}$NH(CH$_2$)$_{1-6}$S(CH$_2$)$_{1-5}$OH, (CH$_2$)$_{0-6}$NH(CH$_2$)$_{1-6}$S(CH$_2$)$_{1-5}$NH$_2$, (CH$_2$)$_{0-6}$NH(CH$_2$)$_{1-6}$S(CH$_2$)$_{1-5}$SH, (CH$_2$)$_{0-3}$C(O)O(CH$_2$)$_{0-3}$, (CH$_2$)$_{0-3}$C(S)O(CH$_2$)$_{0-3}$, (CH$_2$)$_{0-3}$C(O)S(CH$_2$)$_{0-3}$, (CH$_2$)$_{0-3}$C(S)S(CH$_2$)$_{0-3}$, (CH$_2$)$_{0-3}$C(O)NH(CH$_2$)$_{0-3}$, (CH$_2$)$_{0-3}$C(S)NH(CH$_2$)$_{0-3}$, (CH$_2$)$_{0-3}$NHC(O)(CH$_2$)$_{0-3}$, (CH$_2$)$_{0-3}$NHC(S)(CH$_2$)$_{0-3}$, (CH$_2$)$_{0-3}$OC(O)(CH$_2$)$_{0-3}$, (CH$_2$)$_{0-3}$OC(S)(CH$_2$)$_{0-3}$, (CH$_2$)$_{0-3}$SC(O)(CH$_2$)$_{0-3}$, (CH$_2$)$_{0-3}$SC(S)(CH$_2$)$_{0-3}$, (CH$_2$)$_{0-3}$NHC(O)NH(CH$_2$)$_{0-3}$, (CH$_2$)$_{0-3}$NHC(S)NH(CH$_2$)$_{0-3}$, (CH$_2$)$_{0-3}$OC(O)NH(CH$_2$)$_{0-3}$, (CH$_2$)$_{0-3}$OC(S)NH(CH$_2$)$_{0-3}$, (CH$_2$)$_{0-3}$SC(O)NH(CH$_2$)$_{0-3}$, (CH$_2$)$_{0-3}$SC(S)NH(CH$_2$)$_{0-3}$, (CH$_2$)$_{0-3}$NHC(O)O(CH$_2$)$_{0-3}$, (CH$_2$)$_{0-3}$NHC(S)O(CH$_2$)$_{0-3}$, (CH$_2$)$_{0-3}$OC(O)O(CH$_2$)$_{0-3}$, (CH$_2$)$_{0-3}$OC(S)O(CH$_2$)$_{0-3}$, (CH$_2$)$_{0-3}$SC(O)O(CH$_2$)$_{0-3}$, (CH$_2$)$_{0-3}$SC(S)O(CH$_2$)$_{0-3}$, (CH$_2$)$_{0-3}$NHC(O)S(CH$_2$)$_{0-3}$, (CH$_2$)$_{0-3}$NHC(S)S(CH$_2$)$_{0-3}$, (CH$_2$)$_{0-3}$OC(O)S(CH$_2$)$_{0-3}$, (CH$_2$)$_{0-3}$OC(S)S(CH$_2$)$_{0-3}$, (CH$_2$)$_{0-3}$SC(O)S(CH$_2$)$_{0-3}$, (CH$_2$)$_{0-3}$SC(S)S(CH$_2$)$_{0-3}$, (CH$_2$O)$_{1-6}$, and trimethyl methane;

wherein each Q, Q$^1$, and Q$^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), thiadiazole, aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, thiethane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, any suitable C$^3$-C$^7$ cycloalkyl group, and any of the ring structures depicted in Table 4;

wherein each Q, Q$^1$, and Q$^2$, when present, may display one or more additional J groups at any position on the Q ring;

wherein any alkyl or (CH$_2$)$_{x-y}$ groups above may be straight or branched;

wherein any alkyl or (CH$_2$)$_{x-y}$ groups above may additionally comprise OH, =O, NH$_2$, CN, dihaloalkyl (e.g., CF$_2$H), trihaloalkyl (e.g., CF$_3$), or halogen (e.g., F) substituents at one or more carbons; and wherein the number of hydrogens on terminal positions of the groups above may be adjusted if the group is linked to an additional group (e.g., CH$_3$ adjusted to CH$_2$, OH adjusted to O, etc.) or if the group is terminal (e.g., CH$_2$ adjusted to CH$_3$, O adjusted to OH, etc.).

In some embodiments, A, the linker, the ligase ligand, R$^1$, R$^2$, R$^3$, R$^4$, R$^5$, R$^6$, R$^7$, X and/or any other substituents of Formulas (Ia), (Ib), (IIa), and (IIb) are independently any of the substituent groups present on Compounds 1-91 of Table 8, without being limited to the specific combinations of the substituents of Compounds 1-91.

In some embodiments, provided herein are ASH1L-inhibitory compounds comprising a structure of Formula (IIIa):

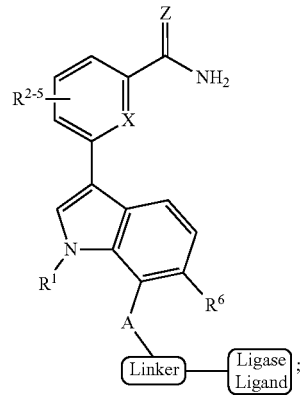

wherein X is CH or N;
wherein Z is O or S;
wherein R$^1$ is selected from H, alkyl, substituted alkyl, (e.g. halogen substituted alkyl), branched alkyl, a substituted branched alkyl (e.g. halogen substituted branched alkyl), alkoxy, amine, substituted amine, thioalkyl, ketone, amide, a substituted amide, cyano, sulfonyl, carboxy, dialkylphosphine oxide, a carbocyclic ring, s substituted carbocyclic ring, an aromatic ring, a substituted aromatic ring, a heterocyclic aromatic ring, a substituted heterocyclic aromatic ring, a substituted or non-substituted heterocyclic non-aromatic ring (e.g. piperidine, methylpiperidine, bridged piperidine, tetrahydropyran, alkylsulfonyl substituted piperidine, sulfonamide substituted piperidine), 1-((trifluoromethyl)sulfonyl)piperidine), difluorocyclohexane, monofluorocyclohexane, cyclohexane, substituted difluorocyclohexane, bicyclooctane, cycloheptane, carbocyclic or heterocyclic aromatic ring fused to another aromatic ring, a hydrogen bond donor, a hydrogen bond acceptor, and combinations thereof;
wherein R$^2$, R$^3$, R, and R$^5$ are independently selected from H, halogen (e.g., Cl, F, Br, I), CH$_3$, OH, SH, NH$_2$, CN, CF$_3$, CCl$_3$, —CH$_2$—CH$_3$, —CH$_2$—OH, —CH$_2$NH$_2$, CH$_3$SH, CH$_2$Cl, CH$_2$Br, CH$_2$F, CHF$_2$, CH$_2$CN, CH$_2$CF$_3$, CH$_2$Cl$_3$, alkyl, haloalkyl, and alcohol;

and wherein R$^6$ is selected from H, alkyl, substituted alkyl, hydroxy, alkoxy, amine, substituted amine, alkylamine, substituted alkylamine, thioalkyl, halogen, ketone, amide, substituted amide, alkylamide, substituted alkylamide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring (e.g. azetidine), carbocyclic or heterocyclic aromatic ring fused to another aromatic ring, a hydrogen bond donor, a hydrogen bond acceptor, and combinations thereof.

In some embodiments, the R$^1$ and/or R$^6$ substituents of Formula ((IIIa) are independently one of Formulas (a-q); wherein one of J, Q$^1$, or J$^1$, when present, is linked to the main scaffold;

wherein each J, J$^1$, J$^2$, J$^3$, and J$^4$, when present, are independently selected from the group consisting of: a covalent bond, H, alkyl$_{1-15}$, alkenyl$_{1-6}$, alkynyl$_{1-6}$, (CH$_2$)$_{0-6}$C(S)NH$_2$, (CH$_2$)$_{0-6}$C(O)NH$_2$, O, S, NH, (CH$_2$)$_{0-6}$C(O)NH(CH$_2$)$_{1-6}$, (CH$_2$)$_{0-6}$NHC(O)(CH$_2$)$_{1-6}$, alkylsulfonyl, sulfonamide, alkylsulfonamide, (CH$_2$)$_{0-6}$C(S)NH(CH$_2$)$_{1-6}$, (CH$_2$)$_{0-6}$O(CH$_2$)$_{1-6}$, (CH$_2$)$_{0-6}$OH, (CH$_2$)$_{0-6}$S(CH$_2$)$_{1-6}$, (CH$_2$)$_{0-6}$SH, (CH$_2$)$_{0-6}$NH(CH$_2$)$_{1-6}$, (CH$_2$)$_{0-6}$N(CH$_2$)$_{1-6}$(CH$_2$)$_{1-6}$, (CH$_2$)$_{0-6}$NH$_2$, (CH$_2$)$_{0-6}$SO$_2$(CH$_2$)$_{1-6}$, (CH$_2$)$_{0-6}$NHSO$_2$(CH$_2$)$_{1-6}$, (CH$_2$)$_{0-6}$SO$_2$NH$_2$, halogen (e.g., F, Cl, Br, or I), haloalkyl (e.g., (CH$_2$)$_{0-6}$ CH$_2$F, (CH$_2$)$_{0-3}$CHF (CH$_2$)$_{0-2}$CH$_3$, or similar with Br, Cl, or I), dihaloalkyl (e.g., (CH$_2$)$_{0-6}$ CF$_2$H, (CH$_2$)$_{0-3}$ CF$_2$(CH$_2$)$_{0-2}$CH$_3$, or similar with Br, Cl, or I), trihaloalkyl (e.g., (CH$_2$)$_{0-6}$ CF$_3$, or similar with Br, Cl, or I), alkyl with 1-3 halogens at two or more positons along its length, (CH$_2$)$_{1-4}$SP(Ph)$_2$=S, (CH$_2$)$_{0-6}$NH(CH$_2$)$_{1-5}$OH, (CH$_2$)$_{0-6}$NH(CH$_2$)$_{1-5}$NH$_2$, (CH$_2$)$_{0-6}$NH(CH$_2$)$_{1-5}$SH, (CH$_2$)$_{0-6}$O(CH$_2$)$_{1-5}$OH, (CH$_2$)$_{0-6}$O(CH$_2$)$_{1-5}$NH$_2$, (CH$_2$)$_{0-6}$O(CH$_2$)$_{1-5}$SH, (CH$_2$)$_{0-6}$S(CH$_2$)$_{1-5}$OH, (CH$_2$)$_{0-6}$S(CH$_2$)$_{1-5}$NH$_2$, (CH$_2$)$_{0-6}$S(CH$_2$)$_{1-5}$SH, (CH$_2$)$_{0-6}$O(CH$_2$)$_{1-6}$NH(CH$_2$)$_{1-5}$OH, (CH$_2$)$_{0-6}$O(CH$_2$)$_{1-6}$NH(CH$_2$)$_{1-5}$NH$_2$, (CH$_2$)$_{0-6}$O(CH$_2$)$_{1-6}$NH(CH$_2$)$_{1-5}$SH, (CH$_2$)$_{0-6}$O(CH$_2$)$_{1-6}$O(CH$_2$)$_{1-5}$OH, (CH$_2$)$_{0-6}$O(CH$_2$)$_{1-6}$O(CH$_2$)$_{1-5}$NH$_2$, (CH$_2$)$_{0-6}$O(CH$_2$)$_{1-6}$O(CH$_2$)$_{1-5}$SH, (CH$_2$)$_{0-6}$O(CH$_2$)$_{1-6}$S(CH$_2$)$_{1-5}$OH, (CH$_2$)$_{0-6}$O(CH$_2$)$_{1-6}$S(CH$_2$)$_{1-5}$NH$_2$, (CH$_2$)$_{0-6}$O(CH$_2$)$_{1-6}$S(CH$_2$)$_{1-5}$SH, (CH$_2$)$_{0-6}$S(CH$_2$)$_{1-6}$NH(CH$_2$)$_{1-6}$OH, (CH$_2$)$_{0-6}$S(CH$_2$)$_{1-6}$NH (CH$_2$)$_{1-5}$NH$_2$, (CH$_2$)$_{0-6}$S(CH$_2$)$_{1-6}$NH(CH$_2$)$_{1-5}$SH, (CH$_2$)$_{0-6}$S(CH$_2$)$_{1-6}$O(CH$_2$)$_{1-5}$OH, (CH$_2$)$_{0-6}$S(CH$_2$)$_{1-6}$O (CH$_2$)$_{1-5}$NH$_2$, (CH$_2$)$_{0-6}$S(CH$_2$)$_{1-6}$O(CH$_2$)$_{1-5}$SH, (CH$_2$)$_{0-6}$S(CH$_2$)$_{1-6}$S(CH$_2$)$_{1-5}$OH, (CH$_2$)$_{0-6}$S(CH$_2$)$_{1-6}$S (CH$_2$)$_{1-5}$NH$_2$, (CH$_2$)$_{0-6}$S(CH$_2$)$_{1-6}$S(CH$_2$)$_{1-5}$SH, (CH$_2$)$_{0-6}$NH(CH$_2$)$_{1-6}$NH(CH$_2$)$_{1-5}$OH, (CH$_2$)$_{0-6}$NH (CH$_2$)$_{1-6}$NH(CH$_2$)$_{1-5}$NH$_2$, (CH$_2$)$_{0-6}$NH(CH$_2$)$_{1-6}$NH (CH$_2$)$_{1-5}$SH, (CH$_2$)$_{0-6}$NH(CH$_2$)$_{1-6}$O(CH$_2$)$_{1-5}$OH, (CH$_2$)$_{0-6}$NH(CH$_2$)$_{1-6}$O(CH$_2$)$_{1-5}$NH$_2$, (CH$_2$)$_{0-6}$NH (CH$_2$)$_{1-6}$O(CH$_2$)$_{1-5}$SH, (CH$_2$)$_{0-4}$NH(CH$_2$)$_{1-6}$ S(CH$_2$)$_{1-5}$OH, (CH$_2$)$_{0-6}$NH(CH$_2$)$_{1-6}$S(CH$_2$)$_{1-5}$NH$_2$, (CH$_2$)$_{0-6}$NH(CH$_2$)$_{1-6}$S(CH$_2$)$_{1-5}$SH, (CH$_2$)$_{0-3}$C(O)O (CH$_2$)$_{0-3}$, (CH$_2$)$_{0-3}$C(S)O(CH$_2$)$_{0-3}$, (CH$_2$)$_{0-3}$C(O)S (CH$_2$)$_{0-3}$, (CH$_2$)$_{0-3}$C(S)S(CH$_2$)$_{0-3}$, (CH$_2$)$_{0-3}$C(O)NH (CH$_2$)$_{0-3}$, (CH$_2$)$_{0-3}$C(S)NH(CH$_2$)$_{0-3}$, (CH$_2$)$_{0-3}$NHC(O) (CH$_2$)$_{0-3}$, (CH$_2$)$_{0-3}$NHC(S)(CH$_2$)$_{0-3}$, (CH$_2$)$_{0-3}$OC(O) (CH$_2$)$_{0-3}$, (CH$_2$)$_{0-3}$OC(S)(CH$_2$)$_{0-3}$, (CH$_2$)$_{0-3}$SC(O) (CH$_2$)$_{0-3}$, (CH$_2$)$_{0-3}$SC(S)(CH$_2$)$_{0-3}$, (CH$_2$)$_{0-3}$NHC(O) NH(CH$_2$)$_{0-3}$, (CH$_2$)$_{0-3}$NHC(S)NH(CH$_2$)$_{0-3}$, (CH$_2$)$_{0-3}$OC(O)NH(CH$_2$)$_{0-3}$, (CH$_2$)$_{0-3}$OC(S)NH (CH$_2$)$_{0-3}$, (CH$_2$)$_{0-3}$SC(O)NH(CH$_2$)$_{0-3}$, (CH$_2$)$_{0-3}$SC(S) NH(CH$_2$)$_{0-3}$, (CH$_2$)$_{0-3}$NHC(O)O(CH$_2$)$_{0-3}$, (CH$_2$)$_{0-3}$NHC(S)O(CH$_2$)$_{0-3}$, (CH$_2$)$_{0-3}$OC(O)O (CH$_2$)$_{0-3}$, (CH$_2$)$_{0-3}$OC(S)O(CH$_2$)$_{0-3}$, (CH$_2$)$_{0-3}$SC(O)O (CH$_2$)$_{0-3}$, (CH$_2$)$_{0-3}$SC(S)O(CH$_2$)$_{0-3}$, (CH$_2$)$_{0-3}$NHC(O) S(CH$_2$)$_{0-3}$, (CH$_2$)$_{0-3}$NHC(S)S(CH$_2$)$_{0-3}$, (CH$_2$)$_{0-3}$OC (O)S(CH$_2$)$_{0-3}$, (CH$_2$)$_{0-3}$OC(S)S(CH$_2$)$_{0-3}$, (CH$_2$)$_{0-3}$SC (O)S(CH$_2$)$_{0-3}$, (CH$_2$)$_{0-3}$SC(S)S(CH$_2$)$_{0-3}$, (CH$_2$O)$_{1-6}$, and trimethyl methane;

wherein each Q, Q$^1$, and Q$^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), thiadiazole, aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, azetidine, oxane, thiane, piperazine, morpholine, thiomorpholine, dioxane, dithiane, trioxane, thiethane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, any suitable C$^3$-C$^7$ cycloalkyl group, and any of the ring structures depicted in Table 4;

wherein each Q, Q$^1$, and Q$^2$, when present, may display one or more additional J groups at any position on the Q ring;

wherein any alkyl or (CH$_2$)$_{x-y}$ groups above may be straight or branched;

wherein any alkyl or (CH$_2$)$_{x-y}$ groups above may additionally comprise OH, =O, NH$_2$, CN, dihaloalkyl (e.g., CF$_2$H), trihaloalkyl (e.g., CF$_3$), or halogen (e.g., F) substituents at one or more carbons; and wherein the number of hydrogens on terminal positions of the groups above may be adjusted if the group is linked to an additional group (e.g., CH$_3$ adjusted to CH$_2$, OH adjusted to O, etc.) or if the group is terminal (e.g., CH$_2$ adjusted to CH$_3$, O adjusted to OH, etc.).

In some embodiments, the linker and A of Formula (IIIa) are selected from one or the combinations listed in Table 5.

In some embodiments, provided herein are ASH1L-degrading compounds comprising a structure of Formula (IIIb):

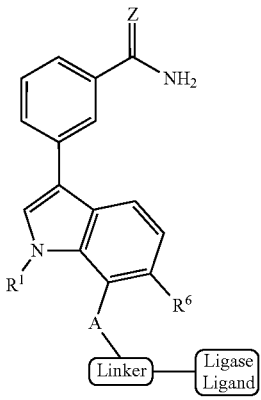

wherein Z is O or S;
wherein $R^1$ is selected from H, alkyl, substituted alkyl, (e.g. halogen substituted alkyl), branched alkyl, a substituted branched alkyl (e.g. halogen substituted branched alkyl), alkoxy, amine, substituted amine, thioalkyl, ketone, amide, a substituted amide, cyano, sulfonyl, carboxy, dialkylphosphine oxide, a carbocyclic ring, s substituted carbocyclic ring, an aromatic ring, a substituted aromatic ring, a heterocyclic aromatic ring, a substituted heterocyclic aromatic ring, a substituted or non-substituted heterocyclic non-aromatic ring (e.g. piperidine, methylpiperidine, bridged piperidine, tetrahydropyran, alkylsulfonyl substituted piperidine, sulfonamide substituted piperidine), 1-((trifluoromethyl)sulfonyl)piperidine), difluorocyclohexane, monofluorocyclohexane, cyclohexane, substituted difluorocyclohexane, bicyclooctane, cycloheptane, carbocyclic or heterocyclic aromatic ring fused to another aromatic ring, a hydrogen bond donor, a hydrogen bond acceptor, and combinations thereof;
wherein $R^6$ is selected from H, alkyl, substituted alkyl, hydroxy, alkoxy, amine, substituted amine, alkylamine, substituted alkylamine, thioalkyl, halogen, ketone, amide, substituted amide, alkylamide, substituted alkylamide, cyano, sulfonyl, carboxy, dialkylphosphine oxide, a carbocyclic ring, a substituted carbocyclic ring, an aromatic ring, a substituted aromatic ring, a heterocyclic aromatic ring, a substituted heterocyclic aromatic ring, a substituted or non-substituted heterocyclic non-aromatic ring (e.g. azetidine), carbocyclic or heterocyclic aromatic ring fused to another aromatic ring, a hydrogen bond donor, a hydrogen bond acceptor, and combinations thereof;
wherein A is a covalent bond (i.e., no atom present) or is selected from the structures listed in Table 1 (wherein n is 0, 1, 2, 3, 4, 5, 6, 7, 8, 9 or 10);
wherein the linker is selected from the structures listed in Table 2 (wherein n, when present, is 0, 1, 2, 3, 4, 5, 6, 7, 8, 9, 10, 11, 12, 13, 14, 15; wherein m, when present, is 0, 1, 2, 3, 4, 5, 6, 7, 8, 9, 10, 11, 12, 13, 14 or 15 or ranges therebetween); wherein k, when present is 0, 1, 2, 3, 4, 5, 6, 7, 8, 9 or 10; wherein l, when present is 0, 1, 2, 3, 4, 5, 6, 7, 8, 9 or 10; and wherein the ligase ligand is selected from those listed in Table 3.

In some embodiments, the $R^1$ and/or $R^6$ substituents of Formula (IIIb) are independently one of Formulas (a-q);
wherein one of J, $Q^1$, or $J^1$, when present, is linked to the main scaffold;
wherein each J, $J^1$, $J^2$, $J^3$, and $J^4$, when present, are independently selected from the group consisting of: a covalent bond, H, $alkyl_{1-15}$, $alkenyl_{1-6}$, $alkynyl_{1-6}$, $(CH_2)_{0-6}C(S)NH_2$, $(CH_2)_{0-6}C(O)NH_2$, O, S, NH, $(CH_2)_{0-6}C(O)NH(CH_2)_{1-6}$, $(CH_2)_{0-6}NHC(O)(CH_2)_{1-6}$, alkylsulfonyl, sulfonamide, alkylsulfonamide, $(CH_2)_{0-6}C(S)NH(CH_2)_{1-6}$, $(CH_2)_{0-6}O(CH_2)_{1-6}$, $(CH_2)_{0-6}OH$, $(CH_2)_{0-6}S(CH_2)_{1-6}$, $(CH_2)_{0-6}SH$, $(CH_2)_{0-6}NH(CH_2)_{1-6}$, $(CH_2)_{0-6}N(CH_2)_{1-6}(CH_2)_{1-6}$, $(CH_2)_{0-6}NH_2$, $(CH_2)_{0-6}SO_2(CH_2)_{1-6}$, $(CH_2)_{0-6}NHSO_2(CH_2)_{1-6}$, $(CH_2)_{0-6}SO_2NH_2$, halogen (e.g., F, Cl, Br, or I), haloalkyl (e.g., $(CH_2)_{0-6}$ $CH_2F$, $(CH_2)_{0-3}CHF(CH_2)_{0-2}CH_3$, or similar with Br, Cl, or I), dihaloalkyl (e.g., $(CH_2)_{0-6}$ $CF_2H$, $(CH_2)_{0-3}$ $CF_2(CH_2)_{0-2}CH_3$, or similar with Br, Cl, or I), trihaloalkyl (e.g., $(CH_2)_{0-6}CF_3$, or similar with Br, Cl, or I), alkyl with 1-3 halogens at two or more positons along its length, $(CH_2)_{1-4}SP(Ph)_2=S$, $(CH_2)_{0-6}NH(CH_2)_{1-5}OH$, $(CH_2)_{0-6}NH(CH_2)_{1-5}NH_2$, $(CH_2)_{0-6}NH(CH_2)_{1-5}SH$, $(CH_2)_{0-6}O(CH_2)_{1-5}OH$, $(CH_2)_{0-6}O(CH_2)_{1-5}NH_2$, $(CH_2)_{0-6}O(CH_2)_{1-5}SH$, $(CH_2)_{0-6}S(CH_2)_{1-5}OH$, $(CH_2)_{0-6}S(CH_2)_{1-5}NH_2$, $(CH_2)_{0-6}S(CH_2)_{1-5}SH$, $(CH_2)_{0-6}O(CH_2)_{1-6}NH(CH_2)_{1-5}OH$, $(CH_2)_{0-6}O(CH_2)_{1-6}NH(CH_2)_{1-5}NH_2$, $(CH_2)_{0-6}O(CH_2)_{1-6}NH(CH_2)_{1-5}SH$, $(CH_2)_{0-6}O(CH_2)_{1-6}O(CH_2)_{1-5}OH$, $(CH_2)_{0-6}O(CH_2)_{1-6}O(CH_2)_{1-5}NH_2$, $(CH_2)_{0-6}O(CH_2)_{1-6}O(CH_2)_{1-5}SH$, $(CH_2)_{0-6}O(CH_2)_{1-6}S(CH_2)_{1-5}OH$, $(CH_2)_{0-6}O(CH_2)_{1-6}S(CH_2)_{1-5}NH_2$, $(CH_2)_{0-6}O(CH_2)_{1-6}S(CH_2)_{1-5}SH$, $(CH_2)_{0-6}S(CH_2)_{1-6}NH(CH_2)_{1-5}OH$, $(CH_2)_{0-6}S(CH_2)_{1-6}NH(CH_2)_{1-6}NH(CH_2)_{1-5}SH$, $(CH_2)_{0-6}S(CH_2)_{1-6}O(CH_2)_{1-5}OH$, $(CH_2)_{0-6}S(CH_2)_{1-6}O(CH_2)_{1-5}NH_2$, $(CH_2)_{0-6}S(CH_2)_{1-6}O(CH_2)_{1-5}SH$, $(CH_2)_{0-6}S(CH_2)_{1-6}S(CH_2)_{1-5}OH$, $(CH_2)_{0-6}S(CH_2)_{1-6}S(CH_2)_{1-5}NH_2$, $(CH_2)_{0-6}S(CH_2)_{1-6}S(CH_2)_{1-5}SH$, $(CH_2)_{0-6}NH(CH_2)_{1-6}NH(CH_2)_{1-5}OH$, $(CH_2)_{0-4}NH(CH_2)_{1-6}NH(CH_2)_{1-5}NH_2$, $(CH_2)_{0-6}NH(CH_2)_{1-6}NH(CH_2)_{1-5}SH$, $(CH_2)_{0-6}NH(CH_2)_{1-6}O(CH_2)_{1-5}OH$, $(CH_2)_{0-6}NH(CH_2)_{1-6}O(CH_2)_{1-5}NH_2$, $(CH_2)_{0-6}NH(CH_2)_{1-6}O(CH_2)_{1-5}SH$, $(CH_2)_{0-4}NH(CH_2)_{1-6}S(CH_2)_{1-5}OH$, $(CH_2)_{0-6}NH(CH_2)_{1-6}S(CH_2)_{1-5}NH_2$, $(CH_2)_{0-6}NH(CH_2)_{1-6}S(CH_2)_{1-5}SH$, $(CH_2)_{0-3}C(O)O(CH_2)_{0-3}$, $(CH_2)_{0-3}C(O)(CH_2)_{0-3}$, $(CH_2)_{0-3}C(O)S(CH_2)_{0-3}$, $(CH_2)_{0-3}C(S)S(CH_2)_{0-3}$, $(CH_2)_{0-3}C(O)NH(CH_2)_{0-3}$, $(CH_2)_{0-3}C(S)NH(CH_2)_{0-3}$, $(CH_2)_{0-3}NHC(O)(CH_2)_{0-3}$, $(CH_2)_{0-3}NHC(S)(CH_2)_{0-3}$, $(CH_2)_{0-3}OC(O)(CH_2)_{0-3}$, $(CH_2)_{0-3}OC(S)(CH_2)_{0-3}$, $(CH_2)_{0-3}SC(O)(CH_2)_{0-3}$, $(CH_2)_{0-3}SC(S)(CH_2)_{0-3}$, $(CH_2)_{0-3}NHC(O)NH(CH_2)_{0-3}$, $(CH_2)_{0-3}NHC(S)NH(CH_2)_{0-3}$, $(CH_2)_{0-3}OC(O)NH(CH_2)_{0-3}$, $(CH_2)_{0-3}OC(S)NH(CH_2)_{0-3}$, $(CH_2)_{0-3}SC(O)NH(CH_2)_{0-3}$, $(CH_2)_{0-3}SC(S)NH(CH_2)_{0-3}$, $(CH_2)_{0-3}NHC(O)O(CH_2)_{0-3}$, $(CH_2)_{0-3}NHC(S)O(CH_2)_{0-3}$, $(CH_2)_{0-3}OC(O)O(CH_2)_{0-3}$, $(CH_2)_{0-3}OC(S)O(CH_2)_{0-3}$, $(CH_2)_{0-3}SC(O)O(CH_2)_{0-3}$, $(CH_2)_{0-3}SC(S)O(CH_2)_{0-3}$, $(CH_2)_{0-3}NHC(O)S(CH_2)_{0-3}$, $(CH_2)_{0-3}NHC(S)S(CH_2)_{0-3}$, $(CH_2)_{0-3}OC(O)S(CH_2)_{0-3}$, $(CH_2)_{0-3}OC(S)S(CH_2)_{0-3}$, $(CH_2)_{0-3}SC(O)S(CH_2)_{0-3}$, $(CH_2)_{0-3}SC(S)S(CH_2)_{0-3}$, $(CH_2O)_{1-6}$, and trimethyl methane;
wherein each Q, $Q^1$, and $Q^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), thiadiazole, aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, azetidine, oxane, thiane, piperazine, morpholine, thiomorpholine, dioxane, dithiane, trioxane, thiethane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, any suitable $C^3$-$C^7$ cycloalkyl group, and any of the ring structures depicted in Table 4;

wherein each Q, $Q^1$, and $Q^2$, when present, may display one or more additional J groups at any position on the Q ring;

wherein any alkyl or $(CH_2)_{x-y}$ groups above may be straight or branched;

wherein any alkyl or $(CH_2)_{x-y}$ groups above may additionally comprise OH, =O, $NH_2$, CN, dihaloalkyl (e.g., $CF_2H$), trihaloalkyl (e.g., $CF_3$), or halogen (e.g., F) substituents at one or more carbons; and wherein the number of hydrogens on terminal positions of the groups above may be adjusted if the group is linked to an additional group (e.g., $CH_3$ adjusted to $CH_2$, OH adjusted to O, etc.) or if the group is terminal (e.g., $CH_2$ adjusted to $CH_3$, O adjusted to OH, etc.).

In some embodiments, the linker and A of Formula (IIb) are selected from one or the combinations listed in Table 5.

TABLE 8

Exemplary compounds

| Number | Structure | $M_w$ calc. (Da) | $[MH]^+$ found (Da) |
|---|---|---|---|
| 1 | 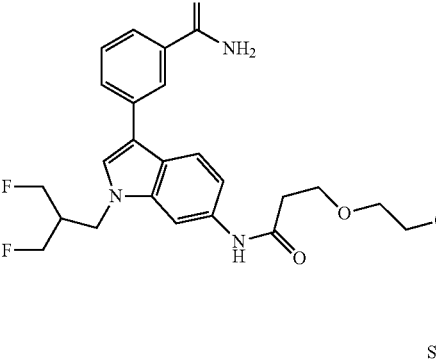 | 819.27 | 820.2812 |
| 2 | 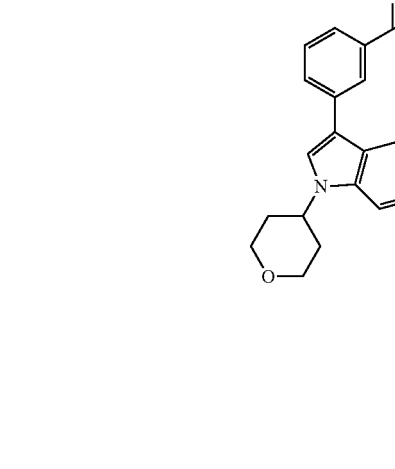 | 825.3044 | 848.2927 (M + Na$^+$) |

TABLE 8-continued
Exemplary compounds
| Number | Structure | $M_w$ calc. (Da) | $[MH]^+$ found (Da) |
|---|---|---|---|
| 3 | 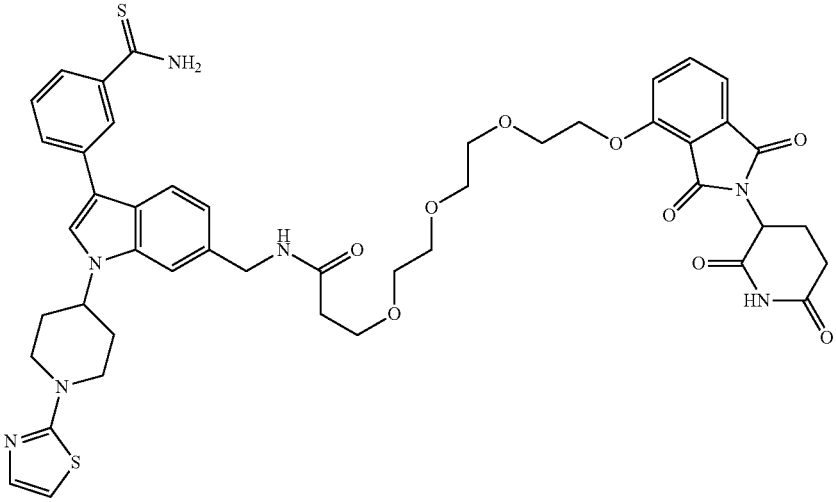 [SMILES: NC(=S)c1cccc(-c2cn(C3CCN(c4nccs4)CC3)c3cc(CNC(=O)CCOCCOCCOCCOc4cccc5c4C(=O)N(C4CCC(=O)NC4=O)C5=O)ccc23)c1] | 908.0580 | 908.3105 |
| 4 | 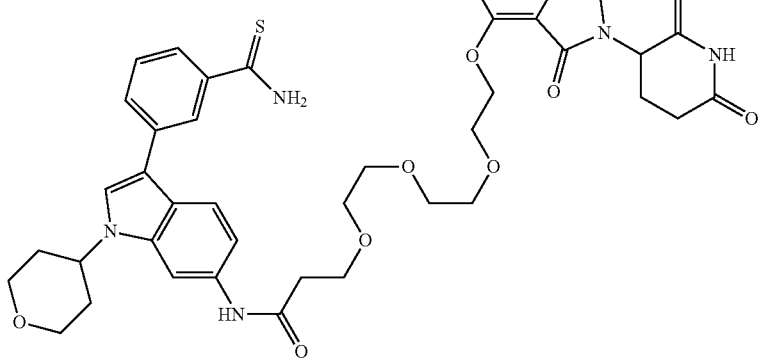 | 811.9070 | 848.2927 (M + Na$^+$) |

TABLE 8-continued

Exemplary compounds

| Number | Structure | $M_w$ calc. (Da) | [MH]+ found (Da) |
|---|---|---|---|
| 5 | 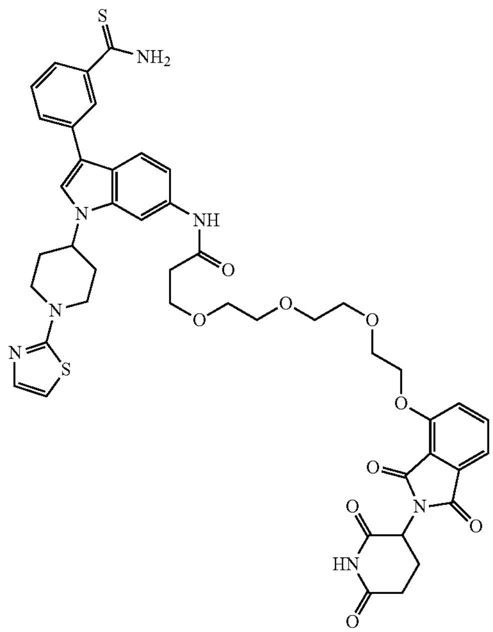 [SMILES: NC(=S)c1cccc(-c2cn(C3CCN(c4nccs4)CC3)c3cc(NC(=O)CCOCCOCCOCCOc4cccc5c4C(=O)N(C4CCC(=O)NC4=O)C5=O)ccc23)c1] | | 894.0310 |
| 6 | 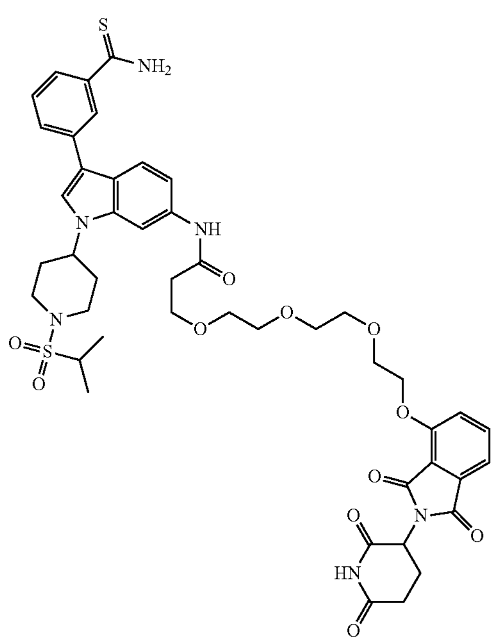 [SMILES: CC(C)S(=O)(=O)N1CCC(n2cc(-c3cccc(C(N)=S)c3)c3ccc(NC(=O)CCOCCOCCOCCOc4cccc5c4C(=O)N(C4CCC(=O)NC4=O)C5=O)cc32)CC1] | | 917.0620 |

TABLE 8-continued

Exemplary compounds

| Number | Structure | $M_w$ calc. (Da) | $[MH]^+$ found (Da) |
|---|---|---|---|
| 7 | 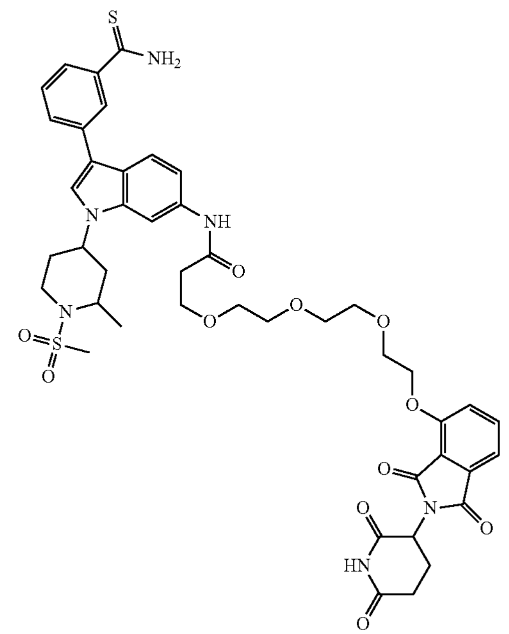 [SMILES: CC1CC(n2cc(-c3cccc(C(N)=S)c3)c3ccc(NC(=O)CCOCCOCCOCCOc4cccc5c4C(=O)N(C4CCC(=O)NC4=O)C5=O)cc32)CCN1S(C)(=O)=O] | | 903.0350 |
| 8 | 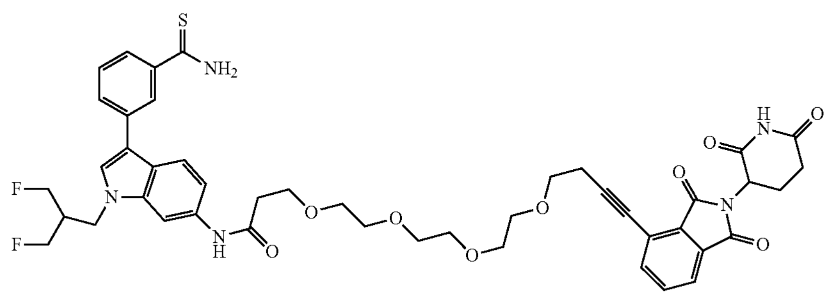 [SMILES: NC(=S)c1cccc(-c2cn(CC(CF)CF)c3cc(NC(=O)CCOCCOCCOCCOCCC#Cc4cccc5c4C(=O)N(C4CCC(=O)NC4=O)C5=O)ccc23)c1] | | 871.31 |
| 9 | 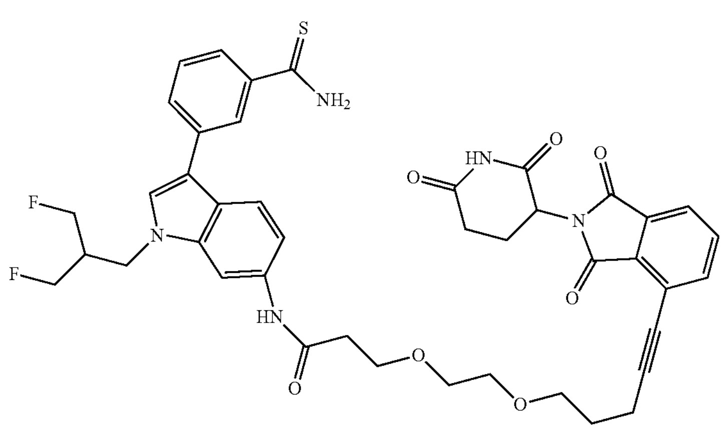 [SMILES: NC(=S)c1cccc(-c2cn(CC(CF)CF)c3cc(NC(=O)CCOCCOCCCC#Cc4cccc5c4C(=O)N(C4CCC(=O)NC4=O)C5=O)ccc23)c1] | | 797.27 |

TABLE 8-continued
Exemplary compounds
| Number | Structure | $M_w$ calc. (Da) | $[MH]^+$ found (Da) |
|---|---|---|---|
| 10 | 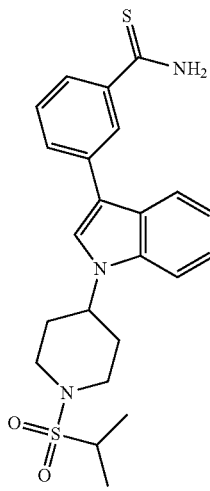 | | 942.1160 |
| 11 | 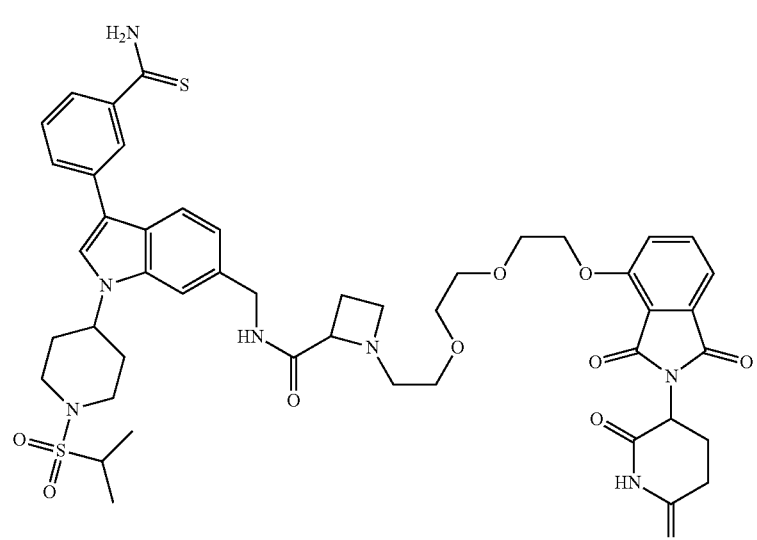 | | 942.1160 |

TABLE 8-continued
Exemplary compounds
| Number | Structure | $M_w$ calc. (Da) | $[MH]^+$ found (Da) |
|---|---|---|---|
| 12 | 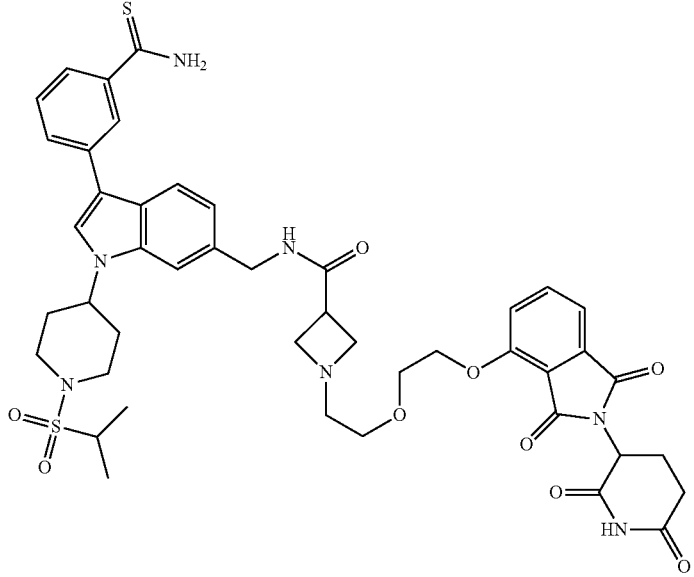 [SMILES: CC(C)S(=O)(=O)N1CCC(n2cc(-c3cccc(C(N)=S)c3)c3ccc(CNC(=O)C4CN(CCOCCOc5cccc6c5C(=O)N(C5CCC(=O)NC5=O)C6=O)C4)cc32)CC1] | | 898.0630 |
| 13 | 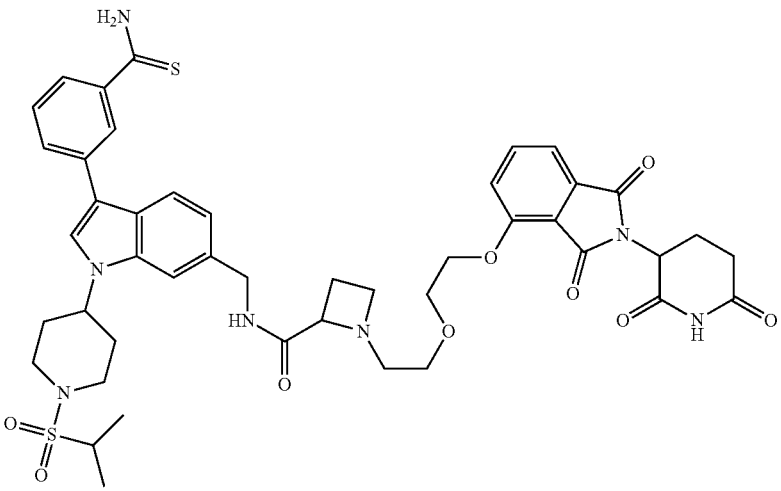 [SMILES: CC(C)S(=O)(=O)N1CCC(n2cc(-c3cccc(C(N)=S)c3)c3ccc(CNC(=O)C4CCN4CCOCCOc4cccc5c4C(=O)N(C4CCC(=O)NC4=O)C5=O)cc32)CC1] | | 898.0630 |

TABLE 8-continued

Exemplary compounds

| Number | Structure | M$_w$ calc. (Da) | [MH]$^+$ found (Da) |
|---|---|---|---|
| 14 | 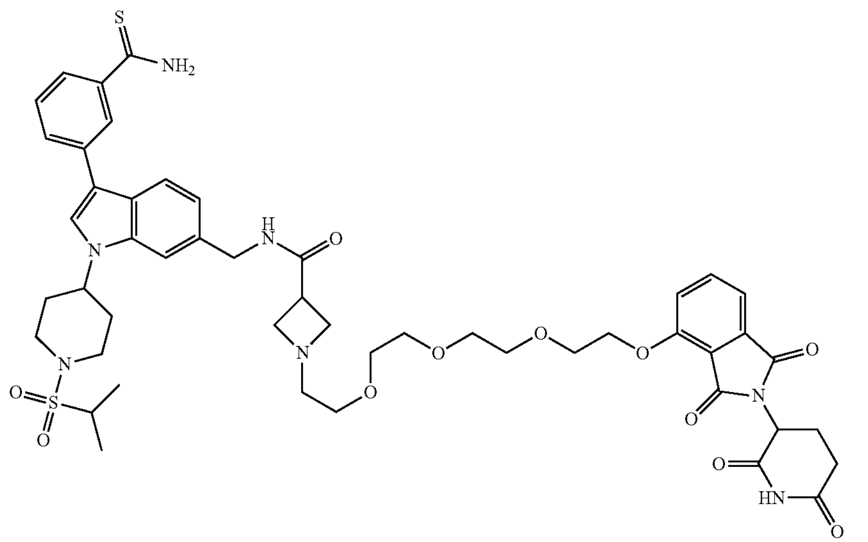 [SMILES: CC(C)S(=O)(=O)N1CCC(n2cc(-c3cccc(C(N)=S)c3)c3ccc(CNC(=O)C4CN(CCOCCOCCOCCOc5cccc6c5C(=O)N(C5CCC(=O)NC5=O)C6=O)C4)cc32)CC1] | | 986.1690 |
| 15 | 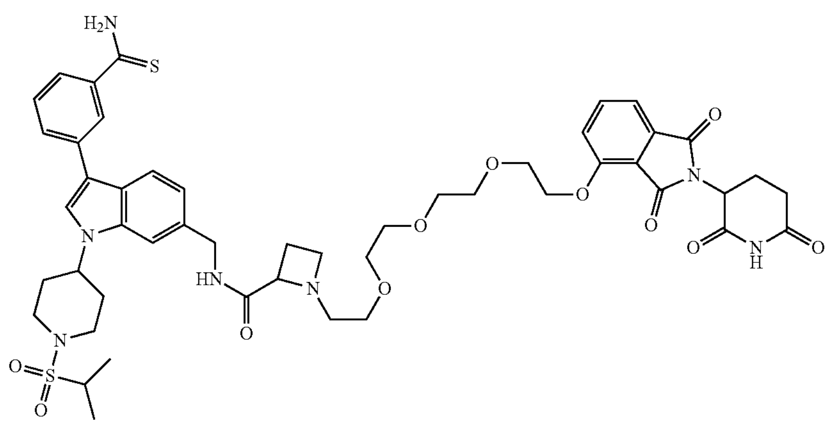 [SMILES: CC(C)S(=O)(=O)N1CCC(n2cc(-c3cccc(C(N)=S)c3)c3ccc(CNC(=O)C4CCN4CCOCCOCCOCCOc4cccc5c4C(=O)N(C4CCC(=O)NC4=O)C5=O)cc32)CC1] | | 986.1690 |
| 16 | 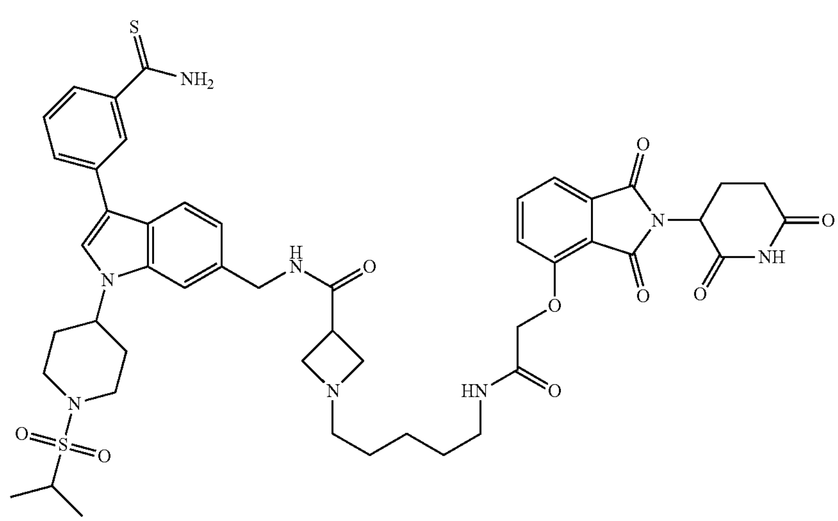 [SMILES: CC(C)S(=O)(=O)N1CCC(n2cc(-c3cccc(C(N)=S)c3)c3ccc(CNC(=O)C4CN(CCCCCNC(=O)COc5cccc6c5C(=O)N(C5CCC(=O)NC5=O)C6=O)C4)cc32)CC1] | | 953.1430 |

TABLE 8-continued

Exemplary compounds

| Number | Structure | $M_w$ calc. (Da) | $[MH]^+$ found (Da) |
|---|---|---|---|
| 17 | 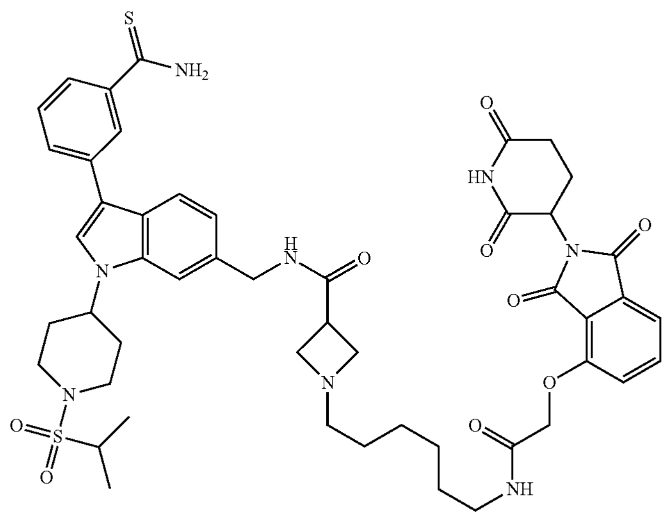 [SMILES: CC(C)S(=O)(=O)N1CCC(n2cc(-c3cccc(C(N)=S)c3)c3ccc(CNC(=O)C4CN(CCCCCCNC(=O)COc5cccc6c5C(=O)N(C5CCC(=O)NC5=O)C6=O)C4)cc32)CC1] | | 967.1700 |
| 18 | 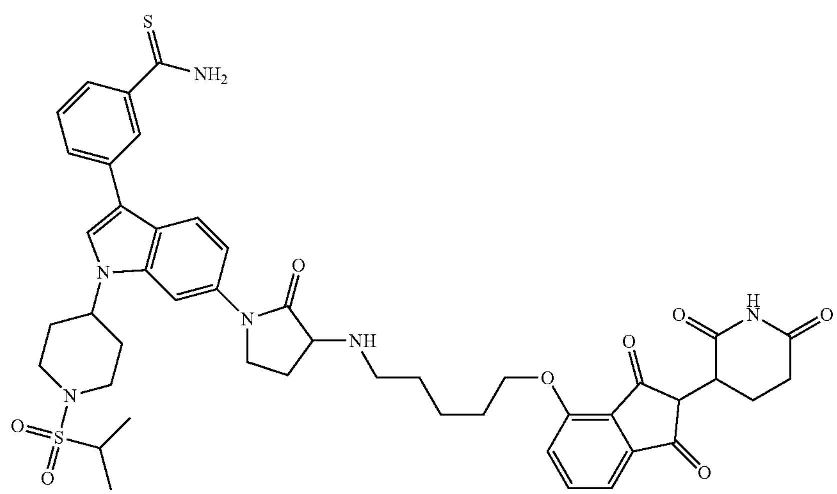 [SMILES: CC(C)S(=O)(=O)N1CCC(n2cc(-c3cccc(C(N)=S)c3)c3ccc(N4CCC(NCCCCCOc5cccc6c5C(=O)C(C5CCC(=O)NC5=O)C6=O)C4=O)cc32)CC1] | | 882.0640 |
| 19 | 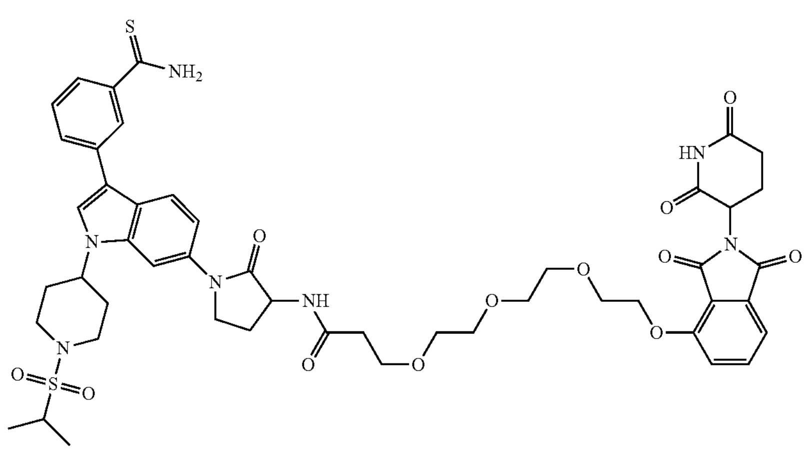 [SMILES: CC(C)S(=O)(=O)N1CCC(n2cc(-c3cccc(C(N)=S)c3)c3ccc(N4CCC(NC(=O)CCOCCOCCOCCOc5cccc6c5C(=O)N(C5CCC(=O)NC5=O)C6=O)C4=O)cc32)CC1] | | 1000.1520 |

TABLE 8-continued
Exemplary compounds
| Number | Structure | $M_w$ calc. (Da) | $[MH]^+$ found (Da) |
|---|---|---|---|
| 20 | 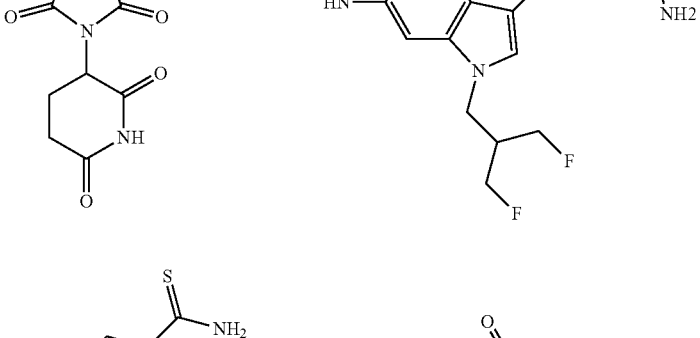 | 695.201 | |
| 21 | 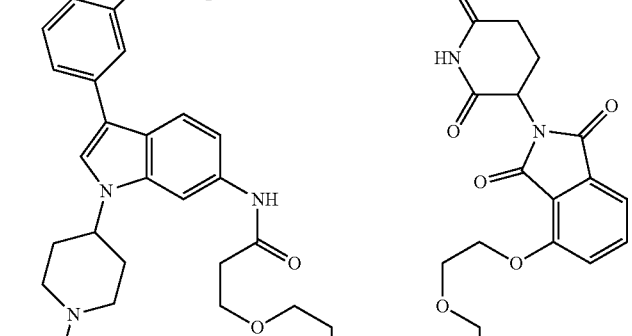 | 987.0322 | 987.2874 |
| 22 | 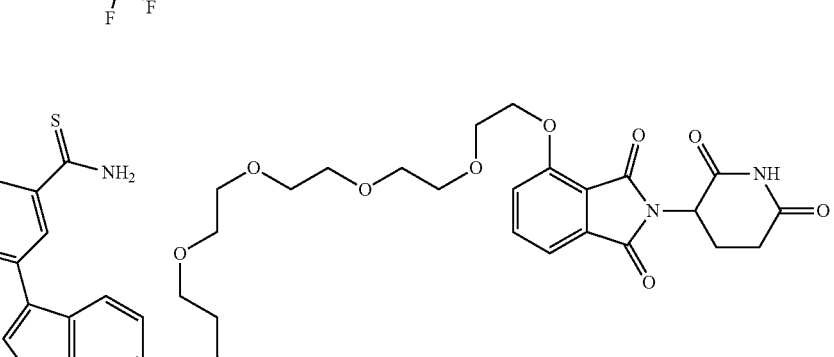 | 933.0610 | 933.3162 |

TABLE 8-continued

Exemplary compounds

| Number | Structure | M_w calc. (Da) | [MH]+ found (Da) |
|---|---|---|---|
| 23 | 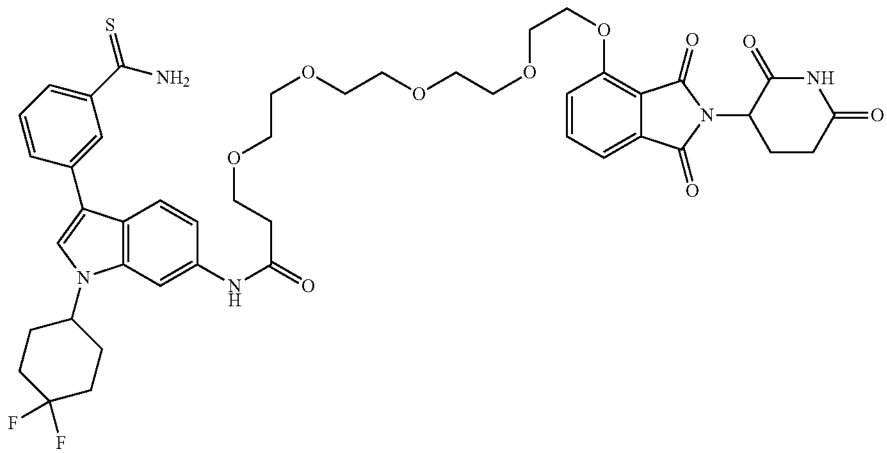 [SMILES: NC(=S)c1cccc(-c2cn(C3CCC(F)(F)CC3)c3cc(NC(=O)CCOCCOCCOCCOCCOc4cccc5c4C(=O)N(C4CCC(=O)NC4=O)C5=O)ccc23)c1] | 889.9688 | 890.3239 |
| 24 | 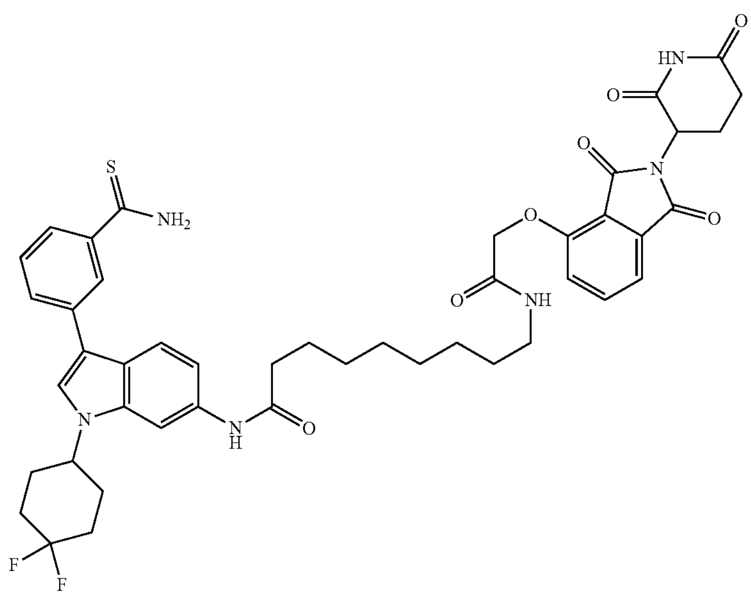 [SMILES: NC(=S)c1cccc(-c2cn(C3CCC(F)(F)CC3)c3cc(NC(=O)CCCCCCCCNC(=O)COc4cccc5c4C(=O)N(C4CCC(=O)NC4=O)C5=O)ccc23)c1] | 854.9708 | 855.3345 |
| 25 | 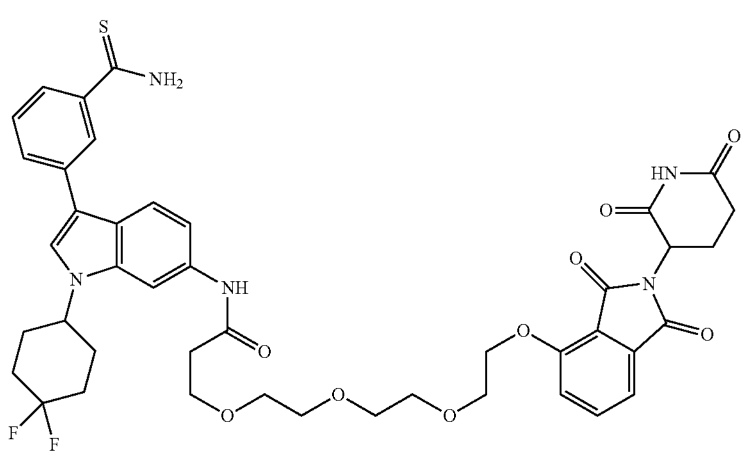 [SMILES: NC(=S)c1cccc(-c2cn(C3CCC(F)(F)CC3)c3cc(NC(=O)CCOCCOCCOCCOc4cccc5c4C(=O)N(C4CCC(=O)NC4=O)C5=O)ccc23)c1] | 845.9158 | 846.2975 |

TABLE 8-continued

Exemplary compounds

| Number | Structure | $M_w$ calc. (Da) | $[MH]^+$ found (Da) |
|---|---|---|---|
| 26 | 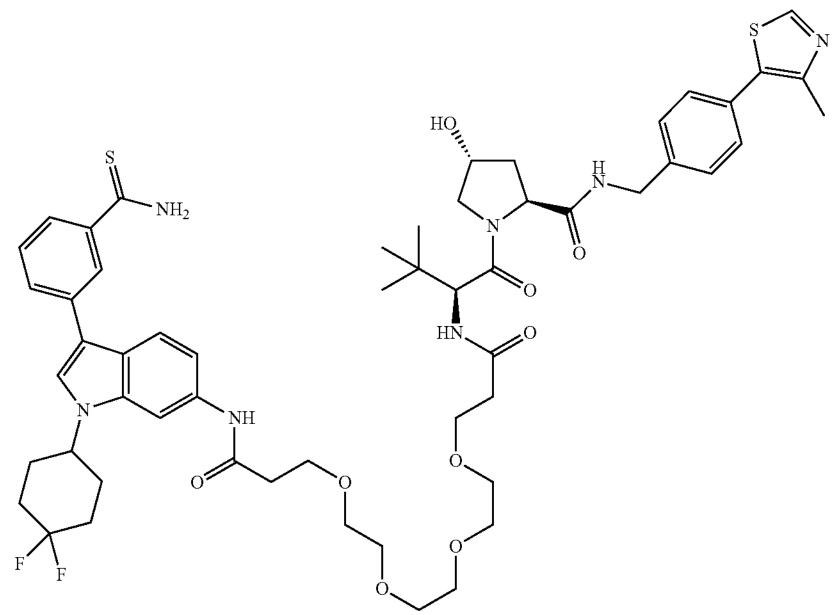 [SMILES: Cc1ncsc1-c1ccc(CNC(=O)[C@@H]2C[C@@H](O)CN2C(=O)[C@@H](NC(=O)CCOCCOCCOCCOCCC(=O)Nc2ccc3c(-c4cccc(C(N)=S)c4)cn(C4CCC(F)(F)CC4)c3c2)C(C)(C)C)cc1] | 1074.3138 | 1074.4636 |
| 27 | 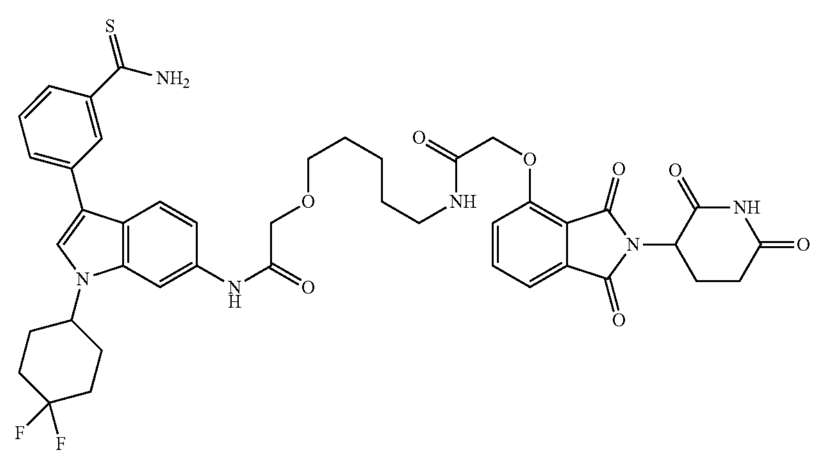 [SMILES: NC(=S)c1cccc(-c2cn(C3CCC(F)(F)CC3)c3cc(NC(=O)COCCCCCNC(=O)COc4cccc5c4C(=O)N(C4CCC(=O)NC4=O)C5=O)ccc23)c1] | 842.9158 | 843.2983 |

TABLE 8-continued

Exemplary compounds

| Number | Structure | $M_w$ calc. (Da) | $[MH]^+$ found (Da) |
|---|---|---|---|
| 28 | 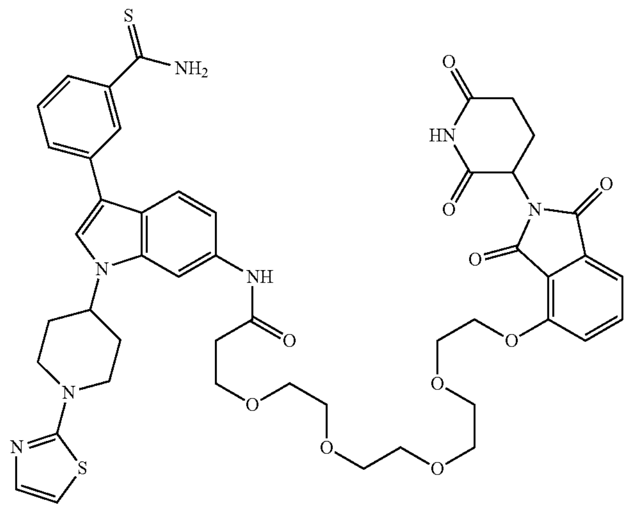 [SMILES: NC(=S)c1cccc(-c2cn(C3CCN(c4nccs4)CC3)c3cc(NC(=O)CCOCCOCCOCCOCCOc4cccc5c4C(=O)N(C4CCC(=O)NC4=O)C5=O)ccc23)c1] | 938.0840 | 938.3212 |
| 29 | 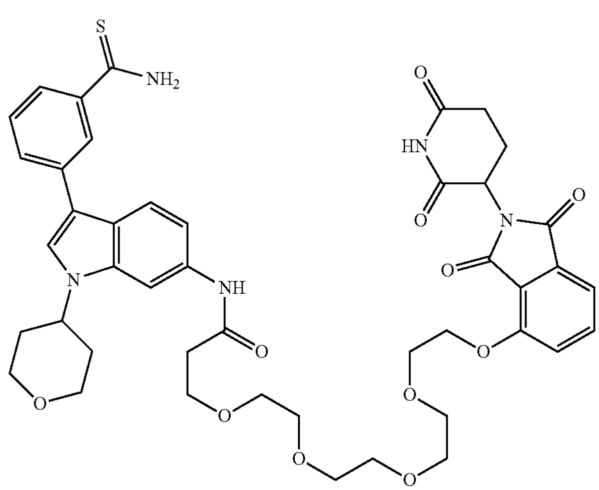 [SMILES: NC(=S)c1cccc(-c2cn(C3CCOCC3)c3cc(NC(=O)CCOCCOCCOCCOCCOc4cccc5c4C(=O)N(C4CCC(=O)NC4=O)C5=O)ccc23)c1] | 855.9600 | 878.3045 (M + Na$^+$) |

TABLE 8-continued

Exemplary compounds

| Number | Structure | $M_w$ calc. (Da) | $[MH]^+$ found (Da) |
|---|---|---|---|
| 30 | 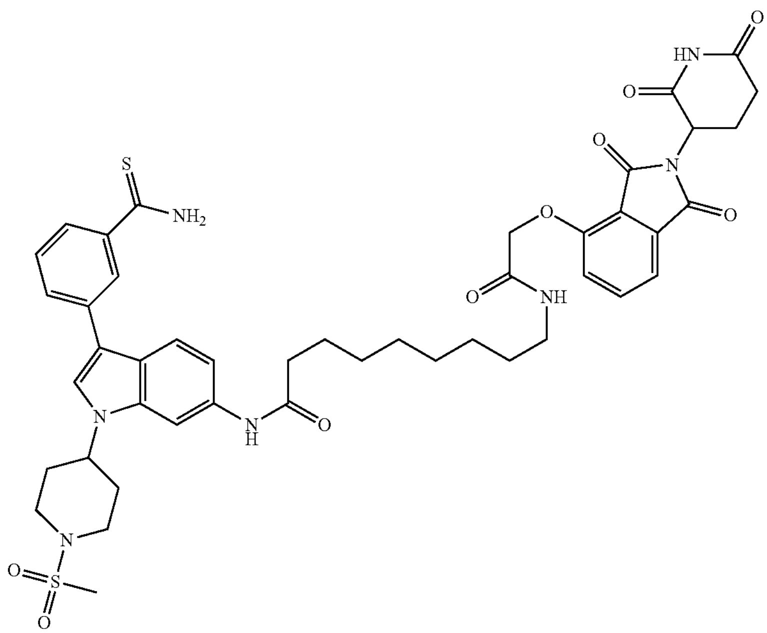 [SMILES: CS(=O)(=O)N1CCC(n2cc(-c3cccc(C(N)=S)c3)c3ccc(NC(=O)CCCCCCCCNC(=O)COc4cccc5c4C(=O)N(C4CCC(=O)NC4=O)C5=O)cc32)CC1] | 898.0630 | 898.3261 |
| 31 | 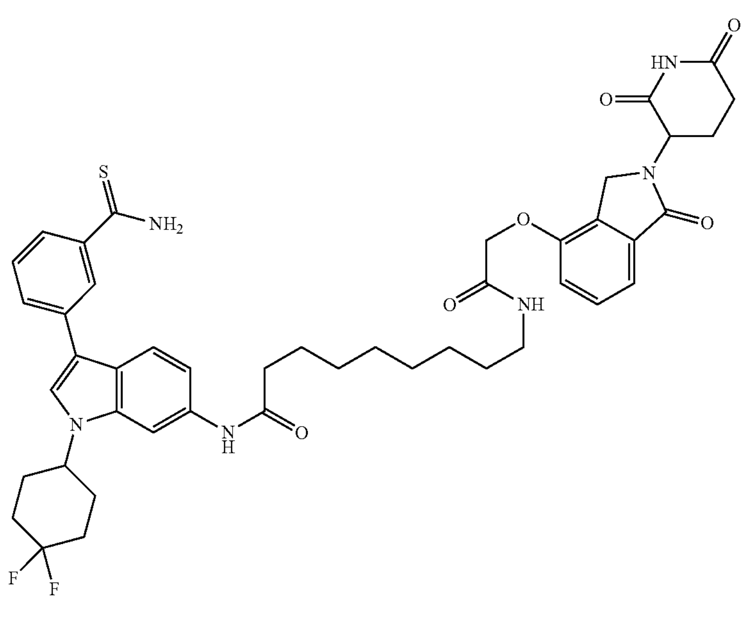 | 840.9878 | 841.3554 |

TABLE 8-continued

Exemplary compounds

| Number | Structure | M_w calc. (Da) | [MH]+ found (Da) |
|---|---|---|---|
| 32 | 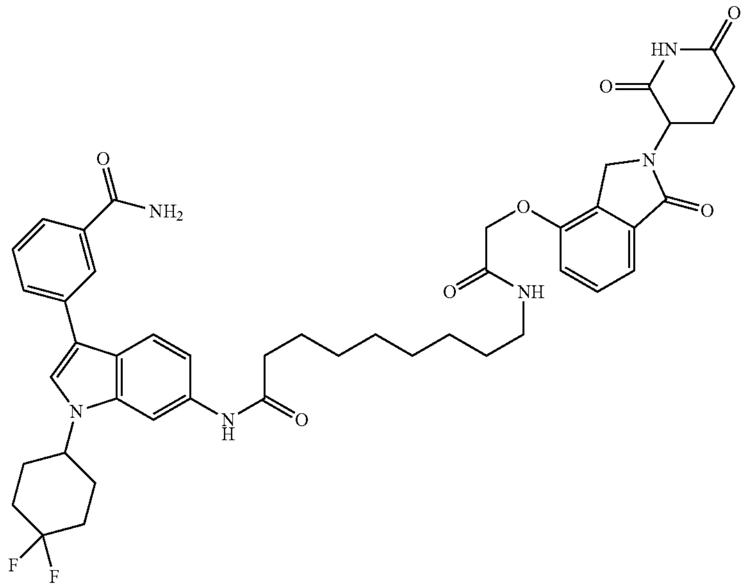 [SMILES: NC(=O)c1cccc(-c2cn(C3CCC(F)(F)CC3)c3cc(NC(=O)CCCCCCCCNC(=O)COc4cccc5c4CN(C4CCC(=O)NC4=O)C5=O)ccc23)c1] | | 824.9268 |
| 33 | 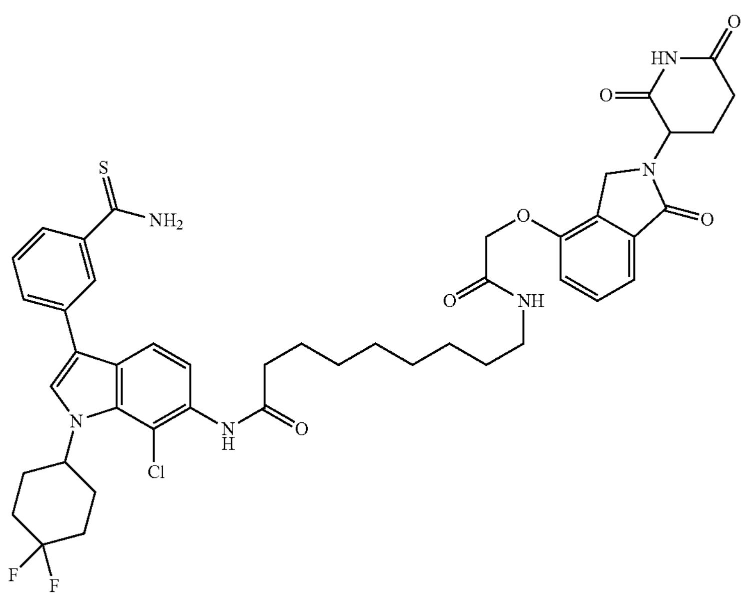 [SMILES: NC(=S)c1cccc(-c2cn(C3CCC(F)(F)CC3)c3c(Cl)c(NC(=O)CCCCCCCCNC(=O)COc4cccc5c4CN(C4CCC(=O)NC4=O)C5=O)ccc23)c1] | | 875.4298 |

TABLE 8-continued

Exemplary compounds

| Number | Structure | $M_w$ calc. (Da) | [MH]+ found (Da) |
|---|---|---|---|
| 34 | 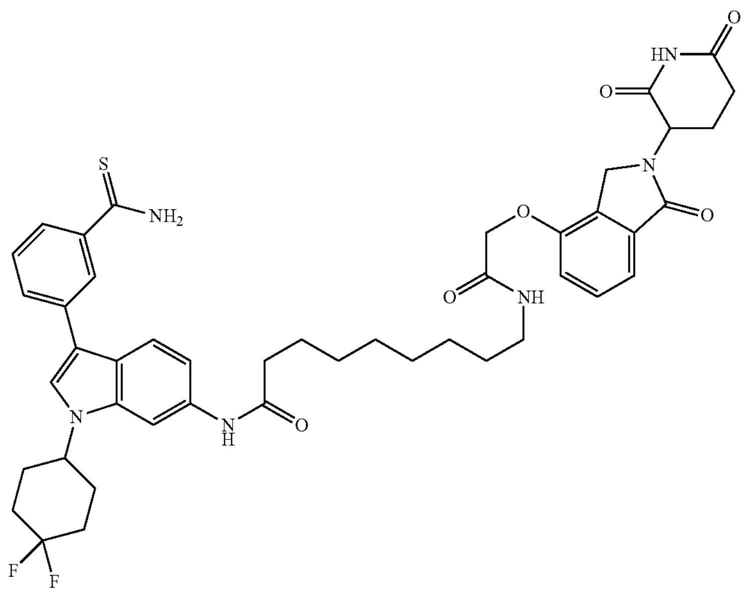 | 839.0158 | 839.3765 |
| 35 | 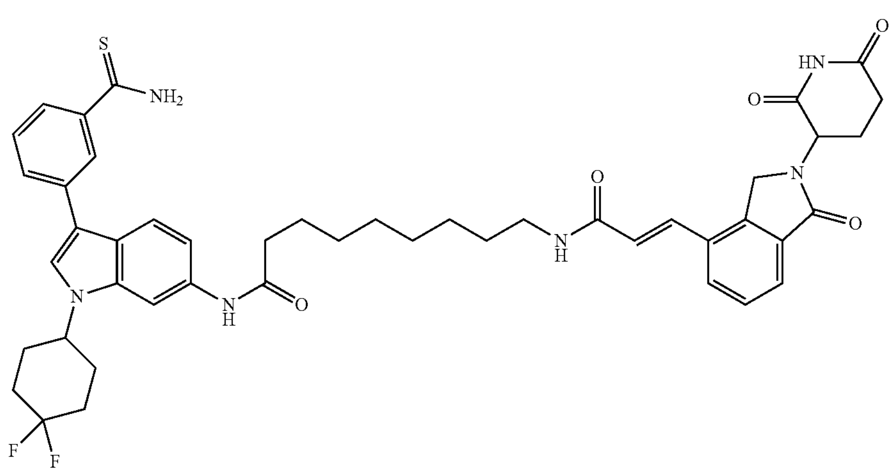 [SMILES: NC(=S)c1cccc(-c2cn(C3CCC(F)(F)CC3)c3cc(NC(=O)CCCCCCCCNC(=O)/C=C/c4cccc5c4CN(C4CCC(=O)NC4=O)C5=O)ccc23)c1] | 836.9998 | 837.3642 |

TABLE 8-continued

Exemplary compounds

| Number | Structure | $M_w$ calc. (Da) | $[MH]^+$ found (Da) |
|---|---|---|---|
| 36 | 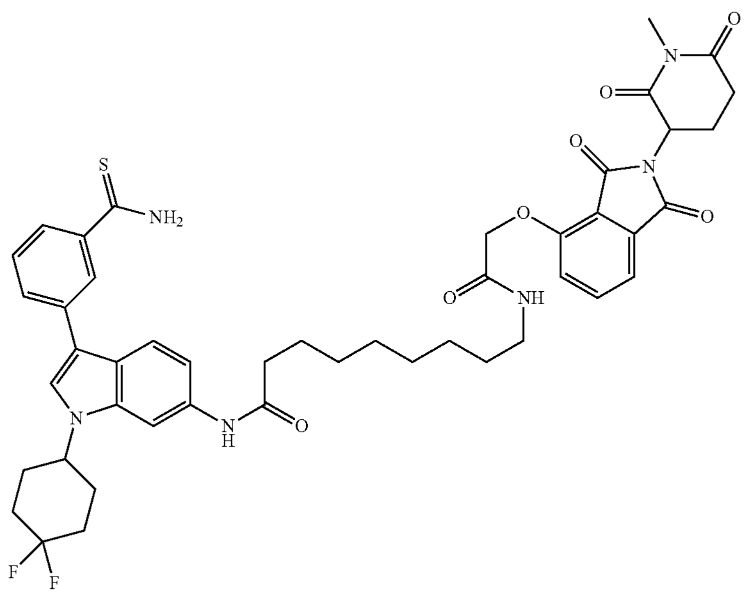 [SMILES: CN1C(=O)CCC(N2C(=O)c3cccc(OCC(=O)NCCCCCCCCC(=O)Nc4ccc5c(-c6cccc(C(N)=S)c6)cn(C6CCC(F)(F)CC6)c5c4)c3C2=O)C1=O] | 868.9978 | 868.3435 |
| 37 | 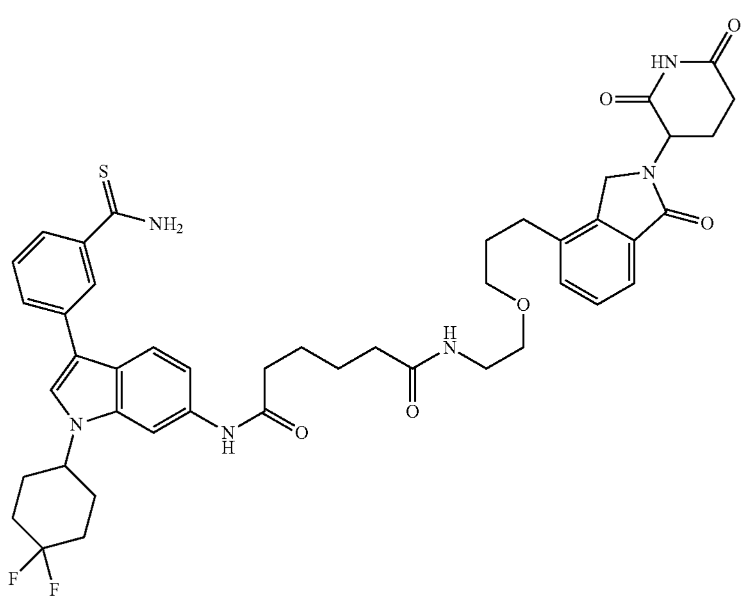 [SMILES: NC(=S)c1cccc(-c2cn(C3CCC(F)(F)CC3)c3cc(NC(=O)CCCCC(=O)NCCOCCCc4cccc5c4CN(C4CCC(=O)NC4=O)C5=O)ccc23)c1] | 840.9878 | |

TABLE 8-continued

| Number | Structure | M$_w$ calc. (Da) | [MH]$^+$ found (Da) |
|---|---|---|---|
| 38 | 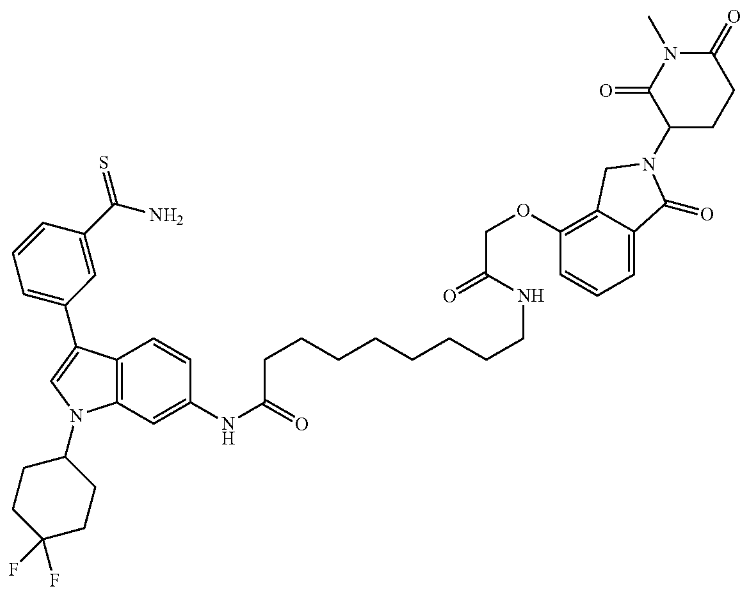 [SMILES: CN1C(=O)CCC(N2Cc3c(OCC(=O)NCCCCCCCCC(=O)Nc4ccc5c(-c6cccc(C(N)=S)c6)cn(C6CCC(F)(F)CC6)c5c4)cccc3C2=O)C1=O] | | 855.0148 |
| 39 | 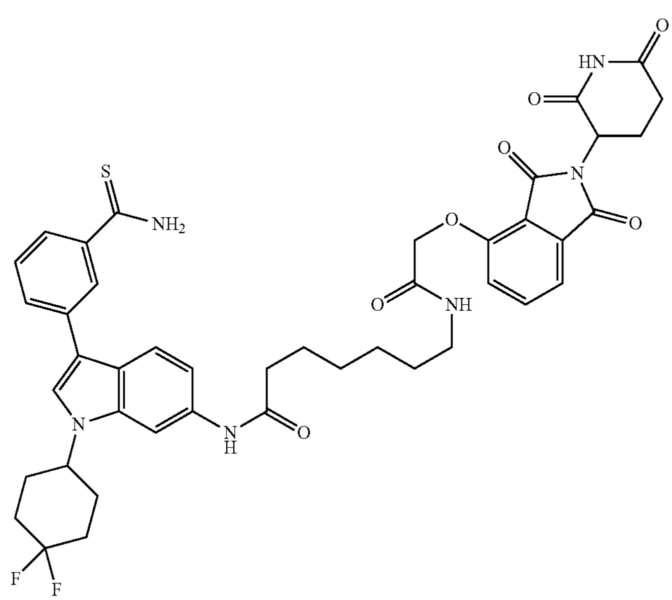 [SMILES: NC(=S)c1cccc(-c2cn(C3CCC(F)(F)CC3)c3cc(NC(=O)CCCCCCNC(=O)COc4cccc5c4C(=O)N(C4CCC(=O)NC4=O)C5=O)ccc23)c1] | | 826.9168 |

TABLE 8-continued

Exemplary compounds

| Number | Structure | $M_w$ calc. (Da) | $[MH]^+$ found (Da) |
|---|---|---|---|
| 40 | 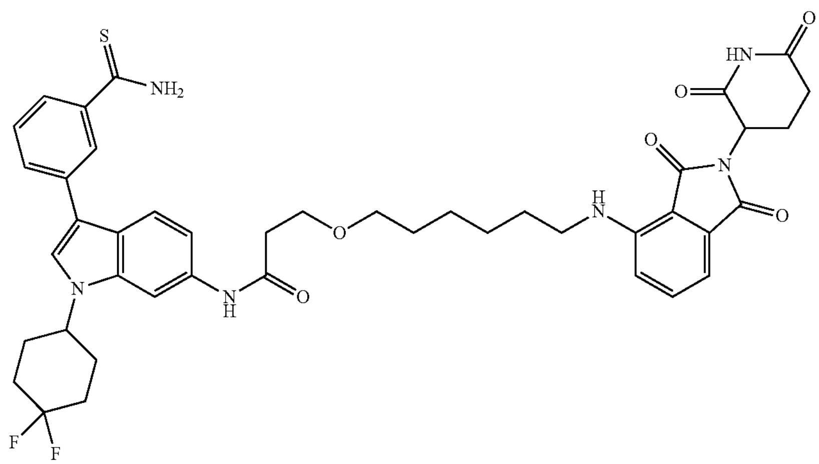 [SMILES: NC(=S)c1cccc(-c2cn(C3CCC(F)(F)CC3)c3cc(NC(=O)CCOCCCCCCNc4cccc5c4C(=O)N(C4CCC(=O)NC4=O)C5=O)ccc23)c1] | 812.9338 | |
| 41 | 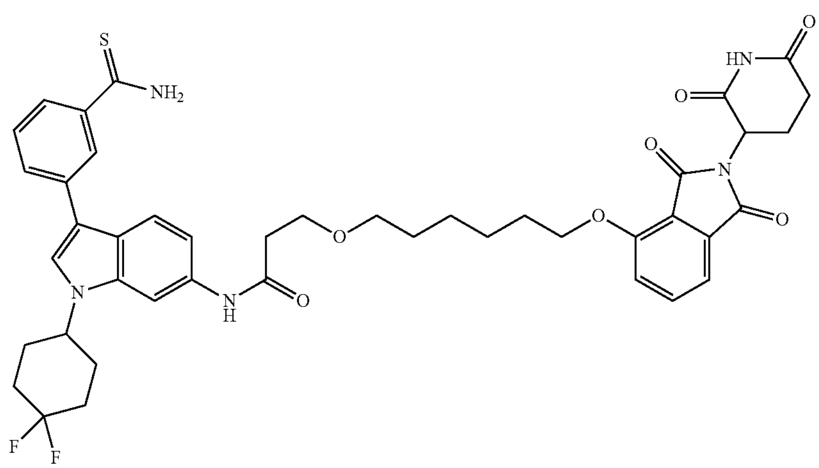 [SMILES: NC(=S)c1cccc(-c2cn(C3CCC(F)(F)CC3)c3cc(NC(=O)CCOCCCCCCOc4cccc5c4C(=O)N(C4CCC(=O)NC4=O)C5=O)ccc23)c1] | 813.9178 | 814.3079 |
| 42 | 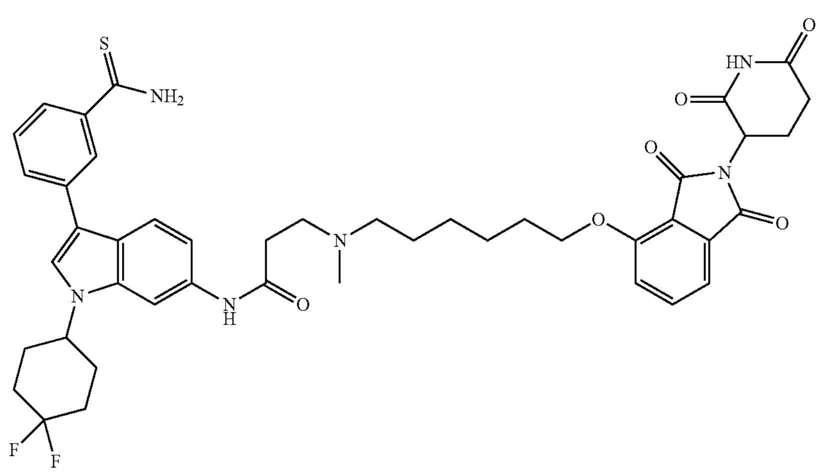 [SMILES: CN(CCCCCCOc1cccc2c1C(=O)N(C1CCC(=O)NC1=O)C2=O)CCC(=O)Nc1ccc2c(-c3cccc(C(N)=S)c3)cn(C3CCC(F)(F)CC3)c2c1] | 826.9608 | |

TABLE 8-continued

Exemplary compounds

| Number | Structure | $M_w$ calc. (Da) | [MH]+ found (Da) |
|---|---|---|---|
| 43 | 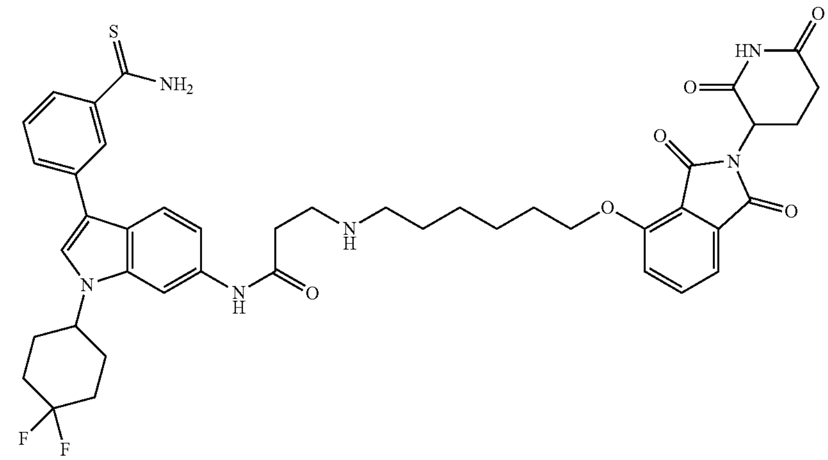 [SMILES: NC(=S)c1cccc(-c2cn(C3CCC(F)(F)CC3)c3cc(NC(=O)CCNCCCCCCOc4cccc5c4C(=O)N(C4CCC(=O)NC4=O)C5=O)ccc23)c1] | | 812.9338 |
| 44 | 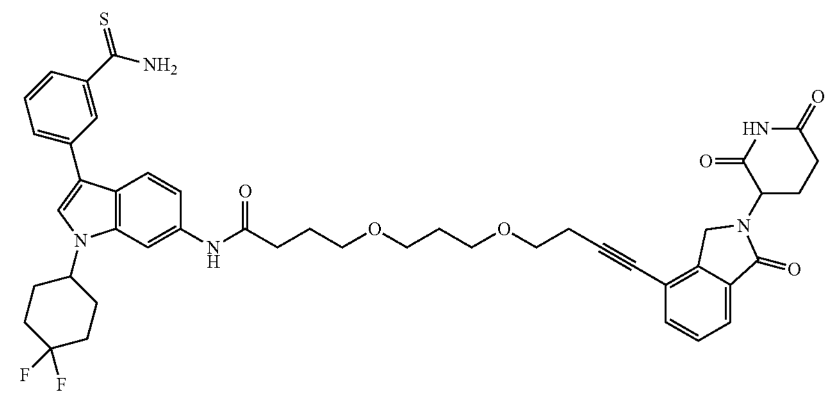 [SMILES: NC(=S)c1cccc(-c2cn(C3CCC(F)(F)CC3)c3cc(NC(=O)CCCOCCCOCCC#Cc4cccc5c4CN(C4CCC(=O)NC4=O)C5=O)ccc23)c1] | | 823.9568 |
| 45 | 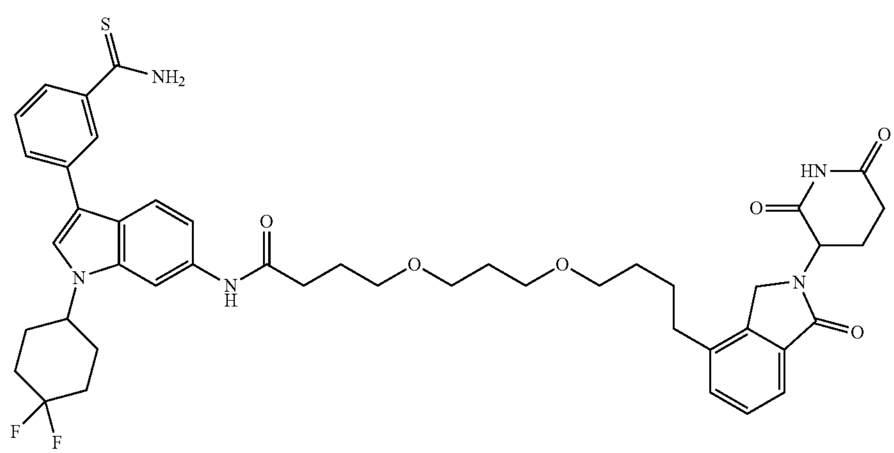 [SMILES: NC(=S)c1cccc(-c2cn(C3CCC(F)(F)CC3)c3cc(NC(=O)CCCOCCCOCCCCc4cccc5c4CN(C4CCC(=O)NC4=O)C5=O)ccc23)c1] | | 827.9888 |

TABLE 8-continued
| Number | Structure | $M_w$ calc. (Da) | [MH]+ found (Da) |
|---|---|---|---|
| 50 | 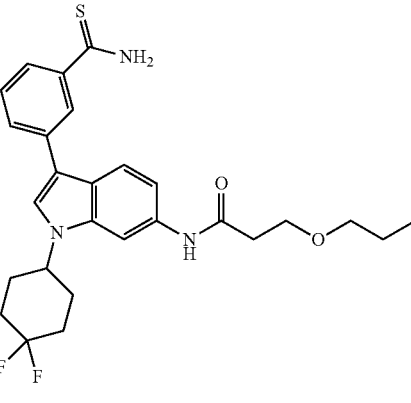 | 823.9568 | |
| 51 | 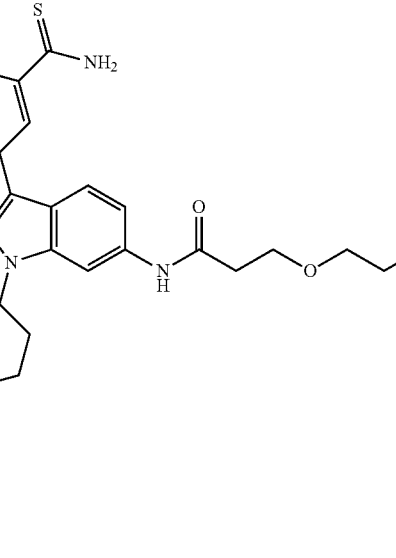 | 827.9888 | |
| 52 | 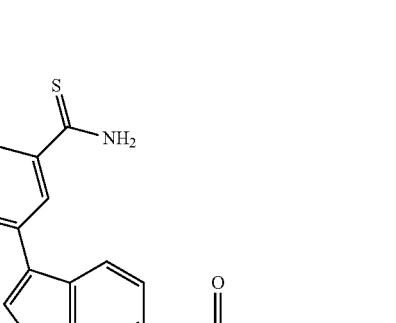 | 793.9308 | |

TABLE 8-continued

Exemplary compounds

| Number | Structure | $M_w$ calc. (Da) | [MH]+ found (Da) |
|---|---|---|---|
| 53 | 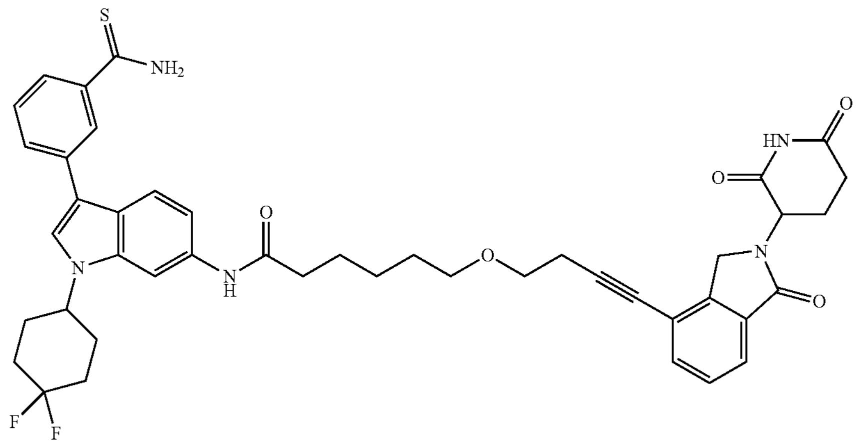 [SMILES: NC(=S)c1cccc(-c2cn(C3CCC(F)(F)CC3)c3cc(NC(=O)CCCCOCCCC#Cc4cccc5c4CN(C4CCC(=O)NC4=O)C5=O)ccc23)c1] | | 793.9308 |
| 54 | 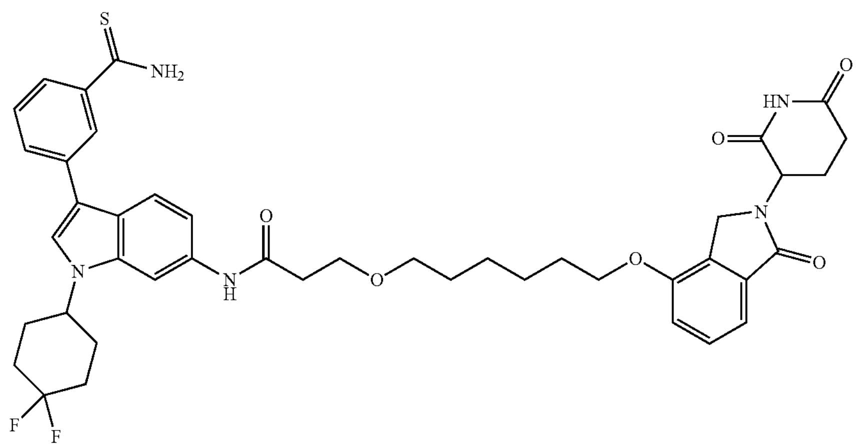 [SMILES: NC(=S)c1cccc(-c2cn(C3CCC(F)(F)CC3)c3cc(NC(=O)CCOCCCCCCOc4cccc5c4CN(C4CCC(=O)NC4=O)C5=O)ccc23)c1] | | 799.9348 |
| 55 | 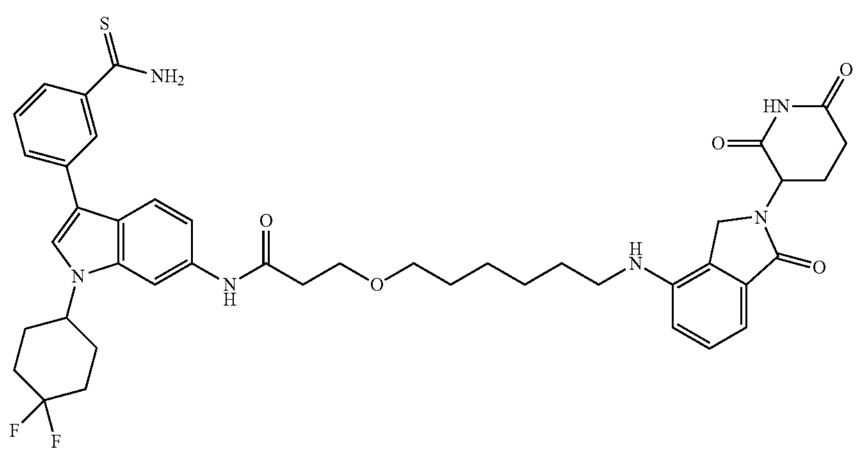 [SMILES: NC(=S)c1cccc(-c2cn(C3CCC(F)(F)CC3)c3cc(NC(=O)CCOCCCCCCNc4cccc5c4CN(C4CCC(=O)NC4=O)C5=O)ccc23)c1] | | 798.9508 |

TABLE 8-continued

Exemplary compounds

| Number | Structure | $M_w$ calc. (Da) | $[MH]^+$ found (Da) |
|---|---|---|---|
| 56 | 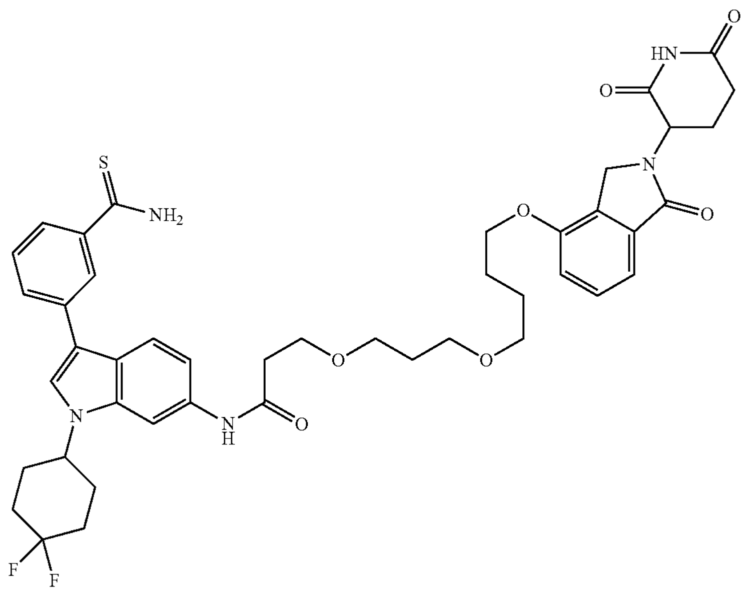 [SMILES: NC(=S)c1cccc(-c2cn(C3CCC(F)(F)CC3)c3cc(NC(=O)CCOCCCOCCCCOc4cccc5c4CN(C4CCC(=O)NC4=O)C5=O)ccc23)c1] | 829.9608 | |
| 57 | 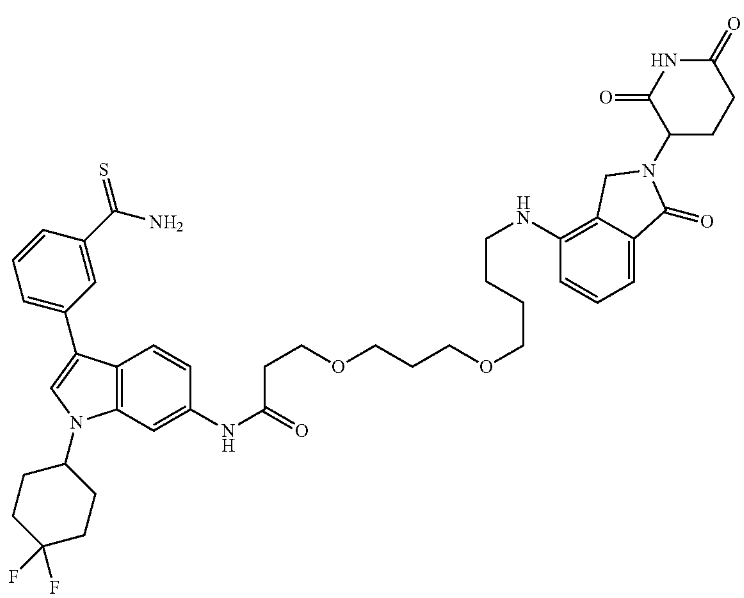 [SMILES: NC(=S)c1cccc(-c2cn(C3CCC(F)(F)CC3)c3cc(NC(=O)CCOCCCOCCCCNc4cccc5c4CN(C4CCC(=O)NC4=O)C5=O)ccc23)c1] | 828.9768 | |

TABLE 8-continued

Exemplary compounds

| Number | Structure | $M_w$ calc. (Da) | $[MH]^+$ found (Da) |
|---|---|---|---|
| 58 | 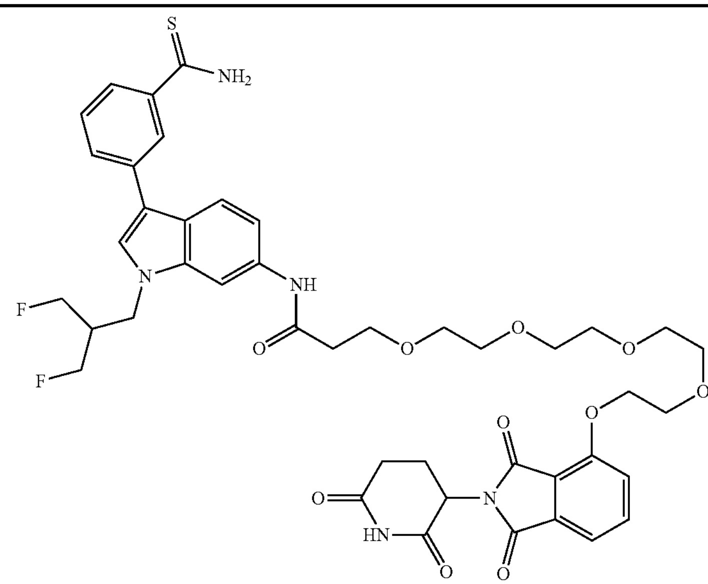 | | 863.9308 |
| 59 | 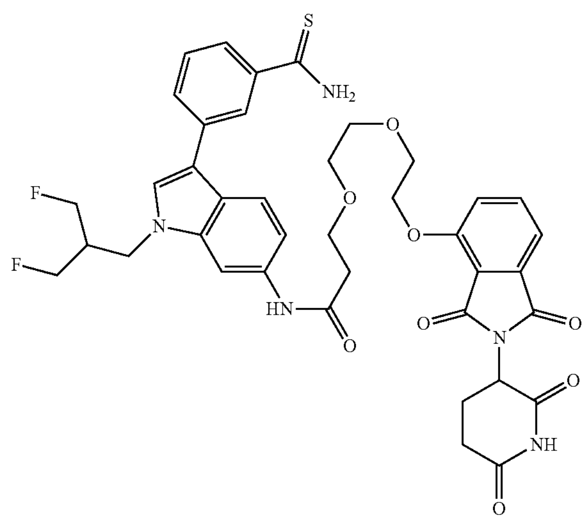 [SMILES: NC(=S)c1cccc(-c2cn(CC(CF)CF)c3cc(NC(=O)CCOCCOCCOc4cccc5c4C(=O)N(C4CCC(=O)NC4=O)C5=O)ccc23)c1] | | 775.8248 |
| 60 | 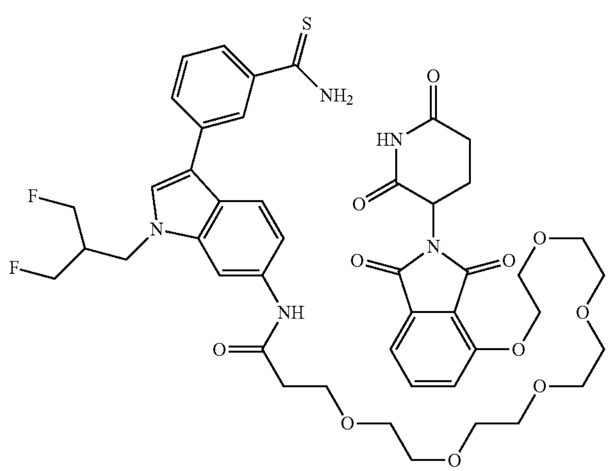 [SMILES: NC(=S)c1cccc(-c2cn(CC(CF)CF)c3cc(NC(=O)CCOCCOCCOCCOCCOCCOc4cccc5c4C(=O)N(C4CCC(=O)NC4=O)C5=O)ccc23)c1] | | 907.9838 |

TABLE 8-continued

Exemplary compounds

| Number | Structure | $M_w$ calc. (Da) | $[MH]^+$ found (Da) |
|---|---|---|---|
| 61 | 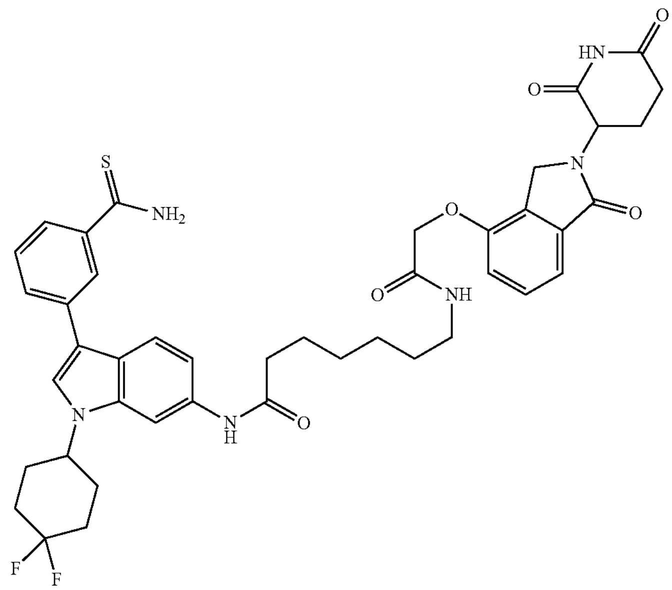 [SMILES: NC(=S)c1cccc(-c2cn(C3CCC(F)(F)CC3)c3cc(NC(=O)CCCCCCNC(=O)COc4cccc5c4CN(C4CCC(=O)NC4=O)C5=O)ccc23)c1] | | 812.9338 |
| 62 | 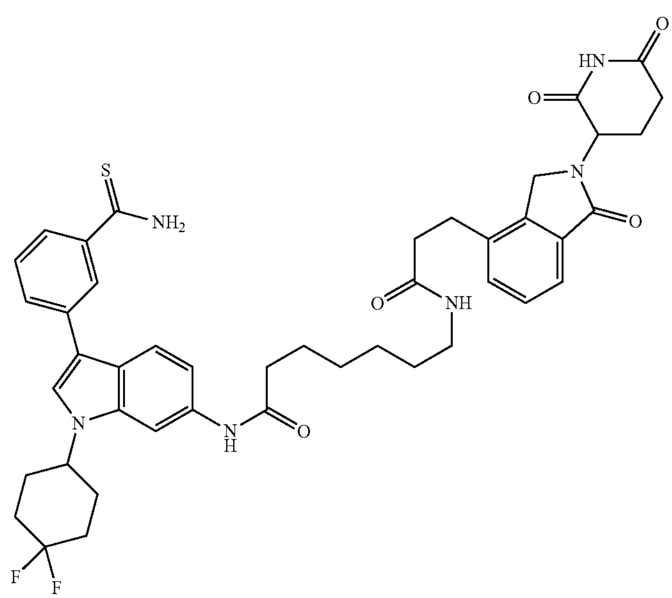 | | 810.9618 |

TABLE 8-continued
Exemplary compounds
| Number | Structure | $M_w$ calc. (Da) | $[MH]^+$ found (Da) |
|---|---|---|---|
| 63 | 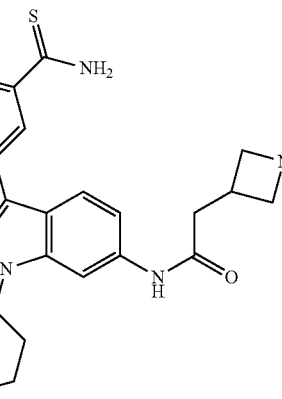 | | 806.9298 |
| 64 | 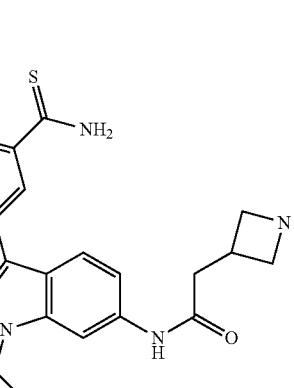 | | 804.9578 |
| 65 | 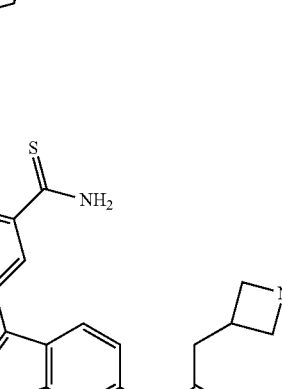 | | 818.9408 |

TABLE 8-continued

Exemplary compounds

| Number | Structure | $M_w$ calc. (Da) | [MH]+ found (Da) |
|---|---|---|---|
| 66 | 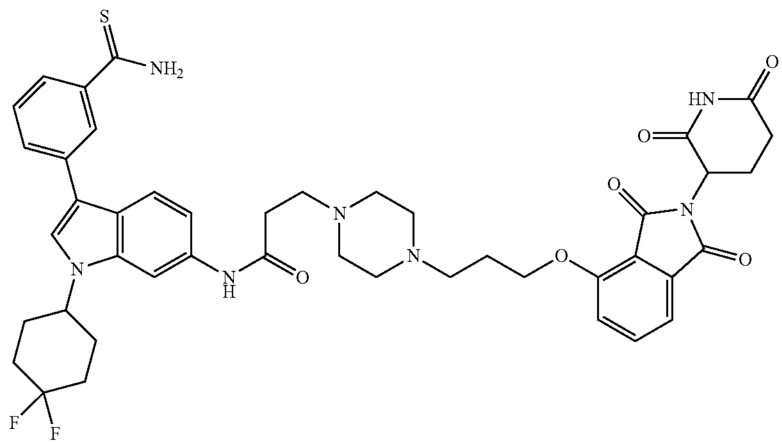 [SMILES: NC(=S)c1cccc(-c2cn(C3CCC(F)(F)CC3)c3cc(NC(=O)CCN4CCN(CCCOc5cccc6c5C(=O)N(C5CCC(=O)NC5=O)C6=O)CC4)ccc23)c1] | | 839.9598 |
| 67 | 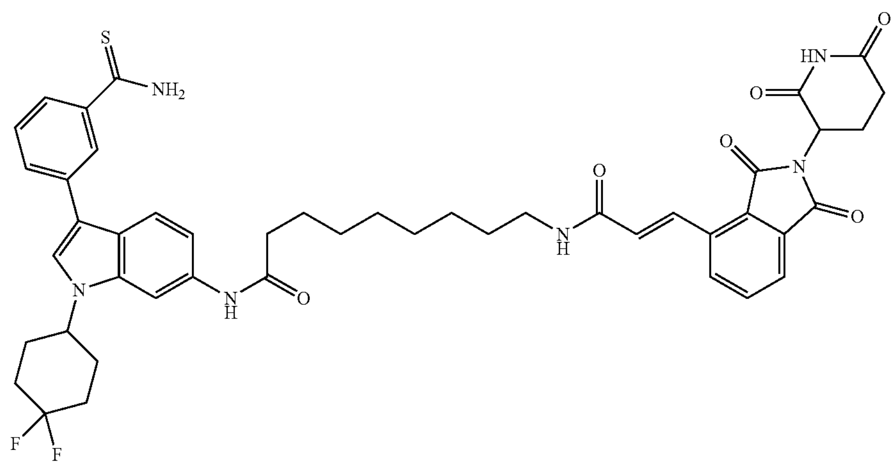 [SMILES: NC(=S)c1cccc(-c2cn(C3CCC(F)(F)CC3)c3cc(NC(=O)CCCCCCCCNC(=O)/C=C/c4cccc5c4C(=O)N(C4CCC(=O)NC4=O)C5=O)ccc23)c1] | | 850.9828 |
| 68 | 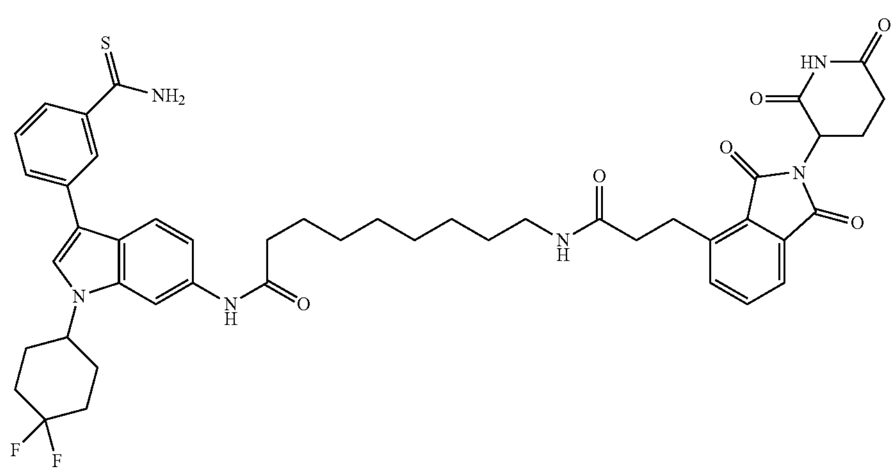 [SMILES: NC(=S)c1cccc(-c2cn(C3CCC(F)(F)CC3)c3cc(NC(=O)CCCCCCCCNC(=O)CCc4cccc5c4C(=O)N(C4CCC(=O)NC4=O)C5=O)ccc23)c1] | | 852.9988 |

TABLE 8-continued
Exemplary compounds
| Number | Structure | $M_w$ calc. (Da) | $[MH]^+$ found (Da) |
|---|---|---|---|
| 69 | 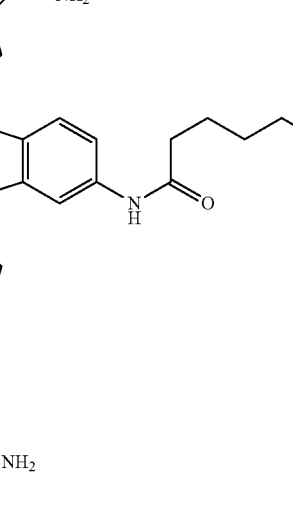 | | 854.9708 |
| 70 | 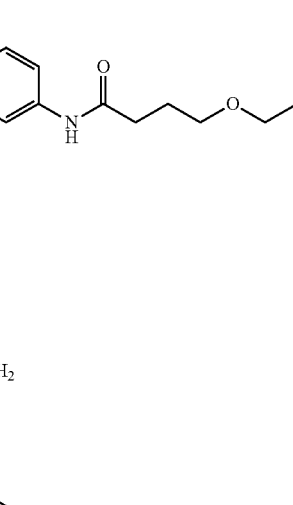 | | 837.9398 |
| 71 | 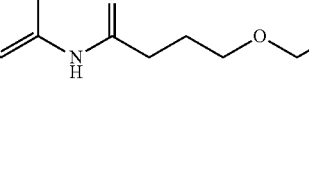 | | 841.9718 |

TABLE 8-continued
Exemplary compounds
| Number | Structure | M_w calc. (Da) | [MH]+ found (Da) |
|---|---|---|---|
| 72 | 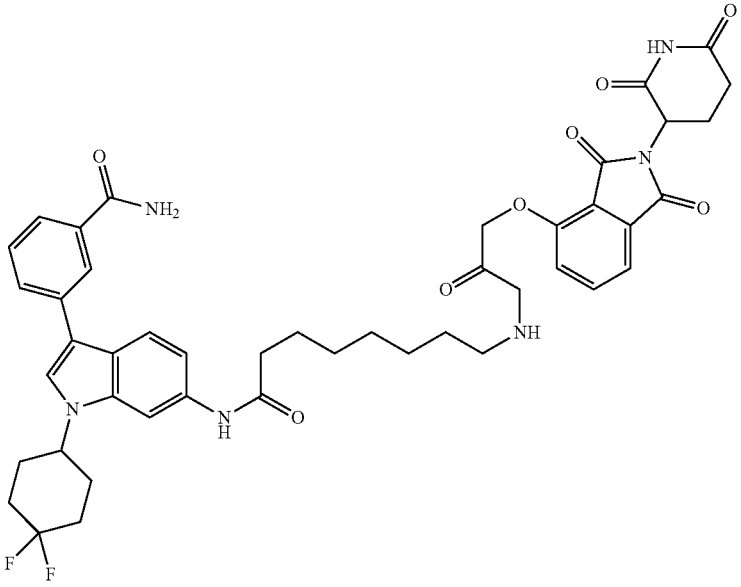 [SMILES: NC(=O)c1cccc(-c2cn(C3CCC(F)(F)CC3)c3cc(NC(=O)CCCCCCCNCC(=O)COc4cccc5c4C(=O)N(C4CCC(=O)NC4=O)C5=O)ccc23)c1] | 838.35 | |
| 73 | 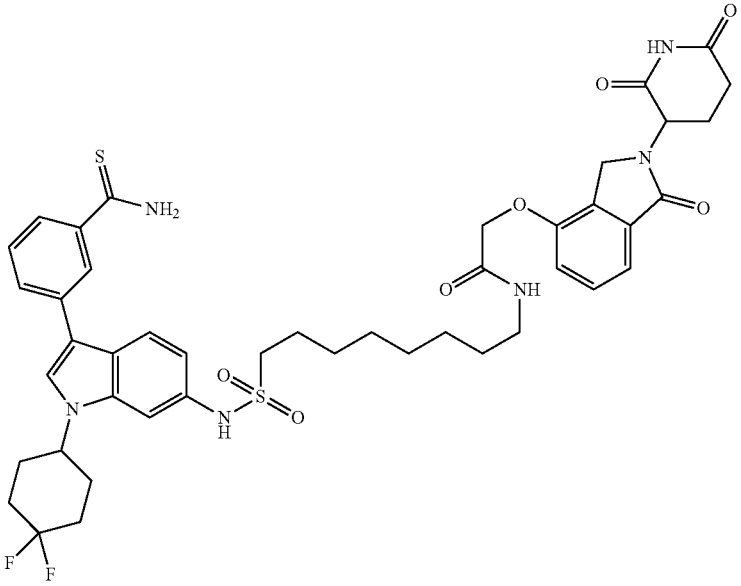 [SMILES: NC(=S)c1cccc(-c2cn(C3CCC(F)(F)CC3)c3cc(NS(=O)(=O)CCCCCCCCNC(=O)COc4cccc5c4CN(C4CCC(=O)NC4=O)C5=O)ccc23)c1] | 876.32 | |

TABLE 8-continued
Exemplary compounds
| Number | Structure | $M_w$ calc. (Da) | [MH]+ found (Da) |
|---|---|---|---|
| 74 | 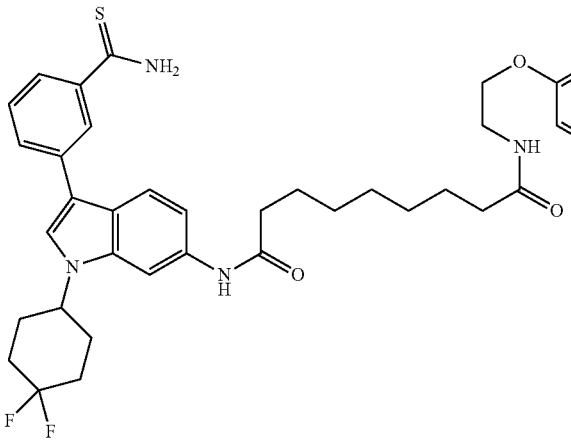 | | 840.35 |
| 75 | 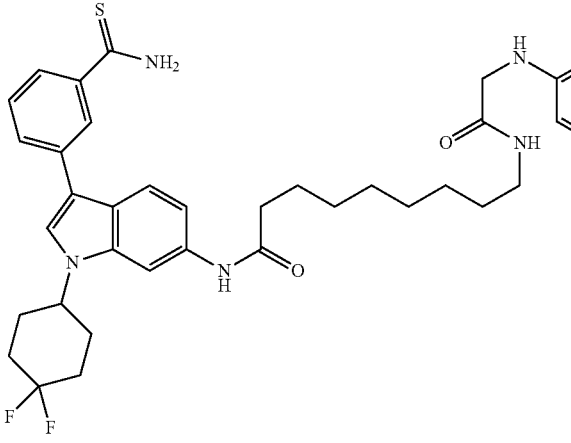 | | 839.36 |

TABLE 8-continued
Exemplary compounds
| Number | Structure | $M_w$ calc. (Da) | [MH]+ found (Da) |
|---|---|---|---|
| 76 | 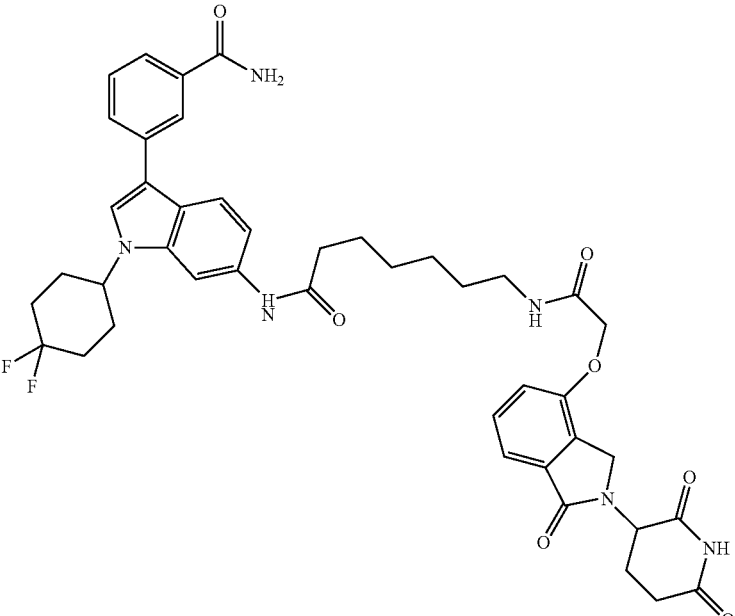 | | 796.34 |
| 77 | 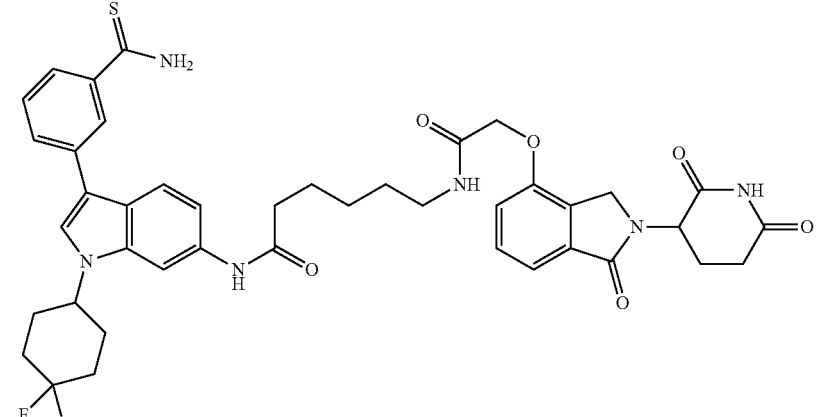 | | 798.9068 |
| 78 | 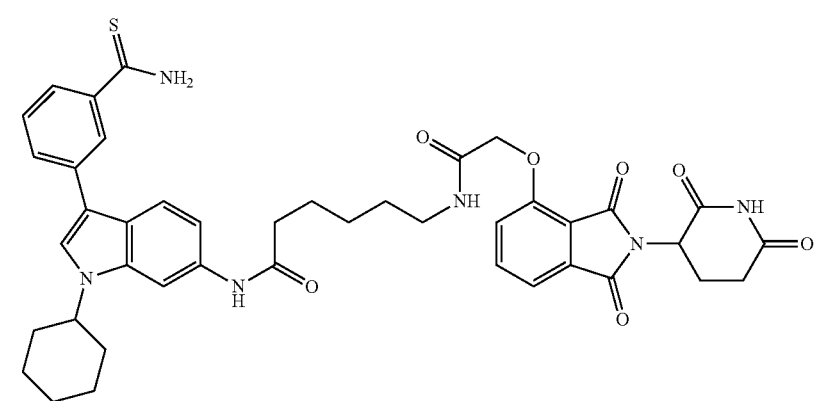 | | 812.8898 |

TABLE 8-continued
Exemplary compounds
| Number | Structure | $M_w$ calc. (Da) | $[MH]^+$ found (Da) |
|---|---|---|---|
| 79 | 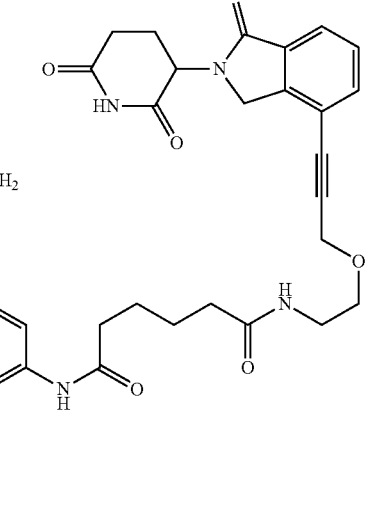 | 836.9558 | |
| 80 | 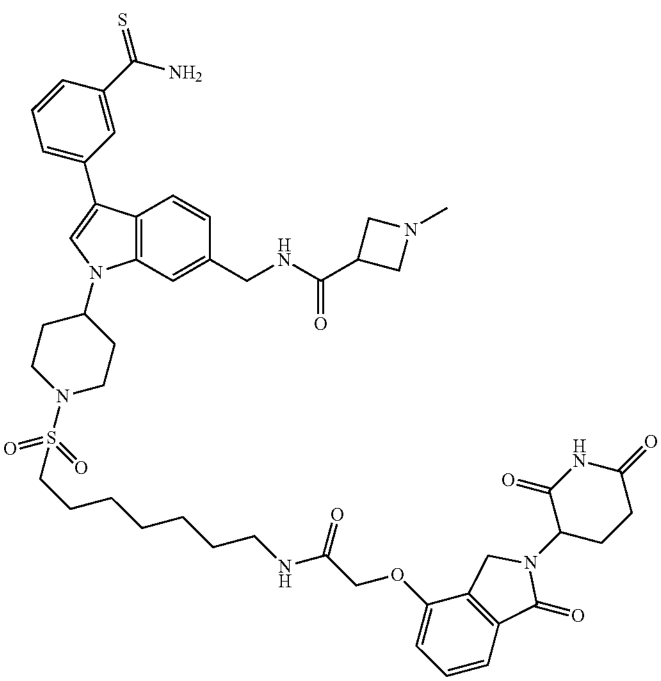 [SMILES: CN1CC(C(=O)NCc2ccc3c(-c4cccc(C(N)=S)c4)cn(C4CCN(S(=O)(=O)CCCCCCCNC(=O)COc5cccc6c5CN(C5CCC(=O)NC5=O)C6=O)CC4)c3c2)C1] | 938.38 | |

TABLE 8-continued

Exemplary compounds

| Number | Structure | $M_w$ calc. (Da) | $[MH]^+$ found (Da) |
|---|---|---|---|
| 81 | 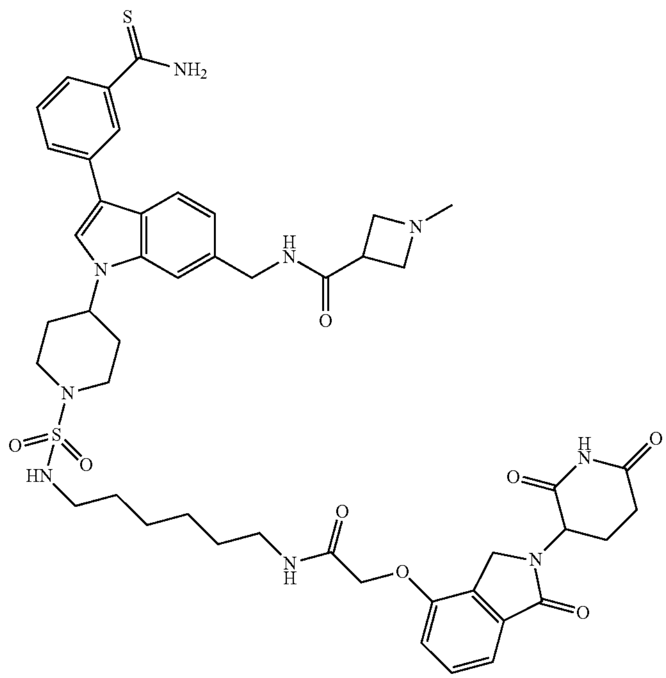 [SMILES: CN1CC(C(=O)NCc2ccc3c(-c4cccc(C(N)=S)c4)cn(C4CCN(S(=O)(=O)NCCCCCCNC(=O)COc5cccc6c5CN(C5CCC(=O)NC5=O)C6=O)CC4)c3c2)C1] | | 939.38 |
| 82 | 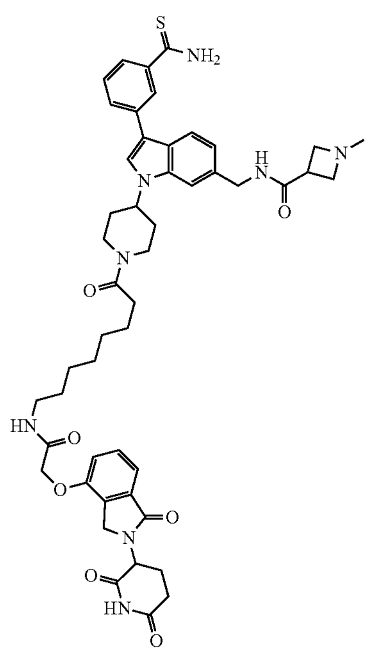 [SMILES: CN1CC(C(=O)NCc2ccc3c(-c4cccc(C(N)=S)c4)cn(C4CCN(C(=O)CCCCCCCNC(=O)COc5cccc6c5CN(C5CCC(=O)NC5=O)C6=O)CC4)c3c2)C1] | | 902.41 |

TABLE 8-continued
| Number | Structure | $M_w$ calc. (Da) | $[MH]^+$ found (Da) |
|---|---|---|---|
| 83 | 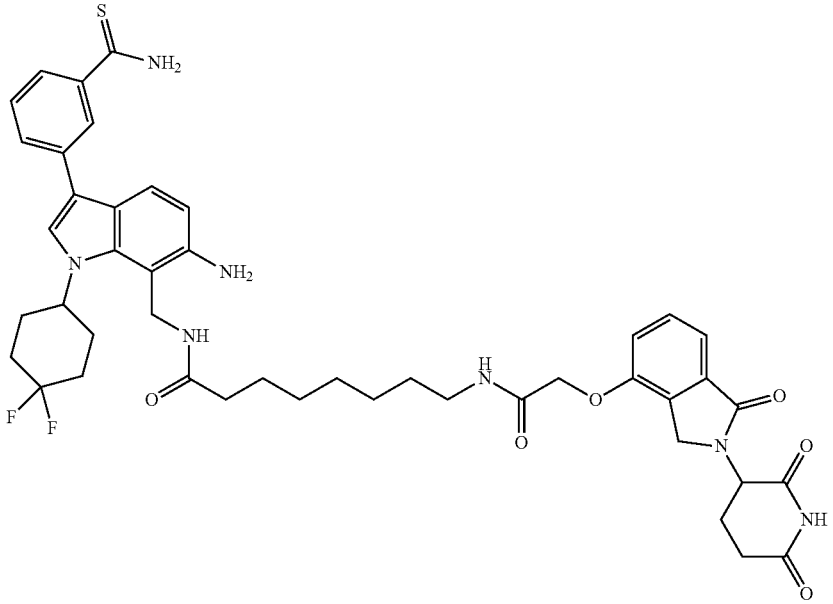 [SMILES: NC(=S)c1cccc(-c2cn(C3CCC(F)(F)CC3)c3c(CNC(=O)CCCCCCCNC(=O)COc4cccc5c4CN(C4CCC(=O)NC4=O)C5=O)c(N)ccc23)c1] | 855.36 | |
| 84 | 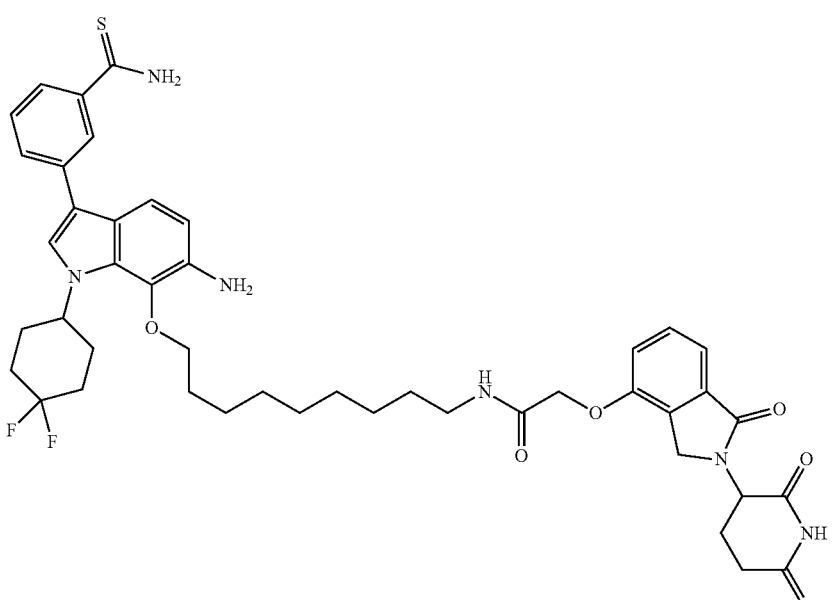 | 842.36 | |

TABLE 8-continued
Exemplary compounds
| Number | Structure | M_w calc. (Da) | [MH]+ found (Da) |
|---|---|---|---|
| 85 | 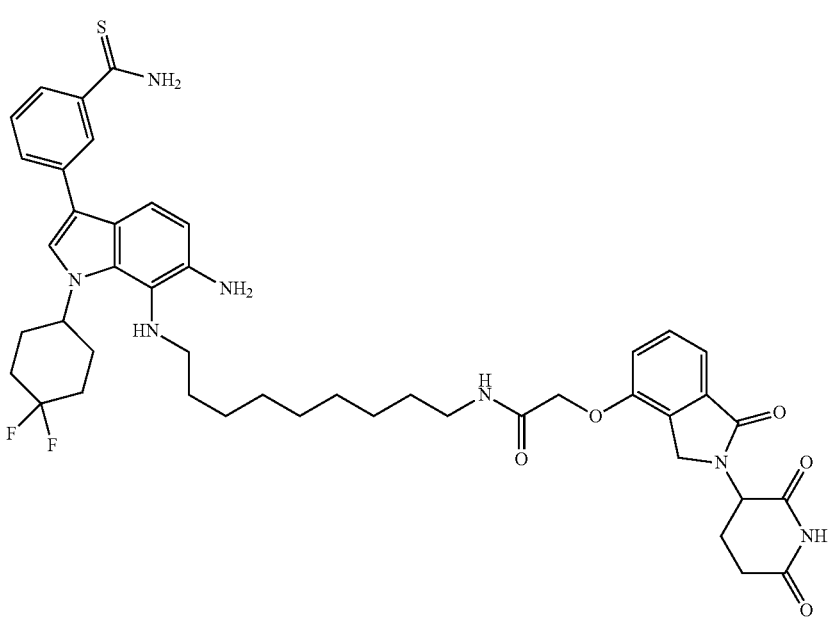 [SMILES: NC(=S)c1cccc(-c2cn(C3CCC(F)(F)CC3)c3c(NCCCCCCCCCNC(=O)COc4cccc5c4CN(C4CCC(=O)NC4=O)C5=O)c(N)ccc23)c1] | | 841.38 |
| 86 | 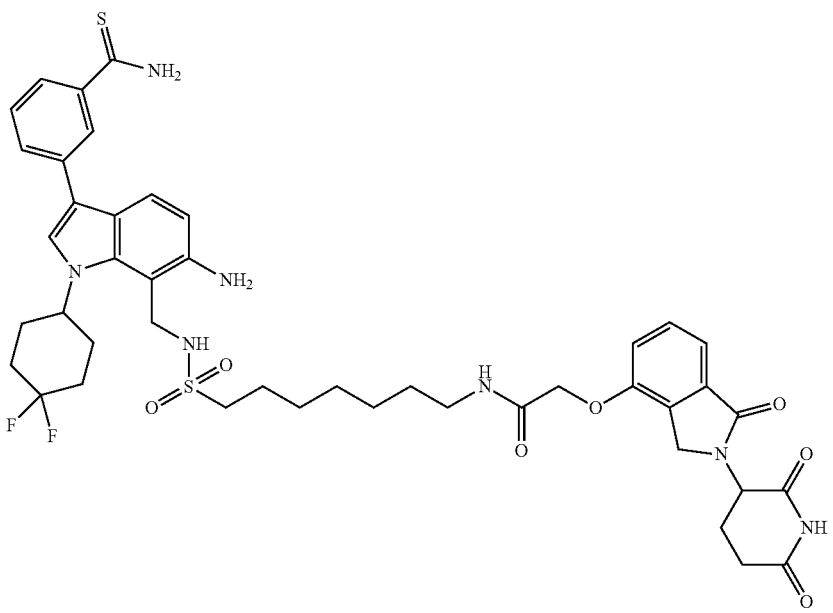 [SMILES: NC(=S)c1cccc(-c2cn(C3CCC(F)(F)CC3)c3c(CNS(=O)(=O)CCCCCCCNC(=O)COc4cccc5c4CN(C4CCC(=O)NC4=O)C5=O)c(N)ccc23)c1] | | 891.33 |

TABLE 8-continued

| Number | Structure | $M_w$ calc. (Da) | $[MH]^+$ found (Da) |
|---|---|---|---|
| 87 | 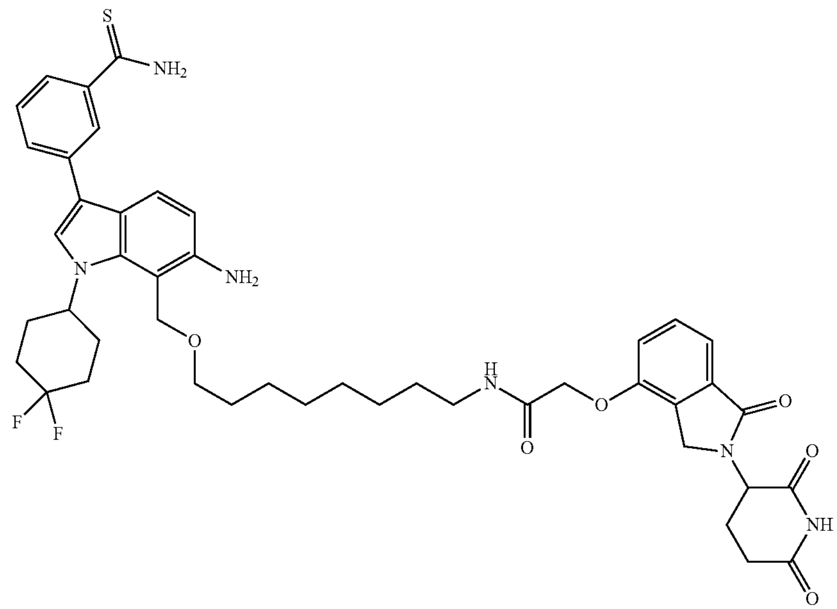 [SMILES: NC(=S)c1cccc(-c2cn(C3CCC(F)(F)CC3)c3c(COCCCCCCCCNC(=O)COc4cccc5c4CN(C4CCC(=O)NC4=O)C5=O)c(N)ccc23)c1] | 842.36 | |
| 88 | 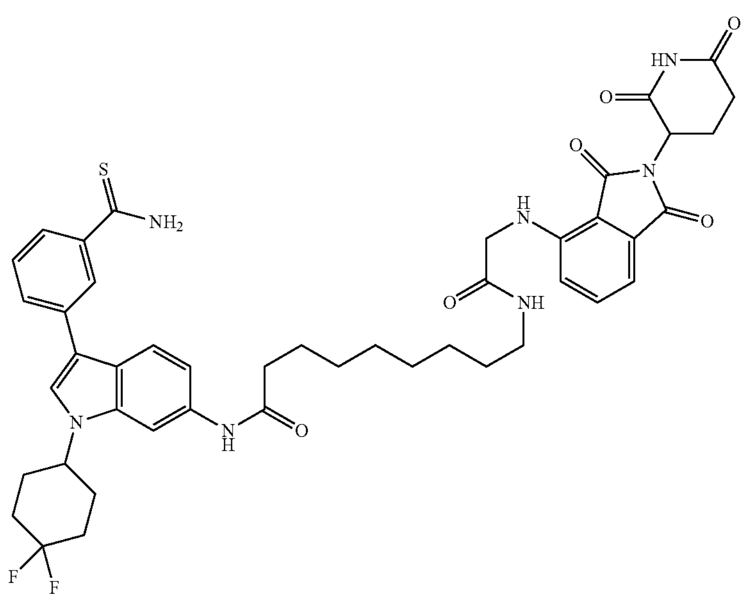 [SMILES: NC(=S)c1cccc(-c2cn(C3CCC(F)(F)CC3)c3cc(NC(=O)CCCCCCCCNC(=O)CNc4cccc5c4C(=O)N(C4CCC(=O)NC4=O)C5=O)ccc23)c1] | 853.34 | |

TABLE 8-continued

Exemplary compounds

| Number | Structure | $M_w$ calc. (Da) | $[MH]^+$ found (Da) |
|---|---|---|---|
| 89 | 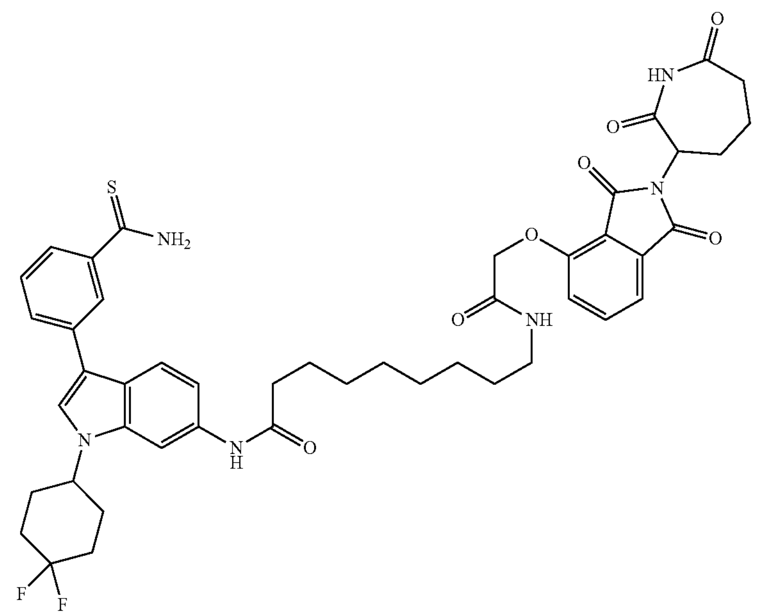 [SMILES: NC(=S)c1cccc(-c2cn(C3CCC(F)(F)CC3)c3cc(NC(=O)CCCCCCCCNC(=O)COc4cccc5c4C(=O)N(C4CCCC(=O)NC4=O)C5=O)ccc23)c1] | 868.34 | |
| 90 | 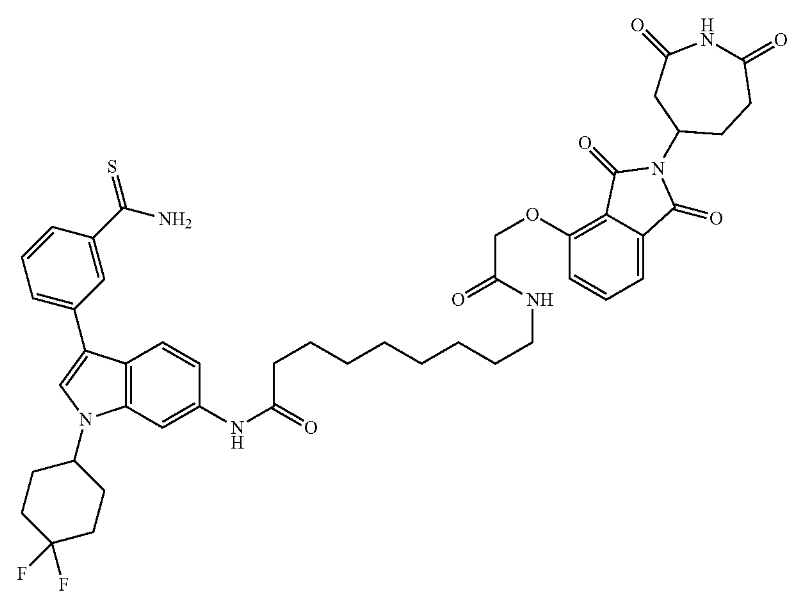 [SMILES: NC(=S)c1cccc(-c2cn(C3CCC(F)(F)CC3)c3cc(NC(=O)CCCCCCCCNC(=O)COc4cccc5c4C(=O)N(C4CCC(=O)NC(=O)C4)C5=O)ccc23)c1] | 868.34 | |

TABLE 8-continued

Exemplary compounds

| Number | Structure | $M_w$ calc. (Da) | $[MH]^+$ found (Da) |
|---|---|---|---|
| 91 | 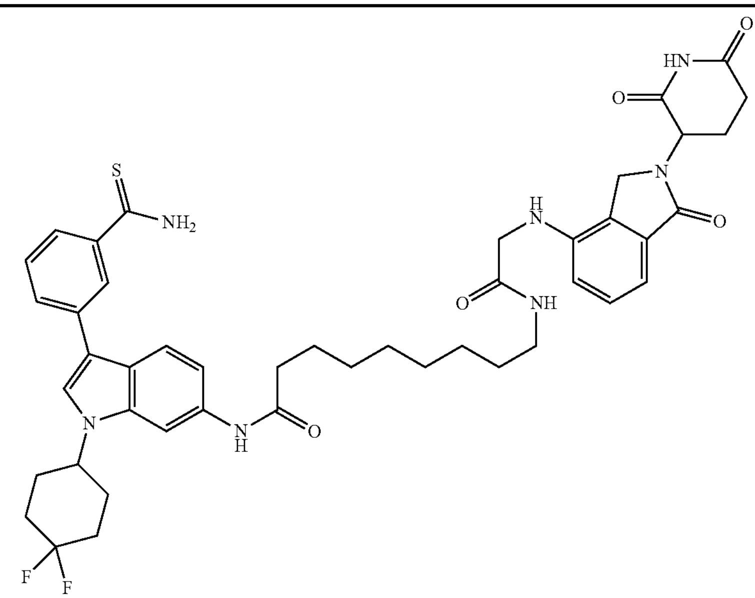 | 839.36 | |

In some embodiments, the compound is selected from the compounds depicted in Table 8 (e.g., Compounds 1-91).

In some embodiments, provided herein are compounds defined by one of Formulas (Ia), (Ib), (IIa), (IIb), (IIIa), and (IIIb), but wherein the benzothioamide (or benzoamide) is linked to the benzene portion of the indole bicyclic structure rather than the pyrrole portion (as is depicted in Formulas (Ia), (Ib), (IIa), (IIb), (IIIa), and (IIIb)). For example, for any Formula (e.g., Formulas (Ia), (Ib), (IIa), (IIb), (IIIa), and (IIIb)) or compound (e.g., Compounds 1-91) described herein as having benzothioamide-pyrrole or benzoamide-pyrrole ring connectivity, such as:

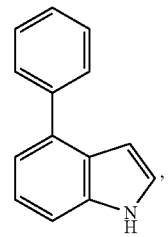

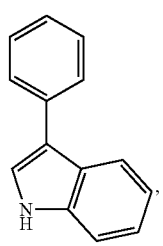 [SMILES: c1ccc(-c2c[nH]c3ccccc23)cc1]

a corresponding Formula (e.g., Formulas (Ic), (Id), (IIc), (IId), (IIIc), (IIId), (IVc), and (IVd)) and compound (e.g., compounds 92-182) having benzothioamide-benzene benzoamide-benzene ring connectivity, such as:

is provided herein and within the scope of embodiments herein. For example, any embodiments, substituents, compounds, etc. described herein in connection with Formula (Ia) may also be provided herein in embodiments in connection with Formula (Ic):

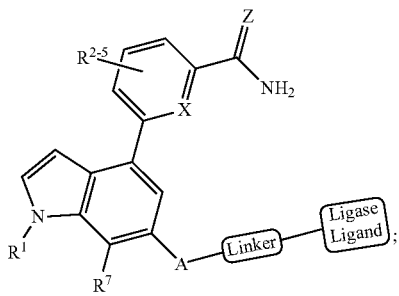

any embodiments, substituents, compounds, etc. described herein in connection with Formula (Ib) may also be provided herein in embodiments related to Formula (Id):

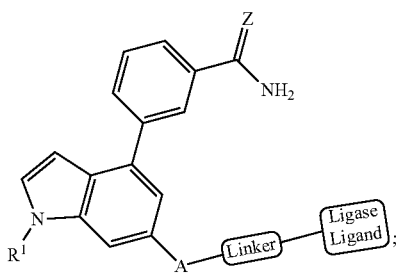

any embodiments, substituents, compounds, etc. described herein in connection with Formula (IIa) may also be provided herein in embodiments related to Formula (IIc):

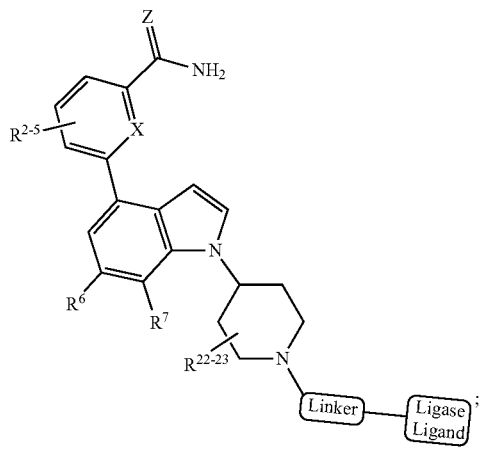

any embodiments, substituents, compounds, etc. described herein in connection with Formula (IIb) may also be provided herein in embodiments related to Formula (IId):

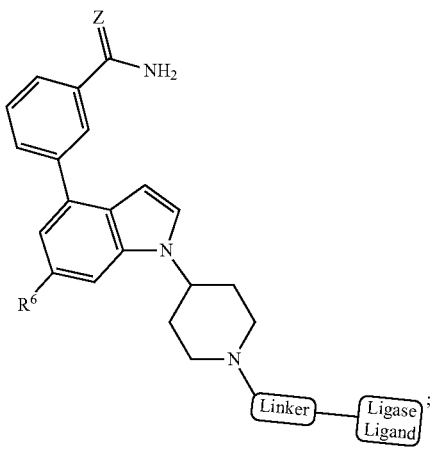

any embodiments, substituents, compounds, etc. described herein in connection with Formula (IIIa) may also be provided herein in embodiments related to Formula (IIIc):

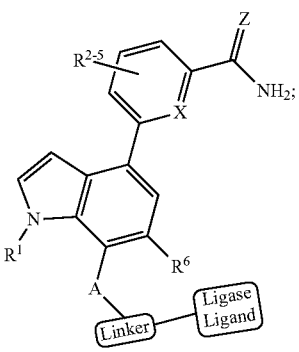

any embodiments, substituents, compounds, etc. described herein in connection with Formula (IIIb) may also be provided herein in embodiments related to Formula (IIId):

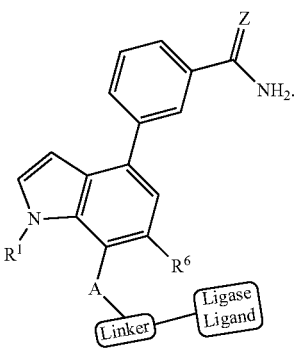

Compounds 92-182 correspond to compounds 1-91 but with the benzothioamide (or benzoamide) linked to the benzene portion of the indole bicyclic structure rather than the pyrrole portion. For example, compound 92 corresponds to compound 1, but with the benzothioamide (or benzoamide) linked to the benzene portion of the indole bicyclic structure rather than the pyrrole portion; compound 93 corresponds to compound 2, but with the benzothioamide (or benzoamide) is linked to the benzene portion of the indole bicyclic structure rather than the pyrrole portion; compound 94 corresponds to compound 3, but with the benzothioamide (or benzoamide) is linked to the benzene portion of the indole bicyclic structure rather than the pyrrole portion; etc.

In some embodiments, provided herein are pharmaceutical compositions comprising a compound described herein and a pharmaceutically acceptable carrier. In some embodiments, the pharmaceutical composition is formulated for oral administration, injection, or any other suitable route of administration.

In some embodiments, provided herein are methods of inhibiting the activity of ASH1L, comprising contacting ASH1L with an effective amount of a compound described herein.

In some embodiments, provided herein are methods of degrading ASH1L by bifunctional compounds, which function to recruit both ASH1L and proteins of E3 Ubiquitin Ligase Complex (e.g. Cereblon, VHL ligase, etc.) for ubiquitination and proteasome-mediated degradation of ASH1L.

In some embodiments, provided herein are methods of treating a disease, comprising administering to a subject a pharmaceutical composition described herein in an amount effective to inhibit the activity of ASH1L and/or degrade ASH1L. In some embodiments, the disease is a cancer. In some embodiments, the disease is a proliferative disorder. In some embodiments, the pharmaceutical composition is co-administered with an additional cancer therapeutic. In some embodiments, the subject is a human.

In some embodiments, provided herein is the use of a compound described herein. In some embodiments, provided herein is the use of a compound described herein for inhibiting ASH1L activity or degradation of ASH1L. In some embodiments, provided herein is the use of a compound described herein for the treatment of a disease (e.g., cancer).

DEFINITIONS

Figure 1:
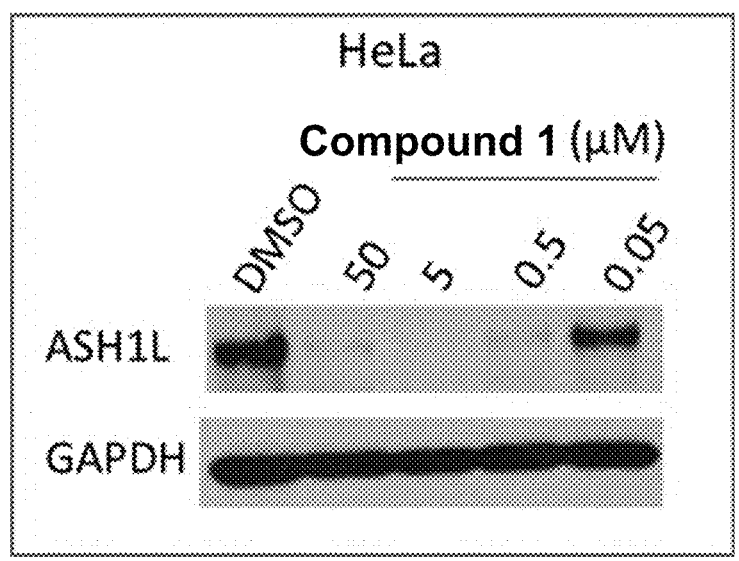
FIG. 1. Degradation of Ash1L induced by compound 1.
Figure 2:
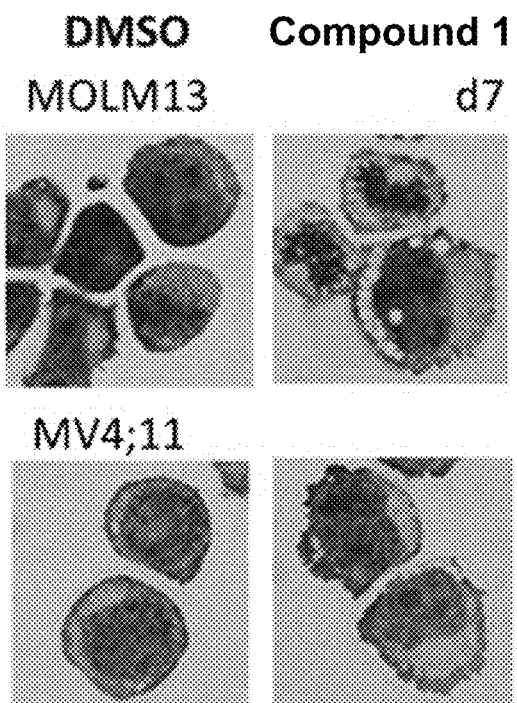
FIG. 2. Compound 1 selectively blocks proliferation and induces differentiation in acute leukemia cell lines. Cell growth inhibition ($GI_{50}$ values) differentiation after 7 days of treatment of various leukemia cell lines are shown.
Figure 3:
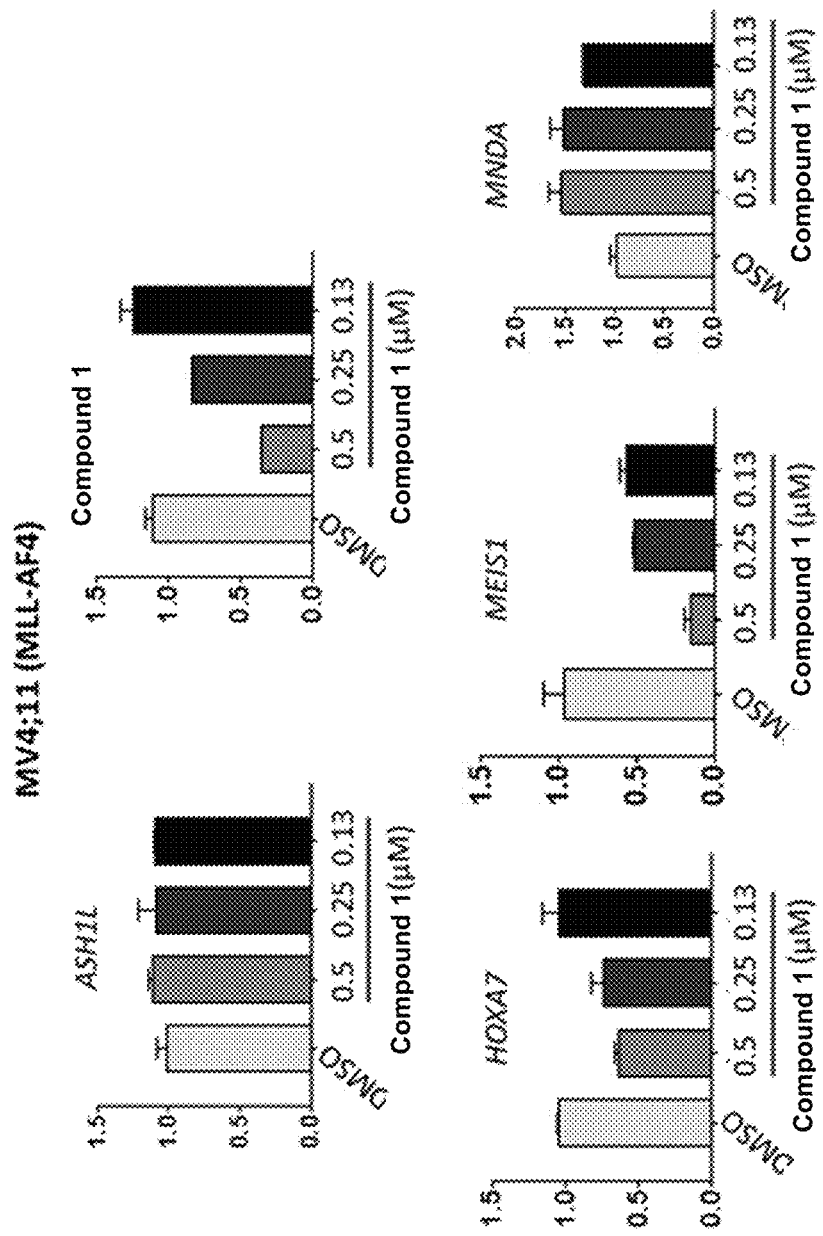
FIG. 3. Compound 1 downregulates expression of MLL fusion target genes in MV4:11 MLL leukemia cell line. Data collected after 7 days of treatment with Compound 1.
Figure 4:
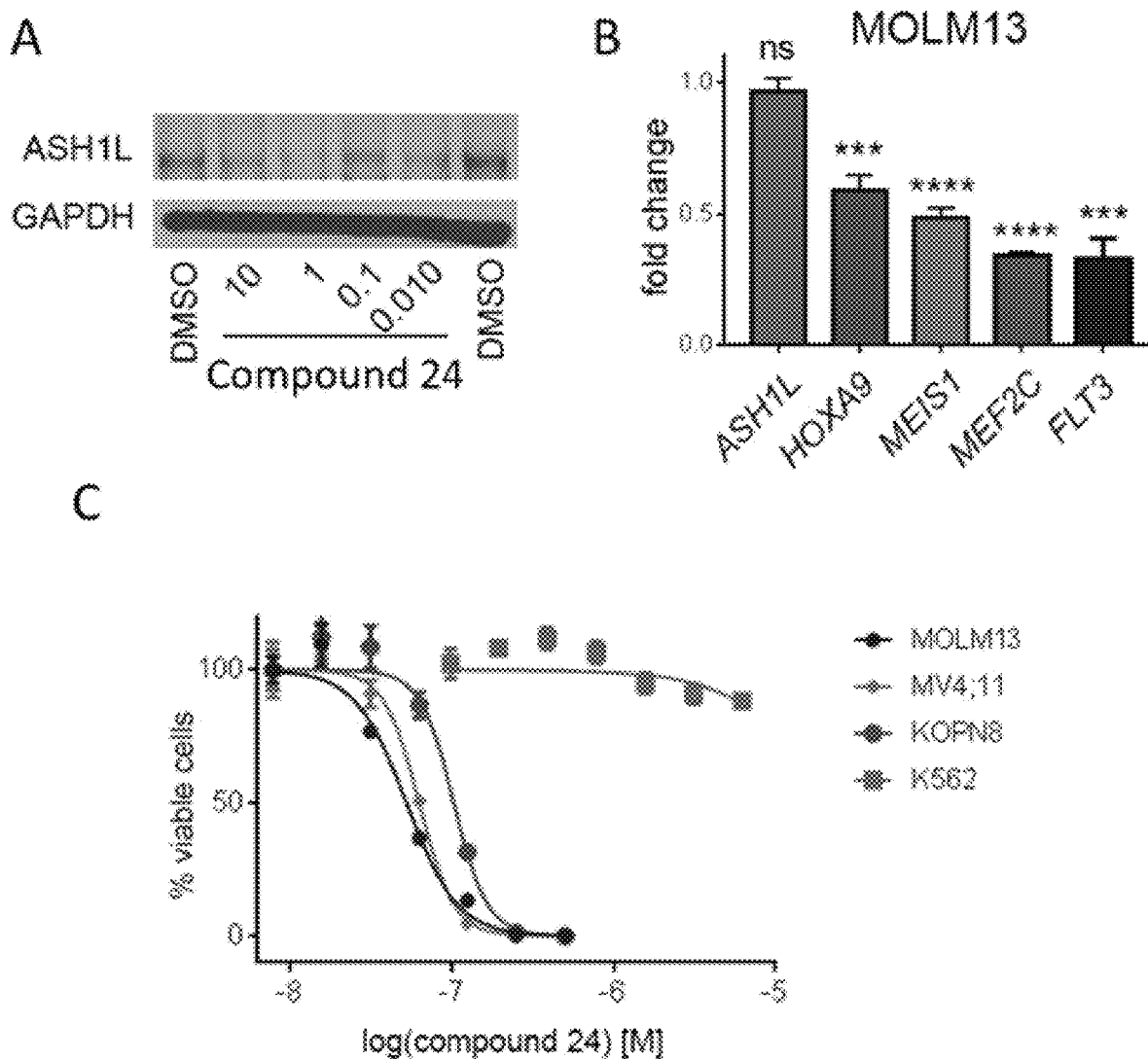
FIG. 4, Panels A-C. (Panel A) Compound 24 induces degradation of ASH1L in HeLa cells after 24 h of treatment. Concentrations of Compound 24 are shown in µM. (Panel B) Gene expression studies upon treatment with Compound 24 in MOLM13 leukemia cell line (after 6 days of treatment at 150 nM). Compound 24 downregulates the expression of MLL fusion protein target genes. (Panel C) Compound 24 inhibits viability of various acute leukemia cells (after 7 days of treatment). $GI_{50}$ values for Compound 24 in leukemia cell lines: 62 nM in MV4:11, 52 nM in MOLM13, 103 nM in KOPN8 and >6 µM in K562 control cell line.
Figure 5:
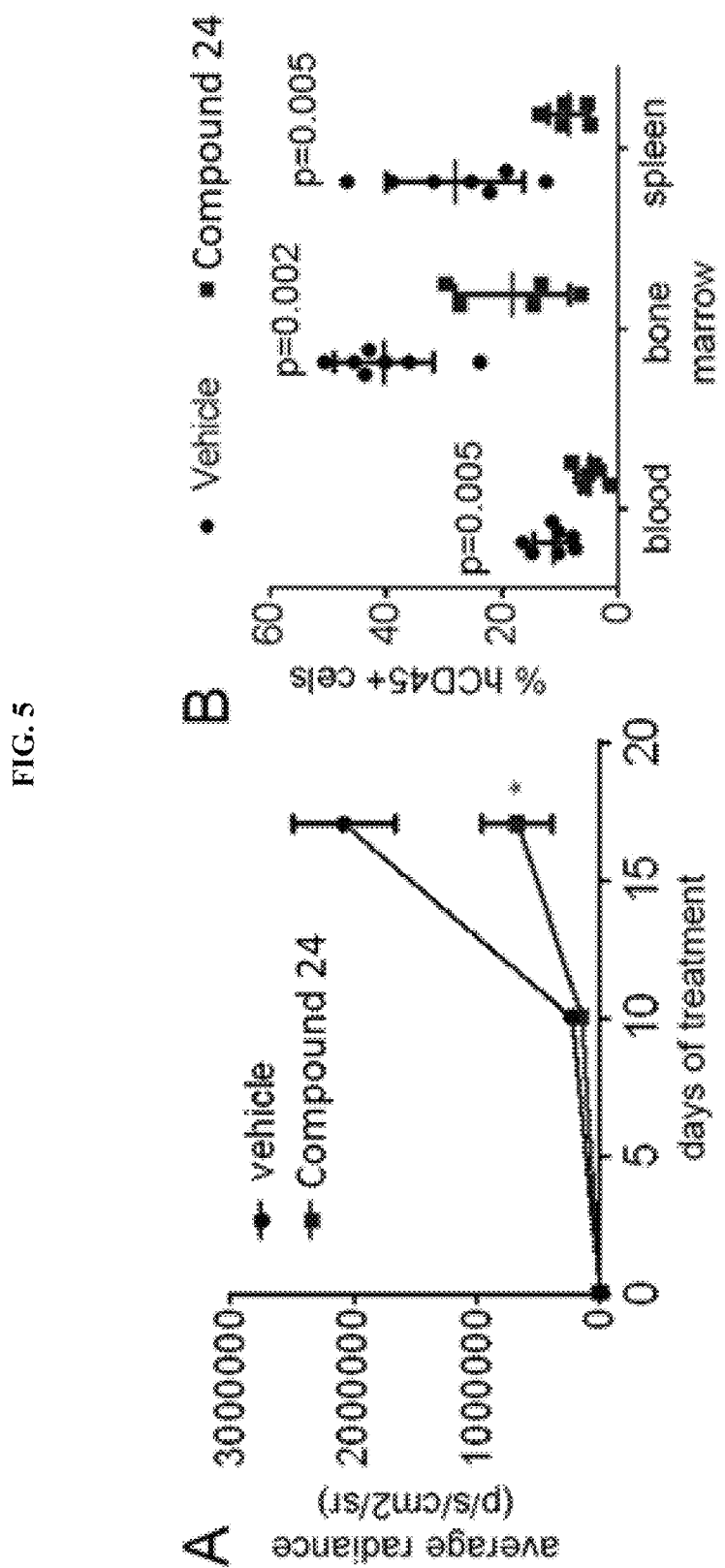
FIG. 5, Panels A-B. Compound 24 blocks leukemia progression in vivo in MV4:11 xenotransplantation model (Compounds 24 was used at 25 mg/kg, i.p., q.d.). Bioluminescence signal in mice (Panel A). Level of hCD45+ cells after 17 days of treatment measured by flow cytometry in bone marrow, spleen and peripheral blood of mice treated with Compound 24 or vehicle (Panel B).

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a ASH1L inhibitor" is a reference to one or more ASH1L inhibitors and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "proteolysis targeting chimera" ("PROTAC") refers to a compound comprising two functional moieties, a target (e.g., ASH1L) binding moiety and a degradation moiety, tethered together by a suitable linker. PROTACs bind to a target molecule (e.g., ASH1L) and signal for degradation of the target molecule (e.g., by recruitment of the E3 ligase, resulting in ubiquitination and subsequent degradation of the target protein by the proteasome). PROTACs may inhibit the activity of the target through their binding to the target active site (e.g., as with a conventional enzyme inhibitor) or may bind to the target without significant inhibition of activity. In some embodiments, the compounds described herein are PROTACs.

All chemical names of substituents should be interpreted in light of IUPAC and/or a modified format in which functional groups within a substituent are read in the order in which they branch from the scaffold or main structure. For example, in the modified nomenclature, methyl-sulfonyl-propanol refers to $CH_2SO_2CH_2CH_2CH_2OH$ or:

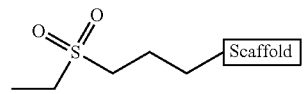

As another example, according to the modified nomenclature, a methyl-amine substituent is:

while an amino-methyl substituent is:

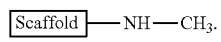

All chemical names of substituents should be interpreted in light of IUPAC and/or the modified nomenclature and with reference to the chemical structures depicted and/or described herein.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "subject at risk for a disease," for example, "a subject at risk for cancer" refers to a subject with one or more risk factors for developing the disease (e.g., cancer). Depending upon the specific disease, risk factors may include, but are not limited to, gender, age, genetic predisposition, environmental exposures, infections, and previous incidents of diseases, lifestyle, etc.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., ASH1L degrader and one or more additional therapeutics) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds herein are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions (e.g., providing dosing, route of administration, decision trees for treating physicians for correlating patient-specific characteristics with therapeutic courses of action).

"Amino" refers to the —$NH_2$ moiety.

"Carbonyl" refers to a moiety of the formula —C(=O)—.

"Carboxy" or "carboxyl" refers to the —$CO_2H$ moiety.

"Cyano" refers to the —CN moiety.

Hydroxy" or "hydroxyl" refers to the —OH moiety.

Imino" refers to the =NH moiety. Unless stated otherwise specifically in the specification, an imino group is optionally substituted.

"Nitro" refers to the —$NO_2$ moiety.

"Oxo" refers to the =O moiety.

"Thioxo" refers to the =S moiety.

"Acyl" refers to the group —C(=O)$R_a$, where $R_a$ is selected from the group consisting of alkyl, cycloalkyl, aryl, heteroaryl (bonded through a ring carbon), heteroalkyl, and heterocyclylalkyl. Unless stated otherwise specifically in the specification, an acyl group is optionally substituted.

"Alkyl" refers to a straight or branched hydrocarbon chain moiety consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds). Unless stated otherwise specifically in the specification, an alkyl group is optionally substituted.

"Alkoxy" refers to a moiety of the formula —$OR_a$ where $R_a$ is an alkyl group as defined herein containing one to twelve carbon atoms. Unless stated otherwise specifically in the specification, an alkoxy group is optionally substituted.

"Alkylamino" refers to a moiety of the formula —$NHR_a$ or —$NR_aR_b$ where $R_a$ and $R_b$ are each independently an alkyl group as defined herein containing one to twelve carbon atoms.

Unless stated otherwise specifically in the specification, an alkylamino group is optionally substituted.

"Alkylaminoalkyl" refers to an alkyl moiety comprising at least one alkylamino substituent. The alkylamino substituent can be on a tertiary, secondary or primary carbon. Unless stated otherwise specifically in the specification, an alkylaminoalkyl group is optionally substituted.

"Amide" or "amido" refers to a moiety with formula —C(=O)$NR_aR_b$ or —$NR_aC$(=O) $R_b$, where $R_a$ and $R_b$ are each independently selected from the group consisting of hydrogen, alkyl, cycloalkyl, aryl, heteroaryl (bonded through a ring carbon), heteroalkyl, and heterocyclylalkyl, each of which moiety may itself be optionally substituted. In some embodiments, it is a $C_1$-$C_4$ amido or amide group, which includes the amide carbonyl in the total number of carbons in the group. The $R_aR_b$ of —$NR_aR_b$ of the amide may optionally be taken together with the nitrogen to which it is attached to form a 4-, 5-, 6-, or 7-membered ring. Unless stated otherwise specifically in the specification, an amido group is optionally substituted.

"Aminoalkyl" refers to an alkyl moiety comprising at least one amino substituent. The amino substituent can be on a tertiary, secondary or primary carbon. Unless stated otherwise specifically in the specification, an aminoalkyl group is optionally substituted.

"Aminocarbonyl" refers to an amide moiety of the formula —C(=O)$NR_aR_b$, where $R_a$ and $R_b$ are each independently H or alkyl. Unless stated otherwise specifically in the specification, an aminocarbonyl group is optionally substituted.

"Aryl" refers to a hydrocarbon ring system moiety comprising 6 to 18 carbon atoms and at least one aromatic ring. For purposes of this invention, the aryl moiety is a monocyclic, bicyclic, tricyclic, or tetracyclic ring system, which may include fused or bridged ring systems. Aryl moieties include, but are not limited to, aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl groups that are optionally substituted.

"Aralkyl" refers to a moiety of the formula —$R_b$—$R_c$ where $R_b$ is an alkylene chain as defined herein and $R_c$ is one or more aryl moieties as defined herein, for example, benzyl, diphenylmethyl, and the like. Unless stated otherwise specifically in the specification, an aralkyl group is optionally substituted.

"Aralkylamino" refers to a aralkyl-$NR_a$— moiety, where $R_a$ is H or alkyl. Unless stated otherwise specifically in the specification, an aralkylamino is optionally substituted.

"Aralkyloxy" refers to an aralkyl-O— moiety. Unless stated otherwise specifically in the specification, an aralkyloxy is optionally substituted.

"Arylamino" refers to a —$NR_a$-aryl moiety, where $R_a$ is H or alkyl. Unless stated otherwise specifically in the specification, an arylamino is optionally substituted.

"Aryloxy" refers to an —O-aryl moiety. Unless stated otherwise specifically in the specification, an aryloxy is optionally substituted.

"Bicycloalkyl" refers to a moiety with two cycloalkyl moieties, that have two or more atoms in common. If the cycloalkyl moieties have exactly two adjacent atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, adamantyl, bicyclo[3.2.1] heptyl ("norbornyl"), bicyclo[2.2.2]octyl, and the like. Unless stated otherwise specifically in the specification, a bicycloalkyl is optionally substituted.

"Carboxyalkyl" refers to a moiety of the formula —$R_b$—$R_c$ where $R_b$ is an alkylene chain as defined herein and $R_c$ is a carboxy group as defined herein. Unless stated otherwise specifically in the specification, carboxyalkyl group is optionally substituted.

"Cyanoalkyl" refers to a moiety of the formula —$R_b$—$R_c$ where $R_b$ is an alkylene chain as defined herein and $R_c$ is a cyano group as defined herein. Unless stated otherwise specifically in the specification, a cyanoalkyl group is optionally substituted.

"Carbocycle" or "carbocyclic ring" refers to a saturated or unsaturated, non-aromatic, monocyclic or polycyclic hydrocarbon moiety, which may include fused or bridged ring systems, having from three to fifteen carbon atoms, preferably having from three to ten carbon atoms, including cycloalkyls, cycloalkenyls, etc. "Cycloalkyl" refers to a saturated, non-aromatic, monocyclic or polycyclic hydrocarbon moiety, which may include fused or bridged ring systems, having from three to fifteen carbon atoms, preferably having from three to ten carbon atoms. Monocyclic cycloalkyl moieties include, for example, cyclopropyl, cyclobutyl, cyclopentyl, cyclopentenyl, cyclohexyl, cyclohexenyl, cycloheptyl, and cyclooctyl. Polycyclic cycloalkyl moieties include, for example, adamantyl, norbornyl, decalinyl, 7,7-dimethyl-bicyclo[2.2.1]heptanyl, and the like. A "cycloalkenyl" is a cycloalkyl comprising one or more carbon-carbon double bonds within the ring, such as cyclopentenyl and cyclohexenyl. Unless otherwise stated specifically in the specification, a cycloalkyl group is optionally substituted.

"Cycloalkylalkyl" refers to a moiety of the formula —$R_bR_d$ where $R_b$ is an alkylene chain as defined herein and $R_d$ is a cycloalkyl moiety as defined herein. Unless stated otherwise specifically in the specification, a cycloalkylalkyl group is optionally substituted.

"Cycloalkylalkylamino" refers to a cycloalkylalkyl-NR$_a$— moiety, where R$_a$ is H or alkyl and where the cycloalkylalkyl moiety is attached via a carbon atom to nitrogen, wherein the nitrogen functions as a linker to attach the moiety to the remainder of the molecule. Unless stated otherwise specifically in the specification, a cycloalkylalkylamino is optionally substituted.

"Cycloalkylalkyloxy" refers to a —O-cycloalkylalkyl moiety, where the cycloalkylalkyl moiety is attached via a carbon atom to oxygen, wherein the oxygen functions as a linker to attach the moiety to the remainder of the molecule. Unless stated otherwise specifically in the specification, a cycloalkylalkyloxy is optionally substituted.

"Cycloalkylamino" refers to a —NR$_a$-cycloalkyl moiety, where R$_a$ is H or alkyl. Unless stated otherwise specifically in the specification, a cycloalkylamino is optionally substituted.

"Cycloalkyloxy" refers to an —O-cycloalkyl moiety. Unless stated otherwise specifically in the specification, a cycloalkyloxy is optionally substituted.

"Halo" or "halogen" refers to fluoro, chloro, bromo, or iodo.

"Haloalkyl" refers to an alkyl group, as defined herein, that is substituted by one or more halo atoms, as defined herein, e.g., trifluoromethyl, difluoromethyl, fluoromethyl, trichloromethyl, —CH$_2$CF$_3$, —CH$_2$CHF$_2$, —CH$_2$CH$_2$F, —CHFCF$_3$, —CHFCHF$_2$, —CHFCH$_2$F, —CHFCH$_3$, —CF$_2$CF$_3$, —CF$_2$CHF$_2$, —CF$_2$CH$_2$F, —CF$_2$CH$_3$, —CH$_2$CF$_2$CH$_3$, —CH$_2$CHFCH$_3$, 3-bromo-2-fluoropropyl, 1,2-dibromoethyl, and the like. Unless stated otherwise specifically in the specification, a haloalkyl group is optionally substituted.

As used herein, the term "heteroatom" or "ring heteroatom" is meant to include any element other than carbon or hydrogen. Preferred heteroatoms are oxygen (O), nitrogen (N), sulfur (S), and phosphorus (P).

"Heteroalkyl," by itself or in combination with another term, means, unless otherwise stated, a straight or branched chain; monocyclic or polycyclic moiety, which may include fused or bridged ring systems; or any combination thereof, comprising at least one carbon atom and at least one heteroatom, such as O, N, P, Si and S, wherein one or more heteroatoms may be oxidized. Heteroatom(s) may be positioned within the alkyl moiety, e.g., —CH$_2$—O—CH$_2$—; at a point of connectivity with the remainder of the molecule, e.g., —SO$_2$CH(CH$_3$)CH$_2$—; or a combination thereof, e.g., —NH$_2$CH$_2$CH$_2$SO$_2$CH$_2$—. Unless stated otherwise specifically in the specification, a heteroalkyl group is optionally substituted.

"Heteroaryl" refers to a 5- to 14-membered ring system moiety comprising one to thirteen carbon atoms; one to six heteroatoms such as nitrogen, oxygen, and sulfur; and one or multiple rings wherein at least one ring is aromatic. For purposes of this invention, the heteroaryl group may be a monocyclic, bicyclic, tricyclic, or tetracyclic ring system, which may include fused or bridged ring systems and one or more heteroatoms may be oxidized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

"Heteroarylalkyl" refers to a moiety of the formula —R$_b$R$_f$ where R$_b$ is an alkylene chain as defined herein and R$_f$ is a heteroaryl group as defined herein. Unless stated otherwise specifically in the specification, a heteroarylalkyl group is optionally substituted.

"Heteroarylalkylamino" refers to a heteroarylalkyl-NR$_a$— moiety, where R$_a$ is H or alkyl. Unless stated otherwise specifically in the specification, an heteroarylalkylamino is optionally substituted.

"Heteroarylalkyloxy" refers to an heteroarylalkyl-O— moiety. Unless stated otherwise specifically in the specification, a heteroarylalkyloxy is optionally substituted.

"Heteroarylamino" refers to a —NR$_a$-heteroaryl moiety, where R$_a$ is H or alkyl. Unless stated otherwise specifically in the specification, a heteroarylamino is optionally substituted.

"Heteroaryloxy" refers to an —O-heteroaryl moiety. Unless stated otherwise specifically in the specification, an heteroaryloxy is optionally substituted.

"Heterobicycloalkyl" refers to a bicycloalkyl structure in which at least one carbon ring atom is replaced with a heteroatom such as oxygen, nitrogen, and sulfur. Unless stated otherwise specifically in the specification, a heterobicycloalkyl is optionally substituted.

"Heterocyclyl" or "heterocyclic ring" refers to a 3- to 18-membered non-aromatic ring which consists of two to twelve carbon atoms and from one to six heteroatoms such as nitrogen, oxygen, and sulfur. Unless stated otherwise specifically in the specification, the heterocyclyl group is a monocyclic, bicyclic, tricyclic, or tetracyclic ring system, which may include fused or bridged ring systems; the heteroatoms may be optionally oxidized; and the heterocyclyl may be unsaturated or saturated. Examples of such heterocyclyl moieties include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group is optionally substituted.

"Heterocyclylalkyl" or "heterocycloalkyl" refers to a moiety of the formula —R$_b$R$_c$ where R$_b$ is an alkylene chain as defined herein and R is a heterocyclyl moiety as defined herein, and if the heterocyclyl is a nitrogen-containing heterocyclyl, the heterocyclyl is optionally attached to the alkyl moiety at the nitrogen atom. Unless stated otherwise specifically in the specification, a heterocyclylalkyl group is optionally substituted.

"Heterocyclylalkylamino" refers to a heterocyclylalkyl-NR$_a$— moiety, where R$_a$ is H or alkyl and where the heterocyclylalkyl moiety is attached via a carbon atom to nitrogen, wherein the nitrogen functions as a linker to attach the moiety to the remainder of the molecule. Unless stated otherwise specifically in the specification, a heterocyclylalkylamino is optionally substituted.

"Heterocyclylalkyloxy" refers to a —O-heterocycloalkyl moiety, where the heterocyclylalkyl moiety is attached via a carbon atom to oxygen, wherein the oxygen functions as a linker to attach the moiety to the remainder of the molecule. Unless stated otherwise specifically in the specification, a heterocyclylalkyloxy is optionally substituted.

"Heterocyclylamino" refers to a —NR$_a$-heterocyclyl moiety, where R$_a$ is H or alkyl and where the heterocyclyl moiety is attached via a carbon atom to nitrogen, wherein the nitrogen functions as a linker to attach the moiety to the remainder of the molecule. Unless stated otherwise specifically in the specification, a heterocyclylamino is optionally substituted.

"Heterocyclyloxy" refers to an —O-heterocyclyl moiety, where the heterocyclyl moiety is attached via a carbon atom to oxygen, wherein the oxygen functions as a linker to attach the moiety to the remainder of the molecule. Unless stated otherwise specifically in the specification, a heterocyclyloxy is optionally substituted.

"Hydroxyalkyl" or "hydroxylalkyl" refers to an alkyl group comprising at least one hydroxyl substituent. The —OH substituent may be on a primary, secondary, or tertiary carbon. Unless stated otherwise specifically in the specification, a hydroxylalkyl group is optionally substituted.

"N-heteroaryl" refers to a heteroaryl moiety as defined herein containing at least one nitrogen and where the point of attachment of the heteroaryl moiety to the rest of the molecule is through a nitrogen atom in the heteroaryl ring. Unless stated otherwise specifically in the specification, an N-heteroaryl group is optionally substituted.

"N-heterocyclyl" refers to a heterocyclyl moiety as defined herein containing at least one nitrogen and where the point of attachment of the heterocyclyl moiety to the rest of the molecule is through a nitrogen atom in the heterocyclyl ring. Unless stated otherwise specifically in the specification, a N-heterocyclyl group is optionally substituted.

"Thioalkyl" refers to a moiety of the formula —SR$_a$ where R$_a$ is an alkyl moiety as defined herein containing one to twelve carbon atoms. Unless stated otherwise specifically in the specification, a thioalkyl group is optionally substituted.

"Alkylene" or "alkylene chain" refers to a straight or branched divalent hydrocarbon chain linking two groups in a molecule, which may be saturated or unsaturated (i.e., contains one or more double and/or triple bonds), and have from one to twelve carbon atoms, preferably one to eight carbon atoms ($C_1$-$C_8$ alkylene) or one to six carbon atoms ($C_1$-$C_6$ alkylene), e.g., methylene, ethylene, propylene, n-butylene, ethenylene, propenylene, n-butenylene, propynylene, n-butynylene, and the like. The alkylene chain is attached to the rest of the molecule through a single or double bond. The points of attachment of the alkylene chain to the rest of the molecule may be through one carbon, e.g., methylene, or any two carbons within the chain, e.g., —CH$_2$CH(CH$_3$)CH$_2$CH$_2$—. Unless stated otherwise specifically in the specification, an alkylene chain is optionally substituted.

"Alkylenecarbonyl" refers to a moiety of the formula —C(=O)R$_a$—, where R$_a$ is an alkylene chain as defined herein. Unless stated otherwise specifically in the specification, an alkylenecarbonyl is optionally substituted.

"Alkenylene" is an unsaturated alkylene, as defined herein, which comprises one or more carbon-carbon double bonds. Unless stated otherwise specifically in the specification, an alkenylene is optionally substituted.

"Alkenylenecarbonyl" refers to an unsaturated alkylenecarbonyl, as defined herein, which comprises one or more carbon-carbon double bonds. Unless stated otherwise specifically in the specification, an alkenylenecarbonyl is optionally substituted.

"Arylene" refers to a divalent aryl group which links one part of the molecule to another part of the molecule. Unless stated specifically otherwise, an arylene is optionally substituted.

"Heteroalkylene" refers to an alkylene group comprising at least one heteroatom (e.g., N, O or S). In some embodiments, the heteroatom is within the alkylene chain (i.e., the heteroalkylene comprises at least one carbon-heteroatom-carbon bond). In other embodiments, the heteroatom is at a terminus of the alkylene and joins the alkylene to the remainder of the molecule (e.g., M1-H-A-M2, where M1 and M2 are portions of a molecule, H is a heteroatom and A is an alkylene). A heteroalkylene may have both internal and terminal heteroatoms, e.g., —OCH$_2$CH$_2$OCH$_2$CH$_2$O—. Unless stated otherwise specifically in the specification, a heteroalkylene is optionally substituted.

"Heteroalkylenecarbonyl" refers to a moiety of the formula —C(=O)R$_a$—, where R$_a$ is a heteroalkylene chain as defined herein. Unless stated otherwise specifically in the specification, a heteroalkylenecarbonyl is optionally substituted.

"Heteroarylene" refers to a divalent heteroaryl group which links one part of the molecule to another part of the molecule. Unless stated specifically otherwise, a heteroarylene is optionally substituted.

"Heteroarylenecarbonyl" refers to a moiety of the formula —C(=O)R$_a$—, wherein R$_a$ is a heteroarylene as defined herein. Unless stated specifically otherwise, a heteroarylenecarbonyl is optionally substituted.

"Heterocyclylalkylene" refers to a divalent heterocyclyl group which links one part of the molecule to another part of the molecule. Unless stated specifically otherwise, a heterocycloalkylene is optionally substituted.

"Heterocyclylalkylenecarbonyl" refers to a moiety of the formula —C(=O)R$_a$—, wherein R$_a$ is a heterocycloalkylene as defined herein. Unless stated specifically otherwise, a heterocycloalkylenecarbonyl is optionally substituted.

The term "substituted" used herein refers to replacement of at least one hydrogen atom with any of the above groups (e.g., amino, carboxy, hydroxyl, imino, acyl, alkyl, alkoxy, alkylamino, alkylaminoalkyl, amide, aminoalkyl, aminocarbonyl, aryl, aralkyl, aralkylamino, aralkyloxy, arylamino, aryloxy, bicycloalkyl, carboxyalkyl, cyanoalkyl, cycloalkyl, cycloalkylalkyl, cycloalkylalkylamino, cycloalkylalkyloxy, cycloalkylamino, cycloalkyloxy, halo, haloalkyl, heteroatom, heteroalkyl, heteroaryl, heteroarylalkyl, heteroarylalkylamino, heteroarylalkyloxy, heteroarylamino, heteroaryloxy, heterobicycloalkyl, heterocyclyl, heterocyclylalkyl, heterocyclylalkylamino, heterocyclylalkyloxy, heterocyclylamino, heterocyclyloxy, hydroxyalkyl, N-heteroaryl, N-heterocyclyl, thioalkyl, alkylene, alkylenecarbonyl, alkenylene, alkenylenecarbonyl, arylene, heteroalkylene, heteroalkylenecarbonyl, heteroarylene, heteroarylenecarbonyl, heterocyclylalkylene, and/or heterocyclylalkylenecarbonyl), wherein the at least one hydrogen atom is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups such as alkyl sulfone groups, sulfonyl groups such as sulfonamide groups and sulfonylalkyl groups such as sulfonylmethane, and sulfoxide groups such as alkyl sulfoxide groups; a nitrogen atom in groups such as amino, amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; a phosphorus atom in groups such as dialkylphosphine oxide groups; and other heteroatoms in various other groups. "Substituted" also means any of the above groups in which one or more hydrogen atoms are replaced by a higher-order bond (e.g., a double- or triple-bond) to a carbon atom or a heteroatom such as oxygen in oxo, carbonyl, carboxyl, and ester groups; and nitrogen in groups such as imines, oximes, hydrazones, and nitriles. "Substituted" includes any of the above groups in which one or more hydrogen atoms are replaced with $—NR_gR_h$, $—NR_gC(=O)R_h$, $—NR_gC(=O)NR_gR_h$, $—NR_gC(=O)OR_h$, $—NR_gSO_2R_h$, $—OC(=O)NR_gR_h$, $—OR_g$, $—SR_g$, $—SOR_g$, $—SO_2R_g$, $—OSO_2R_g$, $—SO_2OR_g$, $=NSO_2R_g$, $—SO_2NR_gR_h$, $—C(=O)R_g$, $—C(=O)OR_g$, $—C(=O)NR_gR_h$, $—CH_2SO_2R_g$, or $—CH_2SO_2NR_gR_h$, where $R_g$ and $R_h$ are independently hydrogen, alkyl, alkoxy, alkylamino, thioalkyl, aryl, aralkyl, cycloalkyl, cycloalkylalkyl, haloalkyl, heteroalkyl, heterocyclyl, N-heterocyclyl, heterocycylalkyl, heteroaryl, N-heteroaryl and/or heteroarylalkyl. "Substituted" further means any of the above groups in which one or more hydrogen atoms are replaced by a bond to an amino, carbonyl, carboxy, cyano, hydroxyl, imino, nitro, oxo, thioxo, acyl, alkyl, alkoxy, alkylamino, alkylaminoalkyl, amide, aminoalkyl, aminocarbonyl, aryl, aralkyl, aralkylamino, aralkyloxy, arylamino, aryloxy, bicycloalkyl, carboxyalkyl, cyanoalkyl, cycloalkyl, cycloalkylalkyl, cycloalkylalkylamino, cycloalkylalkyloxy, cycloalkylamino, cycloalkyloxy, halo, haloalkyl, heteroatom, heteroalkyl, heteroaryl, heteroarylalkyl, heteroarylalkylamino, heteroarylalkyloxy, heteroarylamino, heteroaryloxy, heterobicycloalkyl, heterocyclyl, heterocyclylalkyl, heterocyclylalkylamino, heterocyclylalkyloxy, heterocyclylamino, heterocyclyloxy, hydroxyalkyl, N-heteroaryl, N-heterocyclyl, thioalkyl, alkylene, alkylenecarbonyl, alkenylene, alkenylenecarbonyl, arylene, heteroalkylene, heteroalkylenecarbonyl, heteroarylene, heteroarylenecarbonyl, heterocyclylalkylene, heterocyclylalkylenecarbonyl, trimethylsilanyl, dialkylphosphine oxide, $—OR^a$, $—SR^a$, $—OC(O)—R^a$, $—N(R^a)_2$, $—C(O)R^a$, $—C(O)OR^a$, $—C(O)N(R^a)_2$, $—N(R^a)C(O)OR^a$, $—N(R^a)C(O)R^a$, $—N(R^a)S(O)_tR^a$ (where t is 1 or 2), $—S(O)_tOR^a$ (where t is 1 or 2), $—S(O)_tN(R^a)_2$ (where t is 1 or 2), $—PO(R^a)_2$, or $—PO(OR^a)_2$ group. where each $R^a$ is independently hydrogen, alkyl, haloalkyl, cycloalkyl, cycloalkylalkyl, aryl, aralkyl, heterocyclyl, heterocyclylalkyl, heteroaryl or heteroarylalkyl group. In addition, each of the foregoing substituents is optionally substituted with one or more of the above substituents.

The term "optionally substituted", as used herein, means that the referenced group (e.g., alkyl, cycloalkyl, etc.) may or may not be substituted with one or more additional group(s).

As used herein, the term "absent" when used in reference to functional group or substituent, particularly in reference to the chemical structure of a compound, means that the particular functional group or substituent is not present in the compound being described. When used in reference to a substituent (e.g., a pendant group, not a linking group), the absence of the substituent typically means that the bond to the substituent is absent and that absence of the bond is compensated for with a H atom. When used in reference to a position within a chain or ring (e.g., a linking group, not a pendant group), the absence of the position typically means that the two positions otherwise connected by the absent positon are either (1) directly connected by a covalent bond, or (2) not connected, as will either be apparent from the structure or explicitly indicated.

As used herein, the terms "ring system" and "multiring system" refer to a chemical structure or moiety comprising two or more rings that share at least one bond (and two or more atomic positions). For example, a multiring system comprising a cyclohexane and cyclopentane is:

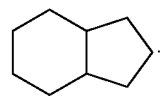

If an aryl or heteroaryl ring is included in a multiring system, the aromaticity of the ring is maintained, unless described otherwise, for example, a multiring system comprising a benzene and cyclohexane is:

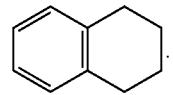

DETAILED DESCRIPTION

Provided herein are small molecules comprising a first domain that binds to ASH1L and a second domain that facilitates ASH1L degradation. In particular, ASH1L-targeting proteolysis targeting chimeras (PROTACs) and methods of use thereof for the treatment of disease (e.g., acute leukemia, solid cancers and other diseases dependent on activity of ASH1L) are provided.

In some embodiments, provided herein are small molecules that directly target the SET domain of ASH1L. In some embodiments, once bound to the SET domain, the compounds described herein block the catalytic activity of ASH1L. In some embodiments, the compounds described bind to and/or recruit agents (e.g., enzymes) to facilitate the degradation of ASH1L. In experiments conducted during development of embodiments herein, small molecule degraders (and/or inhibitors) of ASH1L demonstrated antiproliferative and downregulation of expression of target genes.

In some embodiments, provided herein are bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., acute myeloid leukemia (AML).

Bifunctional compounds such as those that are described in U.S. Patent Application Publications 2015/0291562 and 2014/0356322 (herein incorporated by reference in their entireties), function to recruit endogenous proteins to an E3 ubiquitin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

E3 ubiquitin ligases (of which hundreds are known in humans) confer substrate specificity for ubiquitination, and therefore, are more attractive therapeutic targets than general proteasome inhibitors due to their specificity for certain protein substrates. Recent developments have provided specific ligands which bind to these ligases. For example, since the discovery of nutlins, the first small molecule E3 ligase inhibitors, additional compounds have been reported. For example, since the discovery of Nutlins, the first small molecule E3 ligase mouse double minute 2 homolog (MDM2) inhibitors, additional compounds have been reported that target MDM2 (e.g., human double minute 2 or HDM2) E3 ligases (J. Di, et al. Current Cancer Drug Targets (2011), 11(8), 987-994; herein incorporated by reference in its entirety).

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins.

Inhibitors of Apotosis Proteins (IAPs) are a protein family involved in suppressing apoptosis. The human IAP family includes 8 members, and numerous other organisms contain IAP homologs. IAPs contain an E3 ligase specific domain and baculoviral IAP repeat (BIR) domains that recognize substrates and promote their ubiquitination. IAPs promote ubiquitination.

In some embodiments, provided herein are bifunctional (PROTAC) compounds (e.g., of one of Formulas (Ia-d), (IIa-d), or (IIIa-d), which comprise an E3 ubiquitin ligase ligand (or E3 ligase binding moiety), and a moiety that binds a target protein such that the target protein is placed in proximity to the ubiquitin ligase to effect degradation (inhibition) of that protein. In some embodiments, the Ligase ligand is a Von Hippel-Lindau E3 ubiquitin ligase binding moiety (e.g., hydroxyproline, hydroxyproline derivatives, or binding moieties described in U.S. Patent Application Pub. No. 2014/03022523 (herein incorporated by reference in its entirety)), a cereblon E3 ubiquitin ligase binding moiety (e.g., thalidomide, lenalidomide, pomalidomide, analogs thereof, isosteres thereof, derivatives thereof, or binding moieties described in U.S. Patent Application Publication US 2015/0291562 (herein incorporated by reference in its entirety)), a mouse double minute 2 homolog (MDM2) E3 ubiquitin ligase binding moiety (e.g., binding moieties described in U.S. patent application Ser. No. 15/206,497 (herein incorporated by reference in its entirety)), or an IAP E3 ubiquitin ligase binding moiety. Suitable ligands for binding the aforementioned E3 ubiquitin ligases, as well as other known E3 ubiquitin ligases, are understood in the field and described in, for example, U.S. Pub. Nos. 2015/0291562, 2014/0356322, 2018/0256586, 2018/0228907, 2018/0193470, 2018/0179183, 2018/0134684; 2017/0327469; herein incorporated by reference in their entireties. The compounds and formulas within the scope of embodiments herein are not limited to specific ligase ligand structures described herein, or incorporated by reference, but include ligase ligands understood in the field.

In some embodiments, the compounds described herein find use in the treatment or prevention of disease (e.g., cancer (e.g., leukemia, breast cancer, ovarian cancer, melanoma, prostate cancer, thyroid cancer, or metastasis thereof, muscular dystrophy, liver fibrosis, etc.) and/or the alleviation of symptoms associated therewith. In some embodiments, provided herein are pharmaceutical compositions comprising a compound described and/or within the scope herein. In some embodiments, pharmaceutical compositions comprising a compound described and/or within the scope herein are administered to a subject to treat a disease of condition (e.g., cancer (e.g., leukemia, breast cancer, ovarian cancer, melanoma, prostate cancer, thyroid cancer, or metastasis thereof), muscular dystrophy, liver fibrosis, etc.).

In some embodiments, provided herein are compounds that facilitate/induce ASH1L degradation, the compounds comprising a structure of one or more of Formulas (Ia), (Ib), (IIa), (IIb), (IIa), and/or (IIIb):

[Formula (Ia)]

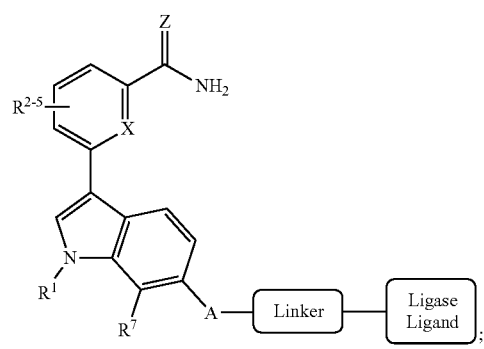

-continued

[Formula (Ib)]

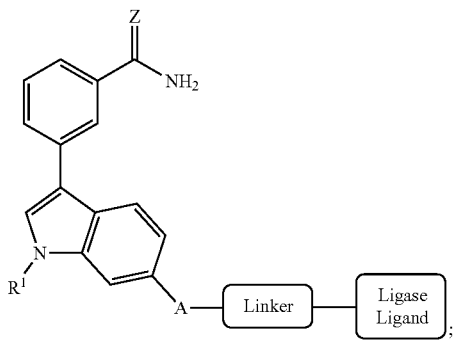

[Formula (IIa)]

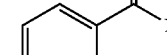

[Formula (IIb)]

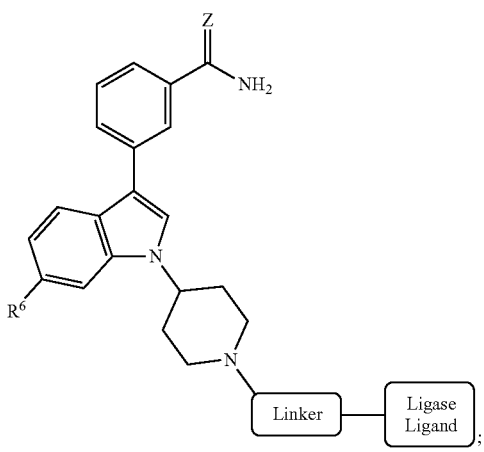

-continued

[Formula (IIIa)]

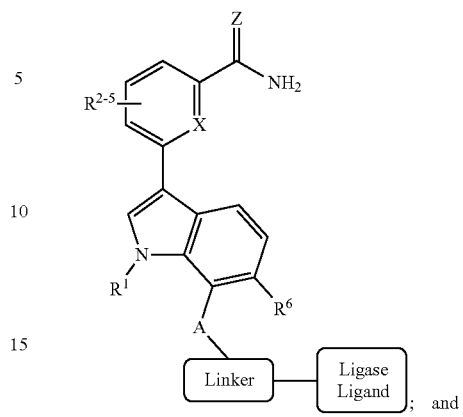
; and

[Formula (IIIb)]

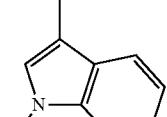
.

In some embodiments, Z is O or S. In some embodiments, Z is S.

In some embodiments, an X group, when present (e.g., in Formulas (Ia), (IIa), and (IIIa), is C (e.g., CH) or N.

In some embodiments, $R^2$, $R^3$, $R^4$, $R^5$, and $R^7$, when present (e.g., when not H), are independently selected from halogen (e.g., Cl, F, Br, I), $CH_3$, OH, SH, $NH_2$, CN, $CF_3$, $CCl_3$, —$CH_2$—$CH_3$, —$CH_2$—OH, —$CH_2NH_2$, $CH_3SH$, $CH_2Cl$, $CH_2Br$, $CH_2F$, $CHF_2$, $CH_2CN$, $CH_2CF_3$, $CH_2Cl_3$, alkyl, haloalkyl, and alcohol.

In some embodiments, $R^1$, when present (e.g., in Formulas (Ia), (Ib), (IIIa), and (IIIb)), is selected from H, alkyl, substituted alkyl, (e.g. halogen substituted alkyl), branched alkyl, a substituted branched alkyl (e.g. halogen substituted branched alkyl) hydroxy, alkoxy, amine, substituted amine, thioalkyl, halogen, ketone, amide, a substituted amide, cyano, sulfonyl, carboxy, dialkylphosphine oxide, a carbocyclic ring, s substituted carbocyclic ring, an aromatic ring, a substituted aromatic ring, a heterocyclic aromatic ring, a substituted heterocyclic aromatic ring, a substituted or non-substituted heterocyclic non-aromatic ring (e.g. piperidine, methylpiperidine, bridged piperidine, tetrahydropyran, alkylsulfonyl substituted piperidine, sulfonamide substituted piperidine, 1-((trifluoromethyl)sulfonyl)piperidine), difluorocyclohexane, monofluorocyclohexane, cyclohexane, substituted difluorocyclohexane, bicyclooctane, cycloheptane, carbocyclic or heterocyclic aromatic ring fused to another aromatic ring, a hydrogen bond donor, a hydrogen bond acceptor, and combinations thereof. In particular embodiments, $R^1$ is selected from the substituents depicted in Table 9 or 12:

TABLE 9
Exemplary R¹ substituents.
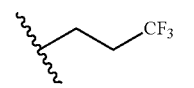 [SMILES: *CCC(F)(F)F]
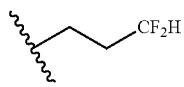
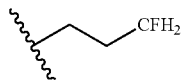
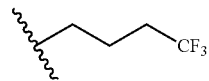 [SMILES: *CCCC(F)(F)F]
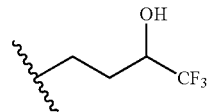 [SMILES: *CCC(O)C(F)(F)F]
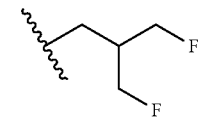 [SMILES: *CC(CF)CF]
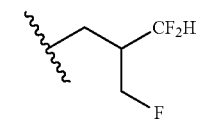
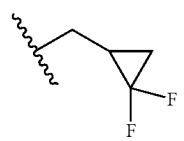 [SMILES: *CC1CC1(F)F]
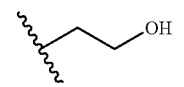 [SMILES: *CCO]
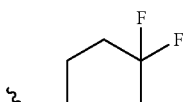
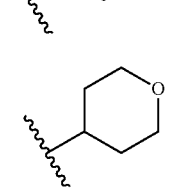
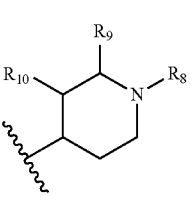
R9, R10 = H, CH₃, F, CFH₂, CF₂H, CF₃, OH
wherein $R^8$, when present in an $R^1$ substituent of Table 9 is selected from the groups depicted in Table 10 or Table 13:
TABLE 10
Exemplary R⁸ substituents.
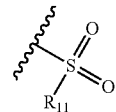
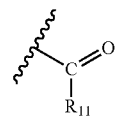
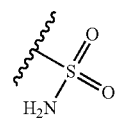
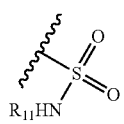
wherein $R^{11}$ is selected from the groups depicted in Table 11:
TABLE 11
Exemplary R¹¹ substituents for the R⁸ substituents of Table 10.
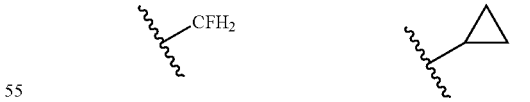

TABLE 12

Exemplary $R^1$ substituents.

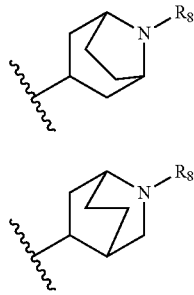

wherein $R^8$, when present in an $R^1$ substituent of Table 9 or 12 is selected from the groups depicted in Table 13:

TABLE 13

Exemplary $R^8$ substituents.

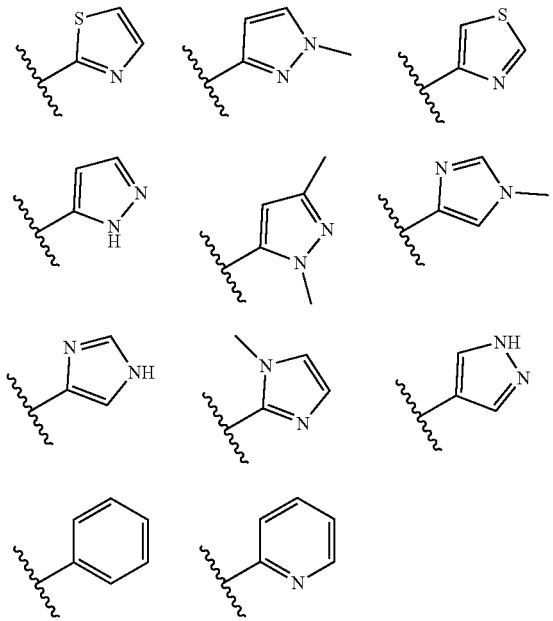

In some embodiments, any of the $R^1$ substituent is one of Formulas (a-q); wherein one of J, $Q^1$, or $J^1$, when present, is linked to the main scaffold; wherein each J, $J^1$, $J^2$, $J^3$, and $J^1$, when present, are independently selected from the group consisting of: a covalent bond, H, alkyl$_{1-15}$, alkenyl$_{1-6}$, alkynyl$_{1-6}$, $(CH_2)_{0-6}C(S)NH_2$, $(CH_2)_{0-6}C(O)NH_2$, O, S, NH, $(CH_2)_{0-4}C(O)NH(CH_2)_{1-6}$, $(CH_2)_{0-6}NHC(O)(CH_2)_{1-6}$, alkylsulfonyl, sulfonamide, alkylsulfonamide, $(CH_2)_{0-6}C(S)NH(CH_2)_{1-6}$, $(CH_2)_{0-6}O(CH_2)_{1-6}$, $(CH_2)_{0-6}OH$, $(CH_2)_{0-6}S(CH_2)_{1-6}$, $(CH_2)_{0-6}SH$, $(CH_2)_{0-6}NH(CH_2)_{1-6}$, $(CH_2)_{0-6}N(CH_2)_{1-6}(CH_2)_{1-6}$, $(CH_2)_{0-6}NH_2$, $(CH_2)_{0-6}SO_2(CH_2)_{1-6}$, $(CH_2)_{0-6}NHSO_2(CH_2)_{1-6}$, $(CH_2)_{0-6}SO_2NH_2$, halogen (e.g., F, Cl, Br, or I), haloalkyl (e.g., $(CH_2)_{0-6}CH_2F$, $(CH_2)_{0-3}CHF(CH_2)_{0-2}CH_3$, or similar with Br, Cl, or I), dihaloalkyl (e.g., $(CH_2)_{0-6}CF_2H$, $(CH_2)_{0-3}CF_2(CH_2)_{0-2}CH_3$, or similar with Br, Cl, or I), trihaloalkyl (e.g., $(CH_2)_{0-6}CF_3$, or similar with Br, Cl, or I), alkyl with 1-3 halogens at two or more positons along its length, $(CH_2)_{1-4}SP(Ph)_2=S$, $(CH_2)_{0-6}NH(CH_2)_{1-5}OH$, $(CH_2)_{0-6}NH(CH_2)_{1-5}NH_2$, $(CH_2)_{0-6}NH(CH_2)_{1-5}SH$, $(CH_2)_{0-6}O(CH_2)_{1-5}OH$, $(CH_2)_{0-6}O(CH_2)_{1-5}NH_2$, $(CH_2)_{0-6}O(CH_2)_{1-5}SH$, $(CH_2)_{0-6}S(CH_2)_{1-5}NH_2$, $(CH_2)_{0-6}S(CH_2)_{1-5}SH$, $(CH_2)_{0-6}O(CH_2)_{1-6}NH(CH_2)_{1-5}OH$, $(CH_2)_{0-6}O(CH_2)_{1-6}NH(CH_2)_{1-5}NH_2$, $(CH_2)_{0-6}O(CH_2)_{1-6}NH(CH_2)_{1-5}SH$, $(CH_2)_{0-6}O(CH_2)_{1-6}O(CH_2)_{1-5}OH$, $(CH_2)_{0-6}O(CH_2)_{1-6}O(CH_2)_{1-5}NH_2$, $(CH_2)_{0-6}O(CH_2)_{1-6}O(CH_2)_{1-5}SH$, $(CH_2)_{0-6}O(CH_2)_{1-6}S(CH_2)_{1-5}OH$, $(CH_2)_{0-6}O(CH_2)_{1-6}S(CH_2)_{1-5}NH_2$, $(CH_2)_{0-6}O(CH_2)_{1-6}S(CH_2)_{1-5}SH$, $(CH_2)_{0-6}S(CH_2)_{1-6}NH(CH_2)_{1-5}OH$, $(CH_2)_{0-6}S(CH_2)_{1-4}NH(CH_2)_{1-5}NH_2$, $(CH_2)_{0-6}S(CH_2)_{1-6}NH(CH_2)_{1-5}SH$, $(CH_2)_{0-6}S(CH_2)_{1-6}O(CH_2)_{1-5}OH$, $(CH_2)_{0-6}S(CH_2)_{1-6}O(CH_2)_{1-5}NH_2$, $(CH_2)_{0-6}S(CH_2)_{1-6}O(CH_2)_{1-5}SH$, $(CH_2)_{0-6}S(CH_2)_{1-6}S(CH_2)_{1-5}OH$, $(CH_2)_{0-6}S(CH_2)_{1-6}S(CH_2)_{1-5}NH_2$, $(CH_2)_{0-6}S(CH_2)_{1-6}S(CH_2)_{1-5}SH$, $(CH_2)_{0-6}NH(CH_2)_{1-6}NH(CH_2)_{1-5}OH$, $(CH_2)_{0-6}NH(CH_2)_{1-6}NH(CH_2)_{1-5}NH_2$, $(CH_2)_{0-6}NH(CH_2)_{1-6}NH(CH_2)_{1-5}SH$, $(CH_2)_{0-6}NH(CH_2)_{1-6}O(CH_2)_{1-5}OH$, $(CH_2)_{0-6}NH(CH_2)_{1-6}O(CH_2)_{1-5}NH_2$, $(CH_2)_{0-6}NH(CH_2)_{1-6}O(CH_2)_{1-5}SH$, $(CH_2)_{0-6}NH(CH_2)_{1-6}S(CH_2)_{1-5}OH$, $(CH_2)_{0-6}NH(CH_2)_{1-6}S(CH_2)_{1-5}NH_2$, $(CH_2)_{0-6}NH(CH_2)_{1-6}S(CH_2)_{1-5}SH$, $(CH_2)_{0-3}C(O)O(CH_2)_{0-3}$, $(CH_2)_{0-3}C(S)O(CH_2)_{0-3}$, $(CH_2)_{0-3}C(O)S(CH_2)_{0-3}$, $(CH_2)_{0-3}C(S)S(CH_2)_{0-3}$, $(CH_2)_{0-3}C(O)NH(CH_2)_{0-3}$, $(CH_2)_{0-3}C(S)NH(CH_2)_{0-3}$, $(CH_2)_{0-3}NHC(O)(CH_2)_{0-3}$, $(CH_2)_{0-3}NHC(S)(CH_2)_{0-3}$, $(CH_2)_{0-3}OC(O)(CH_2)_{0-3}$, $(CH_2)_{0-3}OC(S)(CH_2)_{0-3}$, $(CH_2)_{0-3}SC(O)(CH_2)_{0-3}$, $(CH_2)_{0-3}SC(S)(CH_2)_{0-3}$, $(CH_2)_{0-3}NHC(O)NH(CH_2)_{0-3}$, $(CH_2)_{0-3}NHC(S)NH(CH_2)_{0-3}$, $(CH_2)_{0-3}OC(O)NH(CH_2)_{0-3}$, $(CH_2)_{0-3}OC(S)NH(CH_2)_{0-3}$, $(CH_2)_{0-3}SC(O)NH(CH_2)_{0-3}$, $(CH_2)_{0-3}SC(S)NH(CH_2)_{0-3}$, $(CH_2)_{0-3}NHC(O)O(CH_2)_{0-3}$, $(CH_2)_{0-3}NHC(S)O(CH_2)_{0-3}$, $(CH_2)_{0-3}OC(O)O(CH_2)_{0-3}$, $(CH_2)_{0-3}OC(S)O(CH_2)_{0-3}$, $(CH_2)_{0-3}SC(O)O(CH_2)_{0-3}$, $(CH_2)_{0-3}SC(S)O(CH_2)_{0-3}$, $(CH_2)_{0-3}NHC(O)S(CH_2)_{0-3}$, $(CH_2)_{0-3}NHC(S)S(CH_2)_{0-3}$, $(CH_2)_{0-3}OC(O)S(CH_2)_{0-3}$, $(CH_2)_{0-3}OC(S)S(CH_2)_{0-3}$, $(CH_2)_{0-3}SC(O)S(CH_2)_{0-3}$, $(CH_2)_{0-3}SC(S)S(CH_2)_{0-3}$, $(CH_2O)_{1-6}$, and trimethyl methane; wherein each Q, $Q^1$, and $Q^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), thiadiazole, aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, azetidine morpholine, thiomorpholine, dioxane, dithiane, trioxane, thiethane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, any suitable $C^3$-$C^7$ cycloalkyl group, and any of the ring structures depicted in Table 4; wherein each Q, $Q^1$, and $Q^2$, when present, may display one or more additional J groups at any position on the Q ring; wherein any alkyl or $(CH_2)_{x-y}$ groups above may be straight or branched; wherein any alkyl or $(CH_2)_{x-y}$ groups above may additionally comprise OH, =O, $NH_2$, CN, dihaloalkyl (e.g., $CF_2H$), trihaloalkyl (e.g., $CF_3$), or halogen (e.g., F) substituents at one or more carbons; and wherein the number of hydrogens on terminal positions of the groups above may be adjusted if the group is linked to an additional group (e.g., $CH_3$ adjusted to $CH_2$, OH adjusted to O, etc.) or if the group is terminal (e.g., $CH_2$ adjusted to $CH_3$, O adjusted to OH, etc.).

In some embodiments, $R^6$, when present (e.g., in Formulas (IIa), (IIb), (IIIa), and (IIIb)), is selected from H, alkyl, substituted alkyl, (e.g. halogen substituted alkyl), branched alkyl, a substituted branched alkyl (e.g. halogen substituted branched alkyl) hydroxy, alkoxy, amine, substituted amine, thioalkyl, halogen, ketone, amide, a substituted amide, cyano, sulfonyl, carboxy, dialkylphosphine oxide, a carbocyclic ring, s substituted carbocyclic ring, an aromatic ring, a substituted aromatic ring, a heterocyclic aromatic ring, a substituted heterocyclic aromatic ring, a substituted or non-substituted heterocyclic non-aromatic ring (e.g. piperidine, methylpiperidine, bridged piperidine, tetrahydropyran, alkylsulfonyl substituted piperidine, sulfonamide substituted piperidine), carbocyclic or heterocyclic aromatic ring fused to another aromatic ring, a hydrogen bond donor, a hydrogen bond acceptor, and combinations thereof. In particular embodiments, $R^6$ is selected from the substituents depicted in Table 14:

TABLE 14

Exemplary $R^6$ substituents

| $R^6$ | Additional substituents off $R^6$ |
|---|---|
|  | |
|  | R12 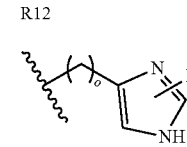<br>o = 0-4; R13 = H, (—CH2)$_{o-8}$CH$_3$ (linear or branched); —NH—(CH$_2$)$_{0-8}$CH$_3$; (—CH$_2$)$_{0-8}$(O)$_{0-1}$(CH$_2$)$_{0-8}$CH$_3$; —NH—(—CH$_2$)$_{0-8}$(O)$_{0-1}$(CH$_2$)$_{0-8}$CH$_3$ |
|  | R14 ;<br>;<br>;<br>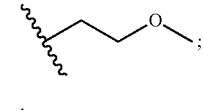;<br> |
| 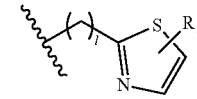 | |

TABLE 14-continued

Exemplary $R^6$ substituents

| $R^6$ | Additional substituents off $R^6$ |
|---|---|
| | 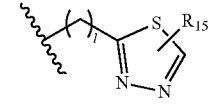<br>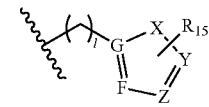<br>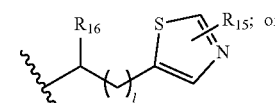 or<br>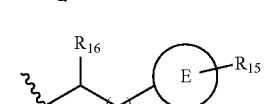<br>X, Y, Z, and F are independently C, S, N, or O<br>G = C, N<br>E is any 5-member heterocycle (see, e.g., the 5 member heterocycles of Table 4).<br>l = 0-4<br>R15 = H, (—CH$_2$)$_{0-8}$CH$_3$ (linear or branched);<br>—NH—(CH$_2$)$_{0-8}$CH$_3$; (—CH$_2$)$_{0-8}$(O)$_{0-1}$(CH$_2$)$_{0-8}$CH$_3$; —NH—(—CH$_2$)0-8(O)$_{0-1}$(CH$_2$)$_{0-8}$CH$_3$<br>R16 = (—CH$_2$)$_{0-8}$CH$_3$ |
|  | |
|  | |
|  | R17 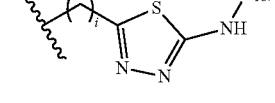<br>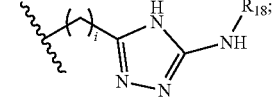<br>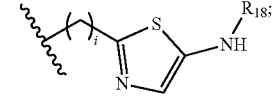<br>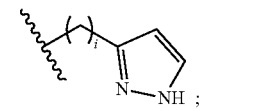 ; |

TABLE 14-continued

Exemplary R⁶ substituents

| R⁶ | Additional substituents off R⁶ |

[structures depicted:
- pyrazole with NHR₁₈
- 5-membered heterocycle G/X/F/Z with NHR₁₈
- R18 = H, (—CH₂)₀₋₈CH₃ (linear or branched); (—CH₂)₀₋₈(O)₀₋₁(CH₂)₀₋₈CH₃; i = 0-4
- amide CH₂NHC(O)R₁₉
- sulfonamide R₁₉NHSO₂
- R19 = —H; —CH₃
- pyrrole with R₂₀
- thiazole with R₂₀
- imidazole with R₂₀
- 5-membered heterocycle G/X/F/Z/Y with R₂₀
- ring E with R₁₆ and R₂₀
- indole with R₂₀
- azetidine with N-R₂₁
- spiro azetidine with N-R₂₁
- azetidine with N-R₂₁]

TABLE 14-continued

Exemplary R⁶ substituents

| R⁶ | Additional substituents off R⁶ |

[pyrrolidine structure with N-R₂₁]

l = 0-4
E is any 5-member heterocycle (see, e.g., the 5 member heterocycles of Table 4).
R20 = H, (—CH₂)₀₋₈CH₃ (could be linear or branched); —NH—(—CH₂)₀₋₈CH₃;
—NH—(—CH₂)₀₋₈(O)₀₋₁(CH₂)₀₋₈CH₃;
(—CH₂)₀₋₈(O)₀₋₁(CH₂)₀₋₈CH₃
R21: H, (—CH₂)₀₋₈CH₃ (linear or branched); (—CH₂)₀₋₈(O)₀₋₁(CH₂)₀₋₈CH₃

In some embodiments, the $R^6$ substituent is one of Formulas (a-q); wherein one of J, $Q^1$, or $J^1$, when present, is linked to the main scaffold; wherein each J, $J^1$, $J^2$, $J^3$, and $J^4$, when present, are independently selected from the group consisting of: a covalent bond, H, alkyl$_{1-15}$, alkenyl$_{1-6}$, alkynyl$_{1-6}$, $(CH_2)_{0-6}C(S)NH_2$, $(CH_2)_{0-6}C(O)NH_2$, O, S, NH, $(CH_2)_{0-6}C(O)NH(CH_2)_{1-6}$, $(CH_2)_{0-6}NHC(O)(CH_2)_{1-6}$, alkylsulfonyl, sulfonamide, alkylsulfonamide, $(CH_2)_{0-6}C(S)NH(CH_2)_{1-6}$, $(CH_2)_{0-6}O(CH_2)_{1-6}$, $(CH_2)_{0-6}OH$, $(CH_2)_{0-6}S(CH_2)_{1-6}$, $(CH_2)_{0-6}SH$, $(CH_2)_{0-6}NH(CH_2)_{1-6}$, $(CH_2)_{0-6}N(CH_2)_{1-6}(CH_2)_{1-6}$, $(CH_2)_{0-6}NH_2$, $(CH_2)_{0-6}SO_2(CH_2)_{1-6}$, $(CH_2)_{0-6}NHSO_2(CH_2)_{1-6}$, $(CH_2)_{0-6}SO_2NH_2$, halogen (e.g., F, Cl, Br, or I), haloalkyl (e.g., $(CH_2)_{0-6}CH_2F$, $(CH_2)_{0-3}CHF(CH_2)_{0-2}CH_3$, or similar with Br, Cl, or I), dihaloalkyl (e.g., $(CH_2)_{0-6}CF_2H$, $(CH_2)_{0-3}CF_2(CH_2)_{0-2}CH_3$, or similar with Br, Cl, or I), trihaloalkyl (e.g., $(CH_2)_{0-6}CF_3$, or similar with Br, Cl, or I), alkyl with 1-3 halogens at two or more positons along its length, $(CH_2)_{1-4}SP(Ph)_2=S$, $(CH_2)_{0-6}NH(CH_2)_{1-5}OH$, $(CH_2)_{0-6}NH(CH_2)_{1-5}NH_2$, $(CH_2)_{0-6}NH(CH_2)_{1-5}SH$, $(CH_2)_{0-6}O(CH_2)_{1-5}OH$, $(CH_2)_{0-6}O(CH_2)_{1-5}NH_2$, $(CH_2)_{0-6}O(CH_2)_{1-5}SH$, $(CH_2)_{0-6}S(CH_2)_{1-5}OH$, $(CH_2)_{0-6}S(CH_2)_{1-5}NH_2$, $(CH_2)_{0-6}S(CH_2)_{1-5}SH$, $(CH_2)_{0-6}O(CH_2)_{1-6}NH(CH_2)_{1-5}OH$, $(CH_2)_{0-6}O(CH_2)_{1-6}NH(CH_2)_{1-5}NH_2$, $(CH_2)_{0-6}O(CH_2)_{1-6}NH(CH_2)_{1-5}SH$, $(CH_2)_{0-6}O(CH_2)_{1-6}O(CH_2)_{1-5}OH$, $(CH_2)_{0-6}O(CH_2)_{1-6}O(CH_2)_{1-5}NH_2$, $(CH_2)_{0-6}O(CH_2)_{1-6}O(CH_2)_{1-5}SH$, $(CH_2)_{0-6}O(CH_2)_{1-6}S(CH_2)_{1-5}OH$, $(CH_2)_{0-6}O(CH_2)_{1-6}S(CH_2)_{1-5}NH_2$, $(CH_2)_{0-6}O(CH_2)_{1-6}S(CH_2)_{1-5}SH$, $(CH_2)_{0-6}S(CH_2)_{1-6}NH(CH_2)_{1-5}OH$, $(CH_2)_{0-6}S(CH_2)_{1-6}NH(CH_2)_{1-5}NH_2$, $(CH_2)_{0-6}S(CH_2)_{1-6}NH(CH_2)_{1-5}SH$, $(CH_2)_{0-6}S(CH_2)_{1-6}O(CH_2)_{1-5}OH$, $(CH_2)_{0-6}S(CH_2)_{1-6}O(CH_2)_{1-5}NH_2$, $(CH_2)_{0-6}S(CH_2)_{1-6}O(CH_2)_{1-5}SH$, $(CH_2)_{0-6}S(CH_2)_{1-6}S(CH_2)_{1-5}OH$, $(CH_2)_{0-6}S(CH_2)_{1-6}S(CH_2)_{1-5}NH_2$, $(CH_2)_{0-6}S(CH_2)_{1-6}S(CH_2)_{1-5}SH$, $(CH_2)_{0-6}NH(CH_2)_{1-6}NH(CH_2)_{1-5}OH$, $(CH_2)_{0-6}NH(CH_2)_{1-6}NH(CH_2)_{1-5}NH_2$, $(CH_2)_{0-6}NH(CH_2)_{1-6}NH(CH_2)_{1-5}SH$, $(CH_2)_{0-6}NH(CH_2)_{1-6}O(CH_2)_{1-5}OH$, $(CH_2)_{0-6}NH(CH_2)_{1-6}O(CH_2)_{1-5}NH_2$, $(CH_2)_{0-6}NH(CH_2)_{1-6}O(CH_2)_{1-5}SH$, $(CH_2)_{0-6}NH(CH_2)_{1-6}S(CH_2)_{1-5}OH$, $(CH_2)_{0-6}NH(CH_2)_{1-6}(CH_2)_{1-5}NH_2$, $(CH_2)_{0-6}NH(CH_2)_{1-6}S(CH_2)_{1-5}SH$, $(CH_2)_{0-3}C(O)O(CH_2)_{0-3}$, $(CH_2)_{0-3}C(S)O(CH_2)_{0-3}$, $(CH_2)_{0-3}C(O)S(CH_2)_{0-3}$, $(CH_2)_{0-3}C(S)S(CH_2)_{0-3}$, $(CH_2)_{0-3}C(O)NH(CH_2)_{0-3}$, $(CH_2)_{0-3}C(S)NH(CH_2)_{0-3}$, $(CH_2)_{0-3}NHC(O)(CH_2)_{0-3}$, $(CH_2)_{0-3}NHC(S)(CH_2)_{0-3}$, $(CH_2)_{0-3}OC(O)(CH_2)_{0-3}$, $(CH_2)_{0-3}OC(S)(CH_2)_{0-3}$, $(CH_2)_{0-3}SC(O)(CH_2)_{0-3}$, $(CH_2)_{0-3}SC(S)(CH_2)_{0-3}$, $(CH_2)_{0-3}NHC(O)NH(CH_2)_{0-3}$, $(CH_2)_{0-3}NHC(S)NH$ (CH$_2$)$_{0-3}$, (CH$_2$)$_{0-3}$OC(O)NH(CH$_2$)$_{0-3}$, (CH$_2$)$_{0-3}$OC(S)NH (CH$_2$)$_{0-3}$, (CH$_2$)$_{0-3}$SC(O)NH(CH$_2$)$_{0-3}$, (CH$_2$)$_{0-3}$SC(S)NH (CH$_2$)$_{0-3}$, (CH$_2$)$_{0-3}$NHC(O)O(CH$_2$)$_{0-3}$, (CH$_2$)$_{0-3}$NHC(S)O (CH$_2$)$_{0-3}$, (CH$_2$)$_{0-3}$OC(O)O(CH$_2$)$_{0-3}$, (CH$_2$)$_{0-3}$OC(S)O (CH$_2$)$_{0-3}$, (CH$_2$)$_{0-3}$SC(O)O(CH$_2$)$_{0-3}$, (CH$_2$)$_{0-3}$SC(S) O(CH$_2$)$_{0-3}$, (CH$_2$)$_{0-3}$NHC(O)S(CH$_2$)$_{0-3}$, (CH$_2$)$_{0-3}$NHC(S) S(CH$_2$)$_{0-3}$, (CH$_2$)$_{0-3}$OC(O)S(CH$_2$)$_{0-3}$, (CH$_2$)$_{0-3}$OC(S)S (CH$_2$)$_{0-3}$, (CH$_2$)$_{0-3}$SC(O)S(CH$_2$)$_{0-3}$, (CH$_2$)$_{0-3}$SC(S) S(CH$_2$)$_{0-3}$, (CH$_2$O)$_{1-6}$, and trimethyl methane; wherein each Q, Q$^1$, and Q$^2$, when present, is independently selected from the group consisting of: furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), thiadiazole, aziridine, thiirane (episulfides), oxirane (ethylene oxide, epoxides), oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, azetidine, morpholine, thiomorpholine, dioxane, dithiane, trioxane, thiethane, azepane, oxepane, thiepane, homopiperazine, azocane, tetrahydropyran, cyclobutene, cyclopentene, cyclohexene, cycloheptene, 1,3-cyclohexadiene, 1,4-cyclohexadiene, 1,5-cyclooctadiene, cyclopropyl, cyclobutyl, cyclopentyl, cyclohexyl, any suitable C$^3$-C$^7$ cycloalkyl group, and any of the ring structures depicted in Table 4; wherein each Q, Q$^1$, and Q$^2$, when present, may display one or more additional J groups at any position on the Q ring; wherein any alkyl or (CH$_2$)$_{x-y}$ groups above may be straight or branched; wherein any alkyl or (CH$_2$)$_{x-y}$ groups above may additionally comprise OH, =O, NH$_2$, CN, dihaloalkyl (e.g., CF$_2$H), trihaloalkyl (e.g., CF$_3$), or halogen (e.g., F) substituents at one or more carbons; and wherein the number of hydrogens on terminal positions of the groups above may be adjusted if the group is linked to an additional group (e.g., CH$_3$ adjusted to CH$_2$, OH adjusted to O, etc.) or if the group is terminal (e.g., CH$_2$ adjusted to CH$_3$, O adjusted to OH, etc.).

In some embodiments, R$^{22}$ and R$^{23}$, when present (e.g., Formula IIa) are independently selected from H, halogen (e.g., Cl, F, Br, I), CH$_3$, OH, SH, NH$_2$, CN, CHF$_2$, CF$_3$, CCl$_3$, —CH$_2$—CH$_3$, —CH$_2$—OH, —CH$_2$NH$_2$, CH$_3$SH, CH$_2$Cl, CH$_2$Br, CH$_2$F, CHF$_2$, CH$_2$CN, CH$_2$CF$_3$, and CH$_2$Cl$_3$.

In some embodiments, an A group, when present (e.g., Formulas (Ia), (Ib), (IIIa), and (IIIb)) is a covalent bond (i.e., no atom present) or is selected from the structures listed in Table 1 (wherein n is 0, 1, 2, or 3).

In some embodiments, the linker, when present (e.g., Formulas (Ia), (Ib), (IIa), (IIb), (IIIa), and (IIIb)), is selected from the structures listed in Tables 2 or 6 (wherein m, when present, is 0, 1, 2, 3, 4 or 5; wherein n, when present, is 0, 1, 2, 3, 4, 5, 6, 7, 8, 9, 10, 11, 12, 13, 14, 15, or ranges therebetween).

In some embodiments, -A-linker, when present (e.g., Formulas (Ia), (Ib), (IIIa), and (IIb)), is selected from the structures listed in Table 5.

In some embodiments, the ligase ligand, when present (e.g., Formulas (Ia), (Ib), (IIa), (IIb), (IIIa), and (IIIb)), is selected from the structures listed in Tables 3 and 7.

In some embodiments, a compound comprises any suitable X, A, R$^1$, R$^2$, R$^3$, R$^4$, R$^5$, R$^6$, R$^7$, A, linker, ligase ligand, R$^8$, R$^9$, R$^{10}$, R$^{11}$, or any other groups or substituents, in any combination, present in the compounds listed in Tables 8 and 9.

In some embodiments, a compound is one of the structures depicted in Tables 8 and 9.

In some embodiments, provided herein are compounds defined by one of Formulas (Ia), (Ib), (IIa), (IIb), (IIIa), and (IIIb), but wherein the benzothioamide (or benzoamide) is linked to the benzene portion of the indole bicyclic structure rather than the pyrrole portion (as is depicted in Formulas (Ia), (Ib), (IIa), (IIb), (IIIa), and (IIIb)). For example, for any Formula (e.g., Formulas (Ia), (Ib), (IIa), (IIb), (IIIa), and (IIIb)) or compound described herein as having benzothioamide-pyrrole or benzoamide-pyrrole ring connectivity, such as:

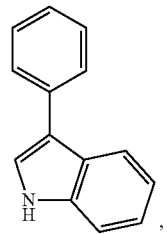

a corresponding Formula (e.g., Formulas (Ic), (Id), (IIc), (Id), (IIc), (IIId), (IVc), and (IVd)) and compound having benzothioamide-benzene benzoamide-benzene ring connectivity, such as:

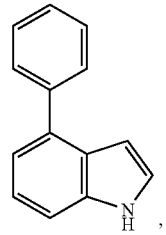 [SMILES: c1ccc(-c2cccc3[nH]ccc23)cc1]

is provided herein and within the scope of embodiments herein. For example, any embodiments, substituents, compounds, etc. described herein in connection with Formula (Ia) may also be provided herein in embodiments in connection with Formula (Ic):

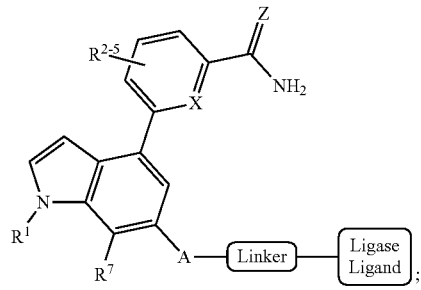

any embodiments, substituents, compounds, etc. described herein in connection with Formula (Ib) may also be provided herein in embodiments related to Formula (Id):

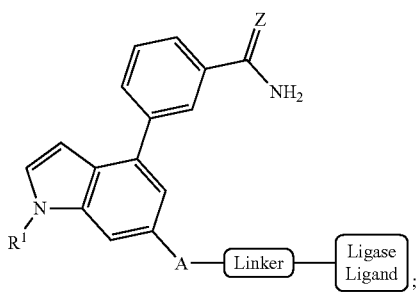

any embodiments, substituents, compounds, etc. described herein in connection with Formula (IIa) may also be provided herein in embodiments related to Formula (IIc):

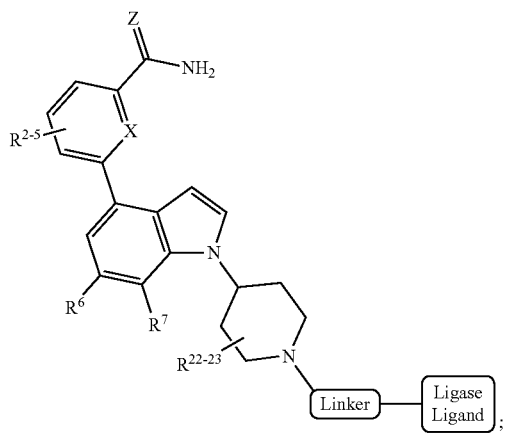

any embodiments, substituents, compounds, etc. described herein in connection with Formula (IIb) may also be provided herein in embodiments related to Formula (IId):

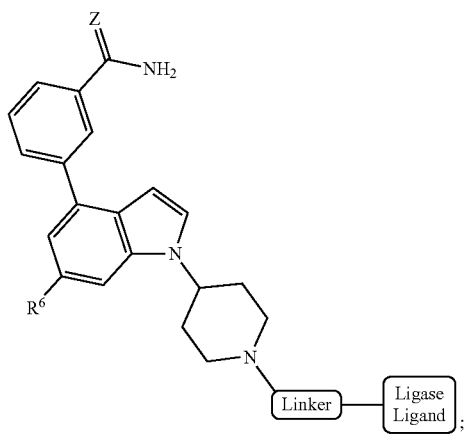

any embodiments, substituents, compounds, etc. described herein in connection with Formula (IIIa) may also be provided herein in embodiments related to Formula (IIIc):

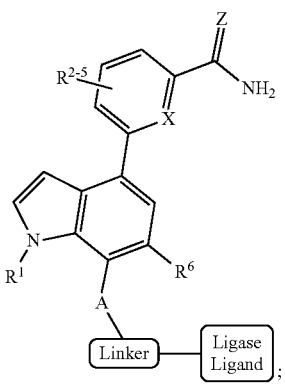

any embodiments, substituents, compounds, etc. described herein in connection with Formula (IIIb) may also be provided herein in embodiments related to Formula (IIId):

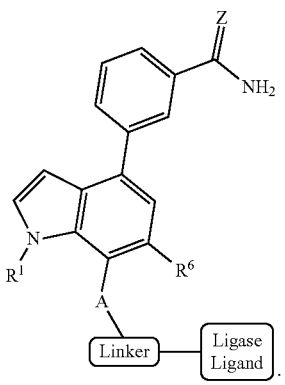

Compounds 86-150 correspond to compounds 21-85 but with the benzothioamide (or benzoamide) is linked to the benzene portion of the indole bicyclic structure rather than the pyrrole portion. For example, compound 86 corresponds to compound 21, but with the benzothioamide (or benzoamide) linked to the benzene portion of the indole bicyclic structure rather than the pyrrole portion; compound 87 corresponds to compound 22, but with the benzothioamide (or benzoamide) is linked to the benzene portion of the indole bicyclic structure rather than the pyrrole portion; compound 88 corresponds to compound 23, but with the benzothioamide (or benzoamide) is linked to the benzene portion of the indole bicyclic structure rather than the pyrrole portion; etc.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by the forming diastereomeric and separation by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In some embodiments, compounds may exist as tautomers. Embodiments comprising all tautomers are included within the formulas described herein.

Unless specified otherwise, divalent variables or groups described herein may be attached in the orientation in which they are depicted or they may be attached in the reverse orientation.

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, etc. The solvated forms of the compounds presented herein are also considered to be disclosed herein.

In some embodiments, compounds or salts described herein may be prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. In some embodiments, by virtue of knowledge of pharmacodynamic processes and drug metabolism in vivo, once a pharmaceutically active compound is determined, prodrugs of the compound are designed. (see, for example, Nogrady (1985) *Medicinal Chemistry A Biochemical Approach,* Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters,* Vol. 4, p. 1985; Rooseboom et al., *Pharmacological Reviews,* 56:53-102, 2004; Miller et al., *J. Med. Chem.* Vol. 46, no. 24, 5097-5116, 2003; Aesop Cho, "Recent Advances in Oral Prodrug Discovery", *Annual Reports in Medicinal Chemistry,* Vol. 41, 395-407, 2006).

The compounds described herein may be labeled isotopically (e.g. with a radioisotope) or by other means, including, but not limited to, the use of chromophores or fluorescent moieties, bioluminescent labels, photoactivatable or chemiluminescent labels, affinity labels (e.g. biotin), degradation tags (e.g. thalidomide conjugates (e.g., compounds 1-91, etc.), VHL ligand conjugates, etc.).

Compounds and salts described herein include isotopically-labeled compounds. In general, isotopically-labeled compounds are identical to those recited in the various formulae and structures presented herein, but for the fact that one or more atoms are replaced by an atom having an atomic mass or mass number different from the atomic mass or mass number most common in nature. Examples of isotopes that can be incorporated into the present compounds include isotopes of hydrogen, carbon, nitrogen, oxygen, fluorine and chlorine, for example, $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

In some embodiments, compounds described herein, such as compounds of any one of Formulas (Ia), (Ib), (IIa), (IIb), (IIIa), and (IIIb), with any suitable substituents and functional groups disclosed herein, are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Pharmaceutical Compositions

In certain embodiments, compounds or salts of any one of Formulas (Ia), (Ib), (IIa), (IIb), (IIIa), and (IIIb), with any suitable substituents and functional groups disclosed herein, are combined with one or more additional agents to form pharmaceutical compositions. Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound or salt of any one of Formulas (Ia), (Ib), (IIa), (IIb), (IIIa), and (IIIb) with any suitable substituents and functional groups disclosed herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds or salts of any one of Formulas (Ia), (Ib), (IIa), (IIb), (IIIa), and (IIIb) with any suitable substituents and functional groups disclosed herein, can be used singly or in combination with one or more therapeutic agents as components of mixtures (as in combination therapy).

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein, which include a compound of any one of Formulas (Ia), (Ib), (IIa), (IIb), (IIIa), and (IIIb) with any suitable substituents and functional groups disclosed herein, can be formulated into any suitable dosage form, including but not limited to, aqueous oral dispersions, liquids, gels, syrups, elixirs, slurries, suspensions, aerosols, fast melt formulations, effervescent formulations, lyophilized formulations, tablets, powders, pills, dragees, and capsules.

One may administer the compounds and/or compositions in a local rather than systemic manner, for example, via injection of the compound directly into an organ or tissue, often in a depot preparation or sustained release formulation. Such long acting formulations may be administered by implantation (for example subcutaneously or intramuscularly) or by intramuscular injection. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of any one of Formulas (Ia), (Ib), (IIa), (IIb), (IIIa), and (IIIb) with any suitable substituents and functional groups disclosed herein, as an active ingredient in free-acid or free-base form, or in a pharmaceutically acceptable salt form.

In certain embodiments, compositions provided herein may also include one or more preservatives to inhibit microbial activity. Suitable preservatives include quaternary ammonium compounds such as benzalkonium chloride, cetyltrimethylammonium bromide and cetylpyridinium chloride.

Pharmaceutical preparations for oral use can be obtained by mixing one or more solid excipients with one or more of the compounds or salts of any one of Formulas (Ia), (Ib), (IIa), (IIb), (IIIa), and (IIIb) with any suitable substituents and functional groups disclosed herein, optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bio-erodible dosage form, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound or salt of any one of Formulas (Ia), (Ib), (IIa), (IIb), (IIIa), and (IIIb) with any suitable substituents and functional groups disclosed herein, with one or more pharmaceutical excipients to form a bulk blend composition. When referring to these bulk blend compositions as homogeneous, it is meant that the particles of the compound or salt of any one of Formulas (Ia), (Ib), (IIa), (IIb), (IIIa), and (IIIb) with any suitable substituents and functional groups disclosed herein, are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

The pharmaceutical solid dosage forms described herein can include a compound of any one of Formulas (Ia), (Ib), (IIa), (IIb), (IIIa), and (IIIb) with any suitable substituents and functional groups disclosed herein, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound or salt of any one of Formulas (Ia), (Ib), (IIa), (IIb), (IIIa), and (IIIb) with any suitable substituents and functional groups disclosed herein, from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. In some embodiments, formulators determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms of the pharmaceutical compositions described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound or salt of any one of Formulas (Ia), (Ib), (IIa), (IIb), (IIIa), and (IIIb) with any suitable substituents and functional groups disclosed herein, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds described herein, which sufficiently isolate the compound from other non-compatible excipients.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound or salt of any one of Formulas (Ia), (Ib), (IIa), (IIb), (IIIa), and (IIIb) with any suitable substituents and functional groups disclosed herein, are solid dispersions. Methods of producing such solid dispersions include, but are not limited to, for example, U.S. Pat. Nos. 4,343,789, 5,340,591, 5,456,923, 5,700,485, 5,723,269, and U.S. patent publication no. 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions include, but are not limited to, for example, U.S. Pat. Nos. 4,151,273, 5,281,420, and 6,083,518.

In some embodiments, pharmaceutical formulations are provided that include particles of the compounds or salt of any one of Formulas (Ia), (Ib), (IIa), (IIb), (IIIa), and (IIIb) with any suitable substituents and functional groups disclosed herein, and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

The pharmaceutical compositions described herein may include sweetening agents such as, but not limited to, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms include, but are not limited to, for example, U.S. Pat. Nos. 5,858,401, 6,667,048, and 6,960, 563.

There is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein.

Potential excipients for intranasal formulations include, for example, U.S. Pat. Nos. 4,476,116, 5,116,817 and 6,391, 452. Formulations solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable non-toxic pharmaceutically acceptable ingredients. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include compounds described herein may be administered using a variety of formulations which include, but are not limited to, U.S. Pat. Nos. 4,229, 447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound is provided essentially throughout. Buccal drug delivery avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, virtually any such carrier can be used, so long as the desired drug release profile is not compromised, and the carrier is compatible with the compounds described herein, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol*, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal formulations described herein may be administered using a variety of devices including but not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound or salt of any one of Formulas (Ia), (Ib), (IIa), (IIb), (IIIa), and (IIb) with any suitable substituents and functional groups disclosed herein; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds described herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally recognized in the field. For other parenteral injections, appropriate formulations may include aqueous or nonaqueous solutions, preferably with physiologically compatible buffers or excipients. Such excipients are generally recognized in the field.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and are formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Generally, an agent, such as a compound of any one of Formulas (Ia), (Ib), (IIa), (IIb), (IIIa), and (IIIb) with any suitable substituents and functional groups disclosed herein, is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

In some embodiments, the compositions described herein are provided as pharmaceutical and/or therapeutic compositions. The pharmaceutical and/or therapeutic compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations for topical administration can include transdermal patches, ointments, lotions, creams, gels, drops, suppositories, sprays, liquids and powders. Conventional carriers; aqueous, powder, or oily bases; thickeners; and the like can be necessary or desirable. Compositions and formulations for oral administration include powders or granules, suspensions or solutions in water or non-aqueous media, capsules, sachets or tablets. Thickeners, flavoring agents, diluents, emulsifiers, dispersing aids or binders can be desirable. Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients. Pharmaceutical and/or therapeutic compositions of the present invention include, but are not limited to, solutions, emulsions, and liposome containing formulations. These compositions can be generated from a variety of components that include, but are not limited to, preformed liquids, self-emulsifying solids and self-emulsifying semisolids.

The pharmaceutical and/or therapeutic formulations, which can conveniently be presented in unit dosage form, can be prepared according to conventional techniques well known in the pharmaceutical/nutriceutical industries. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non-aqueous, oil-based, or mixed media. Suspensions can further contain substances that increase the viscosity of the suspension including, for example, sodium carboxymethylcellulose, sorbitol and/or dextran. The suspension can also contain stabilizers. In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Dosing and administration regimes are tailored by the clinician, or others skilled in the pharmacological arts, based upon well-known pharmacological and therapeutic considerations including, but not limited to, the desired level of therapeutic effect, and the practical level of therapeutic effect obtainable. Generally, it is advisable to follow well-known pharmacological principles for administrating chemotherapeutic agents (e.g., it is generally advisable to not change dosages by more than 50% at time and no more than every 3-4 agent half-lives). For compositions that have relatively little or no dose-related toxicity considerations, and where maximum efficacy is desired, doses in excess of the average required dose are not uncommon. This approach to dosing is commonly referred to as the "maximal dose" strategy. In certain embodiments, the compounds are administered to a subject at a dose of about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone. Dosing may be once per day or multiple times per day for one or more consecutive days.

Methods of Treatment

The present disclosure provides compounds and methods for binding to ASH1L and facilitating degradation of ASH1L protein. In certain embodiments, the disclosure provides compounds that also inhibit ASH1L activity upon binding. A full understanding of the mechanism of ASH1L degradation/inhibition is not required to practice the invention.

Degradation of ASH1L activity may be assessed and demonstrated by a wide variety of ways known in the art. Non-limiting examples include measure (a) a decrease in ASH1L activity; (b) a decrease in cell proliferation and/or cell viability; (c) an increase in cell differentiation; (d) a decrease in the levels of downstream targets of ASH1L activity; and (e) a direct decrease in ASH1L levels, (f) decrease in tumor volume and/or tumor volume growth rate. Kits and commercially available assays can be utilized for determining one or more of the above.

Inhibition of ASH1L activity may be assessed and demonstrated by a wide variety of ways known in the art. Non-limiting examples include measure (a) a direct decrease in ASH1L activity; (b) a decrease in cell proliferation and/or cell viability; (c) an increase in cell differentiation; (d) a decrease in the levels of downstream targets of ASH1L activity; and (e) decrease in tumor volume and/or tumor volume growth rate. Kits and commercially available assays can be utilized for determining one or more of the above.

In some embodiments, it is not necessary to understand the relative contribution of ASH1L degradation and/or inhibition to the overall reduction in ASH1L effect in order to practice the invention.

The disclosure provides compounds and methods for treating a subject suffering from a disease, comprising administering a compound or salt described herein, for example, a compound or salt of any of Formulas (Ia), (Ib), (IIa), (IIb), (IIIa), and (IIIb), with any suitable substituents and functional groups disclosed herein, to the subject. In certain embodiments, the disease is selected from a disease associated with ASH1L expression (e.g., aberrant expression, overexpression, etc.) and/or activity (e.g., cancer). In certain embodiments, the disease is mediated by ASH1L activity and/or expression (e.g., aberrant expression, overexpression, etc.). In certain embodiments, the disease is leukemia, hematologic malignancies, solid tumor cancer, glioma, other cancers, muscular dystrophy, liver fibrosis, etc.

In some embodiments, the disclosure provides a method for treating cancer in a subject, comprising administering a compound or salt described herein, for example, a compound or salt of any of Formulas (Ia), (Ib), (IIa), (IIb), (IIIa), and (IIIb), with any suitable substituents and functional groups disclosed herein, to the subject. In some embodiments, the cancer is mediated by a ASH1L expression (e.g., aberrant expression, overexpression, etc.) and/or activity. In certain embodiments, the cancer is leukemia, breast cancer, prostate cancer, pancreatic cancer, lung cancer, thyroid cancer, liver cancer, skin cancer, or a brain tumor.

In certain embodiments, the disclosure provides method of treating a disease in a subject, wherein the method comprises determining if the subject has an ASH1l-mediated condition (e.g., cancer) and administering to the subject a therapeutically effective dose of a compound or salt described herein, for example, a compound or salt of any one of Formulas (Ia), (Ib), (IIa), (IIb), (IIIa), and (IIIb), with any suitable substituents and functional groups disclosed herein.

In some embodiments, ASH1L expression (e.g., aberrant expression, overexpression, etc.) and/or activity has been identified in hematological malignancies, e.g., cancers that affect blood, bone marrow and/or lymph nodes. Accordingly, certain embodiments are directed to administration of a compound or salt described herein, for example, a compound or salt of any of any one of Formulas (Ia), (Ib), (IIa), (IIb), (IIIa), and (IIIb), with any suitable substituents and functional groups disclosed herein, to a subject with a hematological malignancy. Such malignancies include, but are not limited to, leukemias and lymphomas. For example, the presently disclosed compounds can be used for treatment of diseases such as ALL, AML, Chronic lymphocytic leukemia (CLL), small lymphocytic lymphoma (SLL), Chronic myelogenous leukemia (CML), Acute monocytic leukemia (AMoL), hairy cell leukemia, and/or other leukemias. In certain embodiments, the compounds or salts of the disclosure can be used for treatment of lymphomas such as all subtypes of Hodgkins lymphoma or non-Hodgkins lymphoma.

Determining whether a tumor or cancer expresses (e.g., overexpresses, aberrantly expresses, etc.) ASH1L can be undertaken by assessing the nucleotide sequence encoding ASH1L or by assessing the amino acid sequence of ASH1L. Methods for detecting an ASH1L nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR—SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. Methods for detecting an ASH1L protein are known by those of skill in the art. These methods include, but are not limited to, detection using a binding agent, e.g., an antibody, specific for ASH1L, protein electrophoresis and Western blotting, and direct peptide sequencing.

Methods for determining whether a tumor or cancer expresses (e.g., overexpresses, aberrantly expresses, etc.) ASH1L or is mediated by ASH1L activity can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

In certain embodiments, the disclosure provides a method of inhibiting ASH1L activity in a sample (e.g., by facilitating the degradation of ASH1L, by inhibiting ASH1L activity, by degrading ASH1L and inhibition ASH1L activity, etc.), comprising administering the compound or salt described herein to said sample comprising ASH1L. In some embodiments, the disclosure provides a method of degrading ASH1L protein in a sample, comprising administering the compound or salt described herein to said sample comprising ASH1L.

The disclosure provides methods for treating a disease by administering a compound or salt of any one of Formulas (Ia), (Ib), (IIa), (IIb), (IIIa), and (IIIb), with any suitable substituents and functional groups disclosed herein, to a subject suffering from the disease, wherein the compound binds ASH1L, inhibits ASH1L activity, and/or facilitates degradation of ASH1L by engaging/recruiting the E3 ubiquitin ligase complex. In certain embodiments, the compound covalently binds to ASH1L. In certain embodiments, the compound noncovalently binds to ASH1L. In certain embodiments, the compound covalently binds to the E3 ubiquitin ligase complex. In certain embodiments, the compound noncovalently binds to the E3 ubiquitin ligase complex.

The disclosure also relates to a method of treating a hyperproliferative disorder in a mammal that comprises administering to the mammal a therapeutically effective amount of a compound or salt of any one of Formulas (Ia), (Ib), (IIa), (IIb), (IIIa), and (IIIb), with any suitable substituents and functional groups disclosed herein. In some embodiments, the method relates to the treatment of cancer such as acute myeloid leukemia, cancer in adolescents, adrenocortical carcinoma childhood, AIDS-related cancers, e.g., Lymphoma and Kaposi's Sarcoma, anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, the method relates to the treatment of a non-cancerous hyperproliferative disorder such as benign hyperplasia of the skin, e.g., psoriasis, restenosis, or prostate, e.g., benign prostatic hypertrophy (BPH). In some cases, the method relates to the treatment of leukemia, hematologic malignancy, solid tumor cancer, prostate cancer, e.g., castration-resistant prostate cancer, breast cancer, Ewing's sarcoma, bone sarcoma, primary bone sarcoma, T-cell prolymphocyte leukemia, glioma, glioblastoma, liver cancer, e.g., hepatocellular carcinoma, or diabetes.

Subjects that can be treated with compounds of the invention, or pharmaceutically acceptable salt, ester, prodrug, solvate, tautomer, stereoisomer, isotopologue, hydrate or derivative of the compounds, according to the methods of this invention include, for example, subjects that have been diagnosed as having acute myeloid leukemia, acute myeloid leukemia, cancer in adolescents, adrenocortical carcinoma childhood, AIDS-related cancers, e.g., Lymphoma and Kaposi's Sarcoma, anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, Viral-Induced cancer, leukemia, hematologic malignancy, solid tumor cancer, prostate cancer, castration-resistant prostate cancer, breast cancer, Ewing's sarcoma, bone sarcoma, primary bone sarcoma, T-cell prolymphocyte leukemia, glioma, glioblastoma, hepatocellular carcinoma, liver cancer, or diabetes. In some embodiments subjects that are treated with the compounds of the invention include subjects that have been diagnosed as having a non-cancerous hyperproliferative disorder such as benign hyperplasia of the skin, e.g., psoriasis, restenosis, or prostate, e.g., benign prostatic hypertrophy (BPH).

The invention further provides methods of inhibiting ASH1L activity and/or facilitating degradation of ASH1L by contacting the ASH1L with an effective amount of a compound or salt of any one of Formulas (Ia-d), (IIa-d), and (IIIa-d), with any suitable substituents and functional groups disclosed herein (e.g., by contacting a cell, tissue, or organ that expresses ASH1L). In some embodiments, the invention provides methods of inhibiting ASH1L activity in subject including but not limited to rodents and mammals, e.g., humans, by administering into the subject an effective amount of a compound or salt of any one of Formulas (Ia-d), (IIa-d), and (IIIa-d), with any suitable substituents and functional groups disclosed herein. In some embodiments, the percentage inhibition exceeds 25%, 30%, 40%, 50%, 60%, 70%, 80%, or 90%.

In some embodiments, the disclosure provides methods of inhibiting ASH1L activity and/or inducing degradation of ASH1L in a cell by contacting the cell with an amount of a compound of the invention sufficient to inhibit the activity. In some embodiments, the invention provides methods of inhibiting ASH1L activity in a tissue by contacting the tissue with an amount of a compound or salt of any one of Formulas (Ia-d), (IIa-d), and (IIIa-d), with any suitable substituents and functional groups disclosed herein, sufficient to inhibit the ASH1L activity in the tissue. In some embodiments, the invention provides methods of inhibiting ASH1L activity in an organism (e.g., mammal, human, etc.) by contacting the organism with an amount of a compound or salt of any one of Formulas (Ia-d), (IIa-d), and (IIIa-d), with any suitable substituents and functional groups disclosed herein, sufficient to inhibit the i ASH1L activity in the organism.

The compositions containing the compounds or salts thereof described herein can be administered for prophylactic and/or therapeutic treatments. In therapeutic applications, the compositions are administered to a patient already suffering from a disease, in an amount sufficient to cure or at least partially arrest the symptoms of the disease. Amounts effective for this use will depend on the severity and course of the disease, previous therapy, the patient's health status, weight, and response to the drugs, and the judgment of the treating clinician.

In prophylactic applications, compositions containing the compounds or salts thereof described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating clinician.

In the case wherein the patient's condition does not improve, upon the clinician's discretion the administration of the compounds may be administered chronically, that is, for an extended period of time, including throughout the duration of the patient's life in order to ameliorate or otherwise control or limit the symptoms of the patient's disease.

In the case wherein the patient's status does improve, upon the clinician's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Therapies

Provided herein are methods for combination therapies in which an agent known to modulate other pathways, or other components of the same pathway, or even overlapping sets of target enzymes are used in combination with a compound or salt of any one of Formulas (Ia), (Ib), (IIa), (IIb), (IIIa), and (IIIb), with any suitable substituents and functional groups disclosed herein. In one aspect, such therapy includes but is not limited to the combination of one or more compounds of the invention with chemotherapeutic agents, targeted agents, therapeutic antibodies, and radiation treatment, to provide a synergistic or additive therapeutic effect.

In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving one of the compounds herein, such as a compound or salt of any one of Formulas (Ia), (Ib), (IIa), (IIb), (IIIa), and (IIIb), with any suitable substituents and functional groups disclosed herein, is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis and judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the clinician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound or salt of any one of Formulas (Ia), (Ib), (IIa), (IIb), (IIIa), and (IIIb), with any suitable substituents and functional groups disclosed herein, may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease, and the timing of administering the composition containing a compound can vary. Thus, for example, the compounds can be used as a prophylactic and can be administered continuously to subjects with a propensity to develop conditions or diseases in order to prevent the occurrence of the disease. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Particularly when the compounds and pharmaceutical compositions herein are used for treating cancer, they may be co-administered with one or more chemotherapeutics. Many chemotherapeutics are presently known in the art and can be used in combination with the compounds herein. In some embodiments, the chemotherapeutic is selected from the group consisting of mitotic inhibitors, alkylating agents, anti-metabolites, intercalating antibiotics, growth factor inhibitors, cell cycle inhibitors, enzyme inhibitors, topoisomerase inhibitors, protein-protein interaction inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredepa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

Embodiments herein further relate to methods for using a compound or salt of any of Formulas (Ia-d), (IIa-d), (IIIa-d), with any suitable substituents and functional groups disclosed herein, or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions herein are also used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Other suitable therapeutic agents for coadministration with compounds herein also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated for co-administration with compounds and compositions herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated for co-administration with compounds and compositions herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, Mycobacterium avium complex disease, and leprosy, antifungal agents, antiviral agents including nonretroviral agents and antiretroviral agents.

Examples of therapeutic antibodies that can be combined with a compound herein include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present invention with sorafenib and/or avastin. For treating an endometrial disorder, one may combine a compound of the present invention with doxorubincin, taxotere (taxol), and/or cisplatin (carboplatin). For treating ovarian cancer, one may combine a compound of the present invention with cisplatin (carboplatin), taxotere, doxorubincin, topotecan, and/or tamoxifen. For treating breast cancer, one may combine a compound of the present invention with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present invention with taxotere (taxol), gemcitabine, cisplatin, pemetrexed, Tarceva, PD0325901, and/or avastin.

Further therapeutic agents that can be combined with a compound herein are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein may be used in combination with the agents disclosed herein or other suitable agents, depending on the condition being treated. Hence, in some embodiments the one or more compounds herein will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In some embodiments of the separate administration protocol, a compound of the invention and any of the agents described above are administered a few minutes apart, or a few hours apart, or a few days apart.

In some embodiments, a compound described herein is co-administered with another therapeutic agent effective in treating leukemia and/or other cancers. In some embodiments, a compound described herein is co-administered with one or more therapeutic agents approved for the treatment of Acute Lymphoblastic Leukemia (ALL), for example: ABITREXATE (Methotrexate), ADRIAMYCIN PFS (Doxorubicin Hydrochloride), ADRIAMYCIN RDF (Doxorubicin Hydrochloride), ARRANON (Nelarabine), Asparaginase *Erwinia chrysanthemi*, CERUBIDINE (Daunorubicin Hydrochloride), CLAFEN (Cyclophosphamide), CLOFARABINE, CLOFAREX (Clofarabine), CLOLAR (Clofarabine), Cyclophosphamide, Cytarabine, CYTOSAR-U (Cytarabine), CYTOXAN (Cyclophosphamide), Dasatinib, Daunorubicin Hydrochloride, Doxorubicin Hydrochloride, Erwinaze (Asparaginase *Erwinia chrysanthemi*), FOLEX (Methotrexate), FOLEX PFS (Methotrexate), GLEEVEC (Imatinib Mesylate), ICLUSIG (Ponatinib Hydrochloride), Imatinib Mesylate, MARQIBO (Vincristine Sulfate Liposome), Methotrexate, METHOTREXATE LPF (Methorexate), MEXATE (Methotrexate), MEXATE-AQ (Methotrexate), Nelarabine, NEOSAR (Cyclophosphamide), ONCASPAR (Pegaspargase), Pegaspargase, Ponatinib Hydrochloride, RUBIDOMYCIN (Daunorubicin Hydrochloride), SPRYCEL (Dasatinib), TARABINE PFS (Cytarabine), VINCASAR PFS (Vincristine Sulfate), Vincristine Sulfate, etc.

In some embodiments, a compound described herein is co-administered with one or more therapeutic agents approved for the treatment of Acute Myeloid Leukemia (AML), for example: ADRIAMYCIN PFS (Doxorubicin Hydrochloride), ADRIAMYCIN RDF (Doxorubicin Hydrochloride), Arsenic Trioxide, CERUBIDINE (Daunorubicin Hydrochloride), CLAFEN (Cyclophosphamide), Cyclophosphamide, Cytarabine, CYTOSAR-U (Cytarabine), CYTOXAN (Cyclophosphamide), Daunorubicin Hydrochloride, Doxorubicin Hydrochloride, NEOSAR (Cyclophosphamide), RUBIDOMYCIN (Daunorubicin Hydrochloride), TARABINE PFS (Cytarabine), TRISENOX (Arsenic Trioxide), VINCASAR PFS (Vincristine Sulfate), Vincristine Sulfate, etc.

In some embodiments, a compound described herein is co-administered with one or more therapeutic agents approved for the treatment of Chronic Lymphocytic Leukemia (CLL), for example: Alemtuzumab, AMBOCHLORIN (Chlorambucil), AMBOCLORIN (Chlorambucil), ARZERRA (Ofatumumab), Bendamustine Hydrochloride, CAMPATH (Alemtuzumab), CHLORAMBUCILCLAFEN (Cyclophosphamide), Cyclophosphamide, CYTOXAN (Cyclophosphamide), FLUDARA (Fludarabine Phosphate), Fludarabine Phosphate, LEUKERAN (Chlorambucil), LINFOLIZIN (Chlorambucil), NEOSAR (Cyclophosphamide), Ofatumumab, TREANDA (Bendamustine Hydrochloride), etc.

In some embodiments, a compound described herein is co-administered with one or more therapeutic agents approved for the treatment of Chronic Myelogenous Leukemia (CML), for example: BOSULIF (Bosutinib), Bosutinib, CLAFEN (Cyclophosphamide), Cyclophosphamide, Cytarabine, CYTOSAR-U (Cytarabine), CYTOXAN (Cyclophosphamide), Dasatinib, GLEEVEC (Imatinib Mesylate), ICLUSIG (Ponatinib Hydrochloride), Imatinib Mesylate, NEOSAR (Cyclophosphamide), Nilotinib, Omacetaxine Mepesuccinate, Ponatinib Hydrochloride, SPRYCEL (Dasatinib), SYNRIBO (Omacetaxine Mepesuccinate), TARABINE PFS (Cytarabine), TASIGNA (Nilotinib), etc.

In some embodiments, a compound described herein is co-administered with one or more therapeutic agents approved for the treatment of Meningeal Leukemia, for example: CYTARABINE, CYTOSAR-U (Cytarabine), TARABINE PFS (Cytarabine), etc.

In some embodiments, a compound described herein is co-administered with one or more alkylating agents (e.g., for the treatment of cancer) selected from, for example, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, mitolactol, cisplatin, carboplatin, eptaplatin, lobaplatin, nedaplatin, oxaliplatin, and satraplatin.

In some embodiments, a compound described herein is co-administered with one or more anti-metabolites (e.g., for the treatment of cancer) selected from, for example, methotrexate, 6-mercaptopurineriboside, mercaptopurine, 5-fluorouracil, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosf[iota]te, disodium premetrexed, pentostatin, pelitrexol, raltitrexed, triapine, trimetrexate, vidarabine, vincristine, and vinorelbine;

In some embodiments, a compound described herein is co-administered with one or more hormonal therapy agents (e.g., for the treatment of cancer) selected from, for example, exemestane, Lupron, anastrozole, doxercalciferol, fadrozole, formestane, abiraterone acetate, finasteride, episteride, tamoxifen citrate, fulvestrant, Trelstar, toremifene, raloxifene, lasofoxifene, letrozole, sagopilone, ixabepilone, epothilone B, vinblastine, vinflunine, docetaxel, and paclitaxel;

In some embodiments, a compound described herein is co-administered with one or more cytotoxic topoisomerase inhibiting agents (e.g., for the treatment of cancer) selected from, for example, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, etc.

In some embodiments, a compound described herein is co-administered with one or more anti-angiogenic compounds (e.g., for the treatment of cancer) selected from, for example, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin.

In some embodiments, a compound described herein is co-administered with one or more antibodies (e.g., for the treatment of cancer) selected from, for example, trastuzumab, cetuximab, bevacizumab, rituximab, ticilimumab, ipilimumab, lumiliximab, catumaxomab, atacicept, oregovomab, and alemtuzumab.

In some embodiments, a compound described herein is co-administered with one or more VEGF inhibitors (e.g., for the treatment of cancer) selected from, for example, sorafenib, DAST, bevacizumab, sunitinib, recentin, axitinib, aflibercept, telatinib, brivanib alaninate, vatalanib, pazopanib, and ranibizumab.

In some embodiments, a compound described herein is co-administered with one or more EGFR inhibitors (e.g., for the treatment of cancer) selected from, for example, cetuximab, panitumumab, vectibix, gefitinib, erlotinib, and Zactima.

In some embodiments, a compound described herein is co-administered with one or more HER2 inhibitors (e.g., for the treatment of cancer) selected from, for example, lapatinib, trastuzumab, and pertuzumab; CDK inhibitor is selected from roscovitine and flavopiridol;

In some embodiments, a compound described herein is co-administered with one or more proteasome inhibitors (e.g., for the treatment of cancer) selected from, for example, bortezomib and carfilzomib.

In some embodiments, a compound described herein is co-administered with one or more serine/threonine kinase inhibitors (e.g., for the treatment of cancer), for example, MEK inhibitors and Raf inhibitors such as sorafenib.

In some embodiments, a compound described herein is co-administered with one or more tyrosine kinase inhibitors (e.g., for the treatment of cancer) selected from, for example, dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, trastuzumab and pertuzumab.

In some embodiments, a compound described herein is co-administered with one or more androgen receptor antagonists (e.g., for the treatment of cancer) selected from, for example, nandrolone decanoate, fluoxymesterone, Android, Prostaid, andromustine, bicalutamide, flutamide, apocyproterone, apoflutamide, chlormadinone acetate, Androcur, Tabi, cyproterone acetate, and nilutamide.

In some embodiments, a compound described herein is co-administered with one or more aromatase inhibitors (e.g., for the treatment of cancer) selected from, for example, anastrozole, letrozole, testolactone, exemestane, aminoglutethimide, and formestane.

In some embodiments, a compound described herein is co-administered with one or more other anti-cancer agents including, e.g., alitretinoin, ampligen, atrasentan bexarotene, bortezomib, bosentan, calcitriol, exisulind, fotemustine, ibandronic acid, miltefosine, mitoxantrone, 1-asparaginase, procarbazine, dacarbazine, hydroxycarbamide, pegaspargase, pentostatin, tazaroten, velcade, gallium nitrate, canfosfamide, darinaparsin, and tretinoin. In a preferred embodiment, the compounds of the present disclosure may be used in combination with chemotherapy (e.g., cytotoxic agents), anti-hormones and/or targeted therapies such as other kinase inhibitors, mTOR inhibitors and angiogenesis inhibitors.

In embodiments in which the compounds and pharmaceutical compositions herein are used for the treatment or prevention of non-cancer diseases and/or conditions, the compounds and pharmaceutical compositions herein may be co-administered with therapeutics and/or therapies known in the field to be appropriate for the treatment of such diseases and/or conditions.

Kits

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes a compound or salt of any of Formulas (Ia), (Ib), (IIa), (IIb), (IIIa), and (IIb), with any suitable substituents and functional groups disclosed herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

EXPERIMENTAL

Example 1: Synthesis of N-(3-(3-carbamothioylphenyl)-1-(3-fluoro-2-(fluoromethyl)propyl)-1H-indol-6-yl)-3-(2-(2-(2-((2-(2,6-dioxopiperidin-3-yl)-1,3-dioxoisoindolin-4-yl)oxy)ethoxy)ethoxy)ethoxy)propanamide (Compound 1)

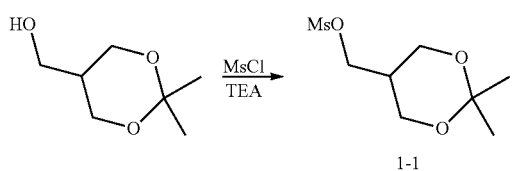

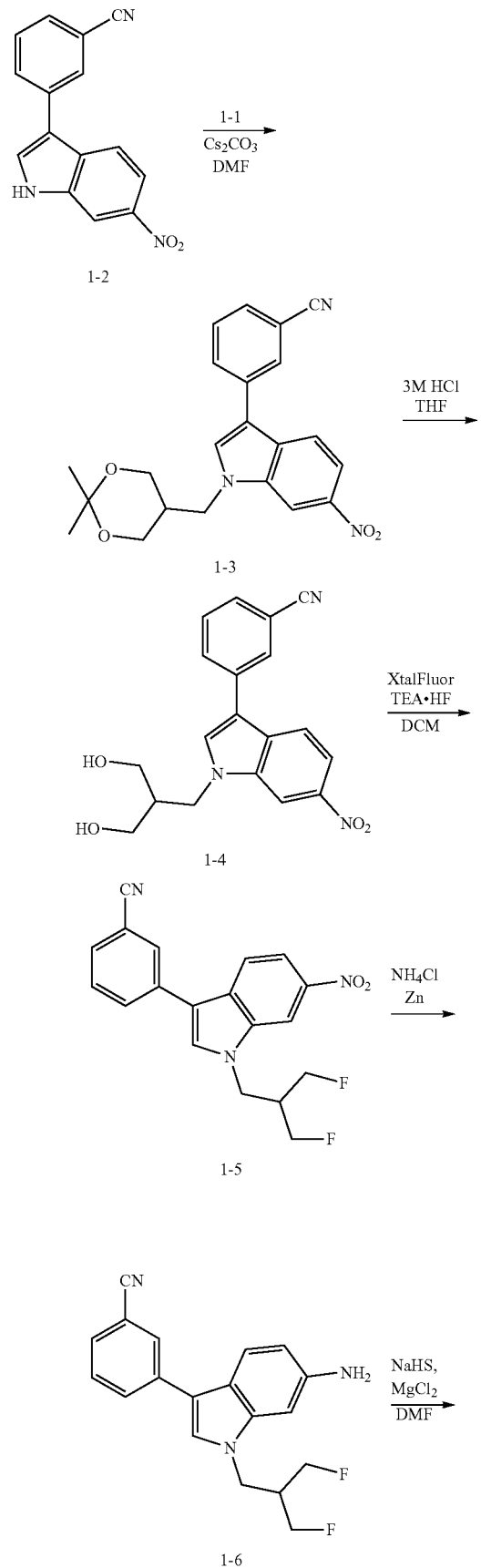

-continued

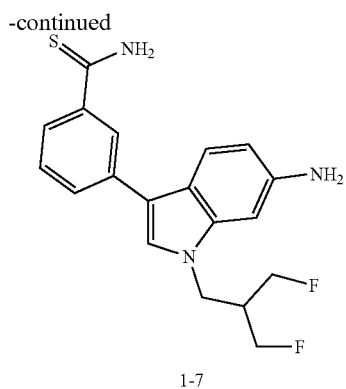

1-7

Step A: Preparation of (2,2-dimethyl-1,3-dioxan-5-yl) methyl methanesulfonate (1-1). Alcohol (50 mg, 0.34 mmol) was dissolved in DCM (0.4 mL). The mixture was cooled in to −78° C. Triethylamine (143 µL, 1 mmol) and methanesulfonyl chloride (32 µL, 0.4 mmol) were added sequentially. The reaction mixture stirred at −78° C.->0° C. After 3 hours, the reaction mixture was transferred to a separatory funnel, diluted with DCM, and washed with sodium bicarbonate. The organic layer was dried over sodium sulfate, filtered, and concentrated. $^1$H NMR (600 MHz, Acetone-$d_6$) δ ppm 1.35 (d, J=2.5 Hz, 3H) 1.42 (d, J=2.9 Hz, 3H) 2.03 (td, J=7.2, 3.3 Hz, 1H) 3.14 (d, J=3.3 Hz, 3H) 3.74-3.83 (m, 2H) 4.04-4.15 (m, 2H) 4.39 (dd, J=7.2, 3.1 Hz, 2H);

Step B: Preparation of 3-(6-nitro-1H-indol-3-yl)benzonitrile (1-2). (3-cyanophenyl)boronic acid (805 mg, 5.5 mmol), 3-bromo-6-nitro-1H-indole (660 mg, 2.7 mmol) Pd$_2$(dba)$_3$ (512 mg 0.6 mmol), tri-t-butyl phosphonium tetrafluoroborate (157 mg, 0.5 mmol) and KF (477 mg, 8.2 mmol) were combined in THF. The mixture was degassed. The reaction was kept under an argon atmosphere and heated to 40° C. The reaction mixture cooled to room temperature and was filtered through a celite pad, which was washed with ethyl acetate (60 mL). The filtrate was concentrated to yield a dark red solid. Purified by column chromatography. $^1$H NMR (600 MHz, ACETONITRILE-$d_3$) δ ppm 7.63-7.71 (m, 2H) 7.93-7.96 (m, 1H) 7.99-8.05 (m, 2H) 8.05-8.09 (m, 2H) 8.47-8.50 (m, 1H) 10.00-10.40 (bs, 1H);

Step C: Preparation of 3-(1-((2,2-dimethyl-1,3-dioxan-5-yl)methyl)-6-nitro-1H-indol-3-yl)benzonitrile (1-3). 3-(6-nitro-1H-indol-3-yl)benzonitrile (540 mg) and cesium carbonate were combined in dry DMF (4 mL). The dark red reaction mixture stirred at room temperature for several minutes. Then suspension of mesylate in DMF (3 mL) was added. The flask stirred under argon, and was heated to 60° C. Water was and compound was extracted by ethyl acetate. Water phase was extracted 2 times with ethyl acetate and combined organic phases were dried over sodium sulfate. After evaporation, crude compound was purified using column chromatography (silica gel, hexane-ethyl acetate). 470 mg (50%) of yellow solid was obtained $^1$H NMR (600 MHz, CDCl$_3$) δ ppm 1.51 (s, 3H) 1.55 (s, 3H) 2.06-2.13 (m, 1H) 3.59 (d, J=11.4 Hz, 2H) 4.13 (dd, J=12.3, 2.8 Hz, 2H) 4.61 (d, J=8.4 Hz, 2H) 7.55-7.67 (m, 3H) 7.86 (d, J=7.7 Hz, 1H) 7.88-7.95 (m, 2H) 8.12 (dd, J=8.8, 2.2 Hz, 1H) 8.46 (d, J=1.5 Hz, 1H); $^{13}$C NMR (150 MHz, CDCl$_3$) δ ppm 19.6, 28.3, 34.8, 46.1, 61.0, 98.9, 107.2, 113.3, 116.1, 116.1, 118.7, 119.6, 129.8, 130.1, 130.2, 130.8, 131.6, 132.0, 135.4, 135.8, 143.7;

Step D: Preparation of 3-(1-(3-hydroxy-2-(hydroxymethyl)propyl)-6-nitro-1H-indol-3-yl)benzonitrile (1-4). 3-(1-((2,2-dimethyl-1,3-dioxan-5-yl)methyl)-6-nitro-1H-indol-3-yl)benzonitrile (350 mg, 0.9 mmol) was dissolved in THF (4.5 mL) and 3M HCl (aq, 0.6 mL) was added. The reaction mixture stirred at room temperature for 1.5 hrs. The mixture was concentrated to remove THF, diluted with water and extracted with several portions of ethyl acetate. The combined organic layers were dried over sodium sulfate, filtered, and concentrated to yield a bright orange solid (280 mg, 89% yield). $^1$H NMR (600 MHz, ACETONITRILE-$d_3$) δ ppm 2.23 (td, J=12.0, 6.1 Hz, 1H) 2.96 (br. s., 2H) 3.51-3.63 (m, 4H) 4.45 (d, J=7.0 Hz, 2H) 7.62-7.72 (m, 2H) 7.96 (m, 1H) 7.99-8.11 (m, 4H) 8.60 (d, J=1.8 Hz, 1H); $^{13}$C NMR (150 MHz, ACETONITRILE-$d_3$) δ ppm 45.5, 46.2, 61.7, 109.1, 114.2, 116.4, 116.7, 120.2, 120.8, 131.1, 131.2, 131.8, 132.9, 135.3, 136.9, 137.4, 144.7;

Step E: Preparation of 3-(1-(3-fluoro-2-(fluoromethyl) propyl)-6-nitro-1H-indol-3-yl)benzonitrile (1-5). To a solution of TEA·HF (93 uL, 0.57 mmol) in dry DCM (0.9 mL), Xtalfluor E (97 mg, 0.42 mmol) was added at 0° C. Then the solution of 3-(1-(3-hydroxy-2-(hydroxymethyl)propyl)-6-nitro-1H-indol-3-yl)benzonitrile (50 mg, 014 mmol) in DCM (0.5 mL) was added dropwise at 0° C. The mixture was stirred for 30 min at 0° C. and 2 h at room temperature. Reaction was then quenched with sat. NaHCO$_3$ and water phase was extracted with DCM and organic phase was dried over sodium sulfate. Volatiles were evaporated and the residue was purified by column chromatography (silica gel, hexane-ethyl acetate) resulting 29 mg of the product (57% yield). $^1$H NMR (600 MHz, DMSO-$d_6$) δ ppm 2.71-2.87 (m, 1H) 4.45-4.52 (m, 1H) 4.53-4.59 (m, 4H) 4.60-4.66 (m, 1H) 7.68-7.73 (m, 1H) 7.78 (d, J=7.7 Hz, 1H) 8.05 (dd, J=8.8, 1.8 Hz, 1H) 8.09 (d, J=8.1 Hz, 1H) 8.13-8.19 (m, 2H) 8.37 (m, 1H) 8.66 (d, J=1.8 Hz, 1H);

Step F: Preparation of 3-(6-amino-1-(3-fluoro-2-(fluoromethyl)propyl)-1H-indol-3-yl)benzonitrile (1-6). To a solution of 3-(1-(3-fluoro-2-(fluoromethyl)propyl)-6-nitro-1H-indol-3-yl)benzonitrile (29 mg, 0.082 mmol) in acetone (1.6 m) water was added (320 µL) followed by ammonium chloride (176 mg) and zinc powder (106 mg). The mixture was stirred for 60 min. Acetone was evaporated, the residue was partitioned between ethyl acetate and conc. ammonia solution. Mixture was filtered through celite and organic phase was dried over MgSO$_4$ and evaporated. Compound was used without further purification for the next step. LR-MS calcd for: [M+H+AcCN]$^+$: 367. found 367.10.

Step G: Preparation of 3-(6-amino-1-(3-fluoro-2-(fluoromethyl)propyl)-1H-indol-3-yl)benzothioamide (1-7). To a solution of 3-(6-amino-1-(3-fluoro-2-(fluoromethyl)propyl)-1H-indol-3-yl)benzonitrile (23 mg, 0.072 mmol) in DMF (0.2 mL) sodium hydrosulfite (60 mg, 1 mmol) and magnesium chloride (101 mg, 0.5 mmol) were added at RT. Mixture was stirred for 2 h. Water was added (0.4 mL) and product was extracted by ethyl acetate (3×5 mL). Organic phase was dried over sodium sulfate and evaporated. Yellow residue was purified using column chromatography (silica gel, hexane-ethyl acetate) affording 10 mg (39%) of thioamide. $^1$H NMR (600 MHz, DMSO-$d_6$) δ ppm 2.50-2.64 (m, 1H) 4.10 (d, J=7.7 Hz, 2H) 4.35-4.53 (m, 4H) 4.88 (s, 2H) 6.48 (dd, J=8.6, 1.7 Hz, 1H) 6.54 (d, J=1.1 Hz, 1H) 7.33-7.39 (m, 2H) 7.53 (d, J=8.4 Hz, 1H) 7.62 (d, J=8.1 Hz, 1H) 7.66 (d, J=8.1 Hz, 1H) 8.05 (m, 1H) 9.47 (br. s., 1H) 9.81 (br. s., 1H); $^{13}$C NMR (150 MHz, DMSO-$d_6$) δ ppm 40.7 (J=18 Hz), 42.2, 80.7, 81.8, 93.4, 110.7, 115.0, 117.0, 119.8, 124.0, 124.2, 128.3, 128.6, 135.4, 138.6, 140.1, 144.8, 200.6 HR-MS [ESI, M+H$^+$] calcd for: C$_{19}$H$_{19}$F$_2$N$_3$S: 360.1346. found: 360.1341

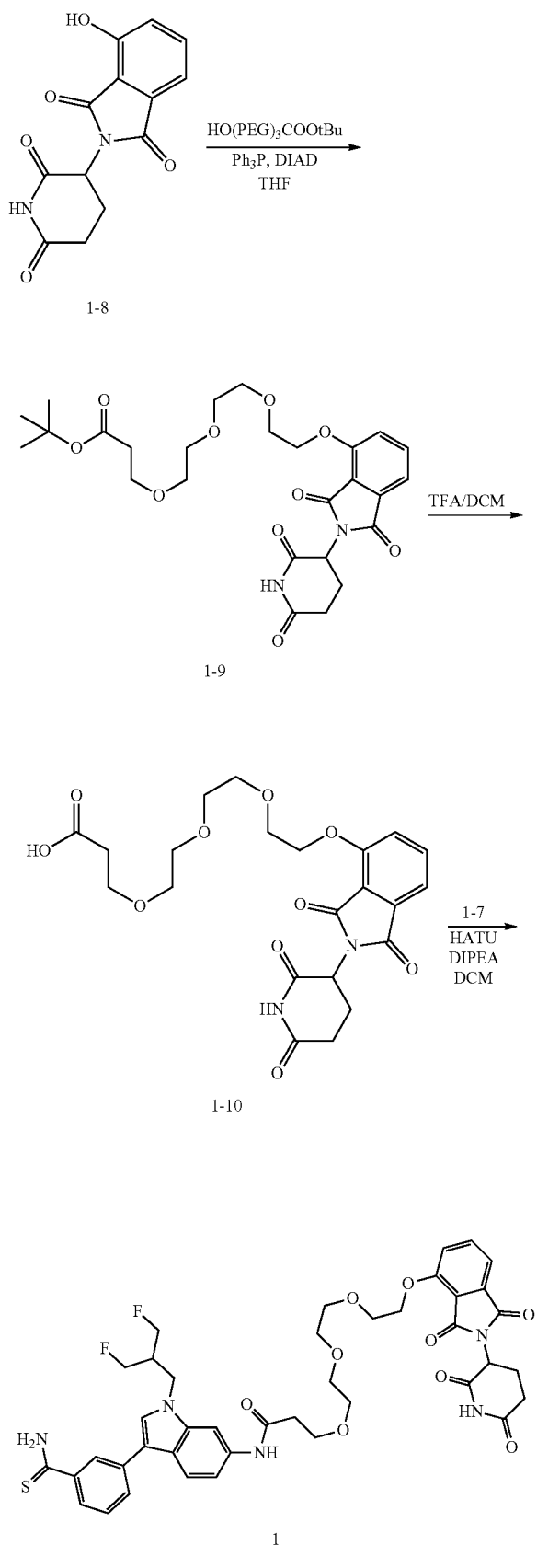

Step H: Preparation of tert-butyl 3-(2-(2-(2-((2-(2,6-dioxopiperidin-3-yl)-1,3-dioxoisoindolin-4-yl)oxy)ethoxy)ethoxy)ethoxy)propanoate. (1-9) tert-Butyl 12-hydroxy-4,7,10-trioxadodecanoate (100 mg, 95 ul, 0.36 mmol, 1 eq) was added to a solution of triphenylphosphine (113 mg, 0.43 mmol, 1.2 eq) in THF (2 ml). The mixture was cooled to 0° C. and DIAD (86 ul, 0.43 mmol, 1.2 eq) in THF (200 uL) was added dropwise. After 15 min 2-(2,6-dioxopiperidin-3-yl)-4-hydroxyisoindoline-1,3-dione (1-8, 99 mg, 0.36 mmol, 1 eq) was added in one portion. The reaction was allowed to warm to room temperature. After 2 h the solvent was removed in vacuo and the residue was purified on column chromatography (silica gel, 12 g cartridge, Hexane:ethyl acetate gradient). Compound was used directly for the next step despite the presence of significant amount of triphenylphosphine oxide.

Step I: Preparation of 3-(2-(2-(2-((2-(2,6-dioxopiperidin-3-yl)-1,3-dioxoisoindolin-4-yl)oxy)ethoxy)ethoxy)ethoxy)propanoic acid (1-10) Compound 1-9 was dissolved in DCM (1 ml) and TFA (500 ul) was added. After 4 hour the reaction was completed. Solvents were evaporated thoroughly and the residue was purified on silica gel column (silica gel, 12 g cartridge, hexane:ethyl acetate gradient). Compound 1-10 was obtained as colorless oil with 56% yield. $^1$H NMR (600 MHz, CHLOROFORM-d) δ 8.84 (br. s., 1H), 7.69 (t, J=7.89 Hz, 1H), 7.48 (d, J=7.34 Hz, 1H), 7.27-7.35 (m, 1H), 4.99 (dd, J=5.32, 12.29 Hz, 1H), 4.37 (t, J=4.77 Hz, 2H), 3.97 (t, J=4.58 Hz, 2H), 3.74-3.85 (m, 4H), 3.62-3.73 (m, 6H), 2.84-2.92 (m, 1H), 2.72-2.84 (m, 2H), 2.57-2.67 (m, 2H), 2.12-2.21 (m, 1H); $^{13}$C NMR (151 MHz, CHLOROFORM-d) δ 174.6, 171.3, 168.7, 167.0, 165.7, 156.5, 136.5, 133.8, 119.5, 117.4, 116.2, 71.2, 70.7, 70.6, 70.3, 69.5, 69.3, 66.4, 49.1, 34.8, 31.3, 22.7;

Step J: Preparation of N-(3-(3-carbamothioylphenyl)-1-(3-fluoro-2-(fluoromethyl)propyl)-1H-indol-6-yl)-3-(2-(2-(2-((2-(2,6-dioxopiperidin-3-yl)-1,3-dioxoisoindolin-4-yl)oxy)ethoxy)ethoxy)ethoxy)-propanamide (1) Compound 1-7(26 mg, 0.08 mmol 1 eq) was added to a solution of acid 1-10 (38.1 mg, 0.08 mmol, 1.1 eq) in DCM (0.6 mL). Then disopropylethylamine (19 μl, 0.1 mmol, 1.2 eq) was added followed by 1-[Bis(dimethylamino)methylene]-1H-1,2,3-triazolo[4,5-b]pyridinium 3-oxide hexafluorophosphate (HATU, 34 mg, 0.08 mmol, 1.1 eq). The mixture was stirred for 15 min and loaded directly on silica gel column (4 g, cartridge). Compound was purified using column chromatography (hexane:ethyl acetate, silica gel, washed at 100% of ethyl acetate). Compound was obtained as yellow solid (54 mg, 77% yield). $^1$H NMR (600 MHz, DMSO-d$_6$) δ 11.06 (s, 1H), 9.96 (s, 1H), 9.84-9.92 (m, 1H), 9.54 (br. s., 1H), 8.15 (s, 1H), 8.02 (s, 1H), 7.83 (d, J=8.44 Hz, 1H), 7.70-7.80 (m, 4H), 7.40-7.51 (m, 3H), 7.23 (d, J=8.44 Hz, 1H), 5.07 (dd, J=5.13, 12.84 Hz, 1H), 4.54-4.61 (m, 1H), 4.47-4.54 (m, 2H), 4.39-4.47 (m, 1H), 4.25-4.33 (m, 4H), 3.75-3.81 (m, 2H), 3.72 (t, J=6.05 Hz, 2H), 3.59-3.63 (m, 2H), 3.51-3.56 (m, 6H), 2.82-2.93 (m, 1H), 2.62-2.76 (m, 1H), 2.53-2.62 (m, 3H), 1.99-2.05 (m, 1H); 13C NMR (151 MHz, DMSO-d$_6$) δ 200.5, 172.7, 169.9, 168.9, 166.8, 165.2, 155.8, 140.2, 136.9, 136.8, 134.8, 134.5, 133.2, 128.8, 128.4, 127.0, 125.0, 124.4, 121.4, 120.0, 119.4, 116.3, 115.3, 115.0, 113.4, 100.5, 81.8, 80.7, 70.1, 69.8, 69.7, 69.6, 68.8, 68.6, 66.7, 59.7, 48.7, 47.7, 37.2, 30.9, 22.0, 20.7, 14.0; HR-MS [M+Na$^+$] m/z calculated for: $C_{41}H_{43}F_2N_5O_9SNa$: 842.2647. found: 842.2637.

Example 2: Synthesis of N-((3-(3-carbamothio-ylphenyl)-1-(tetrahydro-2H-pyran-4-yl)-1H-indol-6-yl)methyl)-3-(2-(2-(2-((2-(2,6-dioxopiperidin-3-yl)-1,3-dioxoisoindolin-4-yl)oxy)ethoxy)ethoxy)ethoxy)propanamide (Compound 2)
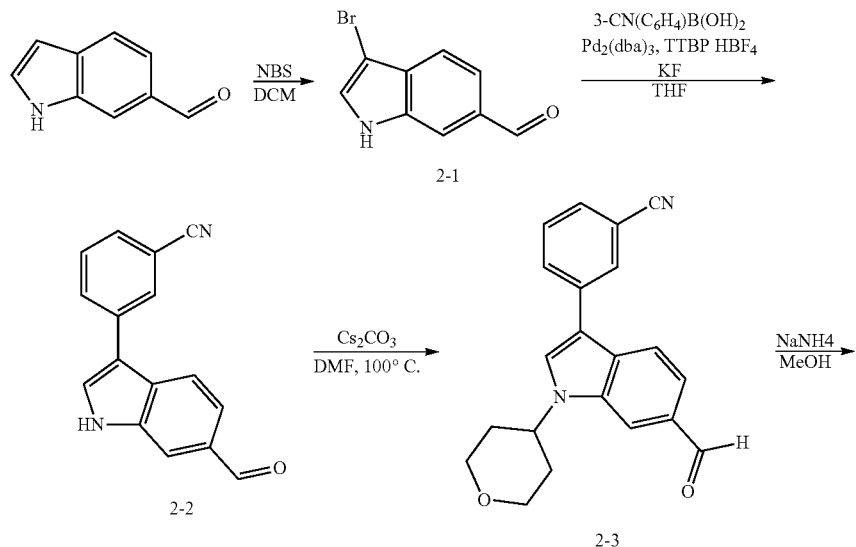
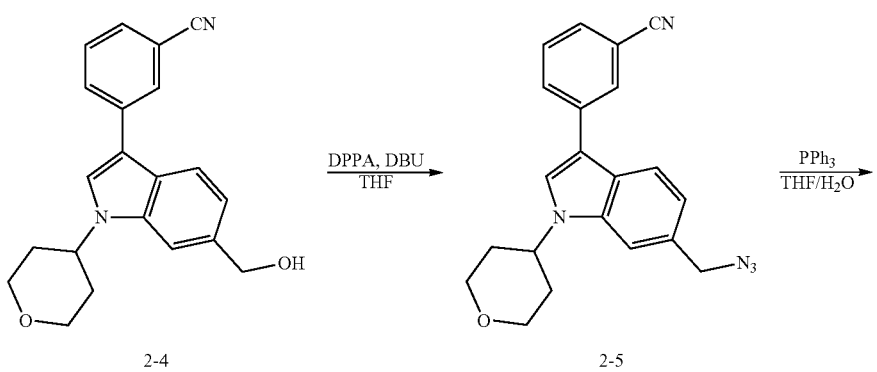
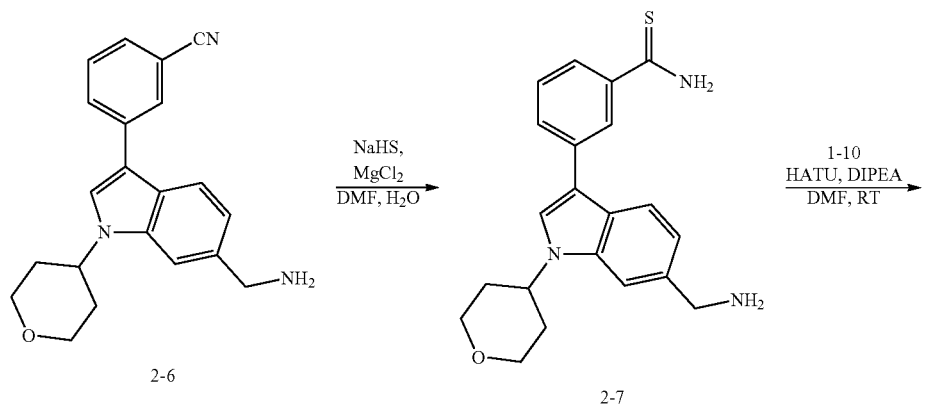

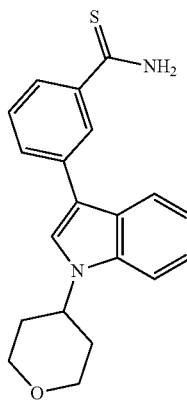

-continued

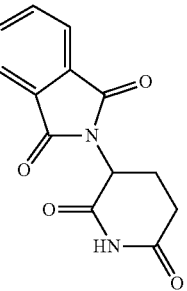

2

Step A: Preparation of 3-bromo-1H-indole-6-carbaldehyde (2-1). To a mixture of 1H-indole-6-carbaldehyde (6 g) in DCM (400 mL) was added NBS (7.36 g). The purple reaction mixture was stirred overnight at room temperature. Water was added to quench the reaction. DCM phase was separated. The water phase was extracted by ethyl acetate. The organic phases were combined and dried with sodium sulfate anhydrous. After filtration and condensation, the crude product was obtained as maroon solid (9221 mg, 100% yield) which was used in the next step directly. $^1$H NMR (400 MHz, CD$_3$OD) δ 9.99 (s, 1H), 7.98 (s, 1H), 7.67 (dd, J=8.0, 1.3 Hz, 1H), 7.59 (m, 2H);

Step B: Preparation of 3-(6-formyl-1H-Indol-3-yl)benzonitrile (2-2). The mixture of 3-bromo-1H-indole-6-carbaldehyde (5000 mg, 22.422 mmol), (3-cyanophenyl)boronic acid (6589 mg, 44.843 mmol), tris(dibenzylideneacetone) dipalladium (0) (2669 mg, 2.915 mmol), tri-tert-butylphosphonium tetrafluoroborate (1952 mg, 6.726 mmol) and anhydrous KF (5211 mg, 89.686 mmol) in anhydrous THF (75 mL) was stirred at 40° C. overnight under argon atmosphere. The mixture was cooled down to room temperature, filtered through celite and washed by ethyl acetate (100 mL). The filtrate was concentrated in vacuo, and the residue (silica gel solid loading) was purified by flash chromatography on silica gel with hexanes and ethyl acetate (0-50%) to give title compound (3 g, 54% yield) as pale yellow solid. $^1$H NMR (400 MHz, CD$_3$OD) δ 10.0 (s, 1H), 8.02 (m, 4H), 7.91 (m, 1H), 7.72 (dd, J=8.0, 1.3 Hz, 1H), 7.62 (m, 2H);

Step C: Preparation of 3-(6-formyl-1-(tetrahydro-2H-pyran-4-yl)-1H-indol-3-yl)benzonitrile (2-3). To an anhydrous DMF solution (5 mL) of 3-(6-formyl-1H-indol-3-yl)benzonitrile (420 mg, 1.707 mmol) at 21° C. was added cesium carbonate (1668 mg, 5.120 mmol) and stirred for 5 min.

Tetrahydro-2H-pyran-4-yl methanesulfonate (1228 mg, 6.826 mmol) was added into the above mixture. The mixture was stirred at 100° C. for 13 hours. Water was added (15 mL) and product was extracted by ethyl acetate (2×20 mL). Organic phase was separated and evaporated to give crude, which was purified by column chromatography (silica gel 12 g, 0-40% ethyl acetate in hexanes) to give product as yellow solid (420 mg, 74% yield). $^1$H NMR (600 MHz, CHLOROFORM-d) δ 10.14 (s, 1H), 8.06 (s, 1H), 7.99 (d, J=8.44 Hz, 1H), 7.92 (s, 1H), 7.88 (d, J=7.70 Hz, 1H), 7.75 (d, J=8.44 Hz, 1H), 7.65 (s, 1H), 7.54-7.62 (m, 2H), 4.62-4.72 (m, 1H), 4.20-4.26 (m, 2H), 3.70 (dt, J=2.57, 11.55 Hz, 2H), 2.12-2.24 (m, 4H);

Step D: Preparation of 3-(6-(hydroxymethyl)-1-(tetrahydro-2H-pyran-4-yl)-1H-indol-3-yl)benzonitrile (2-4). The mixture of 3-(6-formyl-1-(tetrahydro-2H-pyran-4-yl)-1H-indol-3-yl)benzonitrile (310 mg, 0.939 mmol) in methanol (20 mL) and acetonitrile (30 mL) at 0° C. was added sodium borohydride (200 mg, 5.271 mmol). The mixture was stirred at 22° C. for another 5 hours. Aq. NH$_4$Cl was added (5 mL) to quench the reaction. After stirring for 15 mins, the solvent methanol was removed by rotavap. The product was extracted by ethyl acetate (2×20 mL). Organic phase was separated and dried with anhydrous Na$_2$SO$_4$. After filtration and concentration, the crude product (310 mg) was obtained, which was used in the next step directly. LC-MS calcd for: [M–H$_2$O+H]$^+$ 315. found 315.

Step E: Preparation of 3-(6-(azidomethyl)-1-(tetrahydro-2H-pyran-4-yl)-1H-indol-3-yl)benzonitrile (2-5). To a 25-mL round-bottom flask equipped with a magnetic stirrer bar were added 3-(6-(hydroxymethyl)-1-(tetrahydro-2H-pyran-4-yl)-1H-indol-3-yl)benzonitrile (310 mg, 0.933 mmol), diphenylphosphoryl azide (DPPA) (334 mg, 1.213 mmol), and THF (5 mL). After the mixture was stirred at 0° C. for 10 min, 1,8-Diazabicycloundec-7-ene (DBU) (170.5 mg, 1.120 mmol) was added in one portion. The resulting mixture was stirred at room temperature overnight. Aq. NaHCO$_3$ (5 mL) was added. The organic layer was separated and the aqueous layer was extracted with ethyl acetate (10 mL×3). The combined organic layers were washed with water (10 mL×2), dried over anhydrous Na$_2$SO$_4$, filtered, concentrated. The crude was purified by flash chromatography on silica gel (4 g, 0-40% ethyl acetate in hexanes) to give the product as white solid (234 mg, 70% yield). $^1$H NMR (600 MHz, CHLOROFORM-d) δ 7.92 (s, 1H), 7.86-7.91 (m, 2H), 7.52-7.59 (m, 2H), 7.46 (s, 1H), 7.42 (s, 1H), 7.19 (d, J=8.07 Hz, 1H), 4.54-4.58 (m, J=4.77, 4.77 Hz, 1H), 4.52 (s, 2H), 4.19-4.24 (m, 2H), 3.64-3.72 (m, 2H), 2.10-2.22 (m, 4H);

Step F: Preparation of 3-(6-(aminomethyl)-1-(tetrahydro-2H-pyran-4-yl)-1H-indol-3-yl)benzonitrile (2-6). To a solution of the 3-(6-(azidomethyl)-1-(tetrahydro-2H-pyran-4-yl)-1H-indol-3-yl)benzonitrile (234 mg, 0.655 mmol) in THF (6 mL) was added PPh3 (516 mg, 1.966 mmol) at 0° C. The reaction was removed from the ice bath, and water (0.2 mL) was added. The reaction mixture was stirred at room temperature for 18 h. The mixture was acidified to pH=1 with 1N HCl and extracted with EtOAc (100 mL). The aq layer was separated and basified to pH=10 with 1N NaOH. The resulting solution was extracted with EtOAc (30 mL). The organic layer was separated and dried with anhydrous $Na_2SO_4$. After filtration and concentration, the product was obtained as a white solid (210 mg, 97% yield). $^1$H NMR (600 MHz, CHLOROFORM-d) δ 7.93 (s, 1H), 7.81-7.89 (m, 2H), 7.50-7.56 (m, 2H), 7.46 (s, 1H), 7.41 (br. s., OH), 7.19 (d, J=8.07 Hz, 1H), 4.51-4.60 (m, 1H), 4.17-4.23 (m, 2H), 4.06 (s, 2H), 3.67 (t, J=11.55 Hz, 2H), 2.08-2.20 (m, 4H);

Step G: Preparation of 3-(6-(aminomethyl)-1-(tetrahydro-2H-pyran-4-yl)-1H-indol-3-yl)benzothioamide (2-7). To a solution of 3-(6-(aminomethyl)-1-(tetrahydro-2H-pyran-4-yl)-1H-indol-3-yl)benzonitrile (25 mg) in DMF (2 mL) and water (0.1 mL) was added sodium hydrosulfite (200 mg) and magnesium chloride (190 mg) at RT. Mixture was stirred for 18 hours. LCMS indicated that reaction was complete. Water (20 mL) was added and product was extracted by ethyl acetate (2×20 mL). Organic phase was separated and evaporated. The crude was purified using column chromatography (silica gel 4 g, 0~20% methanol (w/5% aq. ammonia solution) in DCM) affording product (25 mg, 91% yield) as yellow solid. $^1$H NMR (600 MHz, Acetone) δ 9.01 (br. s., 1H), 8.92 (br. s., 1H), 8.33 (br. s., 1H), 7.83-7.94 (m, 3H), 7.76-7.83 (m, 1H), 7.63 (s, 1H), 7.44-7.52 (m, 1H), 7.18 (d, J=8.44 Hz, 1H), 4.68-4.79 (m, 1H), 4.58 (s, 2H), 4.06-4.15 (m, 2H), 3.69 (t, J=11.37 Hz, 2H), 3.32 (d, J=4.77 Hz, 1H), 2.13-2.25 (m, 3H);

Step H: Preparation of N-((3-(3-carbamothioylphenyl)-1-(tetrahydro-2H-pyran-4-yl)-1H-indol-6-yl)methyl)-3-(2-(2-(2-((2-(2,6-dioxopiperidin-3-yl)-1,3-dioxoisoindolin-4-yl)oxy)ethoxy)ethoxy)ethoxy)propanamide (2). The mixture of 3-(6-(aminomethyl)-1-(tetrahydro-2H-pyran-4-yl)-1H-indol-3-yl)benzothioamide (25 mg, 0.068 mmol), 3-(2-(2-(2-((2-(2,6-dioxopiperidin-3-yl)-1,3-dioxoisoindolin-4-yl)oxy)ethoxy)ethoxy)ethoxy)propanoic acid (compound 1-10, 36 mg, 0.075 mmol), HATU (42 mg, 0.110 mmol) and DIPEA (24 uL, 0.137 mmol) in DMF (2 mL) was stirred at 22° C. for 1 hour. LCMS indicated desired product formed and the reaction was complete. The reaction mixture was partitioned by acetyl acetate (30 mL) and water (20 mL). The aqueous layer was extracted with EtOAc (10 mL). The organic layer was combined and washed with water and brine. After concentration, the crude was purified by column chromatography (silica gel 4 g, 0~8.8% methanol in DCM) to give product as a yellow solid (20 mg, 36% yield). $^1$H NMR (600 MHz, METHANOL-$d_4$) δ 8.22 (s, 1H), 7.86 (d, J=8.44 Hz, 1H), 7.78 (d, J=7.70 Hz, 1H), 7.71 (d, J=7.70 Hz, 1H), 7.67 (s, 1H), 7.62 (t, J=7.89 Hz, 1H), 7.49 (s, 1H), 7.42 (t, J=7.70 Hz, 1H), 7.34 (d, J=7.34 Hz, 1H), 7.25 (d, J=8.44 Hz, 1H), 7.11 (d, J=8.07 Hz, 1H), 5.03 (dd, J=5.50, 12.47 Hz, 1H), 4.58-4.68 (m, J=8.07, 15.41 Hz, 1H), 4.52 (s, 2H), 4.17 (br. s., 2H), 4.11 (dd, J=2.93, 11.37 Hz, 2H), 3.64-3.79 (m, 6H), 3.48-3.61 (m, 8H), 2.57-2.85 (m, 3H), 2.50 (t, J=5.69 Hz, 2H), 1.98-2.20 (m, 5H); $^{13}$C NMR (151 MHz, METHANOL-$d_4$) δ 204.3, 174.6, 174.0, 171.4, 168.6, 167.3, 157.6, 141.7, 138.0, 137.8, 137.2, 134.9, 133.8, 130.8, 129.5, 127.2, 126.6, 125.1, 124.1, 121.5, 120.9, 120.7, 118.1, 117.2, 116.5, 110.3, 72.0, 71.6, 71.4, 70.3, 68.4, 68.3, 53.4, 50.4, 44.8, 37.9, 34.4, 32.1, 23.6; HR-MS [M+Na$^+$] m/z calculated for: $C_{43}H_{47}N_5O_{10}SNa$: 848.2936. found: 848.2932.

Example 3: Synthesis of N-(3-(3-carbamothioylphenyl)-1-(4,4-difluorocyohexyl)-1H-indol-6-yl)-9-(2-((2-(2,6-dioxopiperidin-3-yl)-1,3-dioxoisoindolin-4-yl)oxy)acetamido)nonanamide (Compound 24)

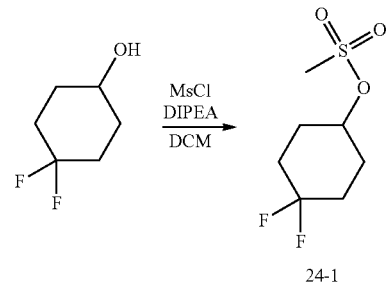

24-1

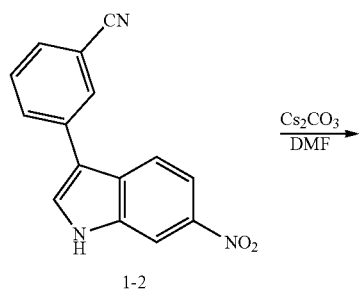

1-2

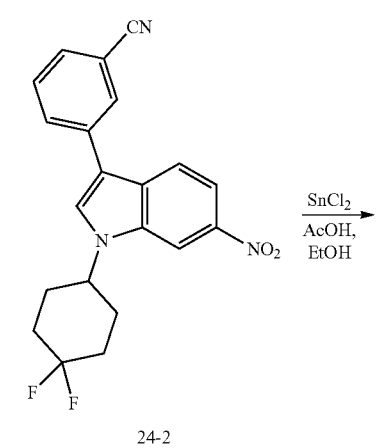

24-2

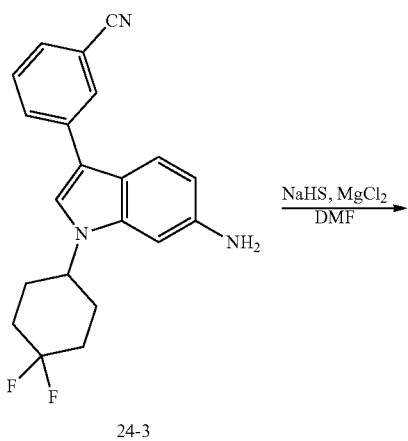

24-3

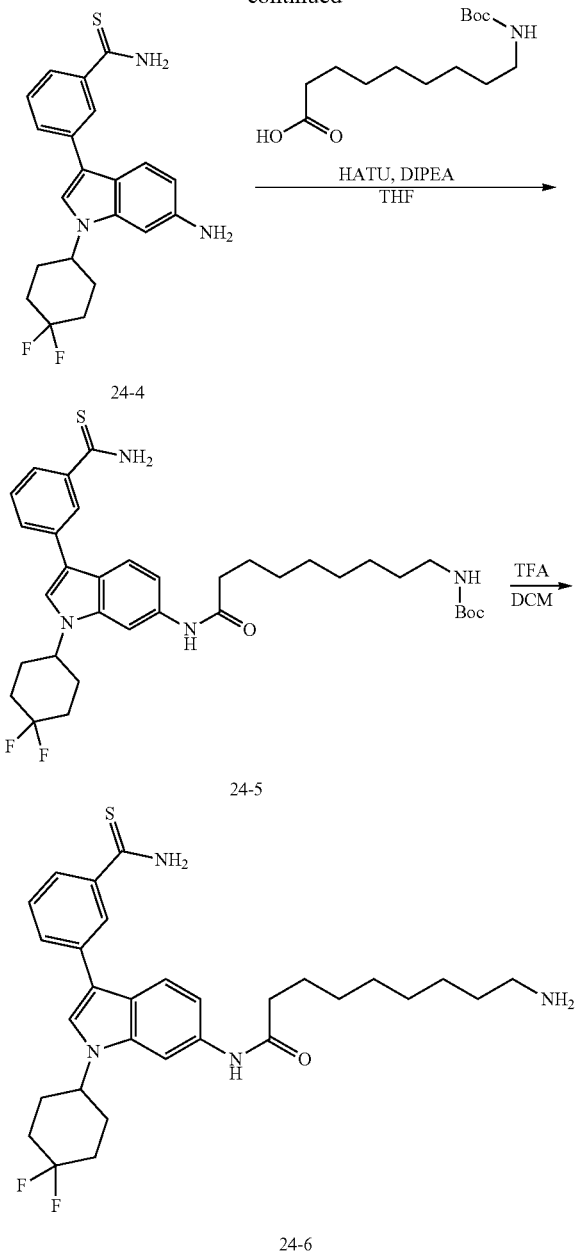

Step A: Preparation of 4,4-difluorocyclohexyl methanesulfonate (24-1). The mixture of 4,4-difluorocyclohexan-1-ol (1000 mg, 7.348 mmol) and DIPEA (2.559 mL, 14.695 mmol) in DCM (30 mL) was added methanesulfonyl chloride (0.853 mL, 11.021 mmol) at 0° C. The reaction mixture was stirred at 22° C. for 24 hours. The mixture was dilute with DCM and quenched with aq. NaHCO₃. After stirred for 5 mins, DCM layer was separated and residue was extracted with DCM (20 mL). Organic layer was washed with water, 0.3 N aq. HCl then conc. aq. NaHCO₃. The organic solution was dried with anhydrous sodium sulfate, separated and concentrated to give product as brown oil. $^1$H NMR (600 MHz, CHLOROFORM-d) δ 4.92 (br. s., 1H), 3.05 (s, 3H), 2.06-2.20 (m, 4H), 1.95-2.00 (m, 4H).

Step B: Preparation of 3-(1-(4,4-difluorocyclohexyl)-6-nitro-1H-indol-3-yl)benzonitrile (24-2). The mixture of 3-(6-nitro-1H-indol-3-yl)benzonitrile (compound 1-2, 600 mg, 2.279 mmol) and cesium carbonate (2970 mg, 9.115 mmol) in dry DMF (9 mL) was stirred at room temperature for several minutes. Then suspension of 4,4-difluorocyclohexyl methanesulfonate (1463 mg, 6.836 mmol) in DMF (1 mL) was added. The flask stirred under argon, and was heated to 100° C. The reaction mixture was stirred at 100° C. for 18 hours. The reaction mixture was partitioned by ethyl acetate (30 mL) and water (10 mL). Organic phase was washed by water for three times. After condensation of organic phase, crude compound was purified by column chromatography (silica gel 12 g, 0~30% ethyl acetate in hexane) to give product (750 mg, 86% yield) as yellow solid. $^1$H NMR (600 MHz, DMSO-$d_6$) δ 8.77 (d, J=2.1 Hz, 1H), 8.59 (s, 1H), 8.23 (s, 1H), 8.13 (d, J=9.0 Hz, 2H), 8.03 (dd, J=8.9, 2.1 Hz, 1H), 7.74 (dt, J=7.6, 1.4 Hz, 1H), 7.67 (t, J=7.8 Hz, 1H), 5.04-4.97 (m, 1H), 2.33-2.07 (m, 8H).

Step C: Preparation of 3-(6-amino-1-(4,4-difluorocyclohexyl)-1H-indol-3-yl)benzonitrile (24-3). To a solution of 3-(1-(4,4-difluorocyclohexyl)-6-nitro-1H-indol-3-yl)benzonitrile (750 mg, 1.968 mmol) in ethanol (500 mL) and acetic acid (10 mL) was added Tin (II) chloride (3731.3 mg, 19.680 mmol). The mixture was stirred at 80° C. for 2 days. The reaction mixture was concentrated under vacuo, diluted by ethyl acetate (50 mL), then basified by con. sodium bicarbonate aq. solution. The mixture was filtered by celite and partitioned by adding water. The organic phase was separated and evaporated. The crude was purified by column chromatography (silica gel 4 g, 0~100% EtOAc in Hexane) to give pure product (370 mg, 54% yield) as yellow oil. $^1$H NMR (600 MHz, DMSO-$d_6$) δ 8.08 (s, 1H), 8.00 (dt, J=6.0, 2.4 Hz, 1H), 7.77 (s, 1H), 7.66-7.51 (m, 3H), 6.70 (d, J=2.3 Hz, 1H), 6.62-6.51 (m, 1H), 4.42 (q, J=8.1 Hz, 1H), 2.13 (dt, J=82.3, 5.0 Hz, 8H).

Step D: Preparation of 3-(6-amino-1-(4,4-difluorocyclohexyl)-1H-indol-3-yl)benzothioamide (24-4). To a solution of 3-(6-amino-1-(4,4-difluorocyclohexyl)-1H-indol-3-yl)benzonitrile in the last step in DMF (3 mL) was added sodium hydrosulfite (210 mg) and magnesium chloride (200 mg) at RT. Mixture was stirred for 2 hours. Water (20 mL) was added and product was extracted by ethyl acetate (2×20 mL). Organic phase was separated and evaporated. The crude was purified by column chromatography (silica gel 4 g, 0~100% ethyl acetate in hexanes) to give product as a yellow oil (200 mg, 91% yield). $^1$H NMR (600 MHz, DMSO-$d_6$) δ 9.85 (s, 1H), 9.49 (s, 1H), 8.11 (t, J=2.0 Hz, 1H), 7.76 (d, J=7.7 Hz, 1H), 7.70 (d, J=7.9 Hz, 1H), 7.62-7.56 (m, 2H), 7.41 (t, J=7.7 Hz, 1H), 6.70 (d, J=2.1 Hz, 1H), 6.55 (dd, J=8.5, 2.0 Hz, 1H), 4.88 (s, 2H), 4.42 (dt, J=11.1, 5.7 Hz, 1H), 2.24-2.01 (m, 8H).

Step E: Preparation of tert-butyl (9-((3-(3-carbamothioylphenyl)-1-(4,4-difluorocyclohexyl)-1H-indol-6-yl)amino)-9-oxononyl)carbamate (24-5). The mixture of 3-(6-amino-1-(4,4-difluorocyclohexyl)-1H-indol-3-yl)benzothioamide (50 mg, 0.130 mmol), 9-((tert-butoxycarbonyl)amino)nonanoic acid (43 mg, 0.156 mmol), HATU (99 mg, 0.259 mmol) and DIPEA (68 uL, 0.389 mmol) in THF (3 mL) was stirred at 25° C. for 2 hours. The reaction mixture was partitioned by acetyl acetate (30 mL) and water (20 mL). The aqueous layer was extracted with EtOAc (10 mL). The organic layer was combined and washed with water and brine. After concentration, the crude was purified by column chromatography (silica gel 4 g, 0-50% ethyl acetate in hexanes) to give product (60 mg, 72% yield) as a yellow oil. $^1$H NMR (600 MHz, Acetone-$d_6$) δ 9.19 (s, 1H), 9.03 (s, 1H), 8.94 (s, 1H), 8.38-8.24 (m, 2H), 7.94-7.84 (m, 3H), 7.78 (d, J=1.5 Hz, 1H), 7.47 (td, J=7.7, 1.5 Hz, 1H), 7.17 (d, J=8.6 Hz, 1H), 5.88 (s, 1H), 4.71-4.57

(m, 1H), 3.07 (q, J=6.7 Hz, 2H), 2.43 (t, J=7.5 Hz, 2H), 2.33-2.17 (m, 8H), 1.75 (p, J=7.4 Hz, 2H), 1.50 (p, J=6.8 Hz, 2H), 1.38 (d, J=32.8 Hz, 17H).

Step F: Preparation of 9-amino-N-(3-(3-carbamothioylphenyl)-1-(4,4-difluorocyclohexyl)-1H-indol-6-yl) nonanamide compound with 2,2,2-trifluoro-1l3-ethan-1-one (24-6). To a solution of tert-butyl (9-((3-(3-cyanophenyl)-1-(4,4-difluorocyclohexyl)-1H-indol-6-yl)amino)-9-oxononyl)carbamate in DCM (15 mL) was added TFA (3 mL) at RT. Mixture was stirred for 3 hours. Volatile reagents were evaporated. The crude was lyophilized to give product (450 mg, 78% yield) as yellow solid as TFA salt. $^1$H NMR (600 MHz, DMSO-d$_6$) δ 9.89 (s, 2H), 9.52 (s, 1H), 8.16 (d, J=1.9 Hz, 1H), 8.10 (d, J=1.8 Hz, 1H), 7.89 (s, 1H), 7.86-7.79 (m, 2H), 7.75 (ddd, J=7.8, 1.9, 1.0 Hz, 1H), 7.60 (s, 4H), 7.46 (t, J=7.7 Hz, 1H), 7.19 (dd, J=8.7, 1.7 Hz, 1H), 4.66-4.45 (m, 1H), 2.84-2.74 (m, 2H), 2.34 (t, J=7.4 Hz, 2H), 2.27-2.05 (m, 8H), 1.72-1.59 (m, 2H), 1.53 (t, J=7.0 Hz, 2H), 1.32 (d, J=9.7 Hz, 8H).

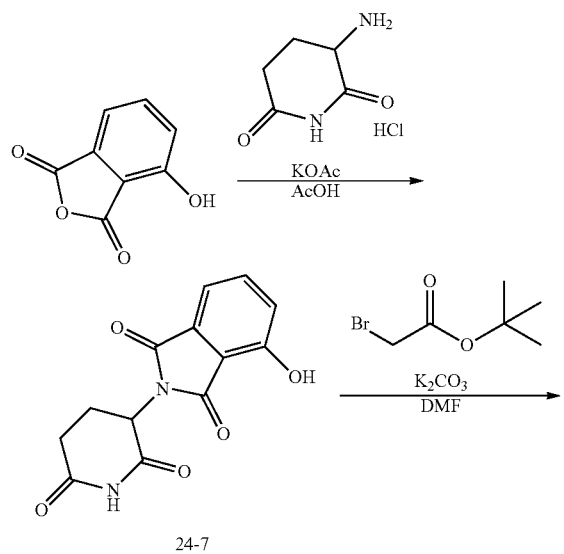

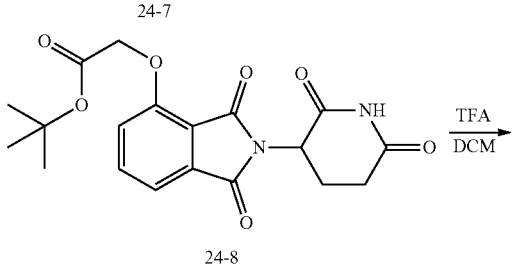

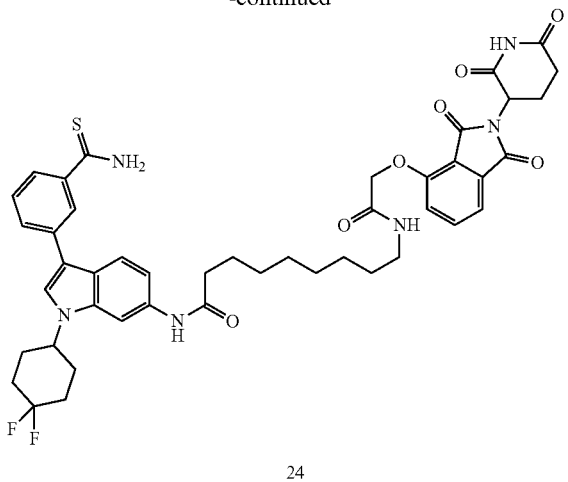

24

Step G: Preparation of 2-(2,6-dioxopiperidin-3-yl)-4-hydroxyisoindoline-1,3-dione (24-7). In a 20 mL glass vial, a mixture of the 4-hydroxyisobenzofuran-1,3-dione (200 mg, 1.220 mmol), Potassium acetate (371 mg, 3.780 mmol) and 3-aminopiperidine-2,6-dione hydrochloride (221 mg, 1.341 mmol) in acetic acid (4 mL) was heated to 90° C. overnight. The black reaction mixture was cooled to room temperature and diluted to 10 mL with water, and subsequently cooled on ice for 30 mins. The resulting slurry was transferred to a 50 mL Falcon tube, which was centrifuged at 3500 rpm for 5 mins. The supernatant was discarded and the black solid was filtered. The solid was washed with water (20 mL) and dried to afford the product as a purple solid (250 mg, 75% yield). $^1$H NMR (600 MHz, DMSO-d$_6$) δ 11.13 (br. s., 1H), 10.96-11.10 (m, 1H), 7.65 (t, J=6.97 Hz, 1H), 7.15-7.40 (m, 2H), 5.07 (dd, J=4.22, 12.29 Hz, 1H), 2.79-2.98 (m, 1H), 2.52-2.66 (m, 2H), 1.94-2.14 (m, 1H). LC-MS calcd for: [M-H]$^-$: 273. found 273.

Step H: Preparation of tert-butyl 2-((2-(2,6-dioxopiperidin-3-yl)-1,3-dioxoisoindolin-4-yl)oxy)acetate (24-8). In a 20 mL glass vial, a mixture of 2-(2,6-dioxopiperidin-3-yl)-4-hydroxyisoindoline-1,3-dione (230 mg, 0.839 mmol) in DMF (4 mL) was added potassium carbonate (174 mg, 1.259 mmol), followed by tert-butyl 2-bromoacetate (163 mg, 0.839 mmol). The mixture was stirred at room temperature for 16 hours. The mixture was diluted with ethyl acetate and washed with water and brine. The organic layer was separated and concentrated. The crude was used in the next step directly. $^1$H NMR (600 MHz, DMSO-d$_6$) δ 11.08 (s, 1H), 7.80 (dd, J=7.34, 8.44 Hz, 1H), 7.48 (d, J=6.97 Hz, 1H), 7.38 (d, J=8.80 Hz, 1H), 5.10 (dd, J=5.50, 12.84 Hz, 1H), 4.96 (s, 2H), 2.84-2.93 (m, 1H), 2.51-2.63 (m, J=17.97 Hz, 2H), 2.01-2.07 (m, 1H).

Step I: Preparation of 2-((2-(2,6-dioxopiperidin-3-yl)-1,3-dioxoisoindolin-4-yl)oxy)acetic acid (24-9). The mixture of tert-butyl 2-((2-(2,6-dioxopiperidin-3-yl)-1,3-dioxoisoindolin-4-yl)oxy)acetate in DCM (2 mL) was added TFA (0.5 mL), which was stirred at 22° C. for 2 hours. The reaction mixture was concentrated under vacuo. The crude was added ethyl acetate, and the precipitate was filtered to give purified product (165 mg, 59% yield over two steps) as white solid. $^1$H NMR (600 MHz, DMSO-d$_6$) δ 13.20 (br. s., 1H), 11.08 (s, 1H), 7.79 (t, J=7.89 Hz, 1H), 7.48 (d, J=7.34 Hz, 1H), 7.39 (d, J=8.80 Hz, 1H), 5.10 (dd, J=5.50, 12.84 Hz, 1H), 4.98 (s, 2H), 2.82-2.95 (m, 1H), 2.52-2.63 (m, 2H), 2.01-2.08 (m, 1H).

Step J: Preparation of N-(3-(3-carbamothioylphenyl)-1-(4,4-difluorocyclohexyl)-1H-indol-6-yl)-9-(2-((2-(2,6-dioxopiperidin-3-yl)-1,3-dioxoisoindolin-4-yl)oxy)acetamido)nonanamide (24). The mixture of 9-amino-N-(3-(3-carbamothioylphenyl)-1-(4,4-difluorocyclohexyl)-1H-indol-6-yl)nonanamide (50 mg, 0.092 mmol), 2-((2-(2,6-dioxopiperidin-3-yl)-1,3-dioxoisoindolin-4-yl)oxy)acetic acid (37 mg, 0.111 mmol), HATU (70 mg, 0.185 mmol) and DIPEA (48 uL, 0.277 mmol) in THF (2 mL) was stirred at 25° C. for 2 hours. The reaction mixture was partitioned by acetyl acetate (30 mL) and water (20 mL). The aqueous layer was extracted with EtOAc (10 mL). The organic layer was combined and washed with water and brine. After concentration, the crude was purified by column chromatography (silica gel 4 g, 0~100% ethyl acetate in hexanes) then reverse phase column chromatography (C18-13 g, 0~80% methanol in water) to give product (13 mg, 17% yield) as a yellow solid. $^1$H NMR (600 MHz, DMSO-$d_6$) δ 11.08 (s, 1H), 9.87 (d, J=7.4 Hz, 2H), 9.52 (s, 1H), 8.14 (s, 1H), 8.11 (s, 1H), 7.90 (t, 1H), 7.88 (s, 1H), 7.84-7.78 (m, 3H), 7.75 (d, J=7.8 Hz, 1H), 7.49 (d, J=7.3 Hz, 1H), 7.45 (t, J=7.7 Hz, 1H), 7.40 (d, J=8.5 Hz, 1H), 7.17 (d, J=8.5 Hz, 1H), 5.11 (dd, J=12.8, 5.4 Hz, 1H), 4.76 (s, 2H), 4.61-4.51 (m, 1H), 3.26-3.22 (m, 1H), 3.15 (q, J=6.3, 5.9 Hz, 2H), 2.96-2.83 (m, 1H), 2.65-2.56 (m, 1H), 2.33 (t, J=7.5 Hz, 2H), 2.28-2.17 (m, 3H), 2.11 (d, J=14.2 Hz, 4H), 1.62 (t, J=10.4 Hz, 2H), 1.45 (d, J=11.2 Hz, 2H), 1.36-1.21 (m, 10H); $^{13}$C NMR (151 MHz, DMSO-$d_6$) δ 200.52, 172.70, 171.01, 169.81, 166.59, 165.50, 155.04, 140.13, 136.89, 136.32, 135.03, 134.27, 133.02, 128.84, 128.34, 124.65, 123.35, 121.35, 120.44, 119.31, 116.86, 116.05, 114.98, 113.69, 100.89, 67.71, 51.78, 48.81, 48.57, 38.30, 36.37, 32.21, 30.92, 28.94, 28.76, 28.66, 28.56, 28.47, 26.25, 25.13, 21.97; HR-MS [M+H$^+$] m/z calculated for: C45H49F2N6O7S: 855.3346. found: 855.3345.

Example 4: Synthesis of N-(3-(3-carbamothioylphenyl)-1-(4,4-difluorocyclohexyl)-1H-indol-6-yl)-9-(3-(2-(2,6-dioxopiperidin-3-yl)-1-oxoisoindolin-4-yl)propanamido)nonanamide (Compound 34)

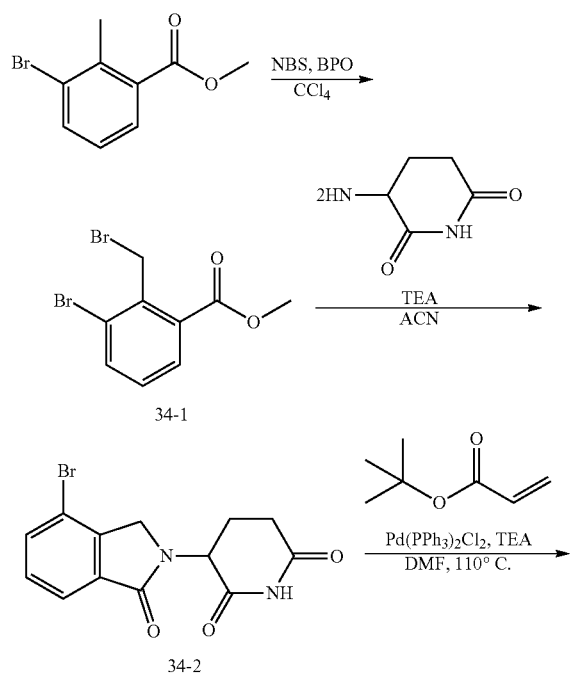

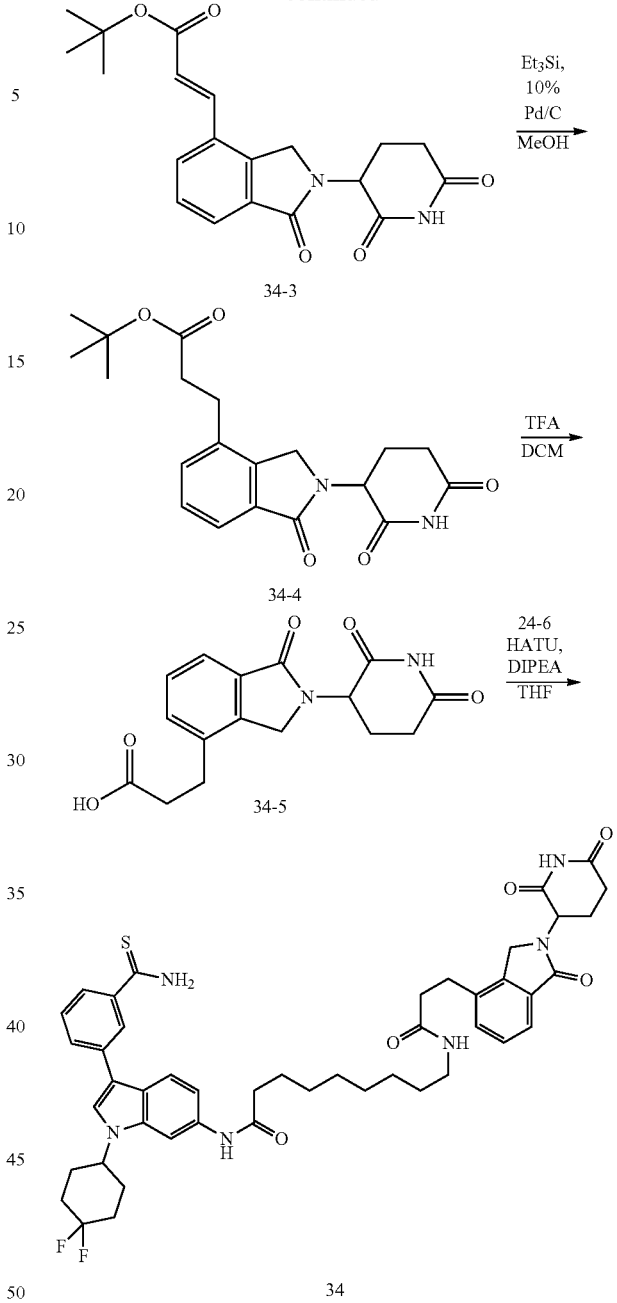

Step A: Preparation of methyl 3-bromo-2-(bromomethyl)benzoate (34-1). Compound 34-2 was prepared according to published procedure in J. Med. Chem. 2018, 61, 462-481. NBS (932 mg, 5.238 mmol, 1.2 equiv) and BPO (106 mg, 0.436 mmol, 0.1 equiv) were added to a stirred solution of methyl 3-bromo-2-methylbenzoate (1 g, 4.365 mmol, 1.0 equiv) in CCl$_4$ (7 mL). The solution was heated at reflux for 6 h. After cooling to room temperature, the solvent was evaporated and the residue was partitioned between ethyl acetate and water. The organic layer was concentrated and purified by flash column chromatography (silica gel 4 g, 0-10% ethyl acetate in hexanes) to afford the desired product (1210 mg, 90% yield) as a colorless oil; $^1$H NMR (600 MHz, Chloroform-d) δ 7.88 (dt, J=7.8, 1.3 Hz, 1H), 7.76 (dt, J=8.1, 1.3 Hz, 1H), 7.23 (td, J=7.9, 1.3 Hz, 1H), 5.13 (s, 2H), 3.96 (s, 3H);

Step B: Preparation of 3-(4-bromo-1-oxoisoindolin-2-yl)piperidine-2,6-dione (34-2). 3-aminopiperidine-2,6-dione (614 mg, 4.793 mmol, 1.22 equiv) and triethylamine (730 uL, 5.225 mmol, 1.33 equiv) were added to a stirred solution of methyl 3-bromo-2-(bromomethyl)benzoate (1210 mg, 3.929 mmol, 1.0 equiv) in MeCN (20 mL). The solution was stirred at 80° C. for 12 h and then cooled to room temperature, and most of the solvent was evaporated. Ethyl acetate (20 mL) and H$_2$O (50 mL) were added to the residue. The mixture was filtered to afford product as a pale purple solid (750 mg, 59% yield); $^1$H NMR (600 MHz, DMSO-d$_6$) δ 10.98 (s, 1H), 7.87 (dd, J=7.9, 0.9 Hz, 1H), 7.77 (dd, J=7.5, 0.9 Hz, 1H), 7.51 (t, J=7.7 Hz, 1H), 5.14 (dd, J=13.3, 5.1 Hz, 1H), 4.42 (d, J=17.5 Hz, 1H), 4.27 (d, J=17.5 Hz, 1H), 2.91 (ddd, J=17.3, 13.7, 5.4 Hz, 1H), 2.63-2.58 (m, 1H), 2.48-2.43 (m, 1H), 2.03 (dtd, J=12.7, 5.3, 2.2 Hz, 1H);

Step C: Preparation of tert-butyl (E)-3-(2-(2,6-dioxopiperidin-3-yl)-1-oxoisoindolin-4-yl)acrylate (34-3). Tert-butyl acrylate (225 uL, 1.548 mmol) and bis(triphenylphosphine)-palladium (II) chloride (22 mg, 0.031 mmol) were heated to reflux in triethylamine (1 mL) and N,N-dimethylformamide (1 mL) for 1 hour. 3-(4-bromo-1-oxoisoindolin-2-yl)piperidine-2,6-dione (100 mg, 0.310 mmol) was added to the mixture and heated at reflux overnight. The reaction mixture was filtered through a bed of celite, washing with ethyl acetate (30 mL). The organic solution was washed with water (2×10 mL), and brine (10 mL). Subsequent drying over Na$_2$SO$_4$ and removal of the solvent in vacuo afforded crude product which was purified by column chromatography using 0-100% EtOAc/hexanes to give product (70 mg, 61% yield) as a yellow solid; $^1$H NMR (600 MHz, DMSO-d$_6$) δ 10.98 (s, 1H), 7.99 (d, J=7.8 Hz, 1H), 7.78 (d, J=7.6 Hz, 1H), 7.65-7.52 (m, 2H), 6.51 (dd, J=16.1, 1.4 Hz, 1H), 5.15 (dd, J=13.4, 5.1 Hz, 1H), 4.69 (d, J=17.6 Hz, 1H), 4.51 (d, J=17.6 Hz, 1H), 2.97-2.88 (m, 1H), 2.62 (d, J=9.1 Hz, 1H), 2.45-2.35 (m, 1H), 2.05-2.00 (m, 1H), 1.50 (s, 9H);

Step D: Preparation of tert-butyl 3-(2-(2,6-dioxopiperidin-3-yl)-1-oxoisoindolin-4-yl)propanoate (34-4). To a stirred solution of tert-butyl (E)-3-(2-(2,6-dioxopiperidin-3-yl)-1-oxoisoindolin-4-yl)acrylate (100 mg, 0.270 mmol) and 10% Pd/C (20 mg) in MeOH (20 mL) was added triethyl silane (430 uL, 2.7 mmol) and the reaction mixture was stirred at RT for 50 min. Subsequently it was filtered through celite and the solvent was removed in vacuo. The crude product was used in the next step directly without purification; $^1$H NMR (600 MHz, DMSO-d$_6$) δ 10.97 (s, 1H), 7.66-7.60 (m, 1H), 7.60-7.54 (m, 1H), 7.50-7.45 (m, 1H), 5.13 (dd, J=13.3, 5.3 Hz, 1H), 4.50 (d, J=17.1 Hz, 1H), 4.35 (d, J=17.1 Hz, 1H), 2.96-2.86 (m, 3H), 2.61 (qd, J=8.0, 3.6 Hz, 3H), 2.44 (qd, J=13.3, 5.2 Hz, 1H), 2.01 (dtd, J=10.3, 5.3, 2.7 Hz, 1H), 1.35 (s, 9H);

Step E: Preparation of (E)-3-(2-(2,6-dioxopiperidin-3-yl)-1-oxoisoindolin-4-yl)acrylic acid (34-5). The mixture of tert-butyl 3-(2-(2,6-dioxopiperidin-3-yl)-1-oxoisoindolin-4-yl)propanoate (compound 34-4) in DCM (2 mL) was added TFA (0.5 mL), which was stirred at 22° C. for 2 hours. The reaction mixture was concentrated under vacuo to give product (165 mg, 59% yield over two steps) as white solid; $^1$H NMR (600 MHz, DMSO-d$_6$) δ 10.99 (s, 1H), 8.00 (d, J=7.7 Hz, 1H), 7.81-7.78 (m, 1H), 7.66-7.54 (m, 2H), 6.55 (d, J=16.2 Hz, 1H), 5.16 (dd, J=13.3, 5.2 Hz, 1H), 4.70 (d, J=17.6 Hz, 1H), 4.51 (d, J=17.6 Hz, 1H), 2.94 (ddd, J=17.3, 13.8, 5.5 Hz, 1H), 2.65-2.59 (m, 2H), 2.02 (dtd, J=12.6, 5.3, 2.3 Hz, 1H);

Step F: Preparation of N-(3-(3-carbamothioylphenyl)-1-(4,4-difluorocyclohexyl)-1H-indol-6-yl)-9-(3-(2-(2,6-dioxopiperidin-3-yl)-1-oxoisoindolin-4-yl)propanamido)nonanamide (34). The mixture of 9-amino-N-(3-(3-carbamothioylphenyl)-1-(4,4-difluorocyclohexyl)-1H-indol-6-yl)nonanamide (50 mg, 0.092 mmol), 3-(2-(2,6-dioxopiperidin-3-yl)-1-oxoisoindolin-4-yl)propanoic acid (35 mg, 0.111 mmol), HATU (42 mg, 0.111 mmol) and DIPEA (50 uL, 0.277 mmol) in THF (2 mL) and DMF (2 mL) was stirred at 0° C. for 10 mins. The reaction mixture was partitioned between ethyl acetate (30 mL) and water (20 mL). The aqueous layer was extracted with ethyl acetate (10 mL). The organic layers were combined and washed with water and brine. After concentration, the crude was purified by column chromatography (silica gel 4 g, 0-10% methanol in DCM) to give product (20 mg, 26% yield) as a yellow solid; $^1$H NMR (600 MHz, Acetonitrile-d$_3$) δ 8.17 (d, J=1.8 Hz, 1H), 8.00 (d, J=1.8 Hz, 1H), 7.79 (d, J=8.6 Hz, 1H), 7.74 (dd, J=7.8, 1.6 Hz, 1H), 7.69 (dd, J=8.1, 1.7 Hz, 1H), 7.63-7.57 (m, 2H), 7.44-7.36 (m, 3H), 7.07 (dd, J=8.5, 1.8 Hz, 1H), 5.08 (dd, J=13.3, 5.2 Hz, 1H), 4.49-4.39 (m, 3H), 3.03 (hept, J=6.6 Hz, 2H), 2.91 (q, J=7.3, 6.5 Hz, 2H), 2.80 (ddd, J=18.4, 13.6, 5.4 Hz, 1H), 2.75-2.66 (m, 1H), 2.50-2.41 (m, 3H), 2.37 (t, J=7.4 Hz, 2H), 2.24-2.01 (m, 9H), 1.69 (p, J=7.6 Hz, 2H), 1.30 (dddt, J=31.8, 24.5, 15.7, 8.4 Hz, 8H), 1.14-1.06 (m, 2H); $^{13}$C NMR (151 MHz, Acetonitrile-d$_3$) δ 204.26, 174.65, 174.60, 174.53, 172.08, 171.70, 142.23, 141.68, 138.09, 137.43, 137.07, 134.77, 133.31, 132.71, 130.82, 129.71, 129.55, 127.09, 125.24, 124.19, 123.82, 122.55, 120.84, 117.46, 115.32, 103.13, 61.53, 54.07, 53.65, 49.85, 40.31, 38.04, 37.19, 33.91 (t, J=25.0 Hz), 32.35, 30.22, 30.15, 30.10, 30.08-29.87 (m), 28.79, 27.67, 26.93, 24.13, 20.84, 14.45; HR-MS [M+Na$^+$] m/z calculated for: C$_{46}$H$_{53}$F$_2$N$_6$O$_5$S: 839.3761. found: 839.3757.

Example 5: Synthesis of N-(3-(3-carbamothioylphenyl)-1-(4,4-difluorocyclohexyl)-1H-indol-6-yl)-3-((6-((2-(2,6-dioxopiperidin-3-yl)-1,3-dioxoisoindolin-4-yl)oxy)hexyl)oxy)propanamide (Compound 41)

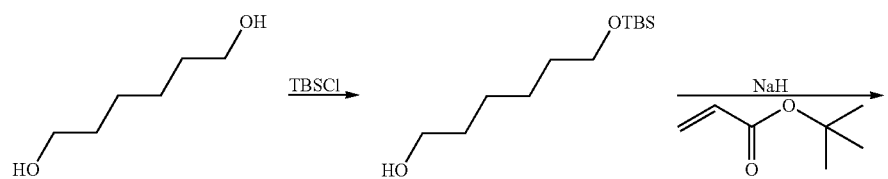

41-1

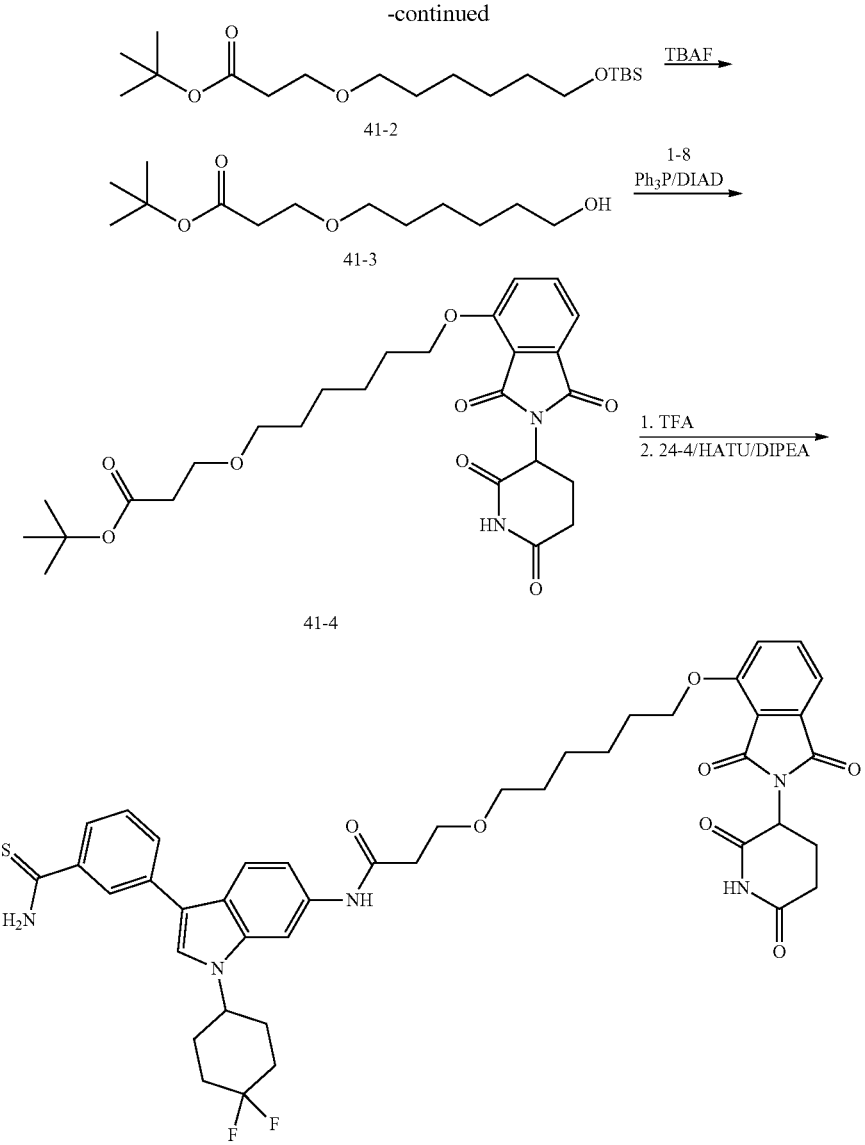

Step A: Preparation of 6-((tert-butyldimethylsilyl)oxy)hexan-1-ol (41-1). Hexan-1,6-diol (2 g, 16.92 mmol) was dissolved in dry DCM. Imidazole (1.15 g, 16.92 mmol) and ter-butyldimethylsilyl chloride (2.55 g, 16.92 mmol) were added, and the mixture was stirred at room temperature for overnight. After dilution with Et$_2$O (20 mL), the solution was washed with water (3×20 mL), dried over anhydrous Na$_2$SO$_4$ and filtered and evaporated under reduced pressure and purified by silica gel column chromatography (10% EtOAc/Hexane) to furnished the product 41-1 (3.57 g, 15.39 mmol, 91%) as a colorless oil. 1H NMR (300 MHz, CDCl3) δ 53.61 (2H, t, J=6.5 Hz), 3.57 (2H, t, J=3.9 Hz), 2.0 (1H, brs), 1.55-1.45 (4H, in), 1.33-1.28 (4H, in), 0.85-0.83 (9H, in), 0.009 (6H, s);

Step B: Preparation of tert-butyl 6-((tert-butyldimethylsilyl)oxy)hexyl)oxy)propanoate (41-2). To a solution of 41-1 (1 g, 4.3 mmol) in anhydrous TH (10 ml) was added NaH (17 mg, 60%, 0.43 mmol), the mixture was stirred at room temperature for 20 min, the tert-butyl acrylate (1.1 g, 8.6 mmol) was added. The resulting mixture was stirred at room temperature for 24 h, then washed with water and brine, dried over Na$_2$SO$_4$ and concentrated on silica. The residue was purified by column chromatography using EtOAc/pentane as eluent to afford tert-butyl 3-((6-((tert-butyldimethylsilyl)oxy)hexyl)oxy)propanoate as a colorless oil (1.2 g, 80%). 1H NMR (600 MHz, CDCl3) δ 7.76 (d, J=2.0 Hz, 2H), 7.63 (d, J=2.9 Hz, 2H), 4.03 (d, J=6.3 Hz, 2H), 3.66 (t, J=6.1 Hz, 2H), 3.38 (t, J=6.4 Hz, 2H), 2.50 (t, J=6.1 Hz, 2H), 1.55-1.45 (4H, m), 1.37 (s, 9H), 1.33-1.28 (4H, m), 0.85-0.83 (9H, m), 0.009 (6H, s);

Steps C & D: Preparation of tert-butyl 3-((6-((2-(2,6-dioxopiperidin-3-yl)-1,3-dioxoisoindolin-4-yl)oxy)hexyl)oxy)propanoate (41-4). To a stirred solution of 41-2 (1 g, 2.7 mmol) in THF (20 mL) was added TBAF (5.5 ml, 1 M in THF, 5.5 mmol), the mixture was stirred at room temperature for 3 h, aqueous NH$_4$Cl was added to the mixture and extracted with EtOAc. The combined organic layer was washed with brine, dried over anhydrous Na$_2$SO$_4$ to afford compound 41-3 as a yellow oil (680 mg, 98%), compound 41-3 was used directly in the next step without further purification. Compound 41-3 (88 mg, 95 µl, 0.36 mmol) was added to a solution of triphenylphosphine (113 mg, 0.43 mmol) in THF (2 ml). The mixture was cooled to 0° C. and DIAD (86 µl, 0.43 mmol) in THF (200 µL) was added dropwise. After 15 min, 2-(2,6-dioxopiperidin-3-yl)-4-hydroxyisoindoline-1,3-dione (1-8, 99 mg, 0.36 mmol,) was added in one portion. The reaction was allowed to warm to room temperature. After 2 h the solvent was removed in vacuo and the residue was purified on column chromatography using DCM/MeOH as eluent to afford compound 41-4 as a yellow oil (108 mg, 60%). LC-MS: 503 [M+H$^+$];

Step E: Preparation of N-(3-(3-carbamothioylphenyl)-1-(4,4-difluorocyclohexyl)-1H-indol-6-yl-3-((6-((2-(2,6-dioxopiperidin-3-yl)-1,3-dioxoisoindolin-4-yl)oxy)hexyl)oxy)propanamide (Compound 41). Compound 41-4 (35 mg, 0.07 mmol) was dissolved in DCM (2.0 mL) and TFA (1.0 mL). After stirring for 1 h, the solvent was evaporated to give the crude acid compound, which was used in the next step without further purification. HATU (27 mg, 0.07 mmol), DIPEA (27 µL, 0.15 mmol,), and the above crude acid compound (0.07 mmol) was added sequentially to a stirred solution of compound 24-4 (19 mg, 0.05 mmol) in DMF (2.0 mL). The solution was stirred at room temperature for 2 h. Then the mixture was poured into H$_2$O, and extracted twice with EtOAc. The combined organic layer was washed with brine, dried over anhydrous Na$_2$SO$_4$, then concentrated on silica. The residue was purified by column chromatography using DCM/MeOH as eluent to afford compound 41 (12 mg, 30%). $^1$H NMR (600 MHz, Acetone) δ 9.72 (s, 1H), 9.03 (s, 1H), 8.86 (s, 1H), 8.75 (s, 1H), 8.20-8.13 (m, 2H), 7.75-7.68 (m, 3H), 7.64 (s, 1H), 7.58 (dd, J=8.3, 7.4 Hz, 1H), 7.31 (t, J=7.7 Hz, 1H), 7.23 (dd, J=11.5, 7.9 Hz, 2H), 7.00 (dd, J=8.6, 1.6 Hz, 1H), 5.01-4.92 (m, 1H), 4.56-4.49 (m, 1H), 4.03 (t, J=6.3 Hz, 2H), 3.66 (t, J=6.1 Hz, 2H), 3.38 (t, J=6.4 Hz, 2H), 3.20-3.16 (m, 1H), 2.72-2.80-2.81 (m, 2H), 2.67-2.71 (m, 2H), 2.50 (t, J=6.1 Hz, 2H), 2.21-1.99 (m, 8H), 1.71-1.62 (m, 2H), 1.49 (dd, J=14.0, 7.0 Hz, 2H), 1.43 (td, J=14.5, 7.3 Hz, 2H), 1.34 (dd, J=15.0, 8.1 Hz, 2H). $^{13}$C NMR (151 MHz, Acetone) δ 202.23, 171.70, 171.63, 169.13, 166.91, 165.35, 156.57, 140.41, 136.95, 136.51, 135.73, 134.60, 129.33, 128.34, 125.30, 124.45, 122.64, 122.16, 119.54, 119.26, 117.07, 115.95, 114.87, 113.43, 113.33, 100.86, 70.46, 69.02, 66.62, 54.00, 52.33, 49.11, 37.82, 35.29, 32.94, 32.72, 32.40, 31.11, 25.69, 25.49, 22.37. HR-MS [M+H$^+$] m/z calculated for: C$_{43}$H$_{46}$F$_2$N$_5$O$_7$S: 814.3081. found: 814.3079.

Experimental Procedures

Western Blot

The 2.5×10$^5$ HeLa cells were treated with compounds for 24 h followed by the lysis in the RIPA buffer. The protein samples were loaded and run in the 3-8% Tris-acetate gel. After transferring proteins to the PVDF membrane, 5% bovine serum albumin solution was used for blocking for 2 h at room temperature. The membranes were incubated with the ASH1L-specific antibody (Bethyl A301-749A) at 4° C. overnight and subsequently with the anti-rabbit secondary antibody (Cell signaling technology, 7074S). The blots were detected by an ECL detection system (Amersham, RPN2236).

Cell Viability Assays

Human leukemia cells were plated at 1×10$^5$ cells/ml in 24-well plates, treated with 0.25% DMSO or compounds and cultured at 37° C. for 7-14 days. Every four days, the volume corresponding to 1×10$^5$ cells of DMSO-treated cells was spun down and resuspended in fresh media with fresh compound. At day 0 and each four day interval, 100 µl aliquots of the cell suspension were transferred to 96-well plates in quadruplicates. The quadruplicate samples were incubated for 3-4 days at 37° C., and then an MTI cell proliferation assay kit (Roche) was used to measure viable cells. Absorbance was read at 570 nm using a PHERAstar (BMG) microplate reader.

Quantitative RT-PCR

Total RNA was extracted from cells using the RNeasy mini kit (QIAGEN), and then 100-2000 ng of total RNA was reverse transcribed using the High Capacity cDNA Reverse Transcription Kit (Applied Biosystems) according to the manufacturer's protocol. Real-time PCR was performed using a CFX96 Real-Time PCR Detection System (Biorad). TaqMan Gene Expression Master Mix and TaqMan Gene Expression Assays were purchased from Thermo Fisher. Relative quantification of each gene transcript was carried out using the ΔΔC$_t$ method as described in the Biorad Real-Time PCR Applications Guide.

Cytospin/Wrigtht-Giemsa Staining

1×10$^5$ of leukemia cells treated with compounds or DMSO were harvested and placed in a Shandon EZ Single Cytofunnel (Thermo Fisher). Samples were centrifuged at 600 rpm for 5 min. The slides were air dried before staining with a Hema-3 kit (Thermo Fisher).

In Vivo Studies

Exemplary compounds disclosed herein, were used for in vivo studies in mice. Immunocompromised 8-10 week-old female NSG mice were used for in vivo efficacy studies in accordance with IACUC guidelines. Luciferase expressing human MV4:11 leukemia cells (MV4:11-luc) were engrafted intravenously via tail vein injection (1×10$^7$ cells/animal). Five days after transplantation mice were randomly assigned to a vehicle control or a compound treatment group (6-7 animals per group). Animals in each of the treatment groups were administered vehicle or compound A of the present disclosure by intraperitoneal (i.p.) injection. Treatment was continued for 17 days. Body weight was measured daily, while mean luminescence signal was measured in all mice at days 10 and 17 after initiating the treatment. At the end point of the experiment, spleen, bone marrow and peripheral blood samples were collected and the level of leukemic blasts (hCD34+ cells) was measured by flow cytometry.

The invention claimed is:

1. A method of treating cancer comprising administering to a subject suffering from cancer with a proteolysis targeting chimera (PROTAC) compound capable binding to ASH1L and an E3 ligase complex, the PROTAC compound comprising a structure of:

[Formula (Ia)]

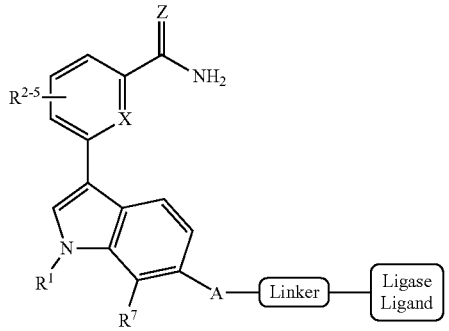

wherein X is CH or N;
wherein Z is S or O;
wherein $R^1$ is selected from

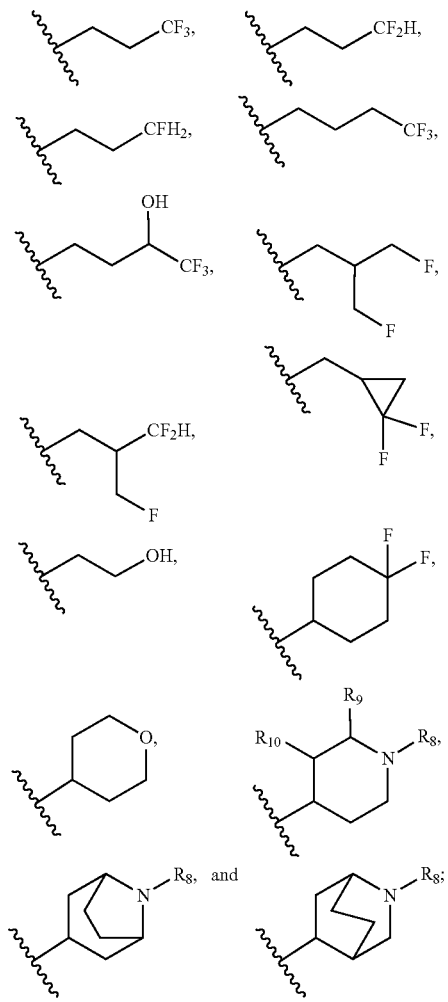

wherein $R_9$ and $R_{10}$, when present in an $R^1$ substituent, are independently selected from H, $CH_3$, F, $CFH_2$, $CF_2H$, $CF_3$, and OH;
wherein $R_8$, when present in an $R^1$ substituent, is selected from

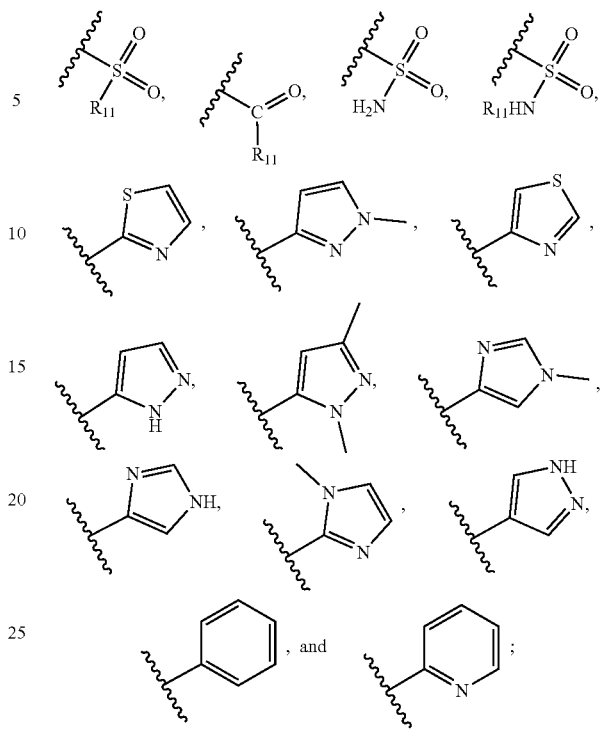

wherein $R^{11}$, when present in an $R_8$ substituent, is selected from

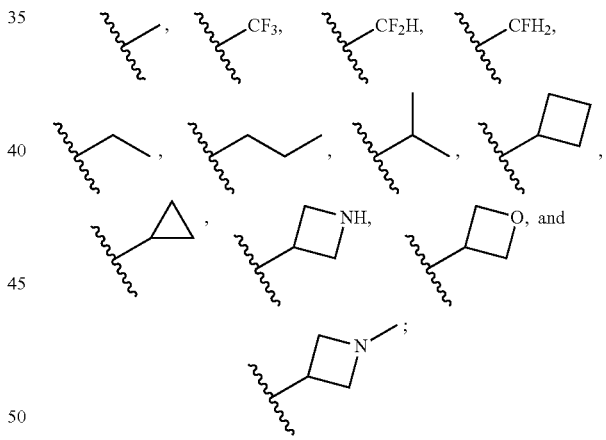

wherein $R^2$-$R^5$ and $R^7$ are independently selected from H, halogen, $CH_3$, OH, SH, $NH_2$, CN, $CF_3$, $CCl_3$, —$CH_2$—$CH_3$, —$CH_2$—OH, —$CH_2NH_2$, $CH_3SH$, $CH_2Cl$, $CH_2Br$, $CH_2F$, $CHF_2$, $CH_2CN$, $CH_2CF_3$, and $CH_2Cl_3$;
wherein A is

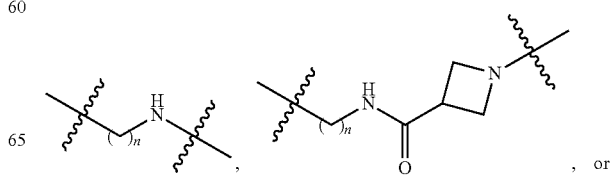

, or

-continued

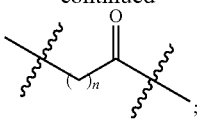

wherein Ligase Ligand is a moiety capable of binding to the E3 ligase complex; and wherein Linker is a functional group tethering the Ligase Ligand to A;

or a salt thereof.

2. The method of claim 1, wherein the Ligase Ligand is capable of binding von Hippel-Lindau (VHL) E3 ligase.

3. The method of claim 2, wherein the Ligase Ligand comprises a hydroxyproline moiety.

4. The method of claim 3, wherein the Ligase Ligand comprises

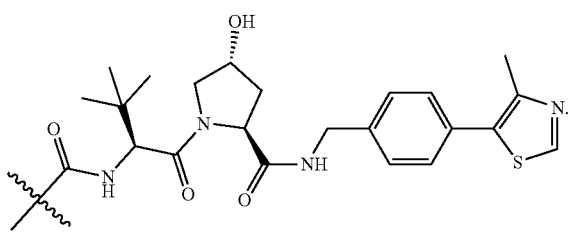 [SMILES: *C(=O)N[C@H](C(=O)N1C[C@H](O)C[C@H]1C(=O)NCc1ccc(-c2scnc2C)cc1)C(C)(C)C]

5. The method of claim 1, wherein the Ligase Ligand is capable of binding a cereblon E3 ubiquitin ligase.

6. The method of claim 5, wherein the Ligase Ligand comprises a thalidomide, lenalidomide, or pomalidomide moiety.

7. The method of claim 5, wherein the Ligase Ligand is selected from:

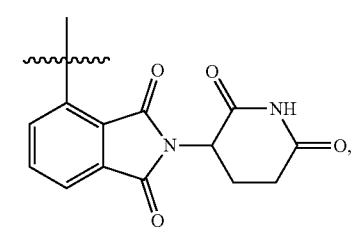

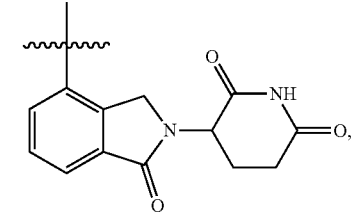

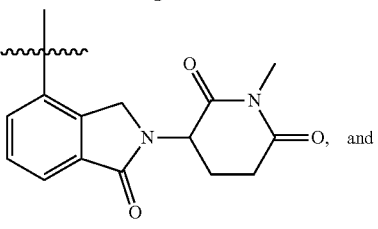

-continued

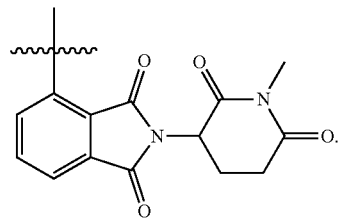

8. The method of claim 1, wherein the Ligase Ligand is capable of binding a mouse double minute 2 homolog (MDM2) E3 ubiquitin ligase or IAP E3 ubiquitin ligase.

9. The method of claim 1, wherein the Ligase Ligand is selected from:

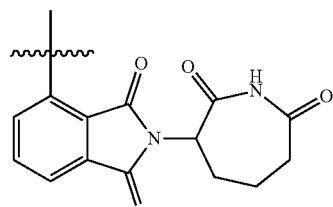

and

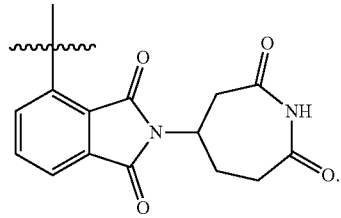

10. The method of claim 1, wherein Z is S and X is CH.
11. The method of claim 1, wherein $R^7$ is H or halogen.
12. The method of claim 1, wherein $R^2$-$R^5$ are H.
13. The method of claim 1, wherein $R^1$ is selected from

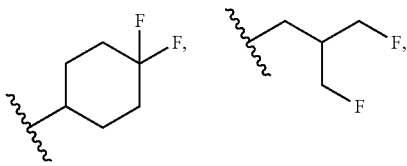

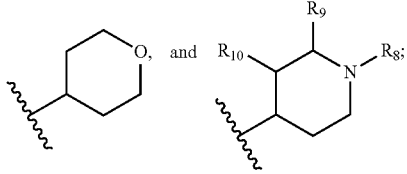

wherein $R_9$ is selected from H and $CH_3$, and $R_{10}$ is H, when present in an $R^1$ substituent;

wherein $R_8$, when present in an $R^1$ substituent, is selected from

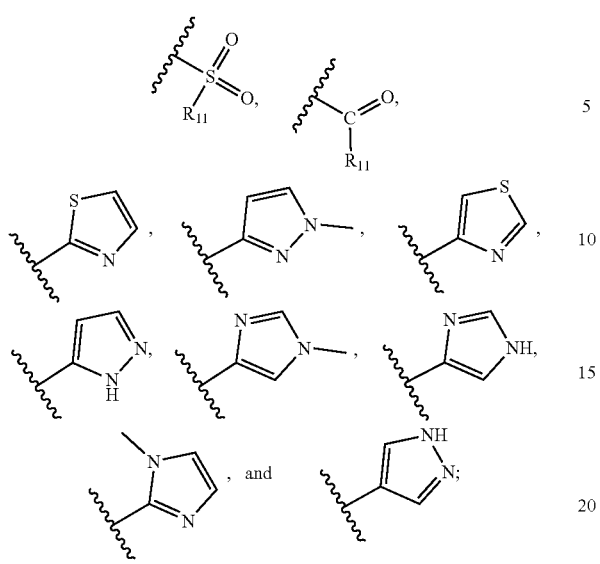

and
wherein $R^{11}$, when present in an $R_8$ substituent, is selected from

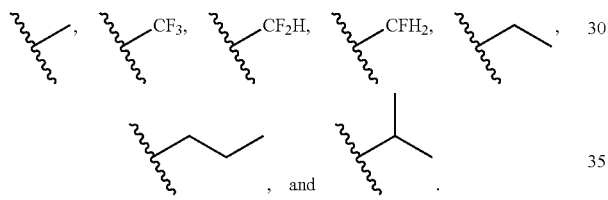

14. The method of claim 1, wherein:
(i)

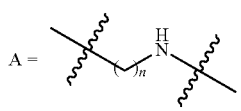

wherein n is 0, and Linker is

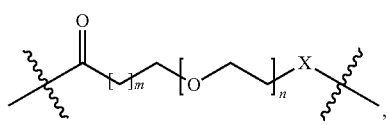

wherein X is O, wherein m is 1, wherein n is 2-4;
(ii)

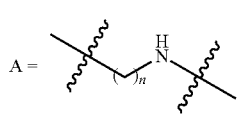

wherein n is 0, and Linker is

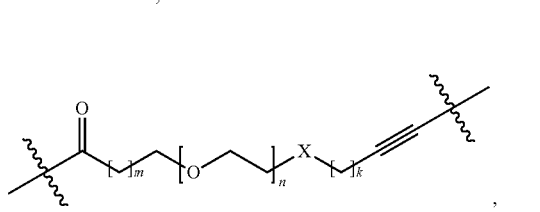

wherein X is O, wherein m is 1, wherein n is 2-4, and wherein k is 1-2;
(iii)

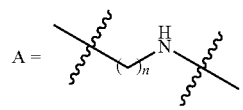

wherein n is 0, and Linker is

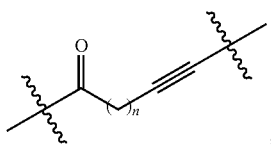

wherein n is 2-4;
(iv) A is

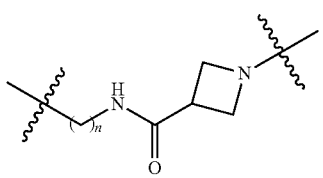

wherein n is 0, and Linker is

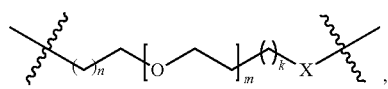

wherein n is 1, wherein m is 1 or 2, wherein X is O, wherein k is 0;
(v) A is

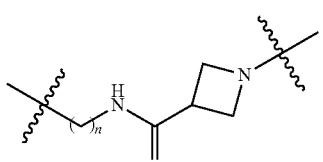

wherein n is 0 and Linker is

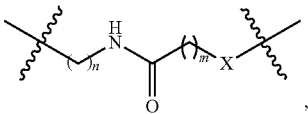

wherein n is 5-6, wherein m is 1, wherein X is O;
(vi) A is

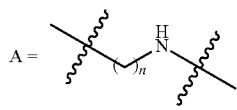

wherein n is 0, and Linker is

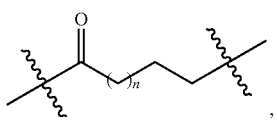

wherein n is 6-10; or
(vii) A is

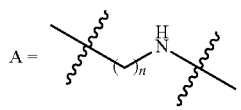

wherein n is 0, and Linker is

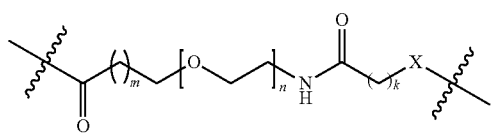

X=O, NH or $CH_2$, wherein m is 6-10, wherein n is 0, wherein k is 1, and wherein X is O.

15. The method of claim 1,
wherein X is CH;
wherein Z is S;
wherein $R^7$ is H or halogen;
wherein $R^2$-$R^5$ are H;
$R^1$ is selected from

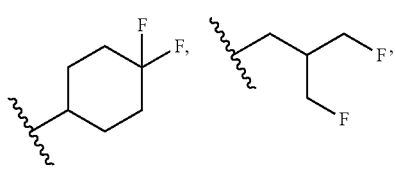

-continued

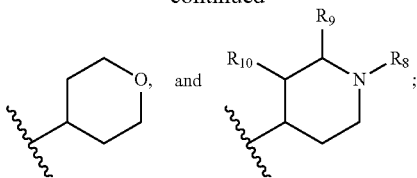

wherein $R_9$ is selected from H and $CH_3$, and $R_{10}$ is H, when present in an $R^1$ substituent;
wherein $R_8$, when present in an $R^1$ substituent, is selected from

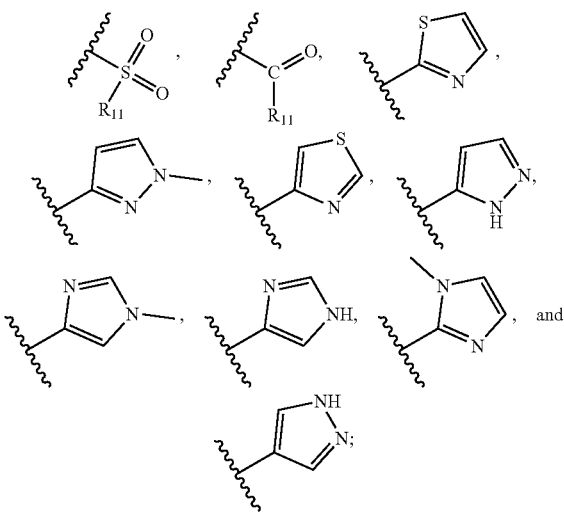

and
wherein $R^{11}$, when present in an $R_8$ substituent, is selected from

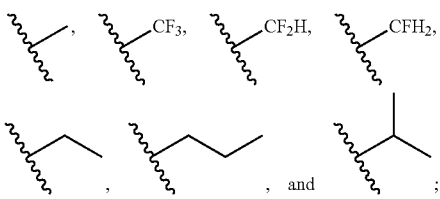

wherein A is

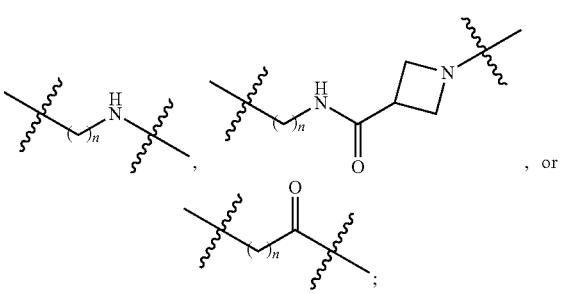

wherein Ligase Ligand is selected from
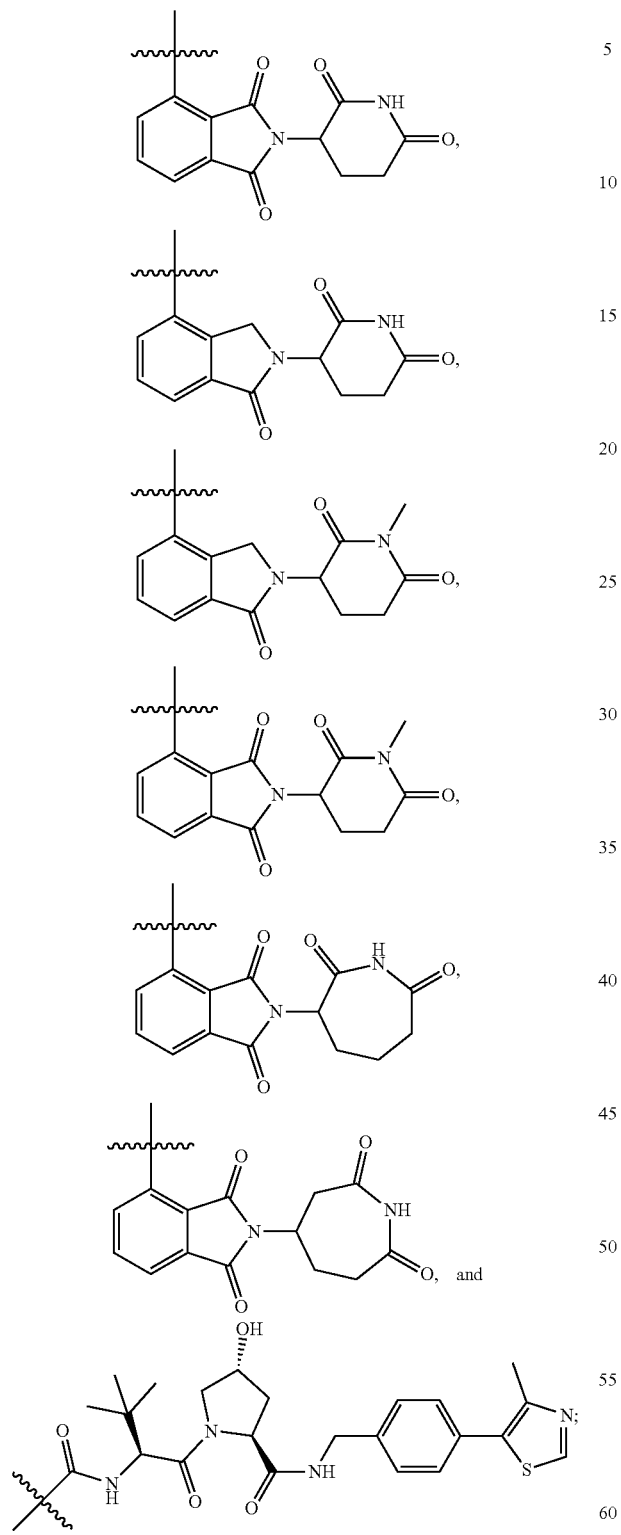
and
wherein Linker is a functional group tethering the Ligase Ligand to A;
or a salt thereof.
16. The method of claim 1, wherein:
(i)
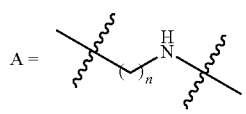
wherein n is 0, and Linker is
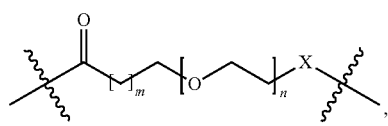
wherein X is O, wherein m is 1, wherein n is 2-4;
(ii)
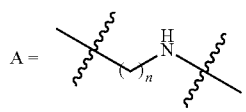
wherein n is 0, and Linker is
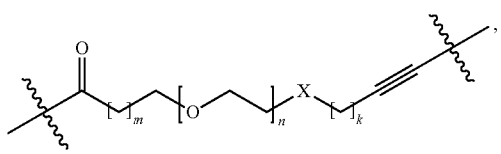
wherein X is O, wherein m is 1, wherein n is 2-4, and wherein k is 1-2;
(iii)
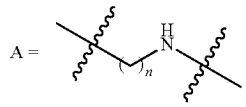
wherein n is 0, and Linker is
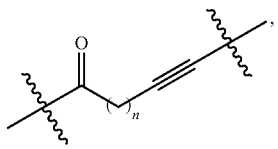

wherein n is 2-4;

(iv) A is

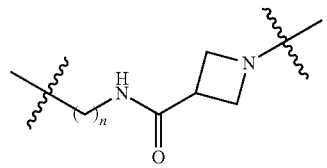

wherein n is 0, and Linker is

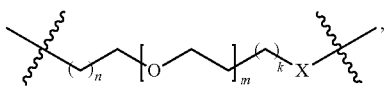

wherein n is 1, wherein m is 1 or 2, wherein X is O, wherein k is 0;

(v) A is

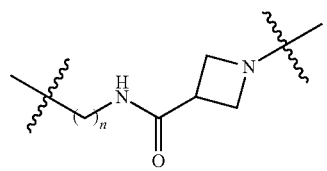

wherein n is 0 and Linker is

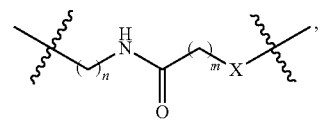

wherein n is 5-6, wherein m is 1, wherein X is O;

(vi) A is

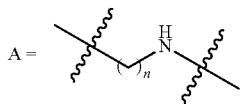

wherein n is 0, and Linker is

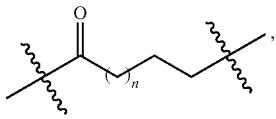

wherein n is 6-10; or (vii) A is

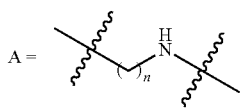

wherein n is 0, and Linker is

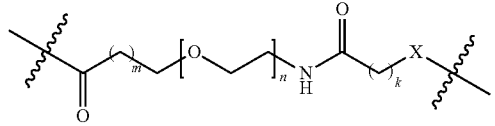

X=O, NH or $CH_2$, wherein m is 6-10, wherein n is 0, wherein k is 1, and wherein X is O.

17. The method of claim 1, selected from Compounds 1-91.

18. The method of claim 1, wherein the cancer is a cancer selected from a leukemia, a hematologic malignancy, and a solid tumor cancer.

19. The method of claim 18, wherein the cancer is a leukemia selected from acute myeloid leukemia (AML), acute lymphoblastic leukemia (ALL), mixed lineage leukemia, or a leukemia with partial tandem duplication of MLL.

* * * * *